US010889556B2

(12) United States Patent
Cohen et al.

(10) Patent No.: US 10,889,556 B2
(45) Date of Patent: Jan. 12, 2021

(54) COMPOSITIONS AND METHODS FOR INHIBITING INFLUENZA RNA POLYMERASE PA ENDONUCLEASE

(71) Applicant: The Regents of the University of California, Oakland, CA (US)

(72) Inventors: Seth M. Cohen, Carlsbad, CA (US); Cy V. Credille, San Diego, CA (US); David T. Puerta, Fallbrook, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/125,468

(22) Filed: Sep. 7, 2018

(65) Prior Publication Data

US 2019/0106398 A1    Apr. 11, 2019

Related U.S. Application Data

(63) Continuation-in-part of application No. PCT/US2017/021457, filed on Mar. 8, 2017.

(60) Provisional application No. 62/305,407, filed on Mar. 8, 2016, provisional application No. 62/608,475, filed on Dec. 20, 2017.

(51) Int. Cl.

| | |
|---|---|
| *C07D 309/32* | (2006.01) |
| *C07D 309/40* | (2006.01) |
| *C07D 213/69* | (2006.01) |
| *C07D 213/90* | (2006.01) |
| *C07D 401/04* | (2006.01) |
| *C07D 401/10* | (2006.01) |
| *C07D 413/04* | (2006.01) |
| *C07C 49/747* | (2006.01) |
| *C07C 49/453* | (2006.01) |
| *C07C 62/38* | (2006.01) |
| *C07C 65/03* | (2006.01) |
| *C07C 65/05* | (2006.01) |
| *C07C 69/757* | (2006.01) |
| *A61P 31/16* | (2006.01) |
| *C07C 49/717* | (2006.01) |
| *C07C 49/753* | (2006.01) |

(52) U.S. Cl.
CPC ............ *C07D 309/32* (2013.01); *A61P 31/16* (2018.01); *C07C 49/717* (2013.01); *C07C 49/747* (2013.01); *C07C 49/753* (2013.01); *C07C 62/38* (2013.01); *C07C 65/03* (2013.01); *C07C 65/05* (2013.01); *C07C 69/757* (2013.01); *C07D 213/69* (2013.01); *C07D 213/90* (2013.01); *C07D 309/40* (2013.01); *C07D 401/04* (2013.01); *C07D 401/10* (2013.01); *C07D 413/04* (2013.01); *C07C 2601/18* (2017.05)

(58) Field of Classification Search
CPC .. C07D 309/32; C07D 309/40; C07D 213/69; C07D 213/90; C07D 401/04; C07D 401/10; C07D 413/04; C07C 49/747; C07C 49/753; C07C 62/38; C07C 654/03; C07C 654/05; C07C 69/757; C07C 2601/18

See application file for complete search history.

(56) References Cited

U.S. PATENT DOCUMENTS

| | | | |
|---|---|---|---|
| 9,260,453 B2 | 2/2016 | Sumino et al. | |
| 2005/0220895 A1 | 10/2005 | Bucalo et al. | |
| 2014/0079666 A1 | 3/2014 | Webb et al. | |
| 2014/0194476 A1* | 7/2014 | Wolkerstorfer | ...... C07D 213/79 514/346 |
| 2015/0322413 A1 | 11/2015 | Tavis et al. | |

FOREIGN PATENT DOCUMENTS

WO    WO-2017/156194 A1    3/2017

OTHER PUBLICATIONS

Belonosov, ,I.S., 22 Zhurnd Prikladnoi Khimii (Sankt-Peterburg, Russian Federation) 1103-7 (1949) (Year: 1949).*
Anonymous (2019). "Table. Adjusted vaccine effectiveness estimates for influenza seasons from 2005-2015," www.cdc.gov/flu/professionals/vaccination/effectivenes-studies.htm (last accessed Jun. 12, 2019), 1 page.
Anonymous (2019). "Tamiflu pediatric adverse events: questions and answers|FDA" located at www.fda.gov/drugs/postmarketdrugsafetyinformationpatientsandproviders/tamiflupediatricadverseeventsquestionsandanswers (last accessed Jun. 12, 2019), 6 pages.
Baughman, B.M. et al. (Mar. 16, 2012, e-published Jan. 19, 2012). "Identification of influenza endonuclease inhibitors using a novel fluorescence polarization assay," *ACS Chem Biol* 7(3):526-534.
Bauman, J.D. et al. (Nov. 15, 2013, e-published Sep. 13, 2013). "Crystallographic fragment screening and structure-based optimization yields a new class of influenza endonuclease inhibitors," *ACS Chem Biol* 8(11):2501-2508.
Beaton, A.R. et al. (Sep. 11, 1981). "Selected host cell capped RNA fragments prime influenza viral RNA transcription in vivo," *Nucleic Acids Res* 9(17):4423-4436.
Blok, V. et al. (May 1996). "Inhibition of the influenza virus RNA-dependent RNA polymerase by antisera directed against the carboxy-terminal region of the PB2 subunit," *J Gen Virol* 77 (Pt 5):1025-1033.

(Continued)

*Primary Examiner* — Timothy R Rozof
(74) *Attorney, Agent, or Firm* — Mintz, Levin, Cohn, Ferris, Glovsky and Popeo, P.C.

(57) ABSTRACT

There are provided inter alia metalloenzyme inhibitors, such as inhibitors of influenza A RNA dependent RNA polymerase PA subunit endonuclease, and methods of synthesis and use of the same.

16 Claims, 10 Drawing Sheets

Specification includes a Sequence Listing.

(56) References Cited

OTHER PUBLICATIONS

Böhm, H.J .et al. (Dec. 2004). "Scaffold hopping," Drug Discov Today Technol 1(3):217-224.
Cianci, C. et al. (Dec. 1, 1996). "Identification of N-Hydroxamic Acid and N-Hydroxyimide Compounds that Inhibit the Influenza Virus Polymerase," Antivir. Chem. Chemother. 7(6):353-360.
Corona, A. et al. (Jan. 22, 2016). "Ribonuclease H/DNA Polymerase HIV-1 Reverse Transcriptase Dual Inhibitor: Mechanistic Studies on the Allosteric Mode of Action of Isatin-Based Compound RMNC6.," PlosOne 11(1):e0147225.
Credille, C.V. et al. (Jul. 14, 2016, e-published Jun. 22, 2016). "Fragment-Based Identification of Influenza Endonuclease Inhibitors," J Med Chem 59(13):6444-6454.
Dias, A. et al. (Apr. 16, 2009, e-published Feb. 4, 2009). "The cap-snatching endonuclease of influenza virus polymerase resides in the PA subunit," Nature 458(7240):914-918.
Drake, J.W. et al. (May 1993). "Rates of spontaneous mutation among RNA viruses," PNAS USA 90(9):4171-4175.
Dubois, R.M. et al. (2012, e-published Aug. 2, 2012). "Structural and biochemical basis for development of influenza virus inhibitors targeting the PA endonuclease," PLoS Pathog 8(8):e1002830.
Dunning, J. et al. (Dec. 2014, e-published Sep. 8, 2014). "Antiviral combinations for severe influenza," Lancet Infect Dis 14(12):1259-1270.
Fiore, A.E. et al. (Jan. 21, 2011). "Antiviral agents for the treatment and chemoprophylaxis of influenza—recommendations of the Advisory Committee on Immunization Practices (ACIP)," MMWR Recomm Rep 60(1):1-24.
Fodor, E. et al. (2013). "The RNA polymerase of influenza a virus: mechanisms of viral transcription and replication," Acta Virol 57(2):113-122.
Furuse, Y. et al. (Oct. 2009, e-published Aug. 3, 2009). "Large-scale sequence analysis of M gene of influenza A viruses from different species: mechanisms for emergence and spread of amantadine resistance," Antimicrob Agents Chremother53(10):4457-4463.
Hastings, J.C. et al. (May 1996). "Anti-influenza virus activities of 4-substituted 2,4-dioxobutanoic acid inhibitors," Antimicrob Agents Chemother40(5):1304-1307.
Hatakeyama, D. et al. (Sep. 5, 2014, e-published Jul. 25, 2014). "A novel functional site in the PB2 subunit of influenza A virus essential for acetyl-CoA interaction, RNA polymerase activity, and viral replication," J Biol Chem 289(36):24980-24994.
Hopkins, A.L. et al. (May 15, 2004). "Ligand efficiency: a useful metric for lead selection," Drug Discov Today 9(10):430-431.
Huang, T.S. et al. (Nov. 1990). "Determination of influenza virus proteins required for genome replication," J Virol 64(11):5669-5673.
International Search Report dated Jul. 7, 2017, for PCT Application No. PCT/US2017/021457, filed Mar. 8, 2017, 5 pages.
Jacobsen, J.A. et al. (Jan. 27, 2011, e-published Dec. 28, 2010). "Identifying chelators for metalloprotein inhibitors using a fragment-based approach," J Med Chem 54(2):591-602.
Kowalinski, E. et al. (2012, e-published Aug. 2, 2012). "Structural analysis of specific metal chelating inhibitor binding to the endonuclease domain of influenza pH1N1 (2009) polymerase," PLoS Pathog. 8(8):e1002831.
Kuzuhara, T.et al. (Oct. 13, 2009). "Green tea catechins inhibit the endonuclease activity of influenza A virus RNA polymerase," PLoS Curr. 1:RRN1052.
Mills, C. E. et al. (Dec. 16, 2004). "Transmissibility of 1918 pandemic influenza," Nature 432:(7019):904-906.
Monod, A. et al. (Apr. 2015). "Learning from structure-based drug design and new antivirals targeting the ribonucleoprotein complex for the treatment of influenza," Expert Opin. Drug Discov.10(4):345-371.
Nakazawa, M. et al. (Jun. 2008, e-published Jan. 17, 2008). PA subunit of RNA polymerase as a promising target for anti-influenza virus agents. Antiviral Res. 78(3):194-201.
Parhi, A.K. et al. (Nov. 1, 2013, e-published Sep. 4, 2013). "Phenyl substituted 3-hydroxypyridin-2(1H)-ones: inhibitors of influenza A endonuclease," Bioorg Med Chem 21(21):6435-6446.
Plotch, S. J. et al. (Mar. 1981). "A unique cap(m$^7$GpppXm)-dependent influenza virion endonuclease cleaves capped RNAs to generate the primers that initiate viral RNA transcription," Cell 23(3): 847-858.
Raha, K. et al. (Feb. 4, 2004, e-published Jan. 9, 2004). "A quantum mechanics-based scoring function: study of zinc ion-mediated ligand binding," J. Am. Chem. Soc. 126(4):1020-1021.
Sagong, H. Y. et al. (May 7, 2013, e-collection Jun. 13, 2013). "3-Hydroxyquinolin-2(1H)-ones As Inhibitors of Influenza A Endonuclease," ACS Med. Chem. Lett. 4(6):547-550.
Sagong, H. Y. et al. (Oct. 9, 2014, e-published Sep. 29, 2014). "Phenyl substituted 4-hydroxypyridazin-3(2H)-ones and 5-hydroxypyrimidin-4(3H)-ones: inhibitors of influenza A endonuclease," J. Med. Chem. 57(19):8086-8098.
Sanna, D. et al. (Feb. 3, 2012). "Coordinating properties of pyrone and pyridinone derivatives, tropolone and catechol toward the VO$^{2+}$ ion: an experimental and computational approach," Eur. J. Inorg. Chem. (7):1079-1092.
Stevaert, A. et al. (Oct. 2013, e-published Jul. 3, 2013). "Mutational analysis of the binding pockets of the diketo acid inhibitor L-742,001 in the influenza virus PA endonuclease," J. Virol. 87(19):10524-10538.
Stiver, G. et al. (Jan. 7, 2003). "The treatment of influenza with antiviral drugs," CMAJ 168(1):49-56.
Tomassini, J. et al. (Dec. 1994). "Inhibition of cap (m7GpppXm)-dependent endonuclease of influenza virus by 4-substituted 2,4-dioxobutanoic acid compounds," Antimicrob. Agents Chemother. 38(12):2827-2837.
Tomassini, J. E. et al. (May 1996). "A novel antiviral agent which inhibits the endonuclease of influenza viruses," Antimicrob. Agents Chemother. 40(5):1189-1193.
Written Opinion dated Jul. 7, 2017, for PCT Application No. PCT/US2017/021457, filed Mar. 8, 2017, 6 pages.
Xie, L. et al. (Jan. 1, 2016, Nov. 11, 2015). "Molecular basis of mRNA cap recognition by Influenza B polymerase PB2 subunit," J. Biol. Chem. 291(1):363-370.
Zhang, J. et al. (Apr. 10, 2012, e-published Jan. 2, 2012). "Modeling structural coordination and ligand binding in zinc proteins with a polarizable potential," J. Chem. Theory Comput 8(4):1314-1324.

* cited by examiner

COMPOSITIONS AND METHODS FOR INHIBITING INFLUENZA RNA POLYMERASE PA ENDONUCLEASE

CROSS-REFERENCES TO RELATED APPLICATION

This application is a Continuation-In-Part of the International Application No. PCT/US2017/021457, filed Mar. 8, 2017, which claims the benefit of U.S. Provisional Patent Application No. 62/305,407, filed Mar. 8, 2016. This application also claims the benefit of U.S. Provisional Patent Application No. 62/608,475, filed Dec. 20, 2017. All prior applications are incorporated herein by reference in their entireties and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048537-573002US_Sequence_Listing.txt, created Dec. 13, 2018, 3,019 bytes, machine format IBM-PC, MS Windows operating system, is hereby incorporated by reference.

STATEMENT AS TO RIGHTS TO INVENTIONS MADE UNDER FEDERALLY SPONSORED RESEARCH AND DEVELOPMENT

This invention was made with Government support under grant number GM098435 awarded by the National Institutes of Health. The Government has certain rights in the invention.

BACKGROUND

The influenza virus is responsible for annual seasonal epidemics, resulting in between 3-5 million yearly cases of severe illness and an estimated 250,000 to 500,000 deaths worldwide (see Reference 1). The last century alone has seen the advent of four influenza pandemics, each resulting in millions of deaths (see Reference 2). While vaccinations are a reasonable prophylactic for healthy adults, they must be re-administered annually and are markedly less effective for individuals with compromised immunity or similar high-risk medical conditions. In addition, efficacy of these vaccines is heavily dependent on correctly predicting the predominant infectious strains for any given year, and incorrect predictions can render vaccination less than 25% effective, as reported by the US Center for Disease Control and Prevention. Existing drugs, such as Zanamivir marketed by GlaxoSmithKline and oseltamivir marketed by Roche, which target viral neuraminidase, can be useful in treating influenza infections, but must be administered within 1-2 days of infection to be effective. These therapeutics also suffer from undesirable side effects, including unusual neurologic or psychiatric events such as delirium, hallucinations, confusion, and abnormal behavior, primarily in children (see References 4, 5, and 6). M2 ion channel blockers such as Rimantadine marketed by Sun Pharma and Amantadine marketed by Endo Pharmaceuticals were previously effective at inhibiting viral replication; however, 100% of seasonal H3N2 and 2009 pandemic H1N1 influenza strains now show resistance to these drugs (see References 7 and 8). Considering this, there is an urgent need for the development of new drugs to prevent and treat influenza infection.

Disclosed herein, inter alia, are solutions to these and other problems in the art.

BRIEF SUMMARY

Herein are provided, inter alia, compounds capable of inhibiting the level of activity of the RNA-dependent RNA polymerase PA subunit endonuclease protein and methods of using the same.

In an aspect is provided a compound having the formula:

$$\text{(I)}$$

$$\text{(II)}$$

$$\text{(IIa)}$$

$$\text{(III)}$$

Y is O, S, or NH. $W^1$ is —O—, —CH($R^1$)—, or —N($R^1$)—. $R^1$ is hydrogen, halogen, —C$X^1_3$, —CH$X^1_2$, —CH$_2X^1$, —OC$X^1_3$, —OCH$_2X^1$, —OCH$X^1_2$, —SO$_{n1}R^{1D}$, —SO$_{v1}$NR$^{1A}R^{1B}$, —NHC(O)NR$^{1A}R^{1B}$, —N(O)$_{m1}$, —NR$^{1A}R^{1B}$, —C(O)$R^{1C}$, —C(O)—O$R^{1C}$, —C(O)NR$^{1A}R^{1B}$, —O$R^{1D}$, —NR$^{1A}$SO$_2R^{1D}$, —NR$^{1A}$C(O)$R^{1C}$, —NR$^{1A}$C(O)O$R^{1C}$, —NR$^{1A}$O$R^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $W^2$ is —C($R^2$)= or —N=. $R^2$ is hydrogen, halogen, —C$X^2_3$, —CH$X^2_2$, —CH$_2X^2$, —OC$X^2_3$, —OCH$_2X^2$, —OCH$X^2_2$, —CN, —SO$_{n2}R^{2D}$, —SO$_{v2}$NR$^{2A}R^{2B}$, —NHC(O)NR$^{2A}R^{2B}$, —N(O)$_{m2}$, —NR$^{2A}R^{2B}$, —C(O)$R^{2C}$, —C(O)—O$R^{2C}$, —C(O)NR$^{2A}R^{2B}$, —O$R^{2D}$, —NR$^{2A}$SO$_2R^{2D}$, —NR$^{2A}$C(O)$R^{2C}$, —NR$^{2A}$C(O)O$R^{2C}$, —NR$^{2A}$O$R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $W^3$ is —C($R^1$)= or —N=. $R^3$ is hydrogen, halogen, —C$X^3_3$, —CH$X^3_2$, —CH$_2X^3$, —OC$X^3_3$, —OCH$_2X^3$, —OCH$X^3_2$, —CN, —SO$_{n3}R^{3D}$, —SO$_{v3}$NR$^{3A}R^{3B}$, —NHC(O)NR$^{3A}R^{3B}$, —N(O)$_{m3}$, —NR$^{3A}R^{3B}$, —C(O)$R^{3C}$, —C(O)—O$R^{3C}$, —C(O)NR$^{3A}R^{3B}$, —O$R^{3D}$, —NR$^{3A}$SO$_2R^{3D}$, —NR$^{3A}$C(O)

R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen, halogen, —CX$^4{}_3$, —CHX$^4{}_2$, —CH$_2$X$^4$, —OCX$^4{}_3$, —OCH$_2$X$^4$, —OCHX$^4{}_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, and R$^{4D}$, is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1A}$ and R$^{1B}$ substituents bonded to the same nitrogen atom may optionally be joined to form a substituted or unsubstituted heterocycloalkyl or substituted or unsubstituted heteroaryl. R$^{2A}$ and R$^{2B}$ substituents bonded to the same nitrogen atom may optionally be joined to form a substituted or unsubstituted heterocycloalkyl or substituted or unsubstituted heteroaryl. R$^{3A}$ and R$^{3B}$ substituents bonded to the same nitrogen atom may optionally be joined to form a substituted or unsubstituted heterocycloalkyl or substituted or unsubstituted heteroaryl. R$^{4A}$ and R$^{4B}$ substituents bonded to the same nitrogen atom may optionally be joined to form a substituted or unsubstituted heterocycloalkyl or substituted or unsubstituted heteroaryl. Each X, X$^1$, X$^2$, X$^3$, and X$^4$ is independently —F, —Cl, —Br, or —I. The symbols n1, n2, n3, and n4 are independently an integer from 0 to 4. The symbols m1, m2, m3, m4, v1, v2, v3, and v4 are independently an integer from 1 to 2.

In an aspect is provided a pharmaceutical composition including a compound described herein, or pharmaceutically acceptable salt thereof, and a pharmaceutically acceptable excipient.

In an aspect is provided a method of inhibiting RNA-dependent RNA polymerase PA subunit endonuclease protein activity. The method includes contacting the RNA-dependent RNA polymerase PA subunit endonuclease protein with an effective amount of a compound described herein.

In an aspect is provided a method of treating a viral infection associated with RNA-dependent RNA polymerase PA subunit endonuclease protein activity. The method including administering to a subject in need thereof an effective amount of a compound described herein.

In an aspect is provided a method of treating an influenza virus infection including administering to a subject in need thereof an effective amount of a compound described herein.

BRIEF DESCRIPTION OF THE DRAWINGS

FIG. 4A depicts a 3-dimensional docking analysis of compound 71 in influenza PA endonuclease (PDB: 4M4Q). FIG. 4B depicts a 2-dimensional representation of the results shown in FIG. 4A. Sequence listing: PDB (4M4Q): SEQ ID NO: 1.

FIG. 5A depicts the cytotoxicity (CC$_{50}$) of compound 71 (squares) and compound L-742,001 (circles) in MDCK cells. FIG. 5B depicts the potency (EC$_{50}$) of compound 71 (squares) and compound L-742,001 (circles) in MDCK cells.

FIG. 6A shows the small crystals grown at room temperature. FIG. 6B shows crystals grown at 35° C. and 37° C.

FIG. 7A depicts the X-ray structure of co-crystal of the endonuclease construct with compound 5. FIG. 7B depicts the X-ray structure of co-crystal of the endonuclease construct with compound 6. FIG. 7C depicts the X-ray structure of co-crystal of the endonuclease construct with compound 101. FIG. 7D depicts the X-ray structure of co-crystal of the endonuclease construct with compound 101 in full active site view. FIG. 7E depicts the X-ray structure of co-crystal of the endonuclease construct with compound 106 in full active site view.

DETAILED DESCRIPTION

I. Definitions

Figure 1A:
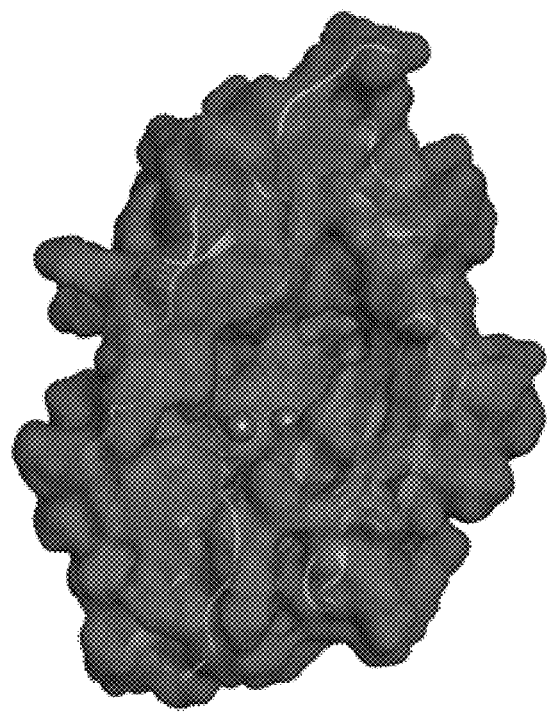
FIG. 1A-1B: Structural model of the influenza RNA-dependent RNA polymerase PA subunit (PDB: 4M5Q). The endonuclease active site employs two divalent metal cations to facilitate the hydrolytic cleavage of the phosphodiester backbone of nucleic acids. Key active site residues and binding pockets are highlighted. Pocket 2 is obscured by residue Tyr24. Sequence listing: PDB (4M5Q): SEQ ID NO:1.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, or S), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, biphenyl, pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded ("=O") to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

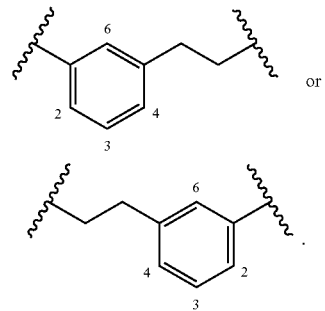

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$-C$_8$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R", —ONR'R", —NR'C (O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group" or "substituent" as used herein, means a group selected from the following moieties:
(A) oxo, halogen, —CF$_3$, —CH$_2$F, —CHF$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
(i) oxo, halogen, —$CF_3$, —$CH_2F$, —$CHF_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, heteroaryl, substituted with at least one substituent selected from:
(a) oxo, halogen, —$CF_3$, —$CH_2F$, —$CHF_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —$CF_3$, —$CH_2F$, —$CHF_2$, —CN, —OH, —$NH_2$, —COOH, —$CONH_2$, $NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$OCH_2F$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted."

Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

The symbol "〰" denotes the point of attachment of a chemical moiety to the remainder of a molecule or chemical formula.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "RNA-dependent RNA polymerase PA subunit endonuclease inhibitor" or 'RNA polymerase PA subunit endonuclease inhibitor" or "influenza endonuclease inhibitor" or "Endonuclease inhibitor" is a composition (e.g., oligonucleotide, protein, or compound) that negatively affects (e.g. decreases) the activity or function of RNA polymerase PA subunit endonuclease relative to the activity or function of the same endonuclease in the absence of the inhibitor (e.g., wherein the endonuclease inhibitor binds endonuclease). A "RNA-dependent RNA polymerase PA subunit endonuclease inhibitor compound" or "RNA polymerase PA subunit endonuclease inhibitor compound" or "influenza endonuclease inhibitor compound" or "endonuclease inhibitor compound" refers to a compound (e.g. compounds described herein) that reduces the activity of RNA polymerase PA subunit endonuclease when compared to a control, such as absence of the compound or a compound with known inactivity.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

An amino acid residue in a protein "corresponds" to a given residue when it occupies the same essential structural position within the protein as the given residue. For example, a selected residue in a selected protein corresponds to Tyr24 of the binding pocket 2 of human influenza endonuclease when the selected residue occupies the same essential spatial or other structural relationship as Tyr24 in human influenza endonuclease. In some embodiments, where a selected protein is aligned for maximum homology with the human influenza endonuclease protein, the position in the aligned selected protein aligning with Tyr24 is said to correspond to Tyr24. Instead of a primary sequence alignment, a three dimensional structural alignment can also be used, e.g., where the structure of the selected protein is aligned for maximum correspondence with the human influenza endonuclease protein and the overall structures compared. In this case, an amino acid that occupies the same essential position as Tyr24 in the structural model is said to correspond to the Tyr24 residue.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

The term "nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer includes a detectable label, as disclosed herein and generally known in the art.

As used herein, the term "infectious disease" refers to a disease or condition related to the presence of an organism (the agent or infectious agent) within or contacting the subject or patient. Examples include a bacterium, fungus, virus, or other microorganism. A "bacterial infectious disease" is an infectious disease wherein the organism is a bacterium. A "viral infectious disease" is an infectious disease wherein the organism is a virus.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. In embodiments, the treating or treatment is no prophylactic treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "associated" or "associated with" in the context of a substance or substance activity or function associated with a disease (e.g. infectious disease, hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with infection may be treated with an agent (e.g. compound as described herein) effective as an antiviral agent.

As used herein, "biomolecule" is used in its customary sense and refers to a molecule found in nature or derivatives thereof, including macromolecules such as proteins, carbohydrates, lipids, and nucleic acids, as well as small molecules such as primary metabolites, secondary metabolites, and natural products. A biomolecule may be present as a moiety attached to the remainder of a compound. A biomolecule includes but is not limited to nucleic acids (e.g. DNA and RNA), peptide nucleic acids, sugars, peptides, proteins, antibodies, lipids, small molecule affinity ligands e.g. inhibitors, biotin and haptens.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The term "RNA-dependent RNA polymerase PA subunit endonuclease" refers to a subunit of a viral RNA polymerase having endonuclease activity (including homologs, isoforms, and functional fragments thereof) which is involved in nucleic acid polymerization. The term includes any recombinant or naturally-occurring form of RNA-dependent RNA polymerase PA subunit endonuclease, or variants thereof, that maintain RNA-dependent RNA polymerase PA subunit endonuclease activity (e.g. within at least 30%, 40%, 50%, 60%, 70%, 80%, 90%, 95%, or 100% activity compared to wildtype RNA-dependent RNA polymerase PA subunit endonuclease). In embodiments, RNA-dependent RNA polymerase PA subunit endonuclease may be part of the polymerase complex. In embodiments, RNA-dependent RNA polymerase PA subunit endonuclease is a Orthomyxoviridae RNA-dependent RNA polymerase PA subunit endonuclease. In embodiments, RNA-dependent RNA polymerase PA subunit endonuclease is a Thogotovirus, Isavirus, Influenzavirus A, Influenzavirus B or Influenzavirus C RNA-dependent RNA polymerase PA subunit endonuclease. In embodiments, RNA-dependent RNA polymerase PA subunit endonuclease is a Influenzavirus A RNA-dependent RNA polymerase PA subunit endonuclease. The RNA-dependent RNA polymerase PA subunit endonuclease is a component of the RNA-dependent RNA polymerase, which includes the polymerase basic 2 and polymerase basic 1 polypeptides. The RNA-dependent RNA polymerase may be referred to as a cap-snatching polymerase. In embodiments, the RNA-dependent RNA polymerase is from the same organism as the included RNA-dependent RNA polymerase PA subunit endonuclease.

II. Compounds

In an aspect is provided a compound having the formula:

(I)

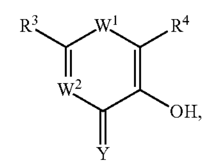

(II)

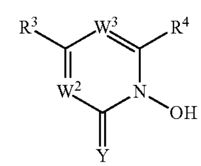

(IIa)

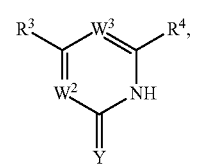

or (III)

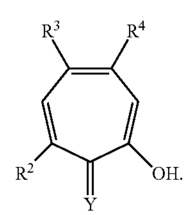

Y is O, S, or NH.

$W^1$ is —O—, —CH($R^1$)—, or —N($R^1$)—.

$R^1$ is hydrogen, halogen, —$CX^1{}_3$, —$CHX^1{}_2$, —$CH_2X^1$, —$OCX^1{}_3$, —$OCH_2X^1$, —$OCHX^1{}_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ and $R^3$ may optionally be joined to form a substituted or unsubstituted heterocycloalkyl or substituted or unsubstituted heteroaryl. $R^1$ and $R^4$ may optionally be joined to form a substituted or unsubstituted heterocycloalkyl or substituted or unsubstituted heteroaryl.

$W^2$ is —C($R^2$)= or —N=.

$R^2$ is hydrogen, halogen, —$CX^2{}_3$, —$CHX^2{}_2$, —$CH_2X^2$, —$OCX^2{}_3$, —$OCH_2X^2$, —$OCHX^2{}_2$, —CN, —$SO_{n2}R^{2D}$, —$SO_{v2}NR^{2A}R^{2B}$, —NHC(O)$NR^{2A}R^{2B}$, —N(O)$_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ and Y may optionally be joined to form a substituted or unsubstituted heterocycloalkyl or substituted or unsubstituted heteroaryl. $R^2$ and $R^3$ may optionally be joined to form a substituted or unsubstituted cycloalkyl, substituted or unsubstituted heterocycloalkyl, substituted or unsubstituted aryl, or substituted or unsubstituted heteroaryl.

$W^3$ is —C($R^1$)= or —N=.

$R^3$ is hydrogen, halogen, —$CX^3{}_3$, —$CHX^3{}_2$, —$CH_2X^3$, —$OCX^3{}_3$, —$OCH_2X^3$, —$OCHX^3{}_2$, —CN, —$SO_{n3}R^{3D}$, —$SO_{v3}NR^{3A}R^{3B}$, —NHC(O)$NR^{3A}R^{3B}$, —N(O)$_{m3}$, —$NR^{3A}R^{3B}$, —C(O)$R^{3C}$, —C(O)—$OR^{3C}$, —C(O)$NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, —$CX^4{}_3$, —$CHX^4{}_2$, —$CH_2X^4$, —$OCX^4{}_3$, —$OCH_2X^4$, —$OCHX^4{}_2$, —CN, —$SO_{n4}R^{4D}$, —$SO_{v4}NR^{4A}R^{4B}$, —NHC(O)$NR^{4A}R^{4B}$, —N(O)$_{m4}$, —$NR^{4A}R^{4B}$, —C(O)$R^{4C}$, —C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and Y may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12, 5 to 10 membered, 5 to 9 membered, or 5 to 6 membered). $R^2$ and Y may optionally be joined to form an $R^{20}$-substituted or unsubstituted heterocycloalkyl (e.g., 3 to 8 membered, 3 to 6 membered, 4 to 6 membered, 4 to 5 membered, or 5 to 6 membered) or $R^{20}$-substituted or unsubstituted heteroaryl (e.g., 5 to 12, 5 to 10 membered, 5 to 9 membered, or 5 to 6 membered). $R^2$ and Y may optionally be joined to form an $R^{20}$-substituted or unsubstituted 4 to 6 membered heterocycloalkyl or $R^{20}$-substituted or unsubstituted 5 to 6 membered heteroaryl. $R^2$ and Y may optionally be joined to form an $R^{20}$-substituted or unsubstituted pyridyl. $R^2$ and Y may optionally be joined to form an $R^{20}$-substituted pyridyl. $R^2$ and Y may optionally be joined to form an unsubstituted pyridyl. In embodiments, $R^2$ and Y are not joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12, 5 to 10 membered, 5 to 9 membered, or 5 to 6 membered).

$R^1$ and $R^3$ may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12, 5 to 10 membered, 5 to 9 membered, or 5 to 6 membered). $R^1$ and $R^3$ may optionally be joined to form an $R^{10}$-substituted or unsubstituted heterocycloalkyl (e.g., 3 to 8 membered, 3 to 6 membered, 4 to 6 membered, 4 to 5 membered, or 5 to 6 membered) or $R^{10}$-substituted or unsubstituted heteroaryl (e.g., 5 to 12, 5 to 10 membered, 5 to 9 membered, or 5 to 6 membered). $R^1$ and $R^3$ may optionally be joined to form an $R^{10}$-substituted or unsubstituted 4 to 6 membered heterocycloalkyl or $R^{10}$-substituted or unsubstituted 5 to 6 membered heteroaryl. $R^1$ and $R^3$ may optionally be joined to form an $R^{10}$-substituted or unsubstituted pyridyl. $R^1$ and $R^3$ may optionally be joined to form an $R^{10}$-substituted pyridyl. $R^1$ and $R^3$ may optionally be joined to form an unsubstituted pyridyl. In embodiments, $R^1$ and $R^3$ are not joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12, 5 to 10 membered, 5 to 9 membered, or 5 to 6 membered).

$R^1$ and $R^4$ may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12, 5 to 10 membered, 5 to 9 membered, or 5 to 6 membered). $R^1$ and $R^4$ may optionally be joined to form an $R^{10}$-substituted or unsubstituted heterocycloalkyl (e.g., 3 to 8 membered, 3 to 6 membered, 4 to 6 membered, 4 to 5 membered, or 5 to 6 membered) or $R^{10}$-substituted or unsubstituted heteroaryl (e.g., 5 to 12, 5 to 10 membered, 5 to 9 membered, or 5 to 6 membered). $R^1$ and $R^4$ may optionally be joined to form an $R^{10}$-substituted or unsubstituted 4 to 6 membered heterocycloalkyl or $R^{10}$-substituted or unsubstituted 5 to 6 membered heteroaryl. $R^1$ and $R^4$ may optionally be joined to form an $R^{10}$-substituted or unsubstituted pyridyl. $R^1$ and $R^4$ may optionally be joined to form an $R^{10}$-substituted pyridyl. $R^1$ and $R^4$ may optionally be joined to form an unsubstituted pyridyl. In embodiments, $R^1$ and $R^4$ are not joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12, 5 to 10 membered, 5 to 9 membered, or 5 to 6 membered).

$R^2$ and $R^3$ may optionally be joined to form a substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered). $R^2$ and $R^3$ may optionally be joined to form a $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 8 membered, 3 to 6 membered, 4 to 6 membered, 4 to 5 membered, or 5 to 6 membered), $R^{30}$-substituted or unsubstituted aryl (e.g., $C_6$-$C_{12}$, $C_6$-$C_{10}$, or phenyl), or $R^{30}$-substituted or unsubstituted heteroaryl (e.g., 5 to 12, 5 to 10 membered, 5 to 9 membered, or 5 to 6 membered). $R^2$ and $R^3$ may optionally be joined to form a $R^{30}$-substituted or unsubstituted $C_4$-$C_6$ cycloalkyl, $R^{30}$-substituted or unsubstituted 4 to 6 membered heterocycloalkyl, $R^{30}$-substituted or unsubstituted phenyl, or $R^{30}$-substituted or unsubstituted 5 to 6 membered heteroaryl. $R^2$ and $R^3$ may optionally be joined to form a $R^{30}$-substituted or unsubstituted pyridyl. $R^2$ and $R^3$ may optionally be joined to form a unsubstituted pyridyl. $R^2$ and $R^3$ may optionally be joined to form a $R^{30}$-substituted or unsubstituted phenyl. $R^2$ and $R^3$ may optionally be joined to form a unsubstituted phenyl. In embodiments, $R^2$ and $R^3$ are not joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 12, 5 to 10 membered, 5 to 9 membered, or 5 to 6 membered).

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, and $R^{4D}$, is independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$ and $R^{1B}$ substituents bonded to the same nitrogen atom may optionally be joined to form a substituted or unsubstituted heterocycloalkyl or substituted or unsubstituted heteroaryl. $R^{2A}$ and $R^{2B}$ substituents bonded to the same nitrogen atom may optionally be joined to form a substituted or unsubstituted heterocycloalkyl or substituted or unsubstituted heteroaryl. $R^{3A}$ and $R^{3B}$ substituents bonded to the same nitrogen atom may optionally be joined to form a substituted or unsubstituted heterocycloalkyl or substituted or unsubstituted heteroaryl. $R^{4A}$ and $R^{4B}$ substituents bonded to the same nitrogen atom may optionally be joined to form a substituted or unsubstituted heterocycloalkyl or substituted or unsubstituted heteroaryl.

Each X, $X^1$, $X^2$, $X^3$, and $X^4$ is independently —F, —Cl, —Br, or —I.

The symbols n1, n2, n3, and n4 are independently an integer from 0 to 4. In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n4 is 0. In embodiments, n4 is 1. In embodiments, n4 is 2. In embodiments, n4 is 3. In embodiments, n4 is 4.

The symbols m1, m2, m3, m4, v1, v2, v3, and v4 are independently an integer from 1 to 2. In embodiments, m1 is 1. In embodiments, m1 is 2. In embodiments, m2 is 1. In embodiments, m2 is 2. In embodiments, m3 is 1. In embodiments, m3 is 2. In embodiments, m4 is 1. In embodiments, m4 is 2. In embodiments, v1 is 1. In embodiments, v1 is 2. In embodiments, v2 is 1. In embodiments, v2 is 2. In embodiments, v3 is 1. In embodiments, v3 is 2. In embodiments, v4 is 1. In embodiments, v4 is 2.

In embodiments, the compound has the formula:

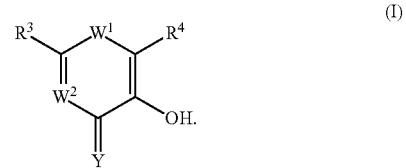

(I)

Y, $W^1$, $W^2$, $R^3$, and $R^4$ are as described herein.

In embodiments, Y is S. In embodiments, Y is O.
In embodiments, $W^1$ is —O—. In embodiments, $W^1$ is —N(R')—. In embodiments, $W^1$ is —CH($R^1$)—.
In embodiments, $W^3$ is —CH($R^1$)=.
In embodiments, $R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —$N(O)_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered).

In embodiments, $R^1$ is independently —$CX^1_3$. In embodiments, $R^1$ is independently —$CHX^{12}$. In embodiments, $R^1$ is independently —$CH_2X^1$. In embodiments, $R^1$ is independently —$OCX^1_3$. In embodiments, $R^1$ is independently —$OCH_2X^1$. In embodiments, $R^1$ is independently —$OCHX^1_2$. In embodiments, $R^1$ is independently —CN. In embodiments, $R^1$ is independently —$SO_{n1}R^{1D}$. In embodiments, $R^1$ is independently —$SO_{v1}NR^{1A}R^{1B}$. In embodiments, $R^1$ is independently —NHC(O)$NR^{1A}R^{1B}$. In embodiments, $R^1$ is independently —$N(O)_{m1}$. In embodiments, $R^1$ is independently —$NR^{1A}R^{1B}$. In embodiments, $R^1$ is independently —C(O)$R^{1C}$. In embodiments, $R^1$ is independently —C(O)—$OR^{1C}$. In embodiments, $R^1$ is independently —C(O)$NR^{1A}R^{1B}$. In embodiments, $R^1$ is independently —$OR^{1D}$. In embodiments, $R^1$ is independently —$NR^{1A}SO_2R^{1D}$. In embodiments, $R^1$ is independently —$NR^{1A}C(O)R^{1C}$. In embodiments, $R^1$ is independently —$NR^{1A}C(O)OR^{1C}$. In embodiments, $R^1$ is independently —$NR^{1A}OR^{1C}$. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$NO_2$. In embodiments, $R^1$ is independently —SH. In embodiments, $R^1$ is independently halogen. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently —$CF_3$. In embodiments, $R^1$ is independently —$CHF_2$. In embodiments, $R^1$ is independently —$CH_2F$. In embodiments, $R^1$ is independently —$OCF_3$. In embodiments, $R^1$ is independently —$OCH_2F$. In embodiments, $R^1$ is independently —$OCHF_2$. In embodiments, $R^1$ is independently —$OCH_3$. In embodiments, $R^1$ is independently —$OCH_2CH_3$. In embodiments, $R^1$ is independently —$OCH_2CH_2CH_3$. In embodiments, $R^1$ is independently —$OCH(CH_3)_2$. In embodiments, $R^1$ is independently —OC(CH$_3$)$_3$. In embodiments, R$^1$ is independently —SCH$_3$. In embodiments, R$^1$ is independently —SCH$_2$CH$_3$. In embodiments, R$^1$ is independently —SCH$_2$CH$_2$CH$_3$. In embodiments, R$^1$ is independently —SCH(CH$_3$)$_2$. In embodiments, R$^1$ is independently —SC(CH$_3$)$_3$. In embodiments, R$^1$ is independently —CH$_3$. In embodiments, R$^1$ is independently —CH$_2$CH$_3$. In embodiments, R$^1$ is independently —CH$_2$CH$_2$CH$_3$. In embodiments, R$^1$ is independently —CH(CH$_3$)$_2$. In embodiments, R$^1$ is independently —C(CH$_3$)$_3$.

In embodiments, R$^1$ is hydrogen, —CX$^1$$_3$, —CHX$^1$$_2$, —CH$_2$X$^1$, —CN, —C(O)R$^{1C}$, —C(O)—OR$^{1C}$, —C(O)NR$^{1A}$R$^{1B}$, —OR$^{1D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^1$ is hydrogen, —CX$^1$$_3$, —CHX$^1$$_2$, —CH$_2$X$^1$, —CN, —C(O)R$^{1C}$, —C(O)—OR$^{1C}$, —C(O)NR$^{1A}$R$^{1B}$, —OR$^{1D}$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{12}$ aryl, or unsubstituted 5 to 12 membered heteroaryl.

In embodiments, R$^1$ is hydrogen, —CX$^1$$_3$, —CHX$^1$$_2$, —CH$_2$X$^1$, —CN, —C(O)R$^{1C}$, —C(O)—OR$^{1C}$, —C(O)NR$^{1A}$R$^{1B}$, —OR$^{1D}$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, R$^1$ is hydrogen. In embodiments, R$^1$ is —C(O)OH, —C(O)NH$_2$, —OH. In embodiments, R$^1$ is —OH.

In embodiments, R$^1$ is substituted or unsubstituted cycloalkyl, substituted or unsubstituted heterocycloalkyl, substituted or unsubstituted aryl, or substituted or unsubstituted heteroaryl.

In embodiments, R$^1$ is substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{12}$, C$_6$-C$_{10}$, or phenyl), or substituted or unsubstituted heteroaryl (e.g., 5 to 12, 5 to 10 membered, 5 to 9 membered, or 5 to 6 membered).

In embodiments, R$^1$ is substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{12}$ aryl, or substituted or unsubstituted 5 to 12 membered heteroaryl.

In embodiments, R$^1$ is substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, R$^1$ is substituted or unsubstituted aryl or substituted or unsubstituted heteroaryl. In embodiments, R$^1$ is substituted or unsubstituted C$_6$-C$_{12}$ aryl or substituted or unsubstituted 5 to 12 membered heteroaryl. In embodiments, R$^1$ is substituted or unsubstituted phenyl or substituted or unsubstituted 5 to 6 membered heteroaryl. In embodiments, R$^1$ is substituted or unsubstituted phenyl. In embodiments, R$^1$ is unsubstituted phenyl. In embodiments, R$^1$ is substituted phenyl.

In embodiments, R$^1$ is independently substituted or unsubstituted alkyl (e.g., C$_1$-C$_8$, C$_1$-C$_6$, C$_1$-C$_4$, or C$_1$-C$_2$). In embodiments, R$^1$ is independently substituted alkyl (e.g., C$_1$-C$_8$, C$_1$-C$_6$, C$_1$-C$_4$, or C$_1$-C$_2$). In embodiments, R$^1$ is independently unsubstituted alkyl (e.g., C$_1$-C$_8$, C$_1$-C$_6$, C$_1$-C$_4$, or C$_1$-C$_2$). In embodiments, R$^1$ is independently unsubstituted methyl. In embodiments, R$^1$ is independently unsubstituted ethyl. In embodiments, R$^1$ is independently unsubstituted propyl. In embodiments, R$^1$ is independently unsubstituted isopropyl. In embodiments, R$^1$ is independently unsubstituted tert-butyl. In embodiments, R$^1$ is independently substituted or unsubstituted heteroalkyl (e.g., 2 to 8 membered, 2 to 6 membered, 4 to 6 membered, 2 to 3 membered, or 4 to 5 membered). In embodiments, R$^1$ is independently substituted heteroalkyl (e.g., 2 to 8 membered, 2 to 6 membered, 4 to 6 membered, 2 to 3 membered, or 4 to 5 membered). In embodiments, R$^1$ is independently unsubstituted heteroalkyl (e.g., 2 to 8 membered, 2 to 6 membered, 4 to 6 membered, 2 to 3 membered, or 4 to 5 membered). In embodiments, R$^1$ is independently substituted or unsubstituted cycloalkyl (e.g., C$_3$-C$_8$, C$_3$-C$_6$, C$_4$-C$_6$, or C$_5$-C$_6$). In embodiments, R$^1$ is independently substituted cycloalkyl (e.g., C$_3$-C$_8$, C$_3$-C$_6$, C$_4$-C$_6$, or C$_5$-C$_6$). In embodiments, R$^1$ is independently unsubstituted cycloalkyl (e.g., C$_3$-C$_8$, C$_3$-C$_6$, C$_4$-C$_6$, or C$_5$-C$_6$). In embodiments, R$^1$ is independently substituted or unsubstituted heterocycloalkyl (e.g., 3 to 8 membered, 3 to 6 membered, 4 to 6 membered, 4 to 5 membered, or 5 to 6 membered). In embodiments, R$^1$ is independently substituted heterocycloalkyl (e.g., 3 to 8 membered, 3 to 6 membered, 4 to 6 membered, 4 to 5 membered, or 5 to 6 membered). In embodiments, R$^1$ is independently unsubstituted heterocycloalkyl (e.g., 3 to 8 membered, 3 to 6 membered, 4 to 6 membered, 4 to 5 membered, or 5 to 6 membered). In embodiments, R$^1$ is independently substituted or unsubstituted aryl (e.g., C$_6$-C$_{12}$, C$_6$-C$_{10}$, or phenyl). In embodiments, R$^1$ is independently substituted aryl (e.g., C$_6$-C$_{12}$, C$_6$-C$_{10}$, or phenyl). In embodiments, R$^1$ is independently unsubstituted aryl (e.g., C$_6$-C$_{12}$, C$_6$-C$_{10}$, or phenyl). In embodiments, R$^1$ is independently substituted or unsubstituted heteroaryl (e.g., 5 to 12 membered, 5 to 10 membered, 5 to 9 membered, or 5 to 6 membered). In embodiments, R$^1$ is independently substituted heteroaryl (e.g., 5 to 12 membered, 5 to 10 membered, 5 to 9 membered, or 5 to 6 membered). In embodiments, R$^1$ is independently unsubstituted heteroaryl (e.g., 5 to 12 membered, 5 to 10 membered, 5 to 9 membered, or 5 to 6 membered).

In embodiments, R$^{1A}$ is independently hydrogen. In embodiments, R$^{1A}$ is independently —CX$^{1A}$$_3$. In embodiments, R$^{1A}$ is independently —CHX$^{1A}$$_2$. In embodiments, R$^{1A}$ is independently —CH$_2$X$^{1A}$. In embodiments, R$^{1A}$ is independently —CN. In embodiments, R$^{1A}$ is independently —COOH. In embodiments, R$^{1A}$ is independently —CONH$_2$. In embodiments, X$^{1A}$ is independently —F, —Cl, —Br, or —I.

In embodiments, R$^{1A}$ is independently substituted or unsubstituted alkyl (e.g., C$_1$-C$_8$, C$_1$-C$_6$, C$_1$-C$_4$, or C$_1$-C$_2$). In embodiments, R$^{1A}$ is independently substituted alkyl (e.g., C$_1$-C$_8$, C$_1$-C$_6$, C$_1$-C$_4$, or C$_1$-C$_2$). In embodiments, R$^{1A}$ is independently unsubstituted alkyl (e.g., C$_1$-C$_8$, C$_1$-C$_6$, C$_1$-C$_4$, or C$_1$-C$_2$). In embodiments, R$^{1A}$ is independently unsubstituted methyl. In embodiments, R$^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl. In embodiments, $R^{1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted heteroalkyl (e.g., 2 to 8 membered, 2 to 6 membered, 4 to 6 membered, 2 to 3 membered, or 4 to 5 membered). In embodiments, $R^{1A}$ is independently unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted or unsubstituted cycloalkyl (e.g., $C_3$-$C_8$, $C_3$-$C_6$, $C_4$-$C_6$, or $C_5$-$C_6$). In embodiments, $R^{1A}$ is independently substituted cycloalkyl (e.g., $C_3$-$C_8$, $C_3$-$C_6$, $C_4$-$C_6$, or $C_5$-$C_6$). In embodiments, $R^{1A}$ is independently unsubstituted cycloalkyl (e.g., $C_3$-$C_8$, $C_3$-$C_6$, $C_4$-$C_6$, or $C_5$-$C_6$). In embodiments, $R^{1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted heterocycloalkyl (e.g., 3 to 8 membered, 3 to 6 membered, 4 to 6 membered, 4 to 5 membered, or 5 to 6 membered). In embodiments, $R^{1A}$ is independently unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted or unsubstituted aryl (e.g., $C_6$-$C_{12}$, $C_6$-$C_{10}$, or phenyl). In embodiments, $R^{1A}$ is independently substituted aryl (e.g., $C_6$-$C_{12}$, $C_6$-$C_{10}$, or phenyl). In embodiments, $R^{1A}$ is independently unsubstituted aryl (e.g., $C_6$-$C_{12}$, $C_6$-$C_{10}$, or phenyl). In embodiments, $R^{1A}$ is independently substituted or unsubstituted heteroaryl (e.g., 5 to 12 membered, 5 to 10 membered, 5 to 9 membered, or 5 to 6 membered). In embodiments, $R^{1A}$ is independently substituted heteroaryl (e.g., 5 to 12 membered, 5 to 10 membered, 5 to 9 membered, or 5 to 6 membered). In embodiments, $R^{1A}$ is independently unsubstituted heteroaryl (e.g., 5 to 12 membered, 5 to 10 membered, 5 to 9 membered, or 5 to 6 membered).

Each $R^{1A}$, $R^{1B}$, $R^{1C}$, and $R^{1D}$ are independently $R^{10}$-substituted or unsubstituted alkyl, $R^{10}$-substituted or unsubstituted heteroalkyl, $R^{10}$-substituted or unsubstituted cycloalkyl, $R^{10}$-substituted or unsubstituted heterocycloalkyl, $R^{10}$-substituted or unsubstituted aryl, or $R^{10}$-substituted or unsubstituted heteroaryl.

Each $R^{2A}$, $R^{2B}$, $R^{2C}$, and $R^{2D}$ are independently $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

Each $R^{3A}$, $R^{3B}$, $R^{3C}$ and $R^{3D}$ are independently $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl.

Each $R^{4A}$, $R^{4B}$, $R^{4C}$, and $R^{4D}$ are independently $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^{1B}$ is independently hydrogen. In embodiments, $R^{1B}$ is independently —$CX^{1B}_3$. In embodiments, $R^{1B}$ is independently —$CHX^{1B}_2$. In embodiments, $R^{1B}$ is independently —$CH_2X^{1B}$. In embodiments, $R^{1B}$ is independently —CN. In embodiments, $R^{1B}$ is independently —COOH. In embodiments, $R^{1B}$ is independently —$CONH_2$. In embodiments, $X^{1B}$ is independently —F, —Cl, —Br, or —I.

In embodiments, $R^{1B}$ is independently substituted or unsubstituted alkyl (e.g., $C_1$-$C_8$, $C_1$-$C_6$, $C_1$-$C_4$, or $C_1$-$C_2$). In embodiments, $R^{1B}$ is independently substituted alkyl (e.g., $C_1$-$C_8$, $C_1$-$C_6$, $C_1$-$C_4$, or $C_1$-$C_2$). In embodiments, $R^{1B}$ is independently unsubstituted alkyl (e.g., $C_1$-$C_8$, $C_1$-$C_6$, $C_1$-$C_4$, or $C_1$-$C_2$). In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl. In embodiments, $R^{1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted heteroalkyl (e.g., 2 to 8 membered, 2 to 6 membered, 4 to 6 membered, 2 to 3 membered, or 4 to 5 membered). In embodiments, $R^{1B}$ is independently unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted or unsubstituted cycloalkyl (e.g., $C_3$-$C_8$, $C_3$-$C_6$, $C_4$-$C_6$, or $C_5$-$C_6$). In embodiments, $R^{1B}$ is independently substituted cycloalkyl (e.g., $C_3$-$C_8$, $C_3$-$C_6$, $C_4$-$C_6$, or $C_5$-$C_6$). In embodiments, $R^{1B}$ is independently unsubstituted cycloalkyl (e.g., $C_3$-$C_8$, $C_3$-$C_6$, $C_4$-$C_6$, or $C_5$-$C_6$). In embodiments, $R^{1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted heterocycloalkyl (e.g., 3 to 8 membered, 3 to 6 membered, 4 to 6 membered, 4 to 5 membered, or 5 to 6 membered). In embodiments, $R^{1B}$ is independently unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted or unsubstituted aryl (e.g., $C_6$-$C_{12}$, $C_6$-$C_{10}$, or phenyl). In embodiments, $R^{1B}$ is independently substituted aryl (e.g., $C_6$-$C_{12}$, $C_6$-$C_{10}$, or phenyl). In embodiments, $R^{1B}$ is independently unsubstituted aryl (e.g., $C_6$-$C_{12}$, $C_6$-$C_{10}$, or phenyl). In embodiments, $R^{1B}$ is independently substituted or unsubstituted heteroaryl (e.g., 5 to 12 membered, 5 to 10 membered, 5 to 9 membered, or 5 to 6 membered). In embodiments, $R^{1B}$ is independently substituted heteroaryl (e.g., 5 to 12 membered, 5 to 10 membered, 5 to 9 membered, or 5 to 6 membered). In embodiments, $R^{1B}$ is independently unsubstituted heteroaryl (e.g., 5 to 12 membered, 5 to 10 membered, 5 to 9 membered, or 5 to 6 membered).

In embodiments, $R^{1A}$ and $R^{1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{1A}$ and $R^{1B}$ substituents bonded to the same nitrogen atom may be joined to form a substituted or unsubstituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may be joined to form a substituted heteroaryl (e.g., 5 to 12 membered, 5 to 10 membered, 5 to 9 membered, or 5 to 6 membered). In embodiments, $R^{1A}$ and $R^{1B}$ substituents bonded to the same nitrogen atom may be joined to form an unsubstituted heteroaryl (e.g., 5 to 12 membered, 5 to 10 membered, 5 to 9 membered, or 5 to 6 membered).

In embodiments, $R^{1C}$ is independently hydrogen. In embodiments, $R^{1C}$ is independently —$CX^{1C}{}_3$. In embodiments, $R^{1C}$ is independently —$CHX^{1C}{}_2$. In embodiments, $R^{1C}$ is independently —$CH_2X^{1C}$. In embodiments, $R^{1C}$ is independently —CN. In embodiments, $R^{1C}$ is independently —COOH. In embodiments, $R^{1C}$ is independently —$CONH_2$. In embodiments, $X^{1C}$ is independently —F, —Cl, —Br, or —I.

In embodiments, $R^{1C}$ is independently substituted or unsubstituted alkyl (e.g., $C_1$-$C_8$, $C_1$-$C_6$, $C_1$-$C_4$, or $C_1$-$C_2$). In embodiments, $R^{1C}$ is independently substituted alkyl (e.g., $C_1$-$C_8$, $C_1$-$C_6$, $C_1$-$C_4$, or $C_1$-$C_2$). In embodiments, $R^{1C}$ is independently unsubstituted alkyl (e.g., $C_1$-$C_8$, $C_1$-$C_6$, $C_1$-$C_4$, or $C_1$-$C_2$). In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl. In embodiments, $R^{1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted heteroalkyl (e.g., 2 to 8 membered, 2 to 6 membered, 4 to 6 membered, 2 to 3 membered, or 4 to 5 membered). In embodiments, $R^{1C}$ is independently unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted or unsubstituted cycloalkyl (e.g., $C_3$-$C_8$, $C_3$-$C_6$, $C_4$-$C_6$, or $C_5$-$C_6$). In embodiments, $R^{1C}$ is independently substituted cycloalkyl (e.g., $C_3$-$C_8$, $C_3$-$C_6$, $C_4$-$C_6$, or $C_5$-$C_6$). In embodiments, $R^{1C}$ is independently unsubstituted cycloalkyl (e.g., $C_3$-$C_8$, $C_3$-$C_6$, $C_4$-$C_6$, or $C_5$-$C_6$). In embodiments, $R^{1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted heterocycloalkyl (e.g., 3 to 8 membered, 3 to 6 membered, 4 to 6 membered, 4 to 5 membered, or 5 to 6 membered). In embodiments, $R^{1C}$ is independently unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted or unsubstituted aryl (e.g., $C_6$-$C_{12}$, $C_6$-$C_{10}$, or phenyl). In embodiments, $R^{1C}$ is independently substituted aryl (e.g., $C_6$-$C_{12}$, $C_6$-$C_{10}$, or phenyl). In embodiments, $R^{1C}$ is independently unsubstituted aryl (e.g., $C_6$-$C_{12}$, $C_6$-$C_{10}$, or phenyl). In embodiments, $R^{1C}$ is independently substituted or unsubstituted heteroaryl (e.g., 5 to 12 membered, 5 to 10 membered, 5 to 9 membered, or 5 to 6 membered). In embodiments, $R^{1C}$ is independently substituted heteroaryl (e.g., 5 to 12 membered, 5 to 10 membered, 5 to 9 membered, or 5 to 6 membered). In embodiments, $R^{1C}$ is independently unsubstituted heteroaryl (e.g., 5 to 12 membered, 5 to 10 membered, 5 to 9 membered, or 5 to 6 membered).

In embodiments, $R^{1D}$ is independently hydrogen. In embodiments, $R^{1D}$ is independently —$CX^{1D}{}_3$. In embodiments, $R^{1D}$ is independently —$CHX^{1D}{}_2$. In embodiments, $R^{1D}$ is independently —$CH_2X^{1D}$. In embodiments, $R^{1D}$ is independently —CN. In embodiments, $R^{1D}$ is independently —COOH. In embodiments, $R^{1D}$ is independently —$CONH_2$. In embodiments, $X^{1D}$ is independently —F, —Cl, —Br, or —I.

In embodiments, $R^{1D}$ is independently substituted or unsubstituted alkyl (e.g., $C_1$-$C_8$, $C_1$-$C_6$, $C_1$-$C_4$, or $C_1$-$C_2$). In embodiments, $R^{1D}$ is independently substituted alkyl (e.g., $C_1$-$C_8$, $C_1$-$C_6$, $C_1$-$C_4$, or $C_1$-$C_2$). In embodiments, $R^{1D}$ is independently unsubstituted alkyl (e.g., $C_1$-$C_8$, $C_1$-$C_6$, $C_1$-$C_4$, or $C_1$-$C_2$). In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl. In embodiments, $R^{1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted heteroalkyl (e.g., 2 to 8 membered, 2 to 6 membered, 4 to 6 membered, 2 to 3 membered, or 4 to 5 membered). In embodiments, $R^{1D}$ is independently unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted or unsubstituted cycloalkyl (e.g., $C_3$-$C_8$, $C_3$-$C_6$, $C_4$-$C_6$, or $C_5$-$C_6$). In embodiments, $R^{1D}$ is independently substituted cycloalkyl (e.g., $C_3$-$C_8$, $C_3$-$C_6$, $C_4$-$C_6$, or $C_5$-$C_6$). In embodiments, $R^{1D}$ is independently unsubstituted cycloalkyl (e.g., $C_3$-$C_8$, $C_3$-$C_6$, $C_4$-$C_6$, or $C_5$-$C_6$). In embodiments, $R^{1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted heterocycloalkyl (e.g., 3 to 8 membered, 3 to 6 membered, 4 to 6 membered, 4 to 5 membered, or 5 to 6 membered). In embodiments, $R^{1D}$ is independently unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted or unsubstituted aryl (e.g., $C_6$-$C_{12}$, $C_6$-$C_{10}$, or phenyl). In embodiments, $R^{1D}$ is independently substituted aryl (e.g., $C_6$-$C_{12}$, $C_6$-$C_{10}$, or phenyl). In embodiments, $R^{1D}$ is independently unsubstituted aryl (e.g., $C_6$-$C_{12}$, $C_6$-$C_{10}$, or phenyl). In embodiments, $R^{1D}$ is independently substituted or unsubstituted heteroaryl (e.g., 5 to 12 membered, 5 to 10 membered, 5 to 9 membered, or 5 to 6 membered). In embodiments, $R^{1D}$ is independently substituted heteroaryl (e.g., 5 to 12 membered, 5 to 10 membered, 5 to 9 membered, or 5 to 6 membered). In embodiments, $R^{1D}$ is independently unsubstituted heteroaryl (e.g., 5 to 12 membered, 5 to 10 membered, 5 to 9 membered, or 5 to 6 membered).

In embodiments, $R^1$ is hydrogen, halogen, —$CX^1{}_3$, —$CHX^1{}_2$, —$CH_2X^1$, —$OCX^1{}_3$, —$OCH_2X^1$, —$OCHX^1{}_2$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, $R^{10}$-substituted or unsubstituted alkyl (e.g., $C_1$-$C_8$, $C_1$-$C_6$, $C_1$-$C_4$, or $C_1$-$C_2$), $R^{10}$-substituted or unsubstituted heteroalkyl (e.g., 2 to 8 membered, 2 to 6 membered, 4 to 6 membered, 2 to 3 membered, or 4 to 5 membered), $R^{10}$-substituted or unsubstituted cycloalkyl (e.g., $C_3$-$C_8$, $C_3$-$C_6$, $C_4$-$C_6$, or $C_5$-$C_6$), $R^{10}$-substituted or unsubstituted heterocycloalkyl (e.g., 3 to 8 membered, 3 to 6 membered, 4 to 6 membered, 4 to 5 membered, or 5 to 6 membered), $R^{10}$-substituted or unsubstituted aryl (e.g., $C_6$-$C_{12}$, $C_6$-$C_{10}$, or phenyl), or $R^{10}$-substituted or unsubstituted heteroaryl (e.g., 5 to 12 membered, 5 to 10 membered, 5 to 9 membered, or 5 to 6 membered). In embodiments, $R^1$ is unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^1$ is $R^{10}$-substituted or unsubstituted alkyl (e.g., $C_1$-$C_8$, $C_1$-$C_6$, $C_1$-$C_4$, or $C_1$-$C_2$), $R^{10}$-substituted or unsubstituted heteroalkyl (e.g., 2 to 8 membered, 2 to 6 membered, 4 to 6 membered, 2 to 3 membered, or 4 to 5 membered), $R^{10}$-substituted or unsubstituted cycloalkyl (e.g., $C_3$-$C_8$, $C_3$-$C_6$, $C_4$-$C_6$, or $C_5$-$C_6$), $R^{10}$-substituted or unsubstituted heterocycloalkyl (e.g., 3 to 8 membered, 3 to 6 membered, 4 to 6 membered, 4 to 5 membered, or 5 to 6 membered), $R^{10}$-substituted or unsubstituted aryl (e.g., $C_6$-$C_{12}$, $C_6$-$C_{10}$, or phenyl), or $R^{10}$-substituted or unsubstituted heteroaryl (e.g., 5 to 12 membered, 5 to 10 membered, 5 to 9 membered, or 5 to 6 membered). In embodiments, $R^1$ is unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, $R^1$ is hydrogen. In embodiments, $R^1$ is unsubstituted methyl. In embodiments, $R^1$ is unsubstituted ethyl.

In embodiments, $R^1$ is $R^{10}$-substituted cyclohexyl. In embodiments, $R^1$ is N—$R^{10}$-substituted piperidinyl. In embodiments, $R^1$ is $R^{10}$-substituted phenyl. In embodiments, $R^1$ is $R^{10}$-substituted methyl.

In embodiments, $R^1$ is independently unsubstituted aryl (e.g., $C_6$-$C_{12}$, $C_6$-$C_{10}$, or phenyl). In embodiments, $R^1$ is independently unsubstituted phenyl. In embodiments, $R^1$ is independently unsubstituted biphenyl. In embodiments, $R^1$ is independently unsubstituted 2-biphenyl. In embodiments, $R^1$ is independently unsubstituted 3-biphenyl. In embodiments, $R^{10}$ is independently unsubstituted 4-biphenyl.

$R^{10}$ is independently oxo, halogen, —$CX^{10}_3$, —$CHX^{10}_2$, —$CH_2X^{10}$, —$OCX^{10}_3$, —$OCH_2X^{10}$, —$OCHX^{10}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{11}$, —$NHR^{11}$, —$COOR^{11}$, —$CONHR^{11}$, —$SR^{11}$, —$SO_2NHR^{11}$, —$SO_2R^{11}$, $R^{11}$-substituted or unsubstituted alkyl (e.g., $C_1$-$C_8$, $C_1$-$C_6$, $C_1$-$C_4$, or $C_1$-$C_2$), $R^{11}$-substituted or unsubstituted heteroalkyl (e.g., 2 to 8 membered, 2 to 6 membered, 4 to 6 membered, 2 to 3 membered, or 4 to 5 membered), $R^1$-substituted or unsubstituted cycloalkyl (e.g., $C_3$-$C_8$, $C_3$-$C_6$, $C_4$-$C_6$, or $C_5$-$C_6$), $R^{11}$-substituted or unsubstituted heterocycloalkyl (e.g., 3 to 8 membered, 3 to 6 membered, 4 to 6 membered, 4 to 5 membered, or 5 to 6 membered), $R^{11}$-substituted or unsubstituted aryl(e.g., $C_6$-$C_{12}$, $C_6$-$C_{10}$, or phenyl), or $R^{11}$-substituted or unsubstituted heteroaryl (e.g., 5 to 12 membered, 5 to 10 membered, 5 to 9 membered, or 5 to 6 membered). In embodiments, $R^{10}$ is independently oxo, halogen, —$CX^{10}_3$, —$CHX^{10}_2$, —$CH_2X^{10}$, —$OCX^{10}_3$, —$OCH_2X^{10}$, —$OCHX^{10}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{11}$, —$NHR^{11}$, —$COOR^{11}$, —$CONHR^{11}$, —$SR^{11}$, —$SO_2NHR^{11}$, —$SO_2R^{11}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{10}$ is independently —F, —Cl, —Br, or —I. In embodiments, $R^{10}$ is independently —$OR^{11}$. In embodiments, $R^{10}$ is independently —$COOR^1$. In embodiments, $R^{10}$ is independently —COOH. In embodiments, $R^{10}$ is independently —$SO_2NHR^{11}$. In embodiments, $R^{10}$ is independently unsubstituted heterocycloalkyl (e.g., 3 to 8 membered, 3 to 6 membered, 4 to 6 membered, 4 to 5 membered, or 5 to 6 membered). In embodiments, $R^{10}$ is independently unsubstituted heteroaryl (e.g., 5 to 12 membered, 5 to 10 membered, 5 to 9 membered, or 5 to 6 membered).

$R^{11}$ is independently oxo, halogen, —$CX^{11}_3$, —$CHX^{11}_2$, —$CH_2X^{11}$, —$OCX^{11}_3$, —$OCH_2X^{11}$, —$OCHX^{11}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{12}$-substituted or unsubstituted alkyl (e.g., $C_1$-$C_8$, $C_1$-$C_6$, $C_1$-$C_4$, or $C_1$-$C_2$), $R^{12}$-substituted or unsubstituted heteroalkyl (e.g., 2 to 8 membered, 2 to 6 membered, 4 to 6 membered, 2 to 3 membered, or 4 to 5 membered), $R^{12}$-substituted or unsubstituted cycloalkyl (e.g., $C_3$-$C_8$, $C_3$-$C_6$, $C_4$-$C_6$, or $C_5$-$C_6$), $R^{12}$-substituted or unsubstituted heterocycloalkyl (e.g., 5 to 12 membered, 5 to 10 membered, 5 to 9 membered, or 5 to 6 membered), $R^{12}$-substituted or unsubstituted aryl (e.g., $C_6$-$C_{12}$, $C_6$-$C_{10}$, or phenyl), or $R^{12}$-substituted or unsubstituted heteroaryl (e.g., 5 to 12 membered, 5 to 10 membered, 5 to 9 membered, or 5 to 6 membered). In embodiments, $R^{11}$ is independently oxo, halogen, —$CX^{11}_3$, —$CHX^{11}_2$, —$CH_2X^{11}$, —$OCX^{11}_3$, —$OCH_2X^{11}$, —$OCHX^{11}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 5 to 12 membered, 5 to 10 membered, 5 to 9 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{11}$ is independently —F, —Cl, —Br, or —I. In embodiments, R" is independently methyl. In embodiments, $R^{12}$ is independently unsubstituted ethyl. In embodiments, R" is independently $R^{12}$-substituted or unsubstituted heteroalkyl (e.g., 2 to 8 membered, 2 to 6 membered, 4 to 6 membered, 2 to 3 membered, or 4 to 5 membered), $R^{12}$-substituted or unsubstituted cycloalkyl (e.g., $C_3$-$C_8$, $C_3$-$C_6$, $C_4$-$C_6$, or $C_5$-$C_6$), $R^{12}$-substituted or unsubstituted heterocycloalkyl (e.g., 5 to 12 membered, 5 to 10 membered, 5 to 9 membered, or 5 to 6 membered), $R^{12}$-substituted or unsubstituted aryl (e.g., $C_6$-$C_{12}$, $C_6$-$C_{10}$, or phenyl), or $R^{12}$-substituted or unsubstituted heteroaryl (e.g., 5 to 12 membered, 5 to 10 membered, 5 to 9 membered, or 5 to 6 membered).

$R^{12}$ is independently oxo, halogen, —$CX^{12}_3$, —$CHX^{12}_2$, —$CH_2X^{12}$, —$OCX^{12}_3$, —$OCH_2X^{12}$, —$OCHX^{12}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl, unsubstituted cycloalkyl (e.g., $C_1$-$C_8$, $C_1$-$C_6$, $C_1$-$C_4$, or $C_1$-$C_2$), unsubstituted heterocycloalkyl (e.g., 2 to 8 membered, 2 to 6 membered, 4 to 6 membered, 2 to 3 membered, or 4 to 5 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{12}$ is independently —F, —Cl, —Br, or —I. In embodiments, $R^{12}$ is independently unsubstituted alkyl (e.g., $C_1$-$C_8$, $C_1$-$C_6$, $C_1$-$C_4$, or $C_1$-$C_2$), unsubstituted heteroalkyl, unsubstituted cycloalkyl (e.g., $C_1$-$C_8$, $C_1$-$C_6$, $C_1$-$C_4$, or $C_1$-$C_2$), unsubstituted heterocycloalkyl (e.g., 2 to 8 membered, 2 to 6 membered, 4 to 6 membered, 2 to 3 membered, or 4 to 5 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{10}$ is independently unsubstituted heteroaryl (e.g., 5 to 12 membered, 5 to 10 membered, 5 to 9 membered, or 5 to 6 membered).

In embodiments, $R^{10}$ is independently unsubstituted 6 membered heteroaryl. In embodiments, $R^{10}$ is independently unsubstituted 5 membered heteroaryl. In embodiments, $R^{10}$ is independently unsubstituted pyridyl. In embodiments, $R^{10}$ is independently unsubstituted 2-pyridyl. In embodiments, $R^{10}$ is independently unsubstituted 3-pyridyl. In embodiments, $R^{10}$ is independently unsubstituted 4-pyridyl. In embodiments, $R^{10}$ is independently unsubstituted pyridazinyl. In embodiments, $R^{10}$ is independently unsubstituted pyrimidinyl. In embodiments, $R^1$ is independently unsubstituted pyrazinyl. In embodiments, $R^{10}$ is independently unsubstituted triazinyl. In embodiments, $R^{10}$ is independently unsubstituted pyrrolyl. In embodiments, $R^0$ is independently unsubstituted 2-pyrrolyl. In embodiments, $R^{10}$ is independently unsubstituted 3-pyrrolyl. In embodiments, $R^{10}$ is independently unsubstituted furanyl. In embodiments, $R^{10}$ is independently unsubstituted 2-furanyl. In embodiments, $R^{10}$ is independently unsubstituted 3-furanyl. In embodiments, $R^{10}$ is independently unsubstituted thienyl. In embodiments, $R^{10}$ is independently unsubstituted 2-thienyl. In embodiments, $R^{10}$ is independently unsubstituted 3-thienyl. In embodiments, $R^{10}$ is independently unsubstituted pyrazolyl. In embodiments, $R^{10}$ is independently unsubstituted isoxazolyl. In embodiments, $R^{10}$ is independently unsubstituted isothiazolyl. In embodiments, $R^{10}$ is independently unsubstituted imidazolyl. In embodiments, $R^{10}$ is independently unsubstituted oxazolyl. In embodiments, $R^{10}$ is independently unsubstituted thiazolyl. In embodiments, $R^{10}$ is independently unsubstituted tetrazolyl. In embodiments, $R^{10}$ is independently unsubstituted triazolyl. In embodiments, $R^{10}$ is independently unsubstituted methoxy. In embodiments, $R^{10}$ is independently unsubstituted phenoxy. In embodiments, $R^0$ is independently unsubstituted —C(O)$OCH_3$. In embodiments, $R^{10}$ is independently unsubstituted —COOH. In embodiments, $R^{10}$ is independently unsubstituted —$COOCH_3$. In embodiments, $R^0$ is independently unsubstituted —C(O)$CH_3$. In embodiments, $R^{10}$ is independently unsubstituted —$SO2CH3$. In embodiments, $R^{10}$ is independently unsubstituted —$SO_2NHCH_3$. In embodiments, $R^{10}$ is independently unsubstituted morpholinyl.

In embodiments, $R^{10}$ is independently unsubstituted aryl (e.g., $C_6$-$C_{12}$, $C_6$-$C_{10}$, or phenyl). In embodiments, $R^{10}$ is independently unsubstituted phenyl. In embodiments, $R^{10}$ is independently unsubstituted biphenyl. In embodiments, $R^{10}$ is independently unsubstituted 2-biphenyl. In embodiments, $R^{10}$ is independently unsubstituted 3-biphenyl. In embodiments, $R^0$ is independently unsubstituted 4-biphenyl.

In embodiments, $R^{10}$ is independently oxo, —OH, —$NH_2$, —COOH, —$CONH_2$, —$SO_3H$, —$SO_4H$, —$SO_2NH_2$, —$OR^{11}$, —$NHR^{11}$, —$COOR^{11}$, —$CONHR^{11}$, —$SO_2NHR^{11}$, or —$SO_2R^{11}$. In embodiments, $R^{10}$ is independently —C(O)$CH_3$, —COOH, —$OCH_3$, —$OC_6H_5$, —$COOCH_3$, —$SO_2NHCH_3$, or —$SO_2CH_3$.

In embodiments, $W^2$ is —N=. In embodiments, $W^2$ is —C($R^2$)=.

In embodiments, $R^2$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered).

In embodiments, $R^2$ is hydrogen, —$OR^{2D}$, —C(O)$R^{2C}$, —C(O)—$OR^{2C}$, —C(O)$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is hydrogen, —$OR^{2D}$, —C(O)$R^{2C}$, —C(O)—$OR^{2C}$, —C(O)$NR^{2A}R^{2B}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{12}$ aryl, or substituted or unsubstituted 5 to 12 membered heteroaryl.

In embodiments, $R^2$ is hydrogen, —$OR^{2D}$, —C(O)$R^{2C}$, —C(O)—$OR^{2C}$, —C(O)$NR^{2A}R^{2B}$, substituted or unsubstituted $C_1$-$C_8$ alkyl, substituted or unsubstituted 2 to 8 membered heteroalkyl; substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^2$ is hydrogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —$OCX^2_3$. In embodiments, $R^2$ is independently —$OCH_2X^2$. In embodiments, $R^2$ is independently —$OCHX^2_2$. In embodiments, $R^2$ is independently —CN. In embodiments, $R^2$ is independently —$SO_{n2}R^{2D}$. In embodiments, $R^2$ is independently —$SO_{v2}NR^{2A}R^{2B}$. In embodiments, $R^2$ is independently —NHC(O)$NR^{2A}R^{2B}$. In embodiments, $R^2$ is independently —N(O)$_{m2}$. In embodiments, R$^2$ is independently —NR$^{2A}$R$^{2B}$. In embodiments, R$^2$ is independently —C(O)R$^{2C}$. In embodiments, R$^2$ is independently —C(O)—OR$^{2C}$. In embodiments, R$^2$ is independently —C(O)NR$^{2A}$R$^{2B}$. In embodiments, R$^2$ is independently —OR$^{2D}$. In embodiments, R$^2$ is independently —NR$^{2A}$SO$_2$R$^{2D}$. In embodiments, R$^2$ is independently —NR$^{2A}$C(O)R$^{2C}$. In embodiments, R$^2$ is independently —NR$^{2A}$C(O)OR$^{2C}$. In embodiments, R$^2$ is independently —NR$^{2A}$OR$^{2C}$. In embodiments, R$^2$ is independently —OH. In embodiments, R$^2$ is independently —NH$_2$. In embodiments, R$^2$ is independently —COOH. In embodiments, R$^2$ is independently —COOCH$_3$. In embodiments, R$^2$ is independently —COOCH$_2$CH$_3$. In embodiments, R$^2$ is independently —CONH$_2$. In embodiments, R$^2$ is independently —NO$_2$. In embodiments, R$^2$ is independently —SH. In embodiments, R$^2$ is independently halogen. In embodiments, R$^2$ is independently —F. In embodiments, R$^2$ is independently —Cl. In embodiments, R$^2$ is independently —Br. In embodiments, R$^2$ is independently —I. In embodiments, R$^2$ is independently —CF$_3$. In embodiments, R$^2$ is independently —CHF$_2$. In embodiments, R$^2$ is independently —CH$_2$F. In embodiments, R$^2$ is independently —OCF$_3$. In embodiments, R$^2$ is independently —OCH$_2$F. In embodiments, R$^2$ is independently —OCHF$_2$. In embodiments, R$^2$ is independently —OCH$_3$. In embodiments, R$^2$ is independently —OCH$_2$CH$_3$. In embodiments, R$^2$ is independently —OCH$_2$CH$_2$CH$_3$. In embodiments, R$^2$ is independently —OCH(CH$_3$)$_2$. In embodiments, R$^2$ is independently —OC(CH$_3$)$_3$. In embodiments, R$^2$ is independently —SCH$_3$. In embodiments, R$^2$ is independently —SCH$_2$CH$_3$. In embodiments, R$^2$ is independently —SCH$_2$CH$_2$CH$_3$. In embodiments, R$^2$ is independently —SCH(CH$_3$)$_2$. In embodiments, R$^2$ is independently —SC(CH$_3$)$_3$. In embodiments, R$^2$ is independently —CH$_3$. In embodiments, R$^2$ is independently —CH$_2$CH$_3$. In embodiments, R$^2$ is independently —CH$_2$CH$_2$CH$_3$. In embodiments, R$^2$ is independently —CH(CH$_3$)$_2$. In embodiments, R$^2$ is independently —C(CH$_3$)$_3$.

In embodiments, R$^2$ is independently substituted or unsubstituted alkyl (e.g., C$_1$-C$_8$, C$_1$-C$_6$, C$_1$-C$_4$, or C$_1$-C$_2$). In embodiments, R$^2$ is independently substituted alkyl (e.g., C$_1$-C$_8$, C$_1$-C$_6$, C$_1$-C$_4$, or C$_1$-C$_2$). In embodiments, R$^2$ is independently unsubstituted alkyl (e.g., C$_1$-C$_8$, C$_1$-C$_6$, C$_1$-C$_4$, or C$_1$-C$_2$). In embodiments, R$^2$ is independently unsubstituted methyl. In embodiments, R$^2$ is independently unsubstituted ethyl. In embodiments, R$^2$ is independently unsubstituted propyl. In embodiments, R$^2$ is independently unsubstituted isopropyl. In embodiments, R$^2$ is independently unsubstituted tert-butyl. In embodiments, R$^2$ is independently substituted or unsubstituted heteroalkyl (e.g., 2 to 8 membered, 2 to 6 membered, 4 to 6 membered, 2 to 3 membered, or 4 to 5 membered). In embodiments, R$^2$ is independently substituted heteroalkyl (e.g., 2 to 8 membered, 2 to 6 membered, 4 to 6 membered, 2 to 3 membered, or 4 to 5 membered). In embodiments, R$^2$ is independently unsubstituted heteroalkyl (e.g., 2 to 8 membered, 2 to 6 membered, 4 to 6 membered, 2 to 3 membered, or 4 to 5 membered). In embodiments, R$^2$ is independently substituted or unsubstituted cycloalkyl (e.g., C$_3$-C$_8$, C$_3$-C$_6$, C$_4$-C$_6$, or C$_5$-C$_6$). In embodiments, R$^2$ is independently substituted cycloalkyl (e.g., C$_3$-C$_8$, C$_3$-C$_6$, C$_4$-C$_6$, or C$_5$-C$_6$). In embodiments, R$^2$ is independently unsubstituted cycloalkyl (e.g., C$_3$-C$_8$, C$_3$-C$_6$, C$_4$-C$_6$, or C$_5$-C$_6$). In embodiments, R$^2$ is independently substituted or unsubstituted heterocycloalkyl (e.g., 3 to 8 membered, 3 to 6 membered, 4 to 6 membered, 4 to 5 membered, or 5 to 6 membered). In embodiments, R$^2$ is independently substituted heterocycloalkyl (e.g., 3 to 8 membered, 3 to 6 membered, 4 to 6 membered, 4 to 5 membered, or 5 to 6 membered). In embodiments, R$^2$ is independently unsubstituted heterocycloalkyl (e.g., 3 to 8 membered, 3 to 6 membered, 4 to 6 membered, 4 to 5 membered, or 5 to 6 membered). In embodiments, R$^2$ is independently substituted or unsubstituted aryl (e.g., C$_6$-C$_{12}$, C$_6$-C$_{10}$, or phenyl). In embodiments, R$^2$ is independently substituted aryl (e.g., C$_6$-C$_{12}$, C$_6$-C$_{10}$, or phenyl). In embodiments, R$^2$ is independently unsubstituted aryl (e.g., C$_6$-C$_{12}$, C$_6$-C$_{10}$, or phenyl). In embodiments, R$^2$ is independently substituted or unsubstituted heteroaryl (e.g., 5 to 12 membered, 5 to 10 membered, 5 to 9 membered, or 5 to 6 membered). In embodiments, R$^2$ is independently substituted heteroaryl (e.g., 5 to 12 membered, 5 to 10 membered, 5 to 9 membered, or 5 to 6 membered). In embodiments, R$^2$ is independently unsubstituted heteroaryl (e.g., 5 to 12 membered, 5 to 10 membered, 5 to 9 membered, or 5 to 6 membered).

In embodiments, R$^{2A}$ is independently hydrogen. In embodiments, R$^{2A}$ is independently —CX$^{2A3}$. In embodiments, R$^{2A}$ is independently —CHX$^{2A2}$. In embodiments, R$^{2A}$ is independently —CH$_2$X$^{2A}$. In embodiments, R$^{2A}$ is independently —CN. In embodiments, R$^{2A}$ is independently —COOH. In embodiments, R$^{2A}$ is independently —CONH$_2$. In embodiments, X$^{2A}$ is independently —F, —Cl, —Br, or —I.

In embodiments, R$^{2A}$ is independently substituted or unsubstituted alkyl (e.g., C$_1$-C$_8$, C$_1$-C$_6$, C$_1$-C$_4$, or C$_1$-C$_2$). In embodiments, R$^{2A}$ is independently substituted alkyl (e.g., C$_1$-C$_8$, C$_1$-C$_6$, C$_1$-C$_4$, or C$_1$-C$_2$). In embodiments, R$^{2A}$ is independently unsubstituted alkyl (e.g., C$_1$-C$_8$, C$_1$-C$_6$, C$_1$-C$_4$, or C$_1$-C$_2$). In embodiments, R$^{2A}$ is independently unsubstituted methyl. In embodiments, R$^{2A}$ is independently unsubstituted ethyl. In embodiments, R$^{2A}$ is independently unsubstituted propyl. In embodiments, R$^{2A}$ is independently unsubstituted isopropyl. In embodiments, R$^{2A}$ is independently unsubstituted tert-butyl. In embodiments, R$^{2A}$ is independently substituted or unsubstituted heteroalkyl (e.g., 2 to 8 membered, 2 to 6 membered, 4 to 6 membered, 2 to 3 membered, or 4 to 5 membered). In embodiments, R$^{2A}$ is independently substituted heteroalkyl (e.g., 2 to 8 membered, 2 to 6 membered, 4 to 6 membered, 2 to 3 membered, or 4 to 5 membered). In embodiments, R$^{2A}$ is independently unsubstituted heteroalkyl (e.g., 2 to 8 membered, 2 to 6 membered, 4 to 6 membered, 2 to 3 membered, or 4 to 5 membered). In embodiments, R$^{2A}$ is independently substituted or unsubstituted cycloalkyl (e.g., C$_3$-C$_8$, C$_3$-C$_6$, C$_4$-C$_6$, or C$_5$-C$_6$). In embodiments, R$^{2A}$ is independently substituted cycloalkyl (e.g., C$_3$-C$_8$, C$_3$-C$_6$, C$_4$-C$_6$, or C$_5$-C$_6$). In embodiments, R$^{2A}$ is independently unsubstituted cycloalkyl (e.g., C$_3$-C$_8$, C$_3$-C$_6$, C$_4$-C$_6$, or C$_5$-C$_6$). In embodiments, R$^{2A}$ is independently substituted or unsubstituted heterocycloalkyl (e.g., 3 to 8 membered, 3 to 6 membered, 4 to 6 membered, 4 to 5 membered, or 5 to 6 membered). In embodiments, R$^{2A}$ is independently substituted heterocycloalkyl (e.g., 3 to 8 membered, 3 to 6 membered, 4 to 6 membered, 4 to 5 membered, or 5 to 6 membered). In embodiments, R$^{2A}$ is independently unsubstituted heterocycloalkyl (e.g., 3 to 8 membered, 3 to 6 membered, 4 to 6 membered, 4 to 5 membered, or 5 to 6 membered). In embodiments, R$^{2A}$ is independently substituted or unsubstituted aryl (e.g., C$_6$-C$_{12}$, C$_6$-C$_{10}$, or phenyl). In embodiments, R$^{2A}$ is independently substituted aryl (e.g., C$_6$-C$_{12}$, C$_6$-C$_{10}$, or phenyl). In embodiments, R$^{2A}$ is independently unsubstituted aryl (e.g., C$_6$-C$_{12}$, C$_6$-C$_{10}$, or phenyl). In embodiments, R$^{2A}$ is independently substituted or unsubstituted heteroaryl (e.g., 5 to 12 membered, 5 to 10 membered, 5 to 9 membered, or 5 to 6 membered). In embodiments, $R^{2A}$ is independently substituted heteroaryl (e.g., 5 to 12 membered, 5 to 10 membered, 5 to 9 membered, or 5 to 6 membered). In embodiments, $R^{2A}$ is independently unsubstituted heteroaryl (e.g., 5 to 12 membered, 5 to 10 membered, 5 to 9 membered, or 5 to 6 membered).

In embodiments, $R^{2B}$ is independently hydrogen. In embodiments, $R^{2B}$ is independently —$CX^{2B}_3$. In embodiments, $R^{2B}$ is independently —$CHX^{2B}_2$. In embodiments, $R^{2B}$ is independently —$CH_2X^{2B}$. In embodiments, $R^{2B}$ is independently —CN. In embodiments, $R^{2B}$ is independently —COOH. In embodiments, $R^{2B}$ is independently —$CONH_2$. In embodiments, $X^{2B}$ is independently —F, —Cl, —Br, or —I.

In embodiments, $R^{2B}$ is independently substituted or unsubstituted alkyl (e.g., $C_1$-$C_8$, $C_1$-$C_6$, $C_1$-$C_4$, or $C_1$-$C_2$). In embodiments, $R^{2B}$ is independently substituted alkyl (e.g., $C_1$-$C_8$, $C_1$-$C_6$, $C_1$-$C_4$, or $C_1$-$C_2$). In embodiments, $R^{2B}$ is independently unsubstituted alkyl (e.g., $C_1$-$C_8$, $C_1$-$C_6$, $C_1$-$C_4$, or $C_1$-$C_2$). In embodiments, $R^{2B}$ is independently unsubstituted methyl. In embodiments, $R^{2B}$ is independently unsubstituted ethyl. In embodiments, $R^{2B}$ is independently unsubstituted propyl. In embodiments, $R^{2B}$ is independently unsubstituted isopropyl. In embodiments, $R^{2B}$ is independently unsubstituted tert-butyl. In embodiments, $R^{2B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted heteroalkyl (e.g., 2 to 8 membered, 2 to 6 membered, 4 to 6 membered, 2 to 3 membered, or 4 to 5 membered). In embodiments, $R^{2B}$ is independently unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted or unsubstituted cycloalkyl (e.g., $C_3$-$C_8$, $C_3$-$C_6$, $C_4$-$C_6$, or $C_5$-$C_6$). In embodiments, $R^{2B}$ is independently substituted cycloalkyl (e.g., $C_3$-$C_8$, $C_3$-$C_6$, $C_4$-$C_6$, or $C_5$-$C_6$). In embodiments, $R^{2B}$ is independently unsubstituted cycloalkyl (e.g., $C_3$-$C_8$, $C_3$-$C_6$, $C_4$-$C_6$, or $C_5$-$C_6$). In embodiments, $R^{2B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted heterocycloalkyl (e.g., 3 to 8 membered, 3 to 6 membered, 4 to 6 membered, 4 to 5 membered, or 5 to 6 membered). In embodiments, $R^{2B}$ is independently unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted or unsubstituted aryl (e.g., $C_6$-$C_{12}$, $C_6$-$C_{10}$, or phenyl). In embodiments, $R^{2B}$ is independently substituted aryl (e.g., $C_6$-$C_{12}$, $C_6$-$C_{10}$, or phenyl). In embodiments, $R^{2B}$ is independently unsubstituted aryl (e.g., $C_6$-$C_{12}$, $C_6$-$C_{10}$, or phenyl). In embodiments, $R^{2B}$ is independently substituted or unsubstituted heteroaryl (e.g., 5 to 12 membered, 5 to 10 membered, 5 to 9 membered, or 5 to 6 membered). In embodiments, $R^{2B}$ is independently substituted heteroaryl (e.g., 5 to 12 membered, 5 to 10 membered, 5 to 9 membered, or 5 to 6 membered). In embodiments, $R^{2B}$ is independently unsubstituted heteroaryl (e.g., 5 to 12 membered, 5 to 10 membered, 5 to 9 membered, or 5 to 6 membered).

In embodiments, $R^{2A}$ and $R^{2B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{2A}$ and $R^{2B}$ substituents bonded to the same nitrogen atom may be joined to form a substituted or unsubstituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may be joined to form a substituted heteroaryl (e.g., 5 to 12 membered, 5 to 10 membered, 5 to 9 membered, or 5 to 6 membered). In embodiments, $R^{2A}$ and $R^{2B}$ substituents bonded to the same nitrogen atom may be joined to form an unsubstituted heteroaryl (e.g., 5 to 12 membered, 5 to 10 membered, 5 to 9 membered, or 5 to 6 membered).

In embodiments, $R^{2C}$ is independently hydrogen. In embodiments, $R^{2C}$ is independently —$CX^{2C}_3$. In embodiments, $R^{2C}$ is independently —$CHX^{2C}_2$. In embodiments, $R^{2C}$ is independently —$CH_2X^{2C}$. In embodiments, $R^{2C}$ is independently —CN. In embodiments, $R^{2C}$ is independently —COOH. In embodiments, $R^{2C}$ is independently —$CONH_2$. In embodiments, $X^{2c}$ is independently —F, —Cl, —Br, or —I.

In embodiments, $R^{2C}$ is independently substituted or unsubstituted alkyl (e.g., $C_1$-$C_8$, $C_1$-$C_6$, $C_1$-$C_4$, or $C_1$-$C_2$). In embodiments, $R^{2C}$ is independently substituted alkyl (e.g., $C_1$-$C_8$, $C_1$-$C_6$, $C_1$-$C_4$, or $C_1$-$C_2$). In embodiments, $R^{2C}$ is independently unsubstituted alkyl (e.g., $C_1$-$C_8$, $C_1$-$C_6$, $C_1$-$C_4$, or $C_1$-$C_2$). In embodiments, $R^{2C}$ is independently unsubstituted methyl. In embodiments, $R^{2C}$ is independently unsubstituted ethyl. In embodiments, $R^{2C}$ is independently unsubstituted propyl. In embodiments, $R^{2C}$ is independently unsubstituted isopropyl. In embodiments, $R^{2C}$ is independently unsubstituted tert-butyl. In embodiments, $R^{2C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted heteroalkyl (e.g., 2 to 8 membered, 2 to 6 membered, 4 to 6 membered, 2 to 3 membered, or 4 to 5 membered). In embodiments, $R^{2C}$ is independently unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted or unsubstituted cycloalkyl (e.g., $C_3$-$C_8$, $C_3$-$C_6$, $C_4$-$C_6$, or $C_5$-$C_6$). In embodiments, $R^{2C}$ is independently substituted cycloalkyl (e.g., $C_3$-$C_8$, $C_3$-$C_6$, $C_4$-$C_6$, or $C_5$-$C_6$). In embodiments, $R^{2C}$ is independently unsubstituted cycloalkyl (e.g., $C_3$-$C_8$, $C_3$-$C_6$, $C_4$-$C_6$, or $C_5$-$C_6$). In embodiments, $R^{2C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted heterocycloalkyl (e.g., 3 to 8 membered, 3 to 6 membered, 4 to 6 membered, 4 to 5 membered, or 5 to 6 membered). In embodiments, $R^{2C}$ is independently unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted or unsubstituted aryl (e.g., $C_6$-$C_{12}$, $C_6$-$C_{10}$, or phenyl). In embodiments, $R^{2C}$ is independently substituted aryl (e.g., $C_6$-$C_{12}$, $C_6$-$C_{10}$, or phenyl). In embodiments, $R^{2C}$ is independently unsubstituted aryl (e.g., $C_6$-$C_{12}$, $C_6$-$C_{10}$, or phenyl). In embodiments, $R^{2C}$ is independently substituted or unsubstituted heteroaryl (e.g., 5 to 12 membered, 5 to 10 membered, 5 to 9 membered, or 5 to 6 membered). In embodiments, $R^{2C}$ is independently substituted heteroaryl (e.g., 5 to 12 membered, 5 to 10 membered, 5 to 9 membered, or 5 to 6 membered). In embodiments, $R^{2C}$ is independently unsubstituted heteroaryl (e.g., 5 to 12 membered, 5 to 10 membered, 5 to 9 membered, or 5 to 6 membered).

In embodiments, $R^{2D}$ is independently hydrogen. In embodiments, $R^{2D}$ is independently —$CX^{2D}{}_3$. In embodiments, $R^{2D}$ is independently —$CHX^{2D}{}_2$. In embodiments, $R^{2D}$ is independently —$CH_2X^{2D}$. In embodiments, $R^{2D}$ is independently —CN. In embodiments, $R^{2D}$ is independently —COOH. In embodiments, $R^{2D}$ is independently —$CONH_2$. In embodiments, $X^{2D}$ is independently —F, —Cl, —Br, or —I.

In embodiments, $R^{2D}$ is independently substituted or unsubstituted alkyl (e.g., $C_1$-$C_8$, $C_1$-$C_6$, $C_1$-$C_4$, or $C_1$-$C_2$). In embodiments, $R^{2D}$ is independently substituted alkyl (e.g., $C_1$-$C_8$, $C_1$-$C_6$, $C_1$-$C_4$, or $C_1$-$C_2$). In embodiments, $R^{2D}$ is independently unsubstituted alkyl (e.g., $C_1$-$C_8$, $C_1$-$C_6$, $C_1$-$C_4$, or $C_1$-$C_2$). In embodiments, $R^{2D}$ is independently unsubstituted methyl. In embodiments, $R^{2D}$ is independently unsubstituted ethyl. In embodiments, $R^{2D}$ is independently unsubstituted propyl. In embodiments, $R^{2D}$ is independently unsubstituted isopropyl. In embodiments, $R^{2D}$ is independently unsubstituted tert-butyl. In embodiments, $R^{2D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted heteroalkyl (e.g., 2 to 8 membered, 2 to 6 membered, 4 to 6 membered, 2 to 3 membered, or 4 to 5 membered). In embodiments, $R^{2D}$ is independently unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted or unsubstituted cycloalkyl (e.g., $C_3$-$C_8$, $C_3$-$C_6$, $C_4$-$C_6$, or $C_5$-$C_6$). In embodiments, $R^{2D}$ is independently substituted cycloalkyl (e.g., $C_3$-$C_8$, $C_3$-$C_6$, $C_4$-$C_6$, or $C_5$-$C_6$). In embodiments, $R^{2D}$ is independently unsubstituted cycloalkyl (e.g., $C_3$-$C_8$, $C_3$-$C_6$, $C_4$-$C_6$, or $C_5$-$C_6$). In embodiments, $R^{2D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted heterocycloalkyl (e.g., 3 to 8 membered, 3 to 6 membered, 4 to 6 membered, 4 to 5 membered, or 5 to 6 membered). In embodiments, $R^{2D}$ is independently unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted or unsubstituted aryl (e.g., $C_6$-$C_{12}$, $C_6$-$C_{10}$, or phenyl). In embodiments, $R^{2D}$ is independently substituted aryl (e.g., $C_6$-$C_{12}$, $C_6$-$C_{10}$, or phenyl). In embodiments, $R^{2D}$ is independently unsubstituted aryl (e.g., $C_6$-$C_{12}$, $C_6$-$C_{10}$, or phenyl). In embodiments, $R^{2D}$ is independently substituted or unsubstituted heteroaryl (e.g., 5 to 12 membered, 5 to 10 membered, 5 to 9 membered, or 5 to 6 membered). In embodiments, $R^{2D}$ is independently substituted heteroaryl (e.g., 5 to 12 membered, 5 to 10 membered, 5 to 9 membered, or 5 to 6 membered). In embodiments, $R^{2D}$ is independently unsubstituted heteroaryl (e.g., 5 to 12 membered, 5 to 10 membered, 5 to 9 membered, or 5 to 6 membered).

In embodiments, $R^2$ is hydrogen, halogen, —$CX^2{}_3$, —$CHX^2{}_2$, —$CH_2X^2$, —$OCX^2{}_3$, —$OCH_2X^2$, —$OCHX^2{}_2$, —CN, —$SO_{n2}R^{2D}$, —$SO_{v2}NR^{2A}R^{2B}$, —NHC(O)$NR^{2A}R^{2B}$, —N(O)$_{m2}$, —$NR^{2A}R^{2B}$, —C—(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{12}$, $C_6$-$C_{10}$, or phenyl), or $R^{20}$-substituted or unsubstituted heteroaryl (e.g., 5 to 12 membered, 5 to 10 membered, 5 to 9 membered, or 5 to 6 membered). In embodiments, $R^2$ is unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^2$ is independently —F, —Cl, —Br, or —I.

In embodiments, $R^2$ is hydrogen, —$OR^{2D}$, —C(O)$R^{2C}$, —C(O)—$OR^{2C}$, —C(O)$NR^{2A}R^{2B}$, $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{12}$, $C_6$-$C_{10}$, or phenyl), or $R^{20}$-substituted or unsubstituted heteroaryl (e.g., 5 to 12 membered, 5 to 10 membered, 5 to 9 membered, or 5 to 6 membered). In embodiments, $R^2$ is unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^2$ is $R^{20}$-substituted or unsubstituted alkyl (e.g., $C_1$-$C_8$, $C_1$-$C_6$, $C_1$-$C_4$, or $C_1$-$C_2$), $R^{20}$-substituted or unsubstituted heteroalkyl (e.g., 2 to 8 membered, 2 to 6 membered, 4 to 6 membered, 2 to 3 membered, or 4 to 5 membered), $R^{20}$-substituted or unsubstituted cycloalkyl (e.g., $C_3$-$C_8$, $C_3$-$C_6$, $C_4$-$C_6$, or $C_5$-$C_6$), $R^{20}$-substituted or unsubstituted heterocycloalkyl (e.g., 3 to 8 membered, 3 to 6 membered, 4 to 6 membered, 4 to 5 membered, or 5 to 6 membered), $R^{20}$-substituted or unsubstituted aryl (e.g., $C_6$-$C_{12}$, $C_6$-$C_{10}$, or phenyl), or $R^{20}$-substituted or unsubstituted heteroaryl (e.g., 5 to 12 membered, 5 to 10 membered, 5 to 9 membered, or 5 to 6 membered). In embodiments, $R^2$ is unsubstituted alkyl (e.g., $C_1$-$C_8$, $C_1$-$C_6$, $C_2$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{21}$, —$NHR^{21}$, —$COOR^{21}$, —$CONHR^{21}$, —$SR^{21}$, —$SO_2NHR^{21}$, —$NHSO_2R^{21}$, —$SO_2R^{21}$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl(e.g., $C_6$-$C_{12}$, $C_6$-$C_{10}$, or phenyl), or $R^{21}$-substituted or unsubstituted heteroaryl (e.g., 5 to 12 membered, 5 to 10 membered, 5 to 9 membered, or 5 to 6 membered). In embodiments, $R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{21}$, —$NHR^{21}$, —$COOR^{21}$, —$CONHR^{21}$, —$SR^{21}$, —$SO_2NHR^{21}$, —$SO_2R^{21}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20}$ is independently —F, —Cl, —Br, or —I.

$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 5 to 12 membered, 5 to 10 membered, 5 to 9 membered, or 5 to 6 membered), $R^{22}$-substituted or unsubstituted aryl (e.g., $C_6$-$C_{12}$, $C_6$-$C_{10}$, or phenyl), or $R^{22}$-substituted or unsubstituted heteroaryl (e.g., 5 to 12 membered, 5 to 10 membered, 5 to 9 membered, or 5 to 6 membered). In embodiments, $R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 5 to 12 membered, 5 to 10 membered, 5 to 9 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21}$ is independently —F, —Cl, —Br, or —I. In embodiments, $R^{21}$ is independently $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 5 to 12 membered, 5 to 10 membered, 5 to 9 membered, or 5 to 6 membered), $R^{22}$-substituted or unsubstituted aryl (e.g., $C_6$-$C_{12}$, $C_6$-$C_{10}$, or phenyl), or $R^{22}$-substituted or unsubstituted heteroaryl (e.g., 5 to 12 membered, 5 to 10 membered, 5 to 9 membered, or 5 to 6 membered).

$R^{22}$ is independently oxo, halogen, —$CX^{22}_3$, —$CHX^{22}_2$, —$CH_2X^{22}$, —$OCX^{22}_3$, —$OCH_2X^{22}$, —$OCHX^{22}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl, unsubstituted cycloalkyl (e.g., $C_1$-$C_8$, $C_1$-$C_6$, $C_1$-$C_4$, or $C_1$-$C_2$), unsubstituted heterocycloalkyl (e.g., 2 to 8 membered, 2 to 6 membered, 4 to 6 membered, 2 to 3 membered, or 4 to 5 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{22}$ is independently —F, —Cl, —Br, or —I. In embodiments, $R^{22}$ is independently unsubstituted alkyl (e.g., $C_1$-$C_8$, $C_1$-$C_6$, $C_1$-$C_4$, or $C_1$-$C_2$), unsubstituted heteroalkyl, unsubstituted cycloalkyl (e.g., $C_1$-$C_8$, $C_1$-$C_6$, $C_1$-$C_4$, or $C_1$-$C_2$), unsubstituted heterocycloalkyl (e.g., 2 to 8 membered, 2 to 6 membered, 4 to 6 membered, 2 to 3 membered, or 4 to 5 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^2$ is —C(O)$NHR^{2A}$.

In embodiments, $R^{2A}$ is independently $R^{20A}$-substituted or unsubstituted methyl, $R^{20A}$-substituted or unsubstituted ethyl, $R^{20A}$-substituted or unsubstituted phenyl, $R^{20A}$-substituted or unsubstituted 1-naphthyl, or $R^{20A}$-substituted or unsubstituted 2-naphthyl. In embodiments, $R^{2A}$ is independently unsubstituted methyl, unsubstituted phenyl, or unsubstituted 1-naphthyl.

In embodiments, $R^{2A}$ is independently $R^{20A}$-substituted methyl. In embodiments, $R^{2A}$ is independently $R^{20A}$-substituted ethyl. In embodiments, $R^{2A}$ is independently $R^{20A}$-substituted phenyl.

$R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{21A}$, —$NHR^{21A}$, —N($CH_3$)$R^{21A}$, —$COOR^{21A}$, —$CONHR^{21A}$, —$SR^{21A}$, $SO_2NHR^{21A}$, $SO_2R^{21A}$, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 to 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 8 membered, 3 to 6 membered, 4 to 6 membered, 4 to 5 membered, or 5 to 6 membered), $R^{21A}$-substituted or unsubstituted aryl (e.g., $C_6$-$C_{12}$, $C_6$-$C_{10}$, or phenyl), or $R^{21A}$-substituted or unsubstituted heteroaryl (e.g., 5 to 12 membered, 5 to 10 membered, 5 to 9 membered, or 5 to 6 membered). In embodiments, $R^{20A}$ is independently oxo, halogen, —$CX^{20A}_3$, —$CHX^{20A}_2$, —$CH_2X^{20A}$, —$OCX^{20A}_3$, —$OCH_2X^{20A}$, —$OCHX^{20A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{21A}$, —$NHR^{21A}$, —$N(CH_3)R^{21A}$, —$COOR^{21A}$, —$CONHR^{21A}$, —$SR^{21A}$, $SO_2NHR^{21A}$, $SO_2R^{21A}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20A}$ is independently —F, —Cl, —Br, or —I. In embodiments, $R^{20A}$ is independently phenyl. In embodiments, $R^{20A}$ is independently 1H-indol-3-yl.

$R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OR^{22A}$, —$NHR^{22A}$, —$N(CH_3)R^{22A}$, —$COOR^{22A}$, —$CONHR^{22A}$, —$SR^{22A}$, $SO_2NHR^{22A}$, $SO_2R^{22A}$, $R^{22A}$-substituted or unsubstituted alkyl, $R^{22A}$-substituted or unsubstituted heteroalkyl (e.g., $C_1$-$C_8$, $C_1$-$C_6$, $C_1$-$C_4$, or $C_1$-$C_2$), $R^{22A}$-substituted or unsubstituted (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 8 membered, 3 to 6 membered, 4 to 6 membered, 4 to 5 membered, or 5 to 6 membered), $R^{22A}$-substituted or unsubstituted aryl (e.g., $C_6$-$C_{12}$, $C_6$-$C_{10}$, or phenyl), or $R^{22A}$-substituted or unsubstituted heteroaryl (e.g., 5 to 12 membered, 5 to 10 membered, 5 to 9 membered, or 5 to 6 membered). In embodiments, $R^{21A}$ is independently oxo, halogen, —$CX^{21A}_3$, —$CHX^{21A}_2$, —$CH_2X^{21A}$, —$OCX^{21A}_3$, —$OCH_2X^{21A}$, —$OCHX^{21A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OR^{22A}$, —$NHR^{22A}$, —$N(CH_3)R^{22A}$, —$COOR^{22A}$, —$CONHR^{22A}$, —$SR^{22A}$, $SO_2NHR^{22A}$, $SO_2R^{22A}$, unsubstituted alkyl, unsubstituted heteroalkyl (e.g., $C_1$-$C_8$, $C_1$-$C_6$, $C_1$-$C_4$, or $C_1$-$C_2$), unsubstituted (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{21A}$ is independently —F, —Cl, —Br, or —I. In embodiments, $R^{21A}$ is independently —F. In embodiments, $R^{21A}$ is independently —$OCH_3$. In embodiments, $R^{21A}$ is independently $R^{22A}$-substituted or unsubstituted alkyl, $R^{22A}$-substituted or unsubstituted heteroalkyl (e.g., $C_1$-$C_8$, $C_1$-$C_6$, $C_1$-$C_4$, or $C_1$-$C_2$), $R^{22A}$-substituted or unsubstituted (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 8 membered, 3 to 6 membered, 4 to 6 membered, 4 to 5 membered, or 5 to 6 membered), $R^{22A}$-substituted or unsubstituted aryl (e.g., $C_6$-$C_{12}$, $C_6$-$C_{10}$, or phenyl), or $R^{22A}$-substituted or unsubstituted heteroaryl (e.g., 5 to 12 membered, 5 to 10 membered, 5 to 9 membered, or 5 to 6 membered).

$R^{22A}$ is independently oxo, halogen, —$CX^{22A}_3$, —$CHX^{22A}_2$, —$CH_2X^{22A}$, —$OCX^{22A}_3$, —$OCH_2X^{22A}$, —$OCHX^{22A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $SO_2CH_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered). $X^{22A}$ is independently —F, —Cl, —Br, or —I. In embodiments, $R^{22A}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered).

In embodiments, $R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —$N(O)_{m3}$, —$NR^{3A}R^{3B}$, —C(O)$R^{3C}$, —C(O)—$OR^{3C}$, —C(O)$NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered).

In embodiments, $R^3$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is hydrogen, halogen, substituted or unsubstituted $C_1$-$C_8$ alkyl, or substituted or unsubstituted 2 to 8 membered heteroalkyl; substituted or unsubstituted $C_3$-$C_8$ cycloalkyl, substituted or unsubstituted 3 to 8 membered heterocycloalkyl, substituted or unsubstituted $C_6$-$C_{12}$ aryl, or substituted or unsubstituted 5 to 12 membered heteroaryl.

In embodiments, $R^3$ is hydrogen, halogen, substituted or unsubstituted $C_1$-$C_8$ alkyl, or substituted or unsubstituted 2 to 8 membered heteroalkyl; substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl.

In embodiments, $R^3$ is hydrogen, halogen, substituted or unsubstituted alkyl, substituted or unsubstituted heteroalkyl, or substituted or unsubstituted aryl.

In embodiments, $R^3$ is hydrogen, halogen, substituted or unsubstituted $C_1$-$C_8$ alkyl, or substituted or unsubstituted 2 to 8 membered heteroalkyl, or substituted or unsubstituted $C_6$-$C_{12}$ aryl.

In embodiments, $R^3$ is hydrogen, halogen, substituted or unsubstituted $C_1$-$C_8$ alkyl, substituted or unsubstituted 2 to 8 membered heteroalkyl, or substituted or unsubstituted phenyl.

In embodiments, $R^3$ is hydrogen. In embodiments, $R^3$ is independently —$CX^3_3$. In embodiments, $R^3$ is independently —$CHX^3_2$. In embodiments, $R^3$ is independently —$CH_2X^3$. In embodiments, $R^3$ is independently —$OCX^3_3$. In embodiments, $R^3$ is independently —$OCH_2X^3$. In embodiments, $R^3$ is independently —$OCHX^3_2$. In embodiments, $R^3$ is independently —CN. In embodiments, $R^3$ is independently —$SO_{n3}R^{3D}$. In embodiments, $R^3$ is independently —$SO_{v3}NR^{3A}R^{3B}$. In embodiments, $R^3$ is independently —NHC(O)$NR^{3A}R^{3B}$. In embodiments, $R^3$ is independently —$N(O)_{m3}$. In embodiments, $R^3$ is independently —$NR^{3A}R^{3B}$. In embodiments, $R^3$ is independently —C(O)$R^{3C}$. In embodiments, $R^3$ is independently —C(O)—$OR^{3C}$. In embodiments, $R^3$ is independently —C(O)$NR^{3A}R^{3B}$. In embodiments, $R^3$ is independently —$OR^{3D}$. In embodiments, $R^3$ is independently —$NR^{3A}SO_2R^{3D}$. In embodiments, $R^3$ is independently —$NR^{3A}C(O)R^{3C}$. In embodiments, $R^3$ is independently —$NR^{3A}C(O)OR^{3C}$. In embodiments, $R^3$ is independently —$NR^{3A}OR^{3C}$. In embodiments, $R^3$ is independently —OH. In embodiments, $R^3$ is independently —$NH_2$. In embodiments, $R^3$ is independently —COOH. In embodiments, $R^3$ is independently —$CONH_2$. In embodiments, $R^3$ is independently —$NO_2$. In embodiments, $R^3$ is independently —SH. In embodiments, $R^3$ is independently halogen. In embodiments, $R^3$ is independently —F. In embodiments, $R^3$ is independently —Cl. In embodiments, $R^3$ is independently —Br. In embodiments, $R^3$ is independently —I. In embodiments, $R^3$ is independently —$CF_3$. In embodiments, $R^3$ is independently —$CHF_2$. In embodiments, $R^3$ is independently —$CH_2F$. In embodiments, $R^3$ is independently —$OCF_3$. In embodiments, $R^3$ is independently —$OCH_2F$. In embodiments, $R^3$ is independently —$OCHF_2$. In embodiments, $R^3$ is independently —$OCH_3$. In embodiments, $R^3$ is independently —$OCH_2CH_3$. In embodiments, $R^3$ is independently —$OCH_2CH_2CH_3$. In embodiments, $R^3$ is independently —$OCH(CH_3)_2$. In embodiments, $R^3$ is independently —$OC(CH_3)_3$. In embodiments, $R^3$ is independently —$SCH_3$. In embodiments, $R^3$ is independently —$SCH_2CH_3$. In embodiments, $R^3$ is independently —$SCH_2CH_2CH_3$. In embodiments, $R^3$ is independently —$SCH(CH_3)_2$. In embodiments, $R^3$ is independently —$SC(CH_3)_3$. In embodiments, $R^3$ is independently —$CH_3$. In embodiments, $R^3$ is independently —$CH_2CH_3$. In embodiments, $R^3$ is independently —$CH_2CH_2CH_3$. In embodiments, $R^3$ is independently —$CH(CH_3)_2$. In embodiments, $R^3$ is independently —$C(CH_3)_3$.

In embodiments, $R^3$ is independently substituted or unsubstituted alkyl (e.g., $C_1$-$C_8$, $C_1$-$C_6$, $C_1$-$C_4$, or $C_1$-$C_2$). In embodiments, $R^3$ is independently substituted alkyl (e.g., $C_1$-$C_8$, $C_1$-$C_6$, $C_1$-$C_4$, or $C_1$-$C_2$). In embodiments, $R^3$ is independently unsubstituted alkyl (e.g., $C_1$-$C_8$, $C_1$-$C_6$, $C_1$-$C_4$, or $C_1$-$C_2$). In embodiments, $R^3$ is independently unsubstituted methyl. In embodiments, $R^3$ is independently unsubstituted ethyl. In embodiments, $R^3$ is independently unsubstituted propyl. In embodiments, $R^3$ is independently unsubstituted isopropyl. In embodiments, $R^3$ is independently unsubstituted tert-butyl. In embodiments, $R^3$ is independently substituted or unsubstituted heteroalkyl (e.g., 2 to 8 membered, 2 to 6 membered, 4 to 6 membered, 2 to 3 membered, or 4 to 5 membered). In embodiments, $R^3$ is independently substituted heteroalkyl (e.g., 2 to 8 membered, 2 to 6 membered, 4 to 6 membered, 2 to 3 membered, or 4 to 5 membered). In embodiments, $R^3$ is independently unsubstituted heteroalkyl (e.g., 2 to 8 membered, 2 to 6 membered, 4 to 6 membered, 2 to 3 membered, or 4 to 5 membered). In embodiments, $R^3$ is independently substituted or unsubstituted cycloalkyl (e.g., $C_3$-$C_8$, $C_3$-$C_6$, $C_4$-$C_6$, or $C_5$-$C_6$). In embodiments, $R^3$ is independently substituted cycloalkyl (e.g., $C_3$-$C_8$, $C_3$-$C_6$, $C_4$-$C_6$, or $C_5$-$C_6$). In embodiments, $R^3$ is independently unsubstituted cycloalkyl (e.g., $C_3$-$C_8$, $C_3$-$C_6$, $C_4$-$C_6$, or $C_5$-$C_6$). In embodiments, $R^3$ is independently substituted or unsubstituted heterocycloalkyl (e.g., 3 to 8 membered, 3 to 6 membered, 4 to 6 membered, 4 to 5 membered, or 5 to 6 membered). In embodiments, $R^3$ is independently substituted heterocycloalkyl (e.g., 3 to 8 membered, 3 to 6 membered, 4 to 6 membered, 4 to 5 membered, or 5 to 6 membered). In embodiments, $R^3$ is independently unsubstituted heterocycloalkyl (e.g., 3 to 8 membered, 3 to 6 membered, 4 to 6 membered, 4 to 5 membered, or 5 to 6 membered). In embodiments, $R^3$ is independently substituted or unsubstituted aryl (e.g., $C_6$-$C_{12}$, $C_6$-$C_{10}$, or phenyl). In embodiments, $R^3$ is independently substituted aryl (e.g., $C_6$-$C_{12}$, $C_6$-$C_{10}$, or phenyl). In embodiments, $R^3$ is independently unsubstituted aryl (e.g., $C_6$-$C_{12}$, $C_6$-$C_{10}$, or phenyl). In embodiments, $R^3$ is independently substituted or unsubstituted heteroaryl (e.g., 5 to 12 membered, 5 to 10 membered, 5 to 9 membered, or 5 to 6 membered). In embodiments, $R^3$ is independently substituted heteroaryl (e.g., 5 to 12 membered, 5 to 10 membered, 5 to 9 membered, or 5 to 6 membered). In embodiments, $R^3$ is independently unsubstituted heteroaryl (e.g., 5 to 12 membered, 5 to 10 membered, 5 to 9 membered, or 5 to 6 membered).

In embodiments, $R^{3A}$ is independently hydrogen. In embodiments, $R^{3A}$ is independently —$CX^{3A}_3$. In embodiments, $R^{3A}$ is independently —$CHX^{3A}_2$. In embodiments, $R^{3A}$ is independently —$CH_2X^{3A}$. In embodiments, $R^{3A}$ is independently —CN. In embodiments, $R^{3A}$ is independently —COOH. In embodiments, $R^{3A}$ is independently —$CONH_2$. In embodiments, $X^{3A}$ is independently —F, —Cl, —Br, or —I.

In embodiments, $R^{3A}$ is independently substituted or unsubstituted alkyl (e.g., $C_1$-$C_8$, $C_1$-$C_6$, $C_1$-$C_4$, or $C_1$-$C_2$). In embodiments, $R^{3A}$ is independently substituted alkyl (e.g., $C_1$-$C_8$, $C_1$-$C_6$, $C_1$-$C_4$, or $C_1$-$C_2$). In embodiments, $R^{3A}$ is independently unsubstituted alkyl (e.g., $C_1$-$C_8$, $C_1$-$C_6$, $C_1$-$C_4$, or $C_1$-$C_2$). In embodiments, $R^{3A}$ is independently unsubstituted methyl. In embodiments, $R^{3A}$ is independently unsubstituted ethyl. In embodiments, $R^{3A}$ is independently unsubstituted propyl. In embodiments, $R^{3A}$ is independently unsubstituted isopropyl. In embodiments, $R^{3A}$ is independently unsubstituted tert-butyl. In embodiments, $R^{3A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted heteroalkyl (e.g., 2 to 8 membered, 2 to 6 membered, 4 to 6 membered, 2 to 3 membered, or 4 to 5 membered). In embodiments, $R^{3A}$ is independently unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted or unsubstituted cycloalkyl (e.g., $C_3$-$C_8$, $C_3$-$C_6$, $C_4$-$C_6$, or $C_5$-$C_6$). In embodiments, $R^{3A}$ is independently substituted cycloalkyl (e.g., $C_3$-$C_8$, $C_3$-$C_6$, $C_4$-$C_6$, or $C_5$-$C_6$). In embodiments, $R^{3A}$ is independently unsubstituted cycloalkyl (e.g., $C_3$-$C_8$, $C_3$-$C_6$, $C_4$-$C_6$, or $C_5$-$C_6$). In embodiments, $R^{3A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ is independently substituted heterocycloalkyl (e.g., 3 to 8 membered, 3 to 6 membered, 4 to 6 membered, 4 to 5 membered, or 5 to 6 membered). In embodiments, $R^{3A}$ is independently unsubstituted heterocycloalkyl (e.g., 3 to 8 membered, 3 to 6 membered, 4 to 6 membered, 4 to 5 membered, or 5 to 6 membered). In embodiments, $R^{3A}$ is independently substituted or unsubstituted aryl (e.g., $C_6$-$C_{12}$, $C_6$-$C_{10}$, or phenyl). In embodiments, $R^{3A}$ is independently substituted aryl (e.g., $C_6$-$C_{12}$, $C_6$-$C_{10}$, or phenyl). In embodiments, $R^{3A}$ is independently unsubstituted aryl (e.g., $C_6$-$C_{12}$, $C_6$-$C_{10}$, or phenyl). In embodiments, $R^{3A}$ is independently substituted or unsubstituted heteroaryl (e.g., 5 to 12 membered, 5 to 10 membered, 5 to 9 membered, or 5 to 6 membered). In embodiments, $R^{3A}$ is independently substituted heteroaryl (e.g., 5 to 12 membered, 5 to 10 membered, 5 to 9 membered, or 5 to 6 membered). In embodiments, $R^{3A}$ is independently unsubstituted heteroaryl (e.g., 5 to 12 membered, 5 to 10 membered, 5 to 9 membered, or 5 to 6 membered).

In embodiments, $R^{3B}$ is independently hydrogen. In embodiments, $R^{3B}$ is independently —$CX^{3B}_3$. In embodiments, $R^{3B}$ is independently —$CHX^{3B}_2$. In embodiments, $R^{3B}$ is independently —$CH_2X^{3B}$. In embodiments, $R^{3B}$ is independently —CN. In embodiments, $R^{3B}$ is independently —COOH. In embodiments, $R^{3B}$ is independently —$CONH_2$. In embodiments, $X^{3B}$ is independently —F, —Cl, —Br, or —I.

In embodiments, $R^{3B}$ is independently substituted or unsubstituted alkyl (e.g., $C_1$-$C_8$, $C_1$-$C_6$, $C_1$-$C_4$, or $C_1$-$C_2$). In embodiments, $R^{3B}$ is independently substituted alkyl (e.g., $C_1$-$C_8$, $C_1$-$C_6$, $C_1$-$C_4$, or $C_1$-$C_2$). In embodiments, $R^{3B}$ is independently unsubstituted alkyl (e.g., $C_1$-$C_8$, $C_1$-$C_6$, $C_1$-$C_4$, or $C_1$-$C_2$). In embodiments, $R^{3B}$ is independently unsubstituted methyl. In embodiments, $R^{3B}$ is independently unsubstituted ethyl. In embodiments, $R^{3B}$ is independently unsubstituted propyl. In embodiments, $R^{3B}$ is independently unsubstituted isopropyl. In embodiments, $R^{3B}$ is independently unsubstituted tert-butyl. In embodiments, $R^{3B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted heteroalkyl (e.g., 2 to 8 membered, 2 to 6 membered, 4 to 6 membered, 2 to 3 membered, or 4 to 5 membered). In embodiments, $R^{3B}$ is independently unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted or unsubstituted cycloalkyl (e.g., $C_3$-$C_8$, $C_3$-$C_6$, $C_4$-$C_6$, or $C_5$-$C_6$). In embodiments, $R^{3B}$ is independently substituted cycloalkyl (e.g., $C_3$-$C_8$, $C_3$-$C_6$, $C_4$-$C_6$, or $C_5$-$C_6$). In embodiments, $R^{3B}$ is independently unsubstituted cycloalkyl (e.g., $C_3$-$C_8$, $C_3$-$C_6$, $C_4$-$C_6$, or $C_5$-$C_6$). In embodiments, $R^{3B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted heterocycloalkyl (e.g., 3 to 8 membered, 3 to 6 membered, 4 to 6 membered, 4 to 5 membered, or 5 to 6 membered). In embodiments, $R^{3B}$ is independently unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted or unsubstituted aryl (e.g., $C_6$-$C_{12}$, $C_6$-$C_{10}$, or phenyl). In embodiments, $R^{3B}$ is independently substituted aryl (e.g., $C_6$-$C_{12}$, $C_6$-$C_{10}$, or phenyl). In embodiments, $R^{3B}$ is independently unsubstituted aryl (e.g., $C_6$-$C_{12}$, $C_6$-$C_{10}$, or phenyl). In embodiments, $R^{3B}$ is independently substituted or unsubstituted heteroaryl (e.g., 5 to 12 membered, 5 to 10 membered, 5 to 9 membered, or 5 to 6 membered). In embodiments, $R^{3B}$ is independently substituted heteroaryl (e.g., 5 to 12 membered, 5 to 10 membered, 5 to 9 membered, or 5 to 6 membered). In embodiments, $R^{3B}$ is independently unsubstituted heteroaryl (e.g., 5 to 12 membered, 5 to 10 membered, 5 to 9 membered, or 5 to 6 membered).

In embodiments, $R^{3A}$ and $R^{3B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{3A}$ and $R^{3B}$ substituents bonded to the same nitrogen atom may be joined to form a substituted or unsubstituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may be joined to form a substituted heteroaryl (e.g., 5 to 12 membered, 5 to 10 membered, 5 to 9 membered, or 5 to 6 membered). In embodiments, $R^{3A}$ and $R^{3B}$ substituents bonded to the same nitrogen atom may be joined to form an unsubstituted heteroaryl (e.g., 5 to 12 membered, 5 to 10 membered, 5 to 9 membered, or 5 to 6 membered).

In embodiments, $R^{3C}$ is independently hydrogen. In embodiments, $R^{3C}$ is independently —$CX^{3C}_3$. In embodiments, $R^{3C}$ is independently —$CHX^{3C}_2$. In embodiments, $R^{3C}$ is independently —$CH_2X^{3C}$. In embodiments, $R^{3C}$ is independently —CN. In embodiments, $R^{3C}$ is independently —COOH. In embodiments, $R^{3C}$ is independently —$CONH_2$. In embodiments, $X^{3C}$ is independently —F, —Cl, —Br, or —I.

In embodiments, $R^{3C}$ is independently substituted or unsubstituted alkyl (e.g., $C_1$-$C_8$, $C_1$-$C_6$, $C_1$-$C_4$, or $C_1$-$C_2$). In embodiments, $R^{3C}$ is independently substituted alkyl (e.g., $C_1$-$C_8$, $C_1$-$C_6$, $C_1$-$C_4$, or $C_1$-$C_2$). In embodiments, $R^{3C}$ is independently unsubstituted alkyl (e.g., $C_1$-$C_8$, $C_1$-$C_6$, $C_1$-$C_4$, or $C_1$-$C_2$). In embodiments, $R^{3C}$ is independently unsubstituted methyl. In embodiments, $R^{3C}$ is independently unsubstituted ethyl. In embodiments, $R^{3C}$ is independently unsubstituted propyl. In embodiments, $R^{3C}$ is independently unsubstituted isopropyl. In embodiments, $R^{3C}$ is independently unsubstituted tert-butyl. In embodiments, $R^{3C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3C}$ is independently substituted heteroalkyl (e.g., 2 to 8 membered, 2 to 6 membered, 4 to 6 membered, 2 to 3 membered, or 4 to 5 membered). In embodiments, $R^{3C}$ is independently unsubstituted heteroalkyl (e.g., 2 to 8 membered, 2 to 6 membered, 4 to 6 membered, 2 to 3 membered, or 4 to 5 membered). In embodiments, $R^{3C}$ is independently substituted or unsubstituted cycloalkyl (e.g., $C_3$-$C_8$, $C_3$-$C_6$, $C_4$-$C_6$, or $C_5$-$C_6$). In embodiments, $R^{3C}$ is independently substituted cycloalkyl (e.g., $C_3$-$C_8$, $C_3$-$C_6$, $C_4$-$C_6$, or $C_5$-$C_6$). In embodiments, $R^{3C}$ is independently unsubstituted cycloalkyl (e.g., $C_3$-$C_8$, $C_3$-$C_6$, $C_4$-$C_6$, or $C_5$-$C_6$). In embodiments, $R^{3C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3C}$ is independently substituted heterocycloalkyl (e.g., 3 to 8 membered, 3 to 6 membered, 4 to 6 membered, 4 to 5 membered, or 5 to 6 membered). In embodiments, $R^{3C}$ is independently unsubstituted heterocycloalkyl (e.g., 3 to 8 membered, 3 to 6 membered, 4 to 6 membered, 4 to 5 membered, or 5 to 6 membered). In embodiments, $R^{3C}$ is independently substituted or unsubstituted aryl (e.g., $C_6$-$C_{12}$, $C_6$-$C_{10}$, or phenyl). In embodiments, $R^{3C}$ is independently substituted aryl (e.g., $C_6$-$C_{12}$, $C_6$-$C_{10}$, or phenyl). In embodiments, $R^{3C}$ is independently unsubstituted aryl (e.g., $C_6$-$C_{12}$, $C_6$-$C_{10}$, or phenyl). In embodiments, $R^{3C}$ is independently substituted or unsubstituted heteroaryl (e.g., 5 to 12 membered, 5 to 10 membered, 5 to 9 membered, or 5 to 6 membered). In embodiments, $R^{3C}$ is independently substituted heteroaryl (e.g., 5 to 12 membered, 5 to 10 membered, 5 to 9 membered, or 5 to 6 membered). In embodiments, $R^{3C}$ is independently unsubstituted heteroaryl (e.g., 5 to 12 membered, 5 to 10 membered, 5 to 9 membered, or 5 to 6 membered).

In embodiments, $R^{3D}$ is independently hydrogen. In embodiments, $R^{3D}$ is independently —$CX^{3D}_3$. In embodiments, $R^{3D}$ is independently —$CHX^{3D}_2$. In embodiments, $R^{3D}$ is independently —$CH_2X^{3D}$. In embodiments, $R^{3D}$ is independently —CN. In embodiments, $R^{3D}$ is independently —COOH. In embodiments, $R^{3D}$ is independently —$CONH_2$. In embodiments, $X^{3D}$ is independently —F, —Cl, —Br, or —I.

In embodiments, $R^{3D}$ is independently substituted or unsubstituted alkyl (e.g., $C_1$-$C_8$, $C_1$-$C_6$, $C_1$-$C_4$, or $C_1$-$C_2$). In embodiments, $R^{3D}$ is independently substituted alkyl (e.g., $C_1$-$C_8$, $C_1$-$C_6$, $C_1$-$C_4$, or $C_1$-$C_2$). In embodiments, $R^{3D}$ is independently unsubstituted alkyl (e.g., $C_1$-$C_8$, $C_1$-$C_6$, $C_1$-$C_4$, or $C_1$-$C_2$). In embodiments, $R^{3D}$ is independently unsubstituted methyl. In embodiments, $R^{3D}$ is independently unsubstituted ethyl. In embodiments, $R^{3D}$ is independently unsubstituted propyl. In embodiments, $R^{3D}$ is independently unsubstituted isopropyl. In embodiments, $R^{3D}$ is independently unsubstituted tert-butyl. In embodiments, $R^{3D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3D}$ is independently substituted heteroalkyl (e.g., 2 to 8 membered, 2 to 6 membered, 4 to 6 membered, 2 to 3 membered, or 4 to 5 membered). In embodiments, $R^{3D}$ is independently unsubstituted heteroalkyl (e.g., 2 to 8 membered, 2 to 6 membered, 4 to 6 membered, 2 to 3 membered, or 4 to 5 membered). In embodiments, $R^{3D}$ is independently substituted or unsubstituted cycloalkyl (e.g., $C_3$-$C_8$, $C_3$-$C_6$, $C_4$-$C_6$, or $C_5$-$C_6$). In embodiments, $R^{3D}$ is independently substituted cycloalkyl (e.g., $C_3$-$C_8$, $C_3$-$C_6$, $C_4$-$C_6$, or $C_5$-$C_6$). In embodiments, $R^{3D}$ is independently unsubstituted cycloalkyl (e.g., $C_3$-$C_8$, $C_3$-$C_6$, $C_4$-$C_6$, or $C_5$-$C_6$). In embodiments, $R^{3D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3D}$ is independently substituted heterocycloalkyl (e.g., 3 to 8 membered, 3 to 6 membered, 4 to 6 membered, 4 to 5 membered, or 5 to 6 membered). In embodiments, $R^{3D}$ is independently unsubstituted heterocycloalkyl (e.g., 3 to 8 membered, 3 to 6 membered, 4 to 6 membered, 4 to 5 membered, or 5 to 6 membered). In embodiments, $R^{3D}$ is independently substituted or unsubstituted aryl (e.g., $C_6$-$C_{12}$, $C_6$-$C_{10}$, or phenyl). In embodiments, $R^{3D}$ is independently substituted aryl (e.g., $C_6$-$C_{12}$, $C_6$-$C_{10}$, or phenyl). In embodiments, $R^{3D}$ is independently unsubstituted aryl (e.g., $C_6$-$C_{12}$, $C_6$-$C_{10}$, or phenyl). In embodiments, $R^{3D}$ is independently substituted or unsubstituted heteroaryl (e.g., 5 to 12 membered, 5 to 10 membered, 5 to 9 membered, or 5 to 6 membered). In embodiments, $R^{3D}$ is independently substituted heteroaryl (e.g., 5 to 12 membered, 5 to 10 membered, 5 to 9 membered, or 5 to 6 membered). In embodiments, $R^{3D}$ is independently unsubstituted heteroaryl (e.g., 5 to 12 membered, 5 to 10 membered, 5 to 9 membered, or 5 to 6 membered).

In embodiments, $R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —C(O)—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 8 membered, 3 to 6 membered, 4 to 6 membered, 4 to 5 membered, or 5 to 6 membered), $R^{30}$-substituted or unsubstituted aryl (e.g., $C_6$-$C_{12}$, $C_6$-$C_{10}$, or phenyl), or $R^{30}$-substituted or unsubstituted heteroaryl (e.g., 5 to 12 membered, 5 to 10 membered, 5 to 9 membered, or 5 to 6 membered). In embodiments, $R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —$N(O)_{m3}$, —$NR^{3A}R^{3B}$, —$C(O)R^{3C}$, —C(O)—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^3$ is independently —F, —Cl, —Br, or —I.

In embodiments, $R^3$ is hydrogen, halogen, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), or $R^{30}$-substituted or unsubstituted aryl (e.g., $C_6$-$C_{12}$, $C_6$-$C_{10}$, or phenyl). In embodiments, $R^3$ is hydrogen, halogen, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), or unsubstituted aryl (e.g., $C_6$-$C_{12}$, $C_6$-$C_{10}$, or phenyl).

In embodiments, $R^3$ is independently $R^{30}$-substituted or unsubstituted methyl, $R^{30}$-substituted or unsubstituted —$CH_2N(CH_3)Ph$, or $R^{30}$-substituted or unsubstituted phenyl. In embodiments, $R^3$ is independently unsubstituted methyl, unsubstituted —$CH_2N(CH_3)Ph$, or unsubstituted phenyl.

In embodiments, $R^3$ is independently $R^{30}$-substituted methyl. In embodiments, $R^{30}$-substituted —$CH_2N(CH_3)Ph$. In embodiments, $R^3$ is independently $R^{30}$-substituted phenyl.

$R^{30}$ is independently oxo, halogen, —$CX^{30}_3$, —$CHX^{30}_2$, —$CH_2X^{30}$, —$OCX^{30}_3$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, —$OR^{31}$, —$NHR^{31}$, —$N(CH_3)R^{31}$, —$COOR^{31}$, —$CONHR^{31}$, —$NHCOR^{31}$, —$SR^{31}$, —$SO_2NHR^{31}$, —$SO_2R^{31}$, —$NHSO_2R^{31}$, $R^{31}$-substituted or unsubstituted alkyl (e.g., $C_1$-$C_8$, $C_1$-$C_6$, $C_1$-$C_4$, or $C_1$-$C_2$), $R^{31}$-substituted or unsubstituted heteroalkyl (e.g., 2 to 8 membered, 2 to 6 membered, 4 to 6 membered, 2 to 3 membered, or 4 to 5 membered), $R^{31}$-substituted or unsubstituted cycloalkyl (e.g., $C_3$-$C_8$, $C_3$-$C_6$, $C_4$-$C_6$, or $C_5$-$C_6$), $R^{31}$-substituted or unsubstituted heterocycloalkyl (e.g., 3 to 8 membered, 3 to 6 membered, 4 to 6 membered, 4 to 5 membered, or 5 to 6 membered), $R^{31}$-substituted or unsubstituted aryl (e.g., $C_6$-$C_{12}$, $C_6$-$C_{10}$, or phenyl), or $R^{31}$-substituted or unsubstituted heteroaryl (e.g., 5 to 12 membered, 5 to 10 membered, 5 to 9 membered, or 5 to 6 membered). In embodiments, $R^{30}$ is independently oxo, halogen, —$CX^{30}_3$, —$CHX^{30}_2$, —$CH_2X^{30}$, —$OCX^{30}_3$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, —$OR^{31}$, —$NHR^{31}$, —$N(CH_3)R^{31}$, —$COOR^{31}$, —$CONHR^{31}$, —$NHCOR^{31}$, —$SR^{31}$, —$SO_2NHR^{31}$, —$SO_2R^{31}$, —$NHSO_2R^{31}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{30}$ is independently —F, —Cl, —Br, or —I. In embodiments, $R^{30}$ is independently methyl. In embodiments, $R^{30}$ is independently phenyl. In embodiments, $R^{30}$ is independently 4-chlorophenyl. In embodiments, $R^{30}$ is independently —COOH. In embodiments, $R^{30}$ is independently —$COONH_2$. In embodiments, $R^{30}$ is independently —$CH_3$. In embodiments, $R^{30}$ is independently unsubstituted heteroaryl (e.g., 5 to 6 membered). In embodiments, $R^{30}$ is independently unsubstituted tetrazolyl. In embodiments, $R^{30}$ is independently

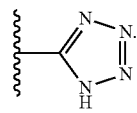

In embodiments, $R^{30}$ is independently unsubstituted tetrazolyl. In embodiments, $R^{30}$ is independently

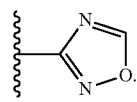

In embodiments, $R^{30}$ is independently $R^{31}$-substituted tetrazolyl. In embodiments, $R^{30}$ is independently methyl-substituted tetrazolyl. In embodiments, $R^{30}$ is independently

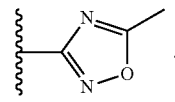 [SMILES: *c1noc(C)n1]

In embodiments, $R^{30}$ is independently

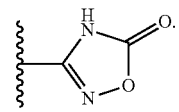

In embodiments, $R^{30}$ is independently unsubstituted oxazolyl. In embodiments, $R^{30}$ is independently

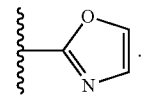

In embodiments, $R^{30}$ is independently $R^{31}$-substituted oxazolyl.

$R^{31}$ is independently oxo, halogen, —$CX^{31}_3$, —$CHX^{31}_2$, —$CH_2X^{31}$, —$OCX^{31}_3$, —$OCH_2X^{31}$, —$OCHX^{31}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O) $NH_2$, —$NHSO_2H$, —$NHC$=(O)H, —NHC(O)—OH, —NHOH, —$OR^{32}$, —$NHR^{32}$, —$N(CH_3)R^{32}$, —$COOR^{32}$, —$CONHR^{32}$, —$SR^{32}$, —$SO_2NHR^{32}$, —$SO_2R^{32}$, $R^{32}$-substituted or unsubstituted alkyl, $R^{32}$-substituted or unsubstituted heteroalkyl (e.g., $C_1$-$C_8$, $C_1$-$C_6$, $C_1$-$C_4$, or $C_1$-$C_2$), $R^{32}$-substituted or unsubstituted (e.g., $C_3$-$C_8$, $C_3$-$C_6$, $C_4$-$C_6$, or $C_5$-$C_6$), $R^{32}$-substituted or unsubstituted heterocycloalkyl (e.g., 3 to 8 membered, 3 to 6 membered, 4 to 6 membered, 4 to 5 membered, or 5 to 6 membered), $R^{32}$-substituted or unsubstituted aryl (e.g., $C_6$-$C_{12}$, $C_6$-$C_{10}$, or phenyl), or $R^{32}$-substituted or unsubstituted heteroaryl (e.g., 5 to 12 membered, 5 to 10 membered, 5 to 9 membered, or 5 to 6 membered). In embodiments, $R^{31}$ is independently oxo, halogen, —$CX^{31}_3$, —$CHX^{31}_2$, —$CH_2X^{31}$, —$OCX^{31}_3$, —$OCH_2X^{31}$, —$OCHX^{31}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O) $NH_2$, —$NHSO_2H$, —$NHC$=(O)H, —NHC(O)—OH, —NHOH, —$OR^{32}$, —$NHR^{32}$, —$N(CH_3)R^{32}$, —$COOR^{32}$, —$CONHR^{32}$, —$SR^{32}$, —$SO_2NHR^{32}$, —$SO_2R^{32}$, unsubstituted alkyl, unsubstituted heteroalkyl (e.g., $C_1$-$C_8$, $C_1$-$C_6$, $C_1$-$C_4$, or $C_1$-$C_2$), unsubstituted (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{31}$ is independently —F, —Cl, —Br, or —I. In embodiments, $R^{31}$ is independently halogen. In embodiments, $R^{31}$ is independently —Cl. In embodiments, $R^{31}$ is independently —F. In embodiments, $R^{31}$ is independently —$OR^{32}$. In embodiments, $R^{31}$ is independently —COOH. In embodiments, $R^{31}$ is independently —$CH_3$. In embodiments, $R^{31}$ is independently unsubstituted heteroaryl (e.g., 5 to 6 membered). In embodiments, $R^{31}$ is independently tetrazolyl. In embodiments, $R^{31}$ is independently $R^{32}$-substituted or unsubstituted alkyl, $R^{32}$-substituted or unsubstituted heteroalkyl (e.g., $C_1$-$C_8$, $C_1$-$C_6$, $C_1$-$C_4$, or $C_1$-$C_2$), $R^{32}$-substituted or unsubstituted (e.g., $C_3$-$C_8$, $C_3$-$C_6$, $C_4$-$C_6$, or $C_5$-$C_6$), $R^{32}$-substituted or unsubstituted heterocycloalkyl (e.g., 3 to 8 membered, 3 to 6 membered, 4 to 6 membered, 4 to 5 membered, or 5 to 6 membered), $R^{32}$-substituted or unsubstituted aryl (e.g., $C_6$-$C_{12}$, $C_6$-$C_{10}$, or phenyl), or $R^{32}$-substituted or unsubstituted heteroaryl (e.g., 5 to 12 membered, 5 to 10 membered, 5 to 9 membered, or 5 to 6 membered).

$R^{32}$ is independently oxo, halogen, —$CX^{32}_3$, —$CHX^{32}_2$, —$CH_2X^{32}$, —$OCX^{32}_3$, —$OCH_2X^{32}$, —$OCHX^{32}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $SO_2CH_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered). $X^{32}$ is independently —F, —Cl, —Br, or —I. In embodiments, $R^{32}$ is independently —$CH_3$. In embodiments, $R^{32}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered).

In embodiments, $R^4$ is hydrogen, halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —$N(O)_{m4}$, —$NR^{4A}R^{4B}$, —C(O)$R^{4C}$, —C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is hydrogen, halogen, —$CX^1_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —NHC(O)$NR^{4A}R^{4B}$, —$N(O)_{m4}$, —$NR^{4A}R^{4B}$, —C(O)$R^{4C}$, —C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered).

In embodiments, $R^4$ is hydrogen, —C(O)$R^{4C}$, —C(O)—$OR^{4C}$, —C(O)$NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is hydrogen, —C(O)$R^{4C}$, —C(O)—$OR^{4C}$, —C(O)$NR^{4A}R^{4B}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{12}$ aryl, or substituted or unsubstituted 5 to 12 membered heteroaryl.

In embodiments, $R^4$ is hydrogen, —C(O)$R^{4C}$, —C(O)—$OR^{4C}$, —C(O)$NR^{4A}R^{4B}$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{12}$ aryl, or substituted or unsubstituted 5 to 6 membered heteroaryl.

In embodiments, $R^4$ is hydrogen, —C(O)$R^{4C}$, —C(O)—$OR^{4C}$, —C(O)$NR^{4A}R^{4B}$, or substituted or unsubstituted heteroaryl.

In embodiments, $R^4$ is hydrogen, —C(O)$R^{4C}$, —C(O)—$OR^{4C}$, —C(O)$NR^{4A}R^{4B}$, or substituted or unsubstituted 5 to 12 membered heteroaryl.

In embodiments, $R^4$ is hydrogen, —C(O)$R^{4C}$, —C(O)—$OR^{4C}$, —C(O)$NR^{4A}R^{4B}$, or substituted or unsubstituted 5 to 6 membered heteroaryl.

In embodiments, $R^4$ is independently —$CX^4_3$. In embodiments, $R^4$ is independently —$CHX^4_2$. In embodiments, $R^4$ is independently —$CH_2X^4$. In embodiments, $R^4$ is independently —$OCX^4_3$. In embodiments, $R^4$ is independently —$OCH_2X^4$. In embodiments, $R^4$ is independently —$OCHX^4_2$. In embodiments, $R^4$ is independently —CN. In embodiments, $R^4$ is independently —$SO_{n4}R^{4D}$. In embodiments, $R^4$ is independently —$SO_{v4}NR^{4A}R^{4B}$. In embodiments, $R^4$ is independently —NHC(O)$NR^{4A}R^{4B}$. In embodiments, $R^4$ is independently —$N(O)_{m4}$. In embodiments, $R^4$ is independently —$NR^{4A}R^{4B}$. In embodiments, $R^4$ is independently —C(O)$R^{4C}$. In embodiments, $R^4$ is independently —C(O)—$OR^{4C}$. In embodiments, $R^4$ is independently —C(O)$NR^{4A}R^{4B}$. In embodiments, $R^4$ is independently —$OR^{4D}$. In embodiments, $R^4$ is independently —$NR^{4A}SO_2R^{4D}$. In embodiments, $R^4$ is independently —$NR^{4A}C(O)R^{4C}$. In embodiments, $R^4$ is independently —$NR^{4A}C(O)OR^{4C}$. In embodiments, $R^4$ is independently —$NR^{4A}OR^{4C}$. In embodiments, $R^4$ is independently —OH. In embodiments, $R^4$ is independently —$NH_2$. In embodiments, $R^4$ is independently —COOH. In embodiments, $R^4$ is independently —$CONH_2$. In embodiments, $R^4$ is independently —$NO_2$. In embodiments, $R^4$ is independently —SH. In embodiments, $R^4$ is independently halogen. In embodiments, $R^4$ is independently —F. In embodiments, $R^4$ is independently —Cl. In embodiments, $R^4$ is independently —Br. In embodiments, $R^4$ is independently —I. In embodiments, $R^4$ is independently —$CF_3$. In embodiments, $R^4$ is independently —$CHF_2$. In embodiments, $R^4$ is independently —$CH_2F$. In embodiments, $R^4$ is independently —$OCF_3$. In embodiments, $R^4$ is independently —$OCH_2F$. In embodiments, $R^4$ is independently —$OCHF_2$. In embodiments, $R^4$ is independently —$OCH_3$. In embodiments, $R^4$ is independently —$OCH_2CH_3$. In embodiments, $R^4$ is independently —$OCH_2CH_2CH_3$. In embodiments, $R^4$ is independently —$OCH(CH_3)_2$. In embodiments, $R^4$ is independently —$OC(CH_3)_3$. In embodiments, $R^4$ is independently —$SCH_3$. In embodiments, $R^4$ is independently —$SCH_2CH_3$.

In embodiments, R⁴ is independently —SCH₂CH₂CH₃. In embodiments, R⁴ is independently —SCH(CH₃)₂. In embodiments, R⁴ is independently —SC(CH₃)₃. In embodiments, R⁴ is independently —CH₃. In embodiments, R⁴ is independently —CH₂CH₃. In embodiments, R⁴ is independently —CH₂CH₂CH₃. In embodiments, R⁴ is independently —CH(CH₃)₂. In embodiments, R⁴ is independently —C(CH₃)₃. In embodiments, R⁴ is independently —COOH. In embodiments, R⁴ is independently —COONH₂. In embodiments, R⁴ is independently —CH₃. In embodiments, R⁴ is independently unsubstituted heteroaryl (e.g., 5 to 6 membered). In embodiments, R⁴ is independently unsubstituted tetrazolyl. In embodiments, R⁴ is independently

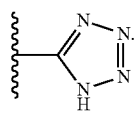

In embodiments, R⁴ is independently unsubstituted tetrazolyl. In embodiments, R⁴ is independently

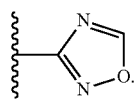

In embodiments, R⁴ is independently R⁴⁰-substituted tetrazolyl. In embodiments, R⁴ is independently methyl-substituted tetrazolyl. In embodiments, R⁴ is independently

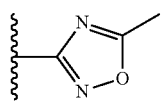

In embodiments, R⁴ is independently unsubstituted oxazolyl. In embodiments, R⁴ is independently

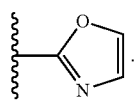

In embodiments, R⁴ is independently R⁴⁰-substituted oxazolyl.

In embodiments, R⁴ is independently substituted or unsubstituted alkyl (e.g., $C_1$-$C_8$, $C_1$-$C_6$, $C_1$-$C_4$, or $C_1$-$C_2$). In embodiments, R⁴ is independently substituted alkyl (e.g., $C_1$-$C_8$, $C_1$-$C_6$, $C_1$-$C_4$, or $C_1$-$C_2$). In embodiments, R⁴ is independently unsubstituted alkyl (e.g., $C_1$-$C_8$, $C_1$-$C_6$, $C_1$-$C_4$, or $C_1$-$C_2$). In embodiments, R⁴ is independently unsubstituted methyl. In embodiments, R⁴ is independently unsubstituted ethyl. In embodiments, R⁴ is independently unsubstituted propyl. In embodiments, R⁴ is independently unsubstituted isopropyl. In embodiments, R⁴ is independently unsubstituted tert-butyl. In embodiments, R⁴ is independently substituted or unsubstituted heteroalkyl (e.g., 2 to 8 membered, 2 to 6 membered, 4 to 6 membered, 2 to 3 membered, or 4 to 5 membered). In embodiments, R⁴ is independently substituted heteroalkyl (e.g., 2 to 8 membered, 2 to 6 membered, 4 to 6 membered, 2 to 3 membered, or 4 to 5 membered). In embodiments, R⁴ is independently unsubstituted heteroalkyl (e.g., 2 to 8 membered, 2 to 6 membered, 4 to 6 membered, 2 to 3 membered, or 4 to 5 membered). In embodiments, R⁴ is independently substituted or unsubstituted cycloalkyl (e.g., $C_3$-$C_8$, $C_3$-$C_6$, $C_4$-$C_6$, or $C_5$-$C_6$). In embodiments, R⁴ is independently substituted cycloalkyl (e.g., $C_3$-$C_8$, $C_3$-$C_6$, $C_4$-$C_6$, or $C_5$-$C_6$). In embodiments, R⁴ is independently unsubstituted cycloalkyl (e.g., $C_3$-$C_8$, $C_3$-$C_6$, $C_4$-$C_6$, or $C_5$-$C_6$). In embodiments, R⁴ is independently substituted or unsubstituted heterocycloalkyl (e.g., 3 to 8 membered, 3 to 6 membered, 4 to 6 membered, 4 to 5 membered, or 5 to 6 membered). In embodiments, R⁴ is independently substituted heterocycloalkyl (e.g., 3 to 8 membered, 3 to 6 membered, 4 to 6 membered, 4 to 5 membered, or 5 to 6 membered). In embodiments, R⁴ is independently unsubstituted heterocycloalkyl (e.g., 3 to 8 membered, 3 to 6 membered, 4 to 6 membered, 4 to 5 membered, or 5 to 6 membered). In embodiments, R⁴ is independently substituted or unsubstituted aryl (e.g., $C_6$-$C_{12}$, $C_6$-$C_{10}$, or phenyl). In embodiments, R⁴ is independently substituted aryl (e.g., $C_6$-$C_{12}$, $C_6$-$C_{10}$, or phenyl). In embodiments, R⁴ is independently unsubstituted aryl (e.g., $C_6$-$C_{12}$, $C_6$-$C_{10}$, or phenyl). In embodiments, R⁴ is independently substituted or unsubstituted heteroaryl (e.g., 5 to 12 membered, 5 to 10 membered, 5 to 9 membered, or 5 to 6 membered). In embodiments, R⁴ is independently substituted heteroaryl (e.g., 5 to 12 membered, 5 to 10 membered, 5 to 9 membered, or 5 to 6 membered). In embodiments, R⁴ is independently unsubstituted heteroaryl (e.g., 5 to 12 membered, 5 to 10 membered, 5 to 9 membered, or 5 to 6 membered).

In embodiments, $R^{4A}$ is independently hydrogen. In embodiments, $R^{4A}$ is independently —$CX^{4A}_3$. In embodiments, $R^{4A}$ is independently —$CHX^{4A}_2$. In embodiments, $R^{4A}$ is independently —$CH_2X^{4A}$. In embodiments, $R^{4A}$ is independently —CN. In embodiments, $R^{4A}$ is independently —COOH. In embodiments, $R^{4A}$ is independently —CONH₂. In embodiments, $X^{4A}$ is independently —F, —Cl, —Br, or —I.

In embodiments, $R^{4A}$ is independently substituted or unsubstituted alkyl (e.g., $C_1$-$C_8$, $C_1$-$C_6$, $C_1$-$C_4$, or $C_1$-$C_2$). In embodiments, $R^{4A}$ is independently substituted alkyl (e.g., $C_1$-$C_8$, $C_1$-$C_6$, $C_1$-$C_4$, or $C_1$-$C_2$). In embodiments, $R^{4A}$ is independently unsubstituted alkyl (e.g., $C_1$-$C_8$, $C_1$-$C_6$, $C_1$-$C_4$, or $C_1$-$C_2$). In embodiments, $R^{4A}$ is independently unsubstituted methyl. In embodiments, $R^{4A}$ is independently unsubstituted ethyl. In embodiments, $R^{4A}$ is independently unsubstituted propyl. In embodiments, $R^{4A}$ is independently unsubstituted isopropyl. In embodiments, $R^{4A}$ is independently unsubstituted tert-butyl. In embodiments, $R^{4A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4A}$ is independently substituted heteroalkyl (e.g., 2 to 8 membered, 2 to 6 membered, 4 to 6 membered, 2 to 3 membered, or 4 to 5 membered). In embodiments, $R^{4A}$ is independently unsubstituted heteroalkyl (e.g., 2 to 8 membered, 2 to 6 membered, 4 to 6 membered, 2 to 3 membered, or 4 to 5 membered). In embodiments, $R^{4A}$ is independently substituted or unsubstituted cycloalkyl (e.g., $C_3$-$C_8$, $C_3$-$C_6$, $C_4$-$C_6$, or $C_5$-$C_6$). In embodiments, $R^{4A}$ is independently substituted cycloalkyl (e.g., $C_3$-$C_8$, $C_3$-$C_6$, $C_4$-$C_6$, or $C_5$-$C_6$). In embodiments, $R^{4A}$ is independently unsubstituted cycloalkyl (e.g., $C_3$-$C_8$, $C_3$-$C_6$, $C_4$-$C_6$, or $C_5$-$C_6$). In embodiments, $R^{4A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ is independently substituted heterocycloalkyl (e.g., 3 to 8 membered, 3 to 6 membered, 4 to 6 membered, 4 to 5 membered, or 5 to 6 membered). In embodiments, $R^{4A}$ is independently unsubstituted heterocycloalkyl (e.g., 3 to 8 membered, 3 to 6 membered, 4 to 6 membered, 4 to 5 membered, or 5 to 6 membered). In embodiments, $R^{4A}$ is independently substituted or unsubstituted aryl (e.g., $C_6$-$C_{12}$, $C_6$-$C_{10}$, or phenyl). In embodiments, $R^{4A}$ is independently substituted aryl (e.g., $C_6$-$C_{12}$, $C_6$-$C_{10}$, or phenyl). In embodiments, $R^{4A}$ is independently unsubstituted aryl (e.g., $C_6$-$C_{12}$, $C_6$-$C_{10}$, or phenyl). In embodiments, $R^{4A}$ is independently substituted or unsubstituted heteroaryl (e.g., 5 to 12 membered, 5 to 10 membered, 5 to 9 membered, or 5 to 6 membered). In embodiments, $R^{4A}$ is independently substituted heteroaryl (e.g., 5 to 12 membered, 5 to 10 membered, 5 to 9 membered, or 5 to 6 membered). In embodiments, $R^{4A}$ is independently unsubstituted heteroaryl (e.g., 5 to 12 membered, 5 to 10 membered, 5 to 9 membered, or 5 to 6 membered).

In embodiments, $R^{4B}$ is independently hydrogen. In embodiments, $R^{4B}$ is independently —$CX^{4B}_3$. In embodiments, $R^{4B}$ is independently —$CHX^{4B}_2$. In embodiments, $R^{4B}$ is independently —$CH_2X^{4B}$. In embodiments, $R^{4B}$ is independently —CN. In embodiments, $R^{4B}$ is independently —COOH. In embodiments, $R^{4B}$ is independently —$CONH_2$. In embodiments, $X^{4B}$ is independently —F, —Cl, —Br, or —I.

In embodiments, $R^{4B}$ is independently substituted or unsubstituted alkyl (e.g., $C_1$-$C_8$, $C_1$-$C_6$, $C_1$-$C_4$, or $C_1$-$C_2$). In embodiments, $R^{4B}$ is independently substituted alkyl (e.g., $C_1$-$C_8$, $C_1$-$C_6$, $C_1$-$C_4$, or $C_1$-$C_2$). In embodiments, $R^{4B}$ is independently unsubstituted alkyl (e.g., $C_1$-$C_8$, $C_1$-$C_6$, $C_1$-$C_4$, or $C_1$-$C_2$). In embodiments, $R^{4B}$ is independently unsubstituted methyl. In embodiments, $R^{4B}$ is independently unsubstituted ethyl. In embodiments, $R^{4B}$ is independently unsubstituted propyl. In embodiments, $R^{4B}$ is independently unsubstituted isopropyl. In embodiments, $R^{4B}$ is independently unsubstituted tert-butyl. In embodiments, $R^{4B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4B}$ is independently substituted heteroalkyl (e.g., 2 to 8 membered, 2 to 6 membered, 4 to 6 membered, 2 to 3 membered, or 4 to 5 membered). In embodiments, $R^{4B}$ is independently unsubstituted heteroalkyl (e.g., 2 to 8 membered, 2 to 6 membered, 4 to 6 membered, 2 to 3 membered, or 4 to 5 membered). In embodiments, $R^{4B}$ is independently substituted or unsubstituted cycloalkyl (e.g., $C_3$-$C_8$, $C_3$-$C_6$, $C_4$-$C_6$, or $C_5$-$C_6$). In embodiments, $R^{4B}$ is independently substituted cycloalkyl (e.g., $C_3$-$C_8$, $C_3$-$C_6$, $C_4$-$C_6$, or $C_5$-$C_6$). In embodiments, $R^{4B}$ is independently unsubstituted cycloalkyl (e.g., $C_3$-$C_8$, $C_3$-$C_6$, $C_4$-$C_6$, or $C_5$-$C_6$). In embodiments, $R^{4B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4B}$ is independently substituted heterocycloalkyl (e.g., 3 to 8 membered, 3 to 6 membered, 4 to 6 membered, 4 to 5 membered, or 5 to 6 membered). In embodiments, $R^{4B}$ is independently unsubstituted heterocycloalkyl (e.g., 3 to 8 membered, 3 to 6 membered, 4 to 6 membered, 4 to 5 membered, or 5 to 6 membered). In embodiments, $R^{4B}$ is independently substituted or unsubstituted aryl (e.g., $C_6$-$C_{12}$, $C_6$-$C_{10}$, or phenyl). In embodiments, $R^{4B}$ is independently substituted aryl (e.g., $C_6$-$C_{12}$, $C_6$-$C_{10}$, or phenyl). In embodiments, $R^{4B}$ is independently unsubstituted aryl (e.g., $C_6$-$C_{12}$, $C_6$-$C_{10}$, or phenyl). In embodiments, $R^{4B}$ is independently substituted or unsubstituted heteroaryl (e.g., 5 to 12 membered, 5 to 10 membered, 5 to 9 membered, or 5 to 6 membered). In embodiments, $R^{4B}$ is independently substituted heteroaryl (e.g., 5 to 12 membered, 5 to 10 membered, 5 to 9 membered, or 5 to 6 membered). In embodiments, $R^{4B}$ is independently unsubstituted heteroaryl (e.g., 5 to 12 membered, 5 to 10 membered, 5 to 9 membered, or 5 to 6 membered).

In embodiments, $R^{4A}$ and $R^{4B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ and $R^{3B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{4A}$ and $R^{4B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{4A}$ and $R^{4B}$ substituents bonded to the same nitrogen atom may be joined to form a substituted or unsubstituted heteroaryl (e.g., 5 to 12 membered, 5 to 10 membered, 5 to 9 membered, or 5 to 6 membered). In embodiments, $R^{4A}$ and $R^{4B}$ substituents bonded to the same nitrogen atom may be joined to form a substituted heteroaryl (e.g., 5 to 12 membered, 5 to 10 membered, 5 to 9 membered, or 5 to 6 membered). In embodiments, $R^{4A}$ and $R^{4B}$ substituents bonded to the same nitrogen atom may be joined to form an unsubstituted heteroaryl (e.g., 5 to 12 membered, 5 to 10 membered, 5 to 9 membered, or 5 to 6 membered).

In embodiments, $R^{4C}$ is independently hydrogen. In embodiments, $R^{4C}$ is independently —$CX^{4C}_3$. In embodiments, $R^{4C}$ is independently —$CHX^{4C}_2$. In embodiments, $R^{4C}$ is independently —$CH_2X^{4C}$. In embodiments, $R^{4C}$ is independently —CN. In embodiments, $R^{4C}$ is independently —COOH. In embodiments, $R^{4C}$ is independently —$CONH_2$. In embodiments, $X^4C$ is independently —F, —Cl, —Br, or —I.

In embodiments, $R^{4C}$ is independently substituted or unsubstituted alkyl (e.g., $C_1$-$C_8$, $C_1$-$C_6$, $C_1$-$C_4$, or $C_1$-$C_2$). In embodiments, $R^{4C}$ is independently substituted alkyl (e.g., $C_1$-$C_8$, $C_1$-$C_6$, $C_1$-$C_4$, or $C_1$-$C_2$). In embodiments, $R^{4C}$ is independently unsubstituted alkyl (e.g., $C_1$-$C_8$, $C_1$-$C_6$, $C_1$-$C_4$, or $C_1$-$C_2$). In embodiments, $R^{4C}$ is independently unsubstituted methyl. In embodiments, $R^{4C}$ is independently unsubstituted ethyl. In embodiments, $R^{4C}$ is independently unsubstituted propyl. In embodiments, $R^{4C}$ is independently unsubstituted isopropyl. In embodiments, $R^{4C}$ is independently unsubstituted tert-butyl. In embodiments, $R^{4C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4C}$ is independently substituted heteroalkyl (e.g., 2 to 8 membered, 2 to 6 membered, 4 to 6 membered, 2 to 3 membered, or 4 to 5 membered). In embodiments, $R^{4C}$ is independently unsubstituted heteroalkyl (e.g., 2 to 8 membered, 2 to 6 membered, 4 to 6 membered, 2 to 3 membered, or 4 to 5 membered). In embodiments, $R^{4C}$ is independently substituted or unsubstituted cycloalkyl (e.g., $C_3$-$C_8$, $C_3$-$C_6$, $C_4$-$C_6$, or $C_5$-$C_6$). In embodiments, $R^{4C}$ is independently substituted cycloalkyl (e.g., $C_3$-$C_8$, $C_3$-$C_6$, $C_4$-$C_6$, or $C_5$-$C_6$). In embodiments, $R^{4C}$ is independently unsubstituted cycloalkyl (e.g., $C_3$-$C_8$, $C_3$-$C_6$, $C_4$-$C_6$, or $C_5$-$C_6$). In embodiments, $R^{4C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4C}$ is independently substituted heterocycloalkyl (e.g., 3 to 8 membered, 3 to 6 membered, 4 to 6 membered, 4 to 5 membered, or 5 to 6 membered). In embodiments, $R^{4C}$ is independently unsubstituted heterocycloalkyl (e.g., 3 to 8 membered, 3 to 6 membered, 4 to 6 membered, 4 to 5 membered, or 5 to 6 membered). In embodiments, $R^{4C}$ is independently substituted or unsubstituted aryl (e.g., $C_6$-$C_{12}$, $C_6$-$C_{10}$, or phenyl). In embodiments, $R^{4C}$ is independently substituted aryl (e.g., $C_6$-$C_{12}$, $C_6$-$C_{10}$, or phenyl). In embodiments, $R^{4C}$ is independently unsubstituted aryl (e.g., $C_6$-$C_{12}$, $C_6$-$C_{10}$, or phenyl). In embodiments, $R^{4C}$ is independently substituted or unsubstituted heteroaryl (e.g., 5 to 12 membered, 5 to 10 membered, 5 to 9 membered, or 5 to 6 membered). In embodiments, $R^{4C}$ is independently substituted heteroaryl (e.g., 5 to 12 membered, 5 to 10 membered, 5 to 9 membered, or 5 to 6 membered). In embodiments, $R^{4C}$ is independently unsubstituted heteroaryl (e.g., 5 to 12 membered, 5 to 10 membered, 5 to 9 membered, or 5 to 6 membered).

In embodiments, $R^{4D}$ is independently hydrogen. In embodiments, $R^{4D}$ is independently —$CX^{4D}_3$. In embodiments, $R^{4D}$ is independently —$CHX^{4D}_2$. In embodiments, $R^{4D}$ is independently —$CH_2X^{4D}$. In embodiments, $R^{4D}$ is independently —CN. In embodiments, $R^{4D}$ is independently —COOH. In embodiments, $R^{4D}$ is independently —$CONH_2$. In embodiments, $X^{4D}$ is independently —F, —Cl, —Br, or —I.

In embodiments, $R^{4D}$ is independently substituted or unsubstituted alkyl (e.g., $C_1$-$C_8$, $C_1$-$C_6$, $C_1$-$C_4$, or $C_1$-$C_2$). In embodiments, $R^{4D}$ is independently substituted alkyl (e.g., $C_1$-$C_8$, $C_1$-$C_6$, $C_1$-$C_4$, or $C_1$-$C_2$). In embodiments, $R^{4D}$ is independently unsubstituted alkyl (e.g., $C_1$-$C_8$, $C_1$-$C_6$, $C_1$-$C_4$, or $C_1$-$C_2$). In embodiments, $R^{4D}$ is independently unsubstituted methyl. In embodiments, $R^{4D}$ is independently unsubstituted ethyl. In embodiments, $R^{4D}$ is independently unsubstituted propyl. In embodiments, $R^{4D}$ is independently unsubstituted isopropyl. In embodiments, $R^{4D}$ is independently unsubstituted tert-butyl. In embodiments, $R^{4D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4D}$ is independently substituted heteroalkyl (e.g., 2 to 8 membered, 2 to 6 membered, 4 to 6 membered, 2 to 3 membered, or 4 to 5 membered). In embodiments, $R^{4D}$ is independently unsubstituted heteroalkyl (e.g., 2 to 8 membered, 2 to 6 membered, 4 to 6 membered, 2 to 3 membered, or 4 to 5 membered). In embodiments, $R^{4D}$ is independently substituted or unsubstituted cycloalkyl (e.g., $C_3$-$C_8$, $C_3$-$C_6$, $C_4$-$C_6$, or $C_5$-$C_6$). In embodiments, $R^{4D}$ is independently substituted cycloalkyl (e.g., $C_3$-$C_8$, $C_3$-$C_6$, $C_4$-$C_6$, or $C_5$-$C_6$). In embodiments, $R^{4D}$ is independently unsubstituted cycloalkyl (e.g., $C_3$-$C_8$, $C_3$-$C_6$, $C_4$-$C_6$, or $C_5$-$C_6$). In embodiments, $R^{4D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4D}$ is independently substituted heterocycloalkyl (e.g., 3 to 8 membered, 3 to 6 membered, 4 to 6 membered, 4 to 5 membered, or 5 to 6 membered). In embodiments, $R^{4D}$ is independently unsubstituted heterocycloalkyl (e.g., 3 to 8 membered, 3 to 6 membered, 4 to 6 membered, 4 to 5 membered, or 5 to 6 membered). In embodiments, $R^{4D}$ is independently substituted or unsubstituted aryl (e.g., $C_6$-$C_{12}$, $C_6$-$C_{10}$, or phenyl). In embodiments, $R^{4D}$ is independently substituted aryl (e.g., $C_6$-$C_{12}$, $C_6$-$C_{10}$, or phenyl). In embodiments, $R^{4D}$ is independently unsubstituted aryl (e.g., $C_6$-$C_{12}$, $C_6$-$C_{10}$, or phenyl). In embodiments, $R^{4D}$ is independently substituted or unsubstituted heteroaryl (e.g., 5 to 12 membered, 5 to 10 membered, 5 to 9 membered, or 5 to 6 membered). In embodiments, $R^{4D}$ is independently substituted heteroaryl (e.g., 5 to 12 membered, 5 to 10 membered, 5 to 9 membered, or 5 to 6 membered). In embodiments, $R^{4D}$ is independently unsubstituted heteroaryl (e.g., 5 to 12 membered, 5 to 10 membered, 5 to 9 membered, or 5 to 6 membered).

In embodiments, $R^4$ is hydrogen, —$C(O)OCH_3$, —$C(O)OH$, —$C(O)NHCH_3$, unsubstituted 2-oxazolyl, or unsubstituted tetrazolyl.

In embodiments, $R^4$ is hydrogen. In embodiments, $R^4$ is —$C(O)OCH_3$. In embodiments, $R^4$ is —$C(O)OH$. In embodiments, $R^4$ is —$C(O)NHCH_3$. In embodiments, $R^4$ is unsubstituted tetrazolyl. In embodiments, $R^4$ is unsubstituted 2-oxazolyl.

In embodiments, $R^4$ is hydrogen, halogen, —$CX^1_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, 2 to 3 membered, or 4 to 5 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 8 membered, 3 to 6 membered, 4 to 6 membered, 4 to 5 membered, or 5 to 6 membered), $R^{40}$-substituted or unsubstituted aryl (e.g., $C_6$-$C_{12}$, $C_6$-$C_{10}$, or phenyl), or $R^{40}$-substituted or unsubstituted heteroaryl (e.g., 5 to 12, 5 to 10 membered, 5 to 9 membered, or 5 to 6 membered). In embodiments, $R^4$ is hydrogen, halogen, —$CX^1_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12, 5 to 10 membered, 5 to 9 membered, or 5 to 6 membered). $X^4$ is independently —F, —Cl, —Br, or —I.

$R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=$(O)NHNH_2$, —$NHC$=$(O)NH_2$, —$NHSO_2H$, —$NHC$=$(O)H$, —$NHC(O)$—$OH$, —NHOH, —$OR^{41}$, —$NHR^{41}$, —$N(CH_3)R^{41}$, —$COOR^{41}$, —$CONHR^{41}$, —$SR^{41}$, —$SO_2NHR^{41}$, —$NHSO_2R^{41}$, $SO_2R^{41}$, $R^{41}$-substituted or unsubstituted alkyl (e.g., $C_1$-$C_8$, $C_1$-$C_6$, $C_1$-$C_4$, or $C_1$-$C_2$), $R^{41}$-substituted or unsubstituted heteroalkyl (e.g., 2 to 8 membered, 2 to 6 membered, 4 to 6 membered, 2 to 3 membered, or 4 to 5 membered), $R^{41}$-substituted or unsubstituted cycloalkyl (e.g., $C_3$-$C_8$, $C_3$-$C_6$, $C_4$-$C_6$, or $C_5$-$C_6$), $R^{41}$-substituted or unsubstituted heterocycloalkyl (e.g., 3 to 8 membered, 3 to 6 membered, 4 to 6 membered, 4 to 5 membered, or 5 to 6 membered), $R^{41}$-substituted or unsubstituted aryl (e.g., $C_6$-$C_{12}$, $C_6$-$C_{10}$, or phenyl), or $R^{41}$-substituted or unsubstituted heteroaryl (e.g., 5 to 12 membered, 5 to 10 membered, 5 to 9 membered, or 5 to 6 membered). In embodiments, $R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{41}$, —$NHR^{41}$, —N($CH_3$)$R^{41}$, —$COOR^{41}$, —$CONHR^{41}$, —$SR^{41}$, $SO_2NHR^{41}$, $SO_2R^{41}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{40}$ is independently —F, —Cl, —Br, or —I. In embodiments, $R^{40}$ is independently phenyl.

$R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OR^{42}$, —$NHR^{42}$, —N($CH_3$)$R^{42}$, —$COOR^{42}$, —$CONHR^{42}$, —$SR^{42}$, $SO_2NHR^{42}$, $SO_2R^{42}$, $R^{42}$-substituted or unsubstituted alkyl, $R^{42}$-substituted or unsubstituted heteroalkyl (e.g., $C_1$-$C_8$, $C_1$-$C_6$, $C_1$-$C_4$, or $C_1$-$C_2$), $R^{42}$-substituted or unsubstituted (e.g., $C_3$-$C_8$, $C_3$-$C_6$, $C_4$-$C_6$, or $C_5$-$C_6$), $R^{42}$-substituted or unsubstituted heterocycloalkyl (e.g., 3 to 8 membered, 3 to 6 membered, 4 to 6 membered, 4 to 5 membered, or 5 to 6 membered), $R^{42}$-substituted or unsubstituted aryl (e.g., $C_6$-$C_{12}$, $C_6$-$C_{10}$, or phenyl), or $R^{42}$-substituted or unsubstituted heteroaryl (e.g., 5 to 12 membered, 5 to 10 membered, 5 to 9 membered, or 5 to 6 membered). In embodiments, $R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{42}$, —$NHR^{42}$, —N($CH_3$)$R^{42}$, —$COOR^{42}$, —$CONHR^{42}$, —$SR^{42}$, $SO_2NHR^{42}$, $SO_2R^{42}$, unsubstituted alkyl, unsubstituted heteroalkyl (e.g., $C_1$-$C_8$, $C_1$-$C_6$, $C_1$-$C_4$, or $C_1$-$C_2$), unsubstituted (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{41}$ is independently —F, —Cl, —Br, or —I. In embodiments, $R^{41}$ is independently $R^{42}$-substituted or unsubstituted alkyl, $R^{42}$-substituted or unsubstituted heteroalkyl (e.g., $C_1$-$C_8$, $C_1$-$C_6$, $C_1$-$C_4$, or $C_1$-$C_2$), $R^{42}$-substituted or unsubstituted (e.g., $C_3$-$C_8$, $C_3$-$C_6$, $C_4$-$C_6$, or $C_5$-$C_6$), $R^{42}$-substituted or unsubstituted heterocycloalkyl (e.g., 3 to 8 membered, 3 to 6 membered, 4 to 6 membered, 4 to 5 membered, or 5 to 6 membered), $R^{42}$-substituted or unsubstituted aryl (e.g., $C_6$-$C_{12}$, $C_6$-$C_{10}$, or phenyl), or $R^{42}$-substituted or unsubstituted heteroaryl (e.g., 5 to 12 membered, 5 to 10 membered, 5 to 9 membered, or 5 to 6 membered).

$R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $SO_2CH_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered). $X^{42}$ is independently —F, —Cl, —Br, or —I. In embodiments, $R^{42}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered).

In embodiments of the compound of Formula I wherein Y is O, $W^1$ is —O—, and $W^2$ is —C($R^2$)=, each $R^2$, $R^3$, and $R^4$ is not hydrogen. In embodiments of the compound of Formula I wherein Y is O, $W^1$ is —O—, and $W^2$ is —C($R^2$)=, $R^3$ is not methyl and each $R^2$ and $R^4$ is not hydrogen. In embodiments of the compound of Formula I wherein Y is O, $W^1$ is —O—, and $W^2$ is —C($R^2$)=, each $R^2$ and $R^3$ is not hydrogen and $R^4$ is not methyl. In embodiments of the compound of Formula I wherein Y is O, $W^1$ is —O—, and $W^2$ is —C($R^2$)=, $R^2$ is not hydrogen, $R^3$ is not methyl, and $R^4$ is not hydroxymethyl. In embodiments of the compound of Formula I wherein Y is O, $W^1$ is —O—, and $W^2$ is —C($R^2$)=, $R^2$ is not —COOH, $R^3$ is not methyl, and $R^4$ is not hydrogen. In embodiments of the compound of Formula I wherein Y is O, $W^1$ is —O—, and $W^2$ is —C($R^2$)=, each $R^2$ and $R^4$ is not hydrogen and $R^3$ is not hydroxymethyl. In embodiments of the compound of Formula I wherein Y is O, $W^1$ is —O—, and $W^2$ is —C($R^2$)=, $R^2$ is not —C(O)NH (para-F-benzyl), $R^3$ is not methyl, and $R^4$ is not hydrogen. In embodiments of the compound of Formula I wherein Y is =O, $W^1$ is —O—, and $W^2$ is —C($R^2$)=, each $R^2$ is not —C(O)NH(ortho-F-benzyl), $R^3$ is not methyl, and $R^4$ is not hydrogen. In embodiments of the compound of Formula I wherein Y is =O, $W^1$ is —O—, and $W^2$ is —C($R^2$)=, each $R^2$ is not —C(O)NH(ortho-F-benzyl), $R^3$ is not methyl, and $R^4$ is not hydrogen. In embodiments of the compound of Formula I wherein Y is =O, $W^1$ is —O—, and $W^2$ is —C($R^2$)=, each $R^2$ is not —C(O)NH(para-F-benzyl), $R^3$ is not methyl, and $R^4$ is not hydrogen. In embodiments of the compound of Formula I wherein Y is =O, $W^1$ is —O—, and $W^2$ is —C($R^2$)=, each $R^2$ is not —C(O)NH(para-F-benzyl), $R^3$ is not methyl, and $R^4$ is not hydrogen.

In embodiments, the compound has the formula:

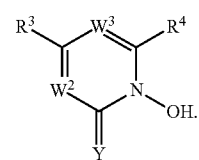

(II)

Y, $W^2$, $R^3$, and $R^4$ are as described herein.

In embodiments, W³ is —C(R¹)═. R¹ is as described herein.

In embodiments, W³ is —N═.

In embodiments of the compound of Formula II wherein Y is O, W² is —C(R²)═, and W³ is —C(R¹)═, each R¹, R², R³, and R⁴ is not hydrogen. In embodiments of the compound of Formula II wherein Y is O, W² is —C(R²)═, and W³ is —C(R¹)═, each R¹, R², and R³ is not hydrogen, and R⁴ is not —COOH. In embodiments of the compound of Formula II wherein Y is S, W² is —C(R²)═, and W³ is —C(R¹)═, each R¹, R², R³, and R⁴ is not hydrogen.

In embodiments, the compound has the formula:

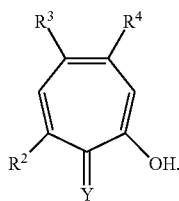

Y, R², R³, and R⁴ are as described herein.

In embodiments, Y is S. In embodiments, Y is O.

In embodiments, R² is hydrogen, —OR²ᴰ, —C(O)R²ᶜ, —C(O)OR²ᶜ, or —C(O)NR²ᴬR²ᴮ. R²ᴬ, R²ᴮ, R²ᶜ, and R²ᴰ are as described herein. In embodiments, R² is hydrogen. In embodiments, R² is —C(O)OR²c or —C(O)NR²ᴬR²ᴮ. In embodiments, R² is —OR²ᴰ. R²ᴬ, R²ᴮ, and R²ᶜ are as described herein. In embodiments, R² is —OCH₃. In embodiments, R² is —OH.

In embodiments, R³ is hydrogen, —C(O)OR³ᶜ, —C(O)NR³ᴬR³ᴮ, —OR³ᴰ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R³ is hydrogen, —C(O)OR³ᶜ, —C(O)NR³ᴬR³ᴮ, —OR³ᴰ, substituted or unsubstituted alkyl (e.g., C₁-C₈, C₁-C₆, C₁-C₄, or C₁-C₂), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C₃-C₈, C₃-C₆, C₄-C₆, or C₅-C₆), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C₆-C₁₂, C₆-C₁₀, or phenyl), or substituted or unsubstituted heteroaryl (e.g., 5 to 12, 5 to 10 membered, 5 to 9 membered, or 5 to 6 membered).

In embodiments, R³ is hydrogen, —C(O)OH, —C(O)NH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R³ is hydrogen, —C(O)OH, —C(O)NH₂, substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₂ aryl, or substituted or unsubstituted 5 to 12 membered heteroaryl.

In embodiments, R³ is hydrogen, —C(O)OH, —C(O)NH₂, substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₂ aryl, or substituted or unsubstituted 5 to 6 membered heteroaryl.

In embodiments, R³ is hydrogen, —C(O)OH, —C(O)NH₂, R³⁰-substituted or unsubstituted alkyl, or R³⁰-substituted or unsubstituted aryl.

In embodiments, R³ is R³⁰-substituted or unsubstituted alkyl or R³⁰-substituted or unsubstituted aryl.

In embodiments, R³ is R³⁰-substituted or unsubstituted alkyl (e.g., C₁-C₈, C₁-C₆, C₁-C₄, or C₁-C₂) or R³⁰-substituted or unsubstituted aryl (e.g., C₆-C₁₂, C₆-C₁₀, or phenyl).

In embodiments, R³ is unsubstituted alkyl (e.g., C₁-C₈, C₁-C₆, C₁-C₄, or C₁-C₂) or unsubstituted aryl (e.g., C₆-C₁₂, C₆-C₁₀, or phenyl).

In embodiments, R³ is independently R³⁰-substituted or unsubstituted methyl or R³⁰-substituted or unsubstituted phenyl. In embodiments, R³ is independently unsubstituted methyl or unsubstituted phenyl.

In embodiments, R³ is independently R³⁰-substituted methyl. In embodiments, R³ is independently R³⁰-substituted phenyl.

R³⁰ is as described herein.

In embodiments, R³ is hydrogen, —C(O)OH, unsubstituted C₁-C₃ alkyl, or unsubstituted phenyl. In embodiments, R³ is hydrogen. In embodiments, R³ is —C(O)OH. In embodiments, R³ is unsubstituted C₁-C₃ alkyl. In embodiments, R³ is unsubstituted methyl. In embodiments, R³ is unsubstituted phenyl.

In embodiments, R⁴ is hydrogen, —C(O)OR⁴ᶜ, —C(O)NR⁴ᴬR⁴ᴮ, —OR⁴ᴰ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R⁴ is hydrogen, —C(O)OR⁴ᶜ, —C(O)NR⁴ᴬR⁴ᴮ, —OR⁴ᴰ, substituted or unsubstituted alkyl (e.g., C₁-C₈, C₁-C₆, C₁-C₄, or C₁-C₂), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C₃-C₈, C₃-C₆, C₄-C₆, or C₅-C₆), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C₆-C₁₂, C₆-C₁₀, or phenyl), or substituted or unsubstituted heteroaryl (e.g., 5 to 12, 5 to 10 membered, 5 to 9 membered, or 5 to 6 membered).

In embodiments, R⁴ is hydrogen, —C(O)OH, —C(O)NHR⁴ᴬ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R⁴ is hydrogen, —C(O)OH, —C(O)NHR⁴ᴬ, substituted or unsubstituted C₁-C₈ alkyl, substituted or unsubstituted 2 to 8 membered heteroalkyl, substituted or unsubstituted C₃-C₅ cycloalkyl, substituted or unsubstituted 3 to 8 membered heterocycloalkyl, substituted or unsubstituted C₆-C₁₂ aryl, or substituted or unsubstituted 5 to 12 membered heteroaryl.

R⁴ᴬ, R⁴ᴮ, R⁴ᶜ, and R⁴ᴰ are as described herein.

In embodiments, R⁴ is hydrogen, —C(O)OH, —C(O)NH₂, R⁴⁰-substituted or unsubstituted alkyl or R⁴⁰-substituted or unsubstituted aryl.

In embodiments, R⁴ is R⁴⁰-substituted or unsubstituted alkyl or R⁴⁰-substituted or unsubstituted aryl.

In embodiments, R⁴ is R⁴⁰-substituted or unsubstituted alkyl (e.g., C₁-C₈, C₁-C₆, C₁-C₄, or C₁-C₂) or R⁴⁰-substituted or unsubstituted aryl (e.g., $C_6$-$C_{12}$, $C_6$-$C_{10}$, or phenyl). In embodiments, $R^4$ is unsubstituted alkyl (e.g., $C_1$-$C_8$, $C_1$-$C_6$, $C_1$-$C_4$, or $C_1$-$C_2$) or unsubstituted aryl (e.g., $C_6$-$C_{12}$, $C_6$-$C_{10}$, or phenyl).

In embodiments, $R^4$ is independently $R^{40}$-substituted or unsubstituted methyl or $R^{40}$-substituted or unsubstituted phenyl. In embodiments, $R^4$ is independently unsubstituted methyl or unsubstituted phenyl.

In embodiments, $R^4$ is independently $R^{40}$-substituted methyl. In embodiments, $R^4$ is independently $R^{40}$-substituted phenyl.

$R^{40}$ is as described herein.

In embodiments, $R^4$ is hydrogen, —C(O)OH, unsubstituted $C_1$-$C_3$ alkyl, or unsubstituted phenyl. In embodiments, $R^4$ is hydrogen. In embodiments, $R^4$ is —C(O)OH. In embodiments, $R^4$ is unsubstituted $C_1$-$C_3$ alkyl. In embodiments, $R^4$ is unsubstituted methyl. In embodiments, $R^4$ is unsubstituted phenyl.

In embodiments, $R^4$ is —C(O)NHR$^{4A}$.

In embodiments, $R^{4A}$ is independently $R^{40A}$-substituted or unsubstituted methyl or $R^{40A}$-substituted or unsubstituted phenyl. In embodiments, $R^{4A}$ is independently unsubstituted methyl or unsubstituted phenyl.

In embodiments, $R^{4A}$ is independently $R^{40A}$-substituted methyl. In embodiments, $R^{4A}$ is independently $R^{40A}$-substituted phenyl.

$R^{40A}$ is independently oxo, halogen, —CX$^{40A}_3$, —CHX$^{40A}_2$, —CH$_2$X$^{40A}$, —OCX$^{40A}_3$, —OCH$_2$X$^{40A}$, —OCHX$^{40A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OR$^{41A}$, —NHR$^{41A}$, —N(CH$_3$)R$^{41A}$, —COOR$^{41A}$, —CONHR$^{41A}$, —SR$^{41A}$, SO$_2$NHR$^{41A}$SO$_2$R$^{41A}$, R$^{41A}$-substituted or unsubstituted alkyl (e.g., $C_1$-$C_8$, $C_1$-$C_6$, $C_1$-$C_4$, or $C_1$-$C_2$), R$^{41A}$-substituted or unsubstituted heteroalkyl (e.g., 2 to 8 membered, 2 to 6 membered, 4 to 6 membered, 2 to 3 membered, or 4 to 5 membered), R$^{41A}$-substituted or unsubstituted cycloalkyl (e.g., $C_3$-$C_8$, $C_3$-$C_6$, $C_4$-$C_6$, or $C_5$-$C_6$), R$^{41A}$-substituted or unsubstituted heterocycloalkyl (e.g., 3 to 8 membered, 3 to 6 membered, 4 to 6 membered, 4 to 5 membered, or 5 to 6 membered), R$^{41A}$-substituted or unsubstituted aryl (e.g., $C_6$-$C_{12}$, $C_6$-$C_{10}$, or phenyl), or R$^{41A}$-substituted or unsubstituted heteroaryl (e.g., 5 to 12 membered, 5 to 10 membered, 5 to 9 membered, or 5 to 6 membered). In embodiments, $R^{40A}$ is independently oxo, halogen, —CX$^{40A}_3$, —CHX$^{40A}_2$, —CH$_2$X$^{40A}$, —OCX$^{40A}_3$, —OCH$_2$X$^{40A}$, —OCHX$^{40A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OR$^{41A}$, —NHR$^{41A}$, —N(CH$_3$)R$^{41A}$, —COOR$^{41A}$, —CONHR$^{41A}$, —SR$^{41A}$, SO$_2$NHR$^{41A}$, SO$_2$R$^{41A}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). X$^{40A}$ is independently —F, —Cl, —Br, or —I. In embodiments, $R^{40A}$ is independently phenyl.

$R^{41A}$ is independently oxo, halogen, —CX$^{41A}_3$, —CHX$^{41A}_2$, —CH$_2$X$^{41A}$, —OCX$^{41A}_3$, —OCH$_2$X$^{41A}$, —OCHX$^{41A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OR$^{42A}$, —NHR$^{42A}$, —N(CH$_3$)R$^{42A}$, —COOR$^{42A}$, —CONHR$^{42A}$, —SR$^{42A}$, SO$_2$NHR$^{42A}$, SO$_2$R$^{42A}$, R$^{42A}$-substituted or unsubstituted alkyl, R$^{42A}$-substituted or unsubstituted heteroalkyl (e.g., $C_1$-$C_8$, $C_1$-$C_6$, $C_1$-$C_4$, or $C_1$-$C_2$), R$^{42A}$-substituted or unsubstituted (e.g., $C_3$-$C_8$, $C_3$-$C_6$, $C_4$-$C_6$, or $C_5$-$C_6$), R$^{42A}$-substituted or unsubstituted heterocycloalkyl (e.g., 3 to 8 membered, 3 to 6 membered, 4 to 6 membered, 4 to 5 membered, or 5 to 6 membered), R$^{42A}$-substituted or unsubstituted aryl (e.g., $C_6$-$C_{12}$, $C_6$-$C_{10}$, or phenyl), or R$^{42A}$-substituted or unsubstituted heteroaryl (e.g., 5 to 12 membered, 5 to 10 membered, 5 to 9 membered, or 5 to 6 membered). In embodiments, $R^{41A}$ is independently oxo, halogen, —CX$^{41A}_3$, —CHX$^{41A}_2$, —CH$_2$X$^{41A}$, —OCX$^{41A}_3$, —OCH$_2$X$^{41A}$, —OCHX$^{41A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OR$^{42A}$, —NHR$^{42A}$, —N(CH$_3$)R$^{42A}$, —COOR$^{42A}$, —CONHR$^{42A}$, —SR$^{42A}$, SO$_2$NHR$^{42A}$, SO$_2$R$^{42A}$, unsubstituted alkyl, unsubstituted heteroalkyl (e.g., $C_1$-$C_8$, $C_1$-$C_6$, $C_1$-$C_4$, or $C_1$-$C_2$), unsubstituted (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). X$^{41A}$ is independently —F, —Cl, —Br, or —I. In embodiments, $R^{41A}$ is independently R$^{42A}$-substituted or unsubstituted alkyl, R$^{42A}$-substituted or unsubstituted heteroalkyl (e.g., $C_1$-$C_8$, $C_1$-$C_6$, $C_1$-$C_4$, or $C_1$-$C_2$), R$^{42A}$-substituted or unsubstituted (e.g., $C_3$-$C_8$, $C_3$-$C_6$, $C_4$-$C_6$, or $C_5$-$C_6$), R$^{42A}$-substituted or unsubstituted heterocycloalkyl (e.g., 3 to 8 membered, 3 to 6 membered, 4 to 6 membered, 4 to 5 membered, or 5 to 6 membered), R$^{42A}$-substituted or unsubstituted aryl (e.g., $C_6$-$C_{12}$, $C_6$-$C_{10}$, or phenyl), or R$^{42A}$-substituted or unsubstituted heteroaryl (e.g., 5 to 12 membered, 5 to 10 membered, 5 to 9 membered, or 5 to 6 membered).

$R^{42A}$ is independently oxo, halogen, —CX$^{42A}_3$, —CHX$^{42A}_2$, —CH$_2$X$^{42A}$, —OCX$^{42A}_3$, —OCH$_2$X$^{42A}$, —OCHX$^{42A}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, SO$_2$CH$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered). X$^{42A}$ is independently —F, —Cl, —Br, or —I. In embodiments, $R^{42A}$ is independently unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl, or unsubstituted heteroaryl (e.g., 5 to 12 membered, 5 to 10 membered, 5 to 9 membered, or 5 to 6 membered).

In embodiments, $R^{4A}$ is hydrogen, unsubstituted $C_1$-$C_3$ alkyl, or unsubstituted phenyl. In embodiments, $R^{4A}$ is hydrogen. In embodiments, $R^{4A}$ is unsubstituted $C_1$-$C_3$ alkyl. In embodiments, $R^{4A}$ is unsubstituted methyl. In embodiments, $R^{4A}$ is unsubstituted phenyl.

In embodiments of the compound of Formula III wherein Y is O, each $R^2$, $R^3$, and $R^4$ is not hydrogen. In embodiments of the compound of Formula III wherein Y is O, each $R^2$ and $R^3$ is not hydrogen, and $R^4$ is not isopropyl.

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, figure, table, scheme, or claim).

In embodiments, unless otherwise indicated, a compound described herein is a tautomer mixture of all structural isomers.

In embodiments, the compound is a tautomer mixture of Formula I and IV:

(I) ↔ (IV)

Y, $W^1$, $W^2$, $R^3$, and $R^4$ are as described herein. In embodiments, the compound of Formula I and IV exists in equilibrium. In embodiments, the compound of Formula I is readily converted to the compound of formula IV. In embodiments, the compound of Formula IV is readily converted to the compound of formula I. In embodiments, the tautomer mixture includes a substantial amount of the compound of Formula I. In embodiments, the tautomer mixture includes a substantial amount of the compound of Formula IV. In embodiments, the compound is a tautomer mixture of Formula I and IV:

(IAA) ↔ (IVAA)

In embodiments, the compound is a tautomer mixture of Formula I and IV:

(IBB) ↔ (IVBB)

In an aspect is provided a compound having the formula

Y, $W^2$, $W^3$, $R^3$, $R^4$ are as described herein.

In an aspect is provided a compound having the formula:

Y, $R^2$, $R^3$, $R^4$ are as described herein.

In an aspect is provided a compound having the formula

Y, $W^2$, $R^3$, $W^3$, $R^4$ are as described herein.

In an aspect is provided a compound having the formula:

Y, $R^2$, $R^3$, $R^4$ are as described herein.

In embodiments, the compound (e.g., compound described herein) contacts one or two divalent metal cations (e.g., $Mn^{2+}$ or $Mg^{2+}$) in influenza virus (e.g., influenza virus type A) RNA-dependent RNA polymerase PA subunit endonuclease, and/or one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts one or two divalent metal cations (e.g., $Mn^{2+}$ or $Mg^{2+}$) in influenza virus (e.g., influenza virus type A) RNA-dependent RNA polymerase PA subunit endonuclease and one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts one or two divalent $Mn^{2+}$ cations in influenza virus (e.g., influenza virus type A) RNA-dependent RNA polymerase PA subunit endonuclease, and/or one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts one or two divalent $Mn^{2+}$ cations in influenza virus (e.g., influenza virus type A) RNA-dependent RNA polymerase PA subunit endonuclease and one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease, and/or one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease and one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts one or two divalent metal cations (e.g., $Mn^{2+}$ or $Mg^{2+}$) in influenza virus (e.g., influenza virus type A) RNA-dependent RNA polymerase PA subunit endonuclease. In embodiments, the compound (e.g., compound described herein) contacts two divalent metal cations (e.g., $Mn^{2+}$ or $Mg^{2+}$) in influenza virus (e.g., influenza virus type A) RNA-dependent RNA polymerase PA subunit endonuclease. In embodiments, the compound (e.g., compound described herein) contacts one or two divalent $Mn^{2+}$ cations in influenza virus (e.g., influenza virus type A) RNA-dependent RNA polymerase PA subunit endonuclease. In embodiments, the compound (e.g., compound described herein) contacts one divalent $Mn^{2+}$ cation in influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease. In embodiments, the compound (e.g., compound described herein) contacts one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts one or more amino acids corresponding to Arg82, Lys34, Arg124, and Lys24 of influenza virus (e.g., influenza virus type A) RNA-dependent RNA polymerase PA subunit endonuclease. In embodiments, the compound (e.g., compound described herein) contacts one or two divalent $Mn^{2+}$ cations in influenza virus (e.g., influenza virus type A) RNA-dependent RNA polymerase PA subunit endonuclease and an amino acid corresponding to Arg82, Lys34, Arg124, Lys24, and Tyr24 of influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease and an amino acid corresponding to Arg82, Lys34, Arg124, Lys24, and Tyr24 of influenza virus (e.g., influenza virus type A) RNA-dependent RNA polymerase PA subunit endonuclease. In embodiments, In embodiments, the compound (e.g., compound described herein) contacts an amino acid corresponding to Arg82, Lys34, Arg124, Lys24, and Tyr24 of influenza virus (e.g., influenza virus type A) RNA-dependent RNA polymerase PA subunit endonuclease. In embodiments, In embodiments, the compound (e.g., compound described herein) contacts an amino acid corresponding to Arg82, Lys34, Arg124, and Lys24 of influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease and an amino acid corresponding to Arg82 of influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease and an amino acid corresponding to Lys34 of influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease and an amino acid corresponding to Lys24 of influenza virus (e.g., influenza virus type A) RNA-dependent RNA polymerase PA subunit endonuclease. In embodiments, the compound (e.g., compound described herein) contacts two divalent $Mn^{2+}$ cations in influenza virus (e.g., influenza virus type A) RNA-dependent RNA polymerase PA subunit endonuclease and an amino acid corresponding to Tyr24 of influenza virus (e.g., influenza virus type A) RNA-dependent RNA polymerase PA subunit endonuclease. In embodiments, the compound (e.g., compound described herein) contacts one divalent $Mn^{2+}$ cation in influenza virus (e.g., influenza virus type A) RNA-dependent RNA polymerase PA subunit endonuclease and an amino acid corresponding to Arg82 of influenza virus (e.g., influenza virus type A) RNA-dependent RNA polymerase PA subunit endonuclease. In embodiments, the compound (e.g., compound described herein) contacts one divalent $Mn^{2+}$ cation in influenza virus (e.g., influenza virus type A) RNA-dependent RNA polymerase PA subunit endonuclease and an amino acid corresponding to Lys34 of influenza virus (e.g., influenza virus type A) RNA-dependent RNA polymerase PA subunit endonuclease. In embodiments, the compound (e.g., compound described herein) contacts one divalent $Mn^{2+}$ cation in influenza virus (e.g., influenza virus type A) RNA-dependent RNA polymerase PA subunit endonuclease and an amino acid corresponding to Lys24, of influenza virus (e.g., influenza virus type A) RNA-dependent RNA polymerase PA subunit endonuclease. In embodiments, the compound (e.g., compound described herein) contacts one divalent $Mn^{2+}$ cation in influenza virus (e.g., influenza virus type A) RNA-dependent RNA polymerase PA subunit endonuclease and an amino acid corresponding to Tyr24 of influenza virus (e.g., influenza virus type A) RNA-dependent RNA polymerase PA subunit endonuclease. In embodiments, the compound (e.g., compound described herein) contacts an amino acid corresponding to Arg82 of influenza virus (e.g., influenza virus type A) RNA-dependent RNA polymerase PA subunit endonuclease. In embodiments, the compound (e.g., compound described herein) contacts an amino acid corresponding to Lys34 of influenza virus (e.g., influenza virus type A) RNA-dependent RNA polymerase PA subunit endonuclease. In embodiments, the compound (e.g., compound described herein) contacts an amino acids corresponding to Arg124 influenza virus (e.g., influenza virus type A) RNA-dependent RNA polymerase PA subunit endonuclease. In embodiments, the compound (e.g., compound described herein) contacts an amino acids corresponding to Tyr24 of influenza virus (e.g., influenza virus type A) RNA-dependent RNA polymerase PA subunit endonuclease. In embodiments, the compound (e.g., compound described herein) chelates to the two divalent $Mn^{2+}$ cations in influenza virus (e.g., influenza virus type A) RNA-dependent RNA polymerase PA subunit endonuclease.

In embodiments, the compound has the formula:

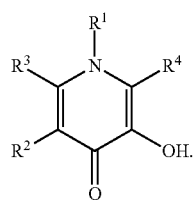

$R^1$, $R^3$, and $R^4$ are as described herein. In embodiments, the compound has the formula:

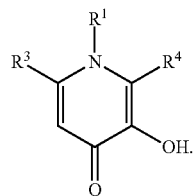

$R^1$, $R^3$, and $R^4$ are as described herein. In embodiments, the compound has the formula:

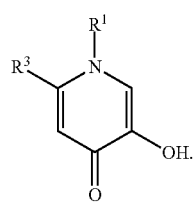

$R^1$ and $R^3$ are as described herein. In embodiments, the compound has the formula:

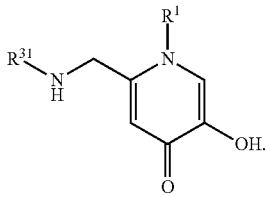

$R^1$ and $R^{31}$ are as described herein. In embodiments, the compound has the formula:

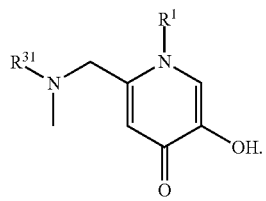

$R^1$ and $R^{31}$ are as described herein. In embodiments, the compound has the formula:

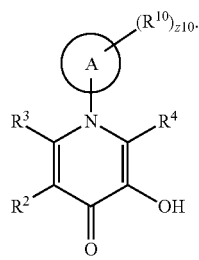

$R^{10}$, $R^2$, $R^3$, and $R^4$ are as described herein. z10 is an integer from 0 to 5. In embodiments, z10 is 0. In embodiments, z10 is 1. In embodiments, z10 is 2. In embodiments, z10 is 3. In embodiments, z10 is 4. In embodiments, z10 is 5. Ring A is a cycloalkyl, heterocycloalkyl, aryl, or heteroaryl. In embodiments, Ring A is a cycloalkyl. In embodiments, Ring A is a heterocycloalkyl. In embodiments, Ring A is an aryl. In embodiments, Ring A is cycloalkyl (e.g., $C_3$-$C_8$, $C_3$-$C_6$, $C_4$-$C_6$, or $C_5$-$C_6$), heterocycloalkyl (e.g., 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12, 5 to 10 membered, 5 to 9 membered, or 5 to 6 membered). In embodiments, Ring A is $C_4$-$C_6$ cycloalkyl, 4 to 6 membered heterocycloalkyl, phenyl, or 5 to 6 membered heteroaryl. In embodiments, Ring A is tetrazolyl. In embodiments, Ring A is pyridyl. In embodiments, Ring A is phenyl. In embodiments, Ring A is a heteroaryl.

In embodiments, the compound has the formula:

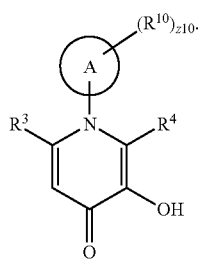

$R^{10}$, z10, Ring A, $R^3$, and $R^4$ are as described herein. In embodiments, the compound has the formula:

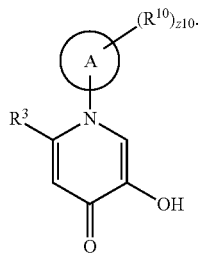

$R^{10}$, z10, Ring A, and $R^3$ are as described herein. In embodiments, the compound has the formula:

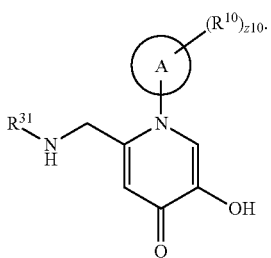

$R^{10}$, z10, Ring A, and $R^{31}$ are as described herein. In embodiments, the compound has the formula:

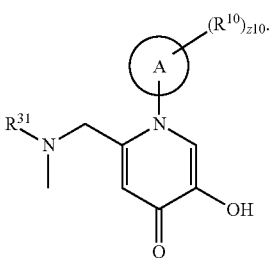

$R^{10}$, z10, Ring A, and $R^{31}$ are as described herein. In embodiments, the compound has the formula:

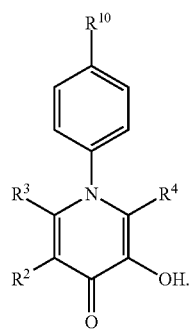

$R^{10}$, $R^2$, $R^3$, and $R^4$ are as described herein. In embodiments, the compound has the formula:

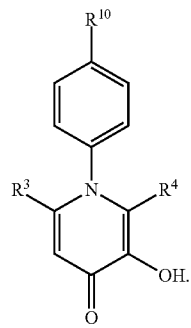

$R^{10}$, $R^3$, and $R^4$ are as described herein. In embodiments, the compound has the formula:

$R^{10}$ and $R^3$ are as described herein. In embodiments, the compound has the formula:

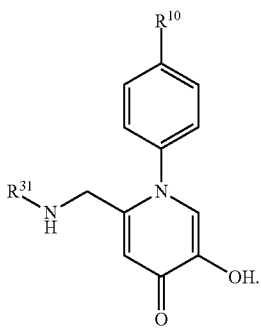

$R^{10}$ and $R^{31}$ are as described herein. In embodiments, the compound has the formula:

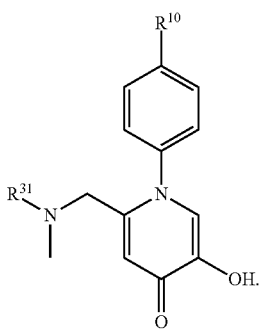

$R^{10}$ and $R^{31}$ are as described herein. In embodiments, the compound has the formula:

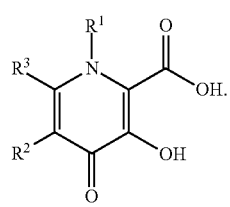

$R^1$, $R^2$, and $R^3$ are as described herein. In embodiments, the compound has the formula:

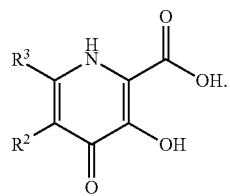

$R^2$ and $R^3$ are as described herein. In embodiments, the compound has the formula:

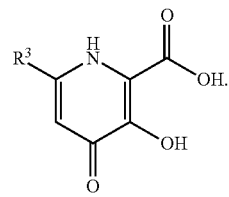

$R^3$ is as described herein. In embodiments, the compound has the formula:

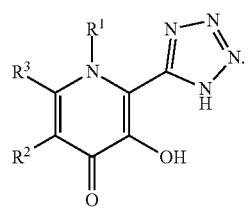

$R^1$, $R^2$, and $R^3$ are as described herein. In embodiments, the compound has the formula:

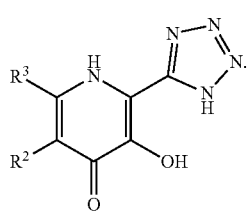

$R^2$ and $R^3$ are as described herein. In embodiments, the compound has the formula:

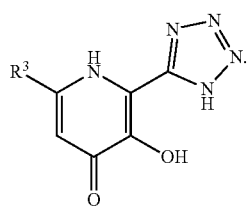

$R^3$ is as described herein. In embodiments, the compound has the formula:

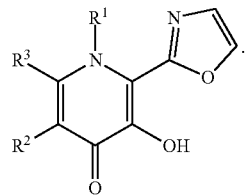

$R^1$, $R^2$, and $R^3$ are as described herein. In embodiments, the compound has the formula:

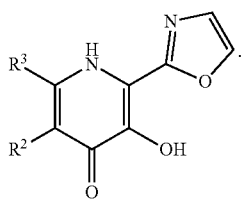

$R^2$ and $R^3$ are as described herein. In embodiments, the compound has the formula:

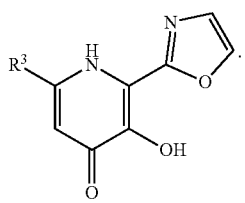

$R^3$ is as described herein.

In embodiments, $R^{10}$ is $R^{11}$-substituted or unsubstituted cycloalkyl (e.g., $C_3$-$C_8$, $C_3$-$C_6$, $C_4$-$C_6$, or $C_5$-$C_6$), $R^{11}$-substituted or unsubstituted heterocycloalkyl (e.g., 3 to 8 membered, 3 to 6 membered, 4 to 6 membered, 4 to 5 membered, or 5 to 6 membered), $R^{11}$-substituted or unsubstituted aryl (e.g., $C_6$-$C_{12}$, $C_6$-$C_{10}$, or phenyl), or $R^{11}$-substituted or unsubstituted heteroaryl (e.g., 5 to 12, 5 to 10 membered, 5 to 9 membered, or 5 to 6 membered). In embodiments, $R^{10}$ is $R^1$-substituted or unsubstituted $C_4$-$C_6$ cycloalkyl, $R^{11}$-substituted or unsubstituted 4 to 6 membered heterocycloalkyl, $R^{11}$-substituted or unsubstituted phenyl, or $R^{11}$-substituted or unsubstituted 5 to 6 membered heteroaryl. In embodiments, $R^{10}$ is $R^{11}$-substituted or unsubstituted tetrazolyl. In embodiments, $R^{10}$ is unsubstituted tetrazolyl. In embodiments, $R^{10}$ is $R^{11}$-substituted or unsubstituted pyridyl. In embodiments, $R^{10}$ is unsubstituted pyridyl. In embodiments, $R^{10}$ is $R^{11}$-substituted or unsubstituted phenyl. In embodiments, $R^{10}$ is unsubstituted phenyl.

In embodiments, $R^3$ is $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 8 membered, 3 to 6 membered, 4 to 6 membered, 4 to 5 membered, or 5 to 6 membered), $R^{30}$-substituted or unsubstituted aryl (e.g., $C_6$-$C_{12}$, $C_6$-$C_{10}$, or phenyl), or $R^{30}$-substituted or unsubstituted heteroaryl (e.g., 5 to 12, 5 to 10 membered, 5 to 9 membered, or 5 to 6 membered). In embodiments, $R^3$ is $R^{30}$-substituted or unsubstituted $C_4$-$C_6$ cycloalkyl, $R^{30}$-substituted or unsubstituted 4 to 6 membered heterocycloalkyl, $R^{30}$-substituted or unsubstituted phenyl, or $R^{30}$-substituted or unsubstituted 5 to 6 membered heteroaryl. In embodiments, $R^3$ is $R^{30}$-substituted or unsubstituted tetrazolyl. In embodiments, $R^3$ is unsubstituted tetrazolyl. In embodiments, $R^3$ is $R^{30}$-substituted or unsubstituted pyridyl. In embodiments, $R^3$ is unsubstituted pyridyl. In embodiments, $R^3$ is $R^{30}$-substituted or unsubstituted phenyl. In embodiments, $R^3$ is unsubstituted phenyl. In embodiments, $R^3$ is independently halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —S H, unsubstituted methyl, unsubstituted ethyl, unsubstituted isopropyl, unsubstituted methoxy, or unsubstituted ethoxy. In embodiments, $R^3$ is independently halogen. In embodiments, $R^3$ is independently —F. In embodiments, $R^3$ is independently —Cl. In embodiments, $R^3$ is independently —Br. In embodiments, $R^3$ is independently —I.

In embodiments, $R^{30}$ is independently halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —S H, unsubstituted methyl, unsubstituted ethyl, unsubstituted isopropyl, unsubstituted methoxy, unsubstituted ethoxy, unsubstituted tetrazolyl, unsubstituted oxazolyl, or unsubstituted 2-oxazolyl. In embodiments, $R^{30}$ is independently halogen. In embodiments, $R^{30}$ is independently —F. In embodiments, $R^{30}$ is independently —Cl. In embodiments, $R^{30}$ is independently —Br. In embodiments, $R^{30}$ is independently —I.

In embodiments, $R^{31}$ is $R^{32}$-substituted or unsubstituted cycloalkyl (e.g., $C_3$-$C_8$, $C_3$-$C_6$, $C_4$-$C_6$, or $C_5$-$C_6$), $R^{32}$-substituted or unsubstituted heterocycloalkyl (e.g., 3 to 8 membered, 3 to 6 membered, 4 to 6 membered, 4 to 5 membered, or 5 to 6 membered), $R^{32}$-substituted or unsubstituted aryl (e.g., $C_6$-$C_{12}$, $C_6$-$C_{10}$, or phenyl), or $R^{32}$-substituted or unsubstituted heteroaryl (e.g., 5 to 12, 5 to 10 membered, 5 to 9 membered, or 5 to 6 membered). In embodiments, $R^{31}$ is $R^{32}$-substituted or unsubstituted $C_4$-$C_6$ cycloalkyl, $R^{32}$-substituted or unsubstituted 4 to 6 membered heterocycloalkyl, $R^{32}$-substituted or unsubstituted phenyl, or $R^{32}$-substituted or unsubstituted 5 to 6 membered heteroaryl. In embodiments, $R^{31}$ is $R^{32}$-substituted or unsubstituted tetrazolyl. In embodiments, $R^{31}$ is unsubstituted tetrazolyl. In embodiments, $R^{31}$ is $R^{32}$-substituted or unsubstituted pyridyl. In embodiments, $R^{31}$ is unsubstituted pyridyl. In embodiments, $R^{31}$ is $R^{32}$-substituted or unsubstituted phenyl. In embodiments, $R^{31}$ is unsubstituted phenyl. In embodiments, $R^{31}$ is independently halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —S H, unsubstituted methyl, unsubstituted ethyl, unsubstituted isopropyl, unsubstituted methoxy, or unsubstituted ethoxy. In embodiments, $R^{31}$ is independently halogen. In embodiments, $R^{31}$ is independently —F. In embodiments, $R^{31}$ is independently —Cl. In embodiments, $R^{31}$ is independently —Br. In embodiments, $R^{31}$ is independently —I.

In embodiments, the compound has the formula:

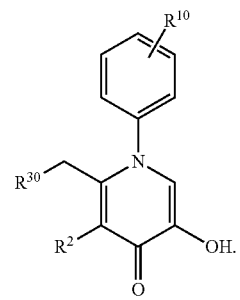

$R^2$, $R^{10}$, and $R^{30}$ are as described herein.
In embodiments, the compound has the formula:

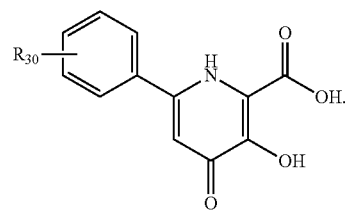

$R^{30}$ is as described herein. In embodiments, the compound has the formula:

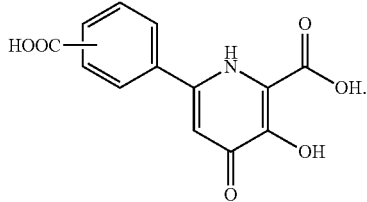

In embodiments, the compound has the formula:

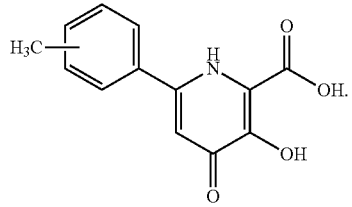

In embodiments, the compound has the formula:

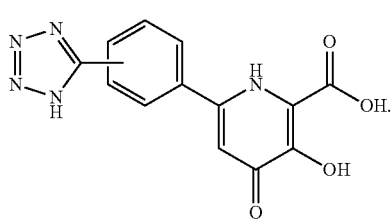

In embodiments, the compound has the formula:

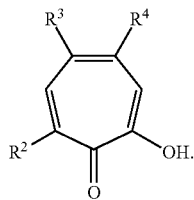

$R^2$, $R^3$, and $R^4$ are as described herein. In embodiments, the compound has the formula:

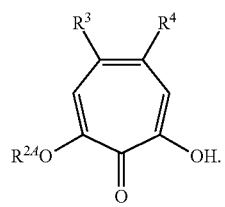

$R^{2A}$, $R^3$, and $R^4$ are as described herein. In embodiments, the compound has the formula:

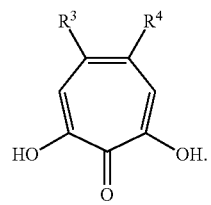

$R^3$ and $R^4$ are as described herein. In embodiments, the compound has the formula:

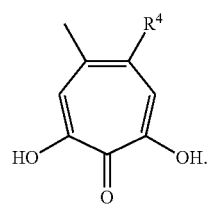

$R^4$ is as described herein. In embodiments, the compound has the formula:

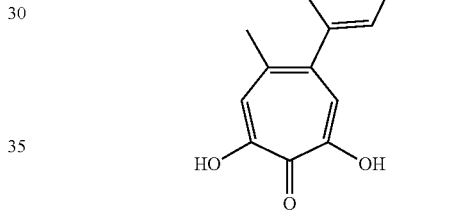

$R^{40}$ is as described herein. z40 is an integer from 0 to 5. In embodiments, z40 is 1. In embodiments, z40 is 2. In embodiments, z40 is 3. In embodiments, z40 is 0. In embodiments, z40 is 4. In embodiments, z40 is 5.

In embodiments, $R^4$ is —C(O)OR$^{4C}$, —C(O)NR$^{4A}$R$^{4B}$, substituted or unsubstituted cycloalkyl, substituted or unsubstituted heterocycloalkyl, substituted or unsubstituted aryl, or substituted or unsubstituted heteroaryl. In embodiments, $R^4$ is —C(O)OR$^4$c. In embodiments, $R^4$ is —C(O)NR$^{4A}$R$^{4B}$. In embodiments, $R^4$ is substituted or unsubstituted cycloalkyl (e.g., $C_3$-$C_8$, $C_3$—$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered). In embodiments, $R^4$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{12}$, $C_6$-$C_{10}$, or phenyl), or substituted or unsubstituted heteroaryl (e.g., 5 to 12, 5 to 10 membered, 5 to 9 membered, or 5 to 6 membered). In embodiments, $R^4$ is $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 8 membered, 3 to 6 membered, 4 to 6 membered, 4 to 5 membered, or 5 to 6 membered), $R^{40}$-substituted or unsubstituted aryl (e.g., $C_6$-$C_{12}$, $C_6$-$C_{10}$, or phenyl), or $R^{40}$-substituted or unsubstituted heteroaryl (e.g., 5 to 12, 5 to 10 membered, 5 to 9 membered, or 5 to 6 membered). In embodiments, $R^4$ is $R^{40}$-substituted or unsubstituted $C_4$-$C_6$ cycloalkyl, $R^{40}$-substituted or unsubstituted 4 to 6 membered heterocycloalkyl, $R^{40}$-substituted or unsubstituted phenyl, or $R^{40}$-substituted or unsubstituted 5 to 6 membered heteroaryl. In embodiments, $R^4$ is $R^{40}$-substituted or unsubstituted tetrazolyl. In embodiments, $R^4$ is unsubstituted tetrazolyl. In embodiments, $R^4$ is $R^{40}$-substituted or unsubstituted pyridyl. In embodiments, $R^4$ is unsubstituted pyridyl. In embodiments, $R^4$ is $R^{40}$-substituted or unsubstituted oxazolyl. In embodiments, $R^4$ is unsubstituted oxazolyl. In embodiments, $R^4$ is $R^{40}$-substituted or unsubstituted 2-oxazolyl. In embodiments, $R^4$ is unsubstituted 2-oxazolyl. In embodiments, $R^4$ is $R^{40}$-substituted or unsubstituted phenyl. In embodiments, $R^4$ is unsubstituted phenyl.

In embodiments, $R^{40}$ is independently halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{41}$, —$NHR^{41}$, —$N(CH_3)R^{41}$, —$COOR^{41}$, —$CONHR^{41}$, —$SR^{41}$, $SO_2NHR^{41}$, $SO_2R^{41}$, $R^{41}$-substituted or unsubstituted $C_1$-$C_4$ alkyl, $R^{41}$-substituted or unsubstituted 2 to 3 membered heteroalkyl, $R^{41}$-substituted or unsubstituted $C_3$-$C_6$ cycloalkyl, $R^{41}$-substituted or unsubstituted 3 to 6 membered heterocycloalkyl, $R^{41}$-substituted or unsubstituted phenyl, or $R^{41}$-substituted or unsubstituted 5 to 6 membered heteroaryl. In embodiments, $R^{40}$ is independently halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, unsubstituted $C_1$-$C_4$ alkyl, unsubstituted 2 to 3 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{40}$ is independently halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —SH, unsubstituted methyl, unsubstituted ethyl, unsubstituted isopropyl, unsubstituted methoxy, or unsubstituted ethoxy. In embodiments, $R^{40}$ is independently $R^{41}$-substituted or unsubstituted phenyl. In embodiments, $R^{40}$ is independently unsubstituted phenyl. In embodiments, $R^{40}$ is independently $R^{41}$-substituted or unsubstituted 5 to 6 membered heteroaryl. In embodiments, $R^{40}$ is independently unsubstituted 5 to 6 membered heteroaryl. In embodiments, $R^{41}$ is independently halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, unsubstituted $C_1$-$C_4$ alkyl, unsubstituted 2 to 3 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{41}$ is independently halogen, —$CF_3$, —$CHF_2$, —$CH_2F$, —$OCF_3$, —$OCH_2F$, —$OCHF_2$, —CN, —OH, —$NH_2$, —COOH, —$CONH_2$, —SH, unsubstituted methyl, unsubstituted ethyl, unsubstituted isopropyl, unsubstituted methoxy, or unsubstituted ethoxy.

In embodiments, the compound has the formula:

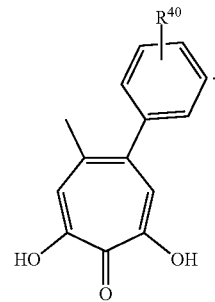

(III-1)

$R^{40}$ is as described herein. In embodiments, the compound has the formula:

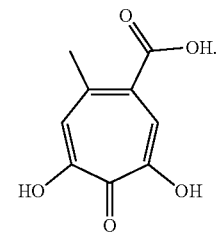

In embodiments, the compound has the formula:

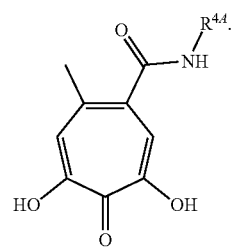

(III-2)

In embodiments, the compound has the formula:

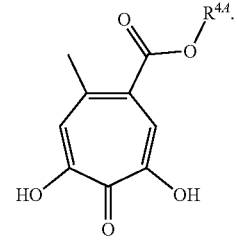

$R^{4A}$ is as described herein. In embodiments, $R^{4A}$ is independently hydrogen, —$CF_3$, —$CHF_2$, —$CH_2F$, unsubstituted methyl, unsubstituted ethyl, unsubstituted isopropyl, or unsubstituted phenyl.

In embodiments, the compound has the formula:

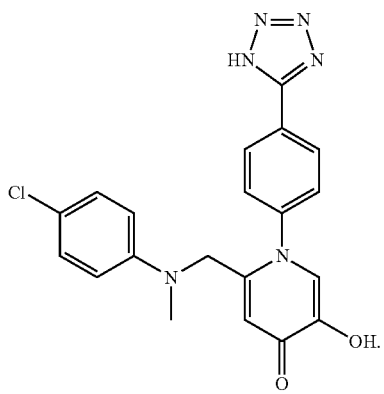

In embodiments, the compound is selected from the group consisting of 3-hydroxy-4-oxo-4H-pyran-2-carboxylic acid, 3-hydroxy-6-methyl-4-oxo-4H-pyran-2-carboxylic acid, 3-hydroxy-6-methyl-4-oxo-1,4-dihydropyridine-2-carboxylic acid, 6-bromo-3-hydroxy-4-oxo-1,4-dihydropyridine-2-carboxylic acid, 6-bromo-3-hydroxy-2-(1H-tetrazol-5-yl)pyridin-4(1H)-one, 3-hydroxy-4-oxo-6-phenyl-1,4-dihydropyridine-2-carboxylic acid, 3-hydroxy-4-oxo-6-(4-phenoxyphenyl)-1,4-dihydropyridine-2-carboxylic acid, 2,7-dihydroxycyclohepta-2,4,6-trien-1-one, 6-hydroxy-4-methoxy-2-methyl-5-oxocyclohepta-1,3,6-triene-1-carboxylic acid, 4,6-dihydroxy-2-methyl-5-oxocyclohepta-1,3,6-triene-1-carboxylic acid, 2,7-dihydroxy-4-methyl-5-phenylcyclohepta-2,4,6-trien-1-one, 1-(4-(1H-tetrazol-5-yl)phenyl)-2-(((4-chlorophenyl)(methyl)amino)methyl)-5-hydroxypyridin-4(1H)-one, 1,3-dihydroxy-6-methyl-4-oxo-1,4-dihydropyridine-2-carboxylic acid, 3-hydroxy-2-(1H-tetrazol-5-yl)pyridin-4(1H)-one, 3-hydroxy-2-(oxazol-2-yl)pyridin-4(1H)-one, 6-(4-carboxyphenyl)-3-hydroxy-4-oxo-1,4-dihydropyridine-2-carboxylic acid, 6-(3-carboxyphenyl)-3-hydroxy-4-oxo-1,4-dihydropyridine-2-carboxylic acid, 3-hydroxy-4-oxo-6-(m-tolyl)-1,4-dihydropyridine-2-carboxylic acid, 3-hydroxy-4-oxo-6-(o-tolyl)-1,4-dihydropyridine-2-carboxylic acid, and 6-(4-(1H-tetrazol-5-yl)phenyl)-3-hydroxy-4-oxo-1,4-dihydropyridine-2-carboxylic acid. In embodiments, the compound is 3-hydroxy-4-oxo-4H-pyran-2-carboxylic acid. In embodiments, the compound is 3-hydroxy-6-methyl-4-oxo-4H-pyran-2-carboxylic acid. In embodiments, the compound is 3-hydroxy-6-methyl-4-oxo-1,4-dihydropyridine-2-carboxylic acid. In embodiments, the compound is 6-bromo-3-hydroxy-4-oxo-1,4-dihydropyridine-2-carboxylic acid. In embodiments, the compound is 6-bromo-3-hydroxy-2-(1H-tetrazol-5-yl)pyridin-4(1H)-one. In embodiments, the compound is 3-hydroxy-4-oxo-6-phenyl-1,4-dihydropyridine-2-carboxylic acid. In embodiments, the compound is 3-hydroxy-4-oxo-6-(4-phenoxyphenyl)-1,4-dihydropyridine-2-carboxylic acid. In embodiments, the compound is 2,7-dihydroxycyclohepta-2,4,6-trien-1-one. In embodiments, the compound is 6-hydroxy-4-methoxy-2-methyl-5-oxocyclohepta-1,3,6-triene-1-carboxylic acid. In embodiments, the compound is 4,6-dihydroxy-2-methyl-5-oxocyclohepta-1,3,6-triene-1-carboxylic acid. In embodiments, the compound is 2,7-dihydroxy-4-methyl-5-phenylcyclohepta-2,4,6-trien-1-one. In embodiments, the compound is 1-(4-(1H-tetrazol-5-yl)phenyl)-2-(((4-chlorophenyl)(methyl)amino)methyl)-5-hydroxypyridin-4(1H)-one. In embodiments, the compound is 1,3-dihydroxy-6-methyl-4-oxo-1,4-dihydropyridine-2-carboxylic acid. In embodiments, the compound is 3-hydroxy-2-(1H-tetrazol-5-yl)pyridin-4(1H)-one. In embodiments, the compound is 3-hydroxy-2-(oxazol-2-yl)pyridin-4(1H)-one. In embodiments, the compound is 6-(4-carboxyphenyl)-3-hydroxy-4-oxo-1,4-dihydropyridine-2-carboxylic acid. In embodiments, the compound is 6-(3-carboxyphenyl)-3-hydroxy-4-oxo-1,4-dihydropyridine-2-carboxylic acid. In embodiments, the compound is 3-hydroxy-4-oxo-6-(m-tolyl)-1,4-dihydropyridine-2-carboxylic acid. In embodiments, the compound is 3-hydroxy-4-oxo-6-(o-tolyl)-1,4-dihydropyridine-2-carboxylic acid. In embodiments, the compound is 6-(4-(1H-tetrazol-5-yl)phenyl)-3-hydroxy-4-oxo-1,4-dihydropyridine-2-carboxylic acid.

In embodiments, $R^1$ is methyl. In embodiments, $R^1$ is unsubstituted isopropyl. In embodiments, $R^1$ is —OH. In embodiments, $R^1$ is unsubstituted phenyl. In embodiments, $R^1$ is

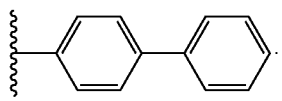

In embodiments, $R^1$ is

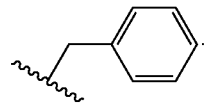 [SMILES: *Cc1ccccc1]

In embodiments, $R^1$ is

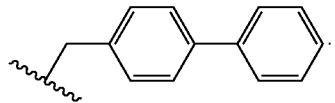 [SMILES: *Cc1ccc(-c2ccccc2)cc1]

In embodiments, $R^1$ is

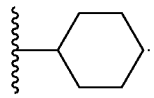

In embodiments, $R^1$ is

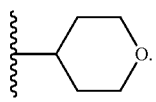

In embodiments, $R^1$ is

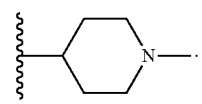

In embodiments, R¹ is
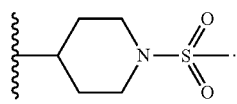 [SMILES: *C1CCN(S(C)(=O)=O)CC1]
In embodiments, R¹ is
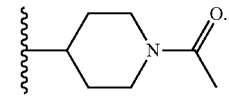 [SMILES: *C1CCN(C(C)=O)CC1]
In embodiments, R¹ is
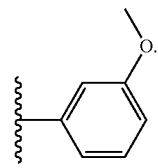 [SMILES: *c1cccc(OC)c1]
In embodiments, R¹ is
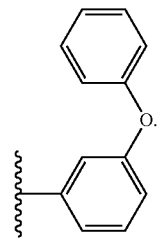 [SMILES: *c1cccc(Oc2ccccc2)c1]
In embodiments, R¹ is
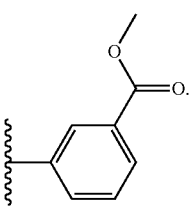 [SMILES: *c1cccc(C(=O)OC)c1]
In embodiments, R¹ is
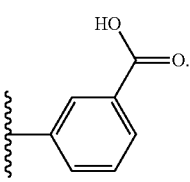 [SMILES: *c1cccc(C(=O)O)c1]
In embodiments, R¹ is
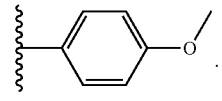
In embodiments, R¹ is
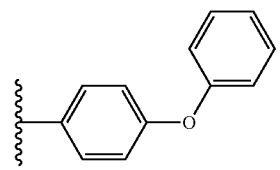
In embodiments, R¹ is
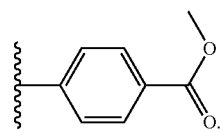
In embodiments, R¹ is
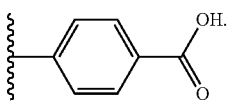 [SMILES: *c1ccc(C(=O)O)cc1]
In embodiments, R¹ is
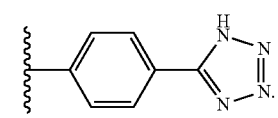
In embodiments, R¹ is
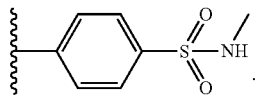 [SMILES: *c1ccc(S(=O)(=O)NC)cc1]
In embodiments, R¹ is
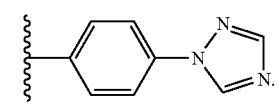
In embodiments, R¹ is
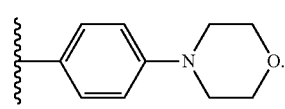

In embodiments, $R^{10}$ is unsubstituted phenyl. In embodiments, $R^{10}$ is —COOH. In embodiments, $R^{10}$ is —S(O)$_2$CH$_3$. In embodiments, $R^{10}$ is —OCH$_3$. In embodiments, $R^{10}$ is —COCH$_3$. In embodiments, $R^{10}$ is

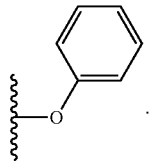 [SMILES: *Oc1ccccc1]

In embodiments, $R^{10}$ is C(O)OCH$_3$. In embodiments, $R^{10}$ is S(O)$_2$NHCH$_3$. In embodiments, $R^{10}$ is

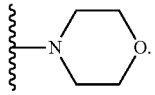

In embodiments, $R^{10}$ is

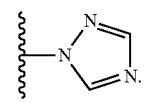

In embodiments, $R^{10}$ is

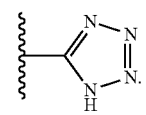

In embodiments, $R^2$ is COOH. In embodiments, $R^2$ is C(O)NH$_2$. In embodiments, $R^2$ is

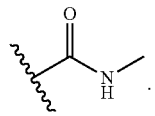 [SMILES: *C(=O)NC]

In embodiments, $R^2$ is CH$_2$OH. In embodiments, $R^2$ is OCH$_3$. In embodiments, $R^2$ is OH. In embodiments, $R^2$ is

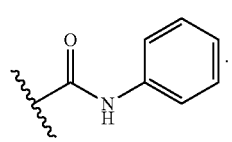 [SMILES: *C(=O)Nc1ccccc1]

In embodiments, $R^2$ is

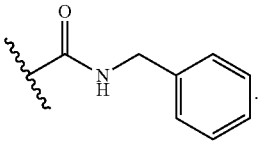 [SMILES: *C(=O)NCc1ccccc1]

In embodiments, $R^2$ is

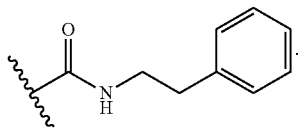 [SMILES: *C(=O)NCCc1ccccc1]

In embodiments, $R^2$ is

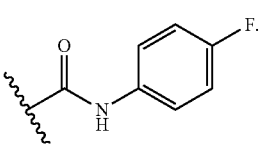 [SMILES: *C(=O)Nc1ccc(F)cc1]

In embodiments, $R^2$ is

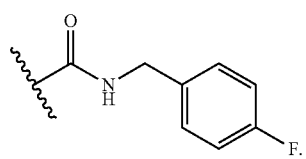 [SMILES: *C(=O)NCc1ccc(F)cc1]

In embodiments, $R^2$ is

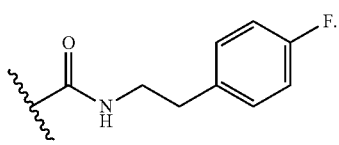 [SMILES: *C(=O)NCCc1ccc(F)cc1]

In embodiments, $R^2$ is

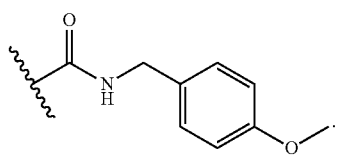 [SMILES: *C(=O)NCc1ccc(OC)cc1]

In embodiments, $R^2$ is

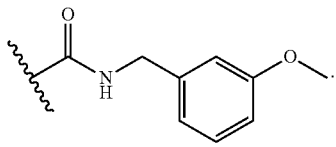 [SMILES: *C(=O)NCc1cccc(OC)c1]

In embodiments, $R^2$ is

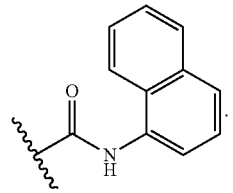 [SMILES: *C(=O)Nc1cccc2ccccc12]

In embodiments, $R^2$ is

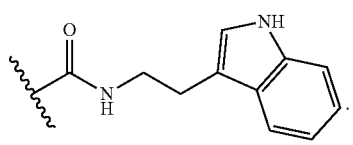 [SMILES: *C(=O)NCCc1c[nH]c2ccccc12]

In embodiments, $R^2$ is

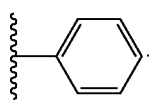

In embodiments, $R^{2A}$ is hydrogen. In embodiments, $R^{2A}$ is

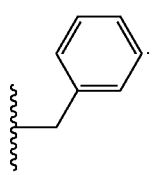 [SMILES: *Cc1ccccc1]

In embodiments, $R^{2A}$ is

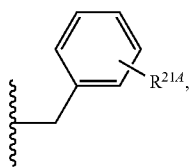

In embodiments, $R^{2A}$ is wherein $R^{21A}$ is as described herein.

In embodiments, $R^{2A}$ is

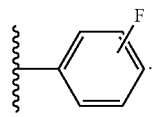

In embodiments, $R^{2A}$ is

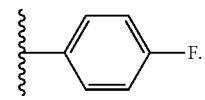

In embodiments, $R^{2A}$ is

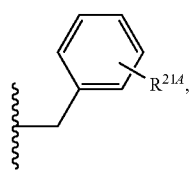

wherein $R^{21A}$ is as described herein. In embodiments, $R^{2A}$ is

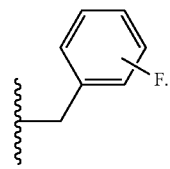

In embodiments, $R^{2A}$ is

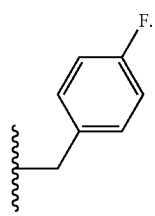 [SMILES: *Cc1ccc(F)cc1]

In embodiments, $R^{2A}$ is

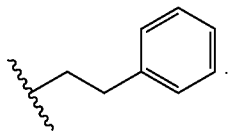 [SMILES: *CCc1ccccc1]

In embodiments, $R^{2A}$ is

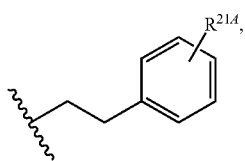

wherein $R^{21A}$ is as described herein. In embodiments, $R^{2A}$ is

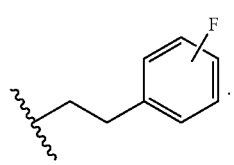

In embodiments, $R^{2A}$ is

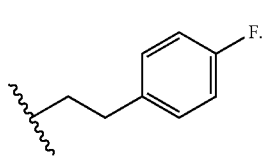 [SMILES: *CCc1ccc(F)cc1]

In embodiments, $R^{2A}$ is

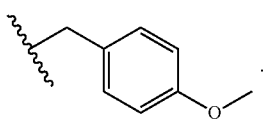 [SMILES: *Cc1ccc(OC)cc1]

In embodiments, $R^{2A}$ is

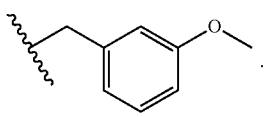 [SMILES: *Cc1cccc(OC)c1]

In embodiments, $R^{2A}$ is

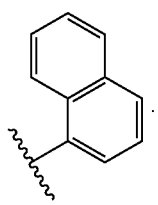 [SMILES: *c1cccc2ccccc12]

In embodiments, $R^{2A}$ is

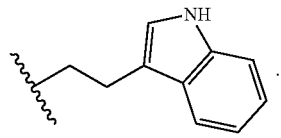 [SMILES: *CCc1c[nH]c2ccccc12]

In embodiments, $R^{2A}$ is

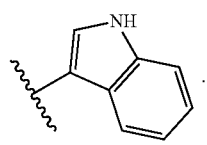

In embodiments, $R^{21A}$ is $OCH_3$. In embodiments, $R^{21A}$ is halogen. In embodiments, $R^{21A}$ is F. In embodiments, $R^{21A}$ is methyl.

In embodiments, $R^{20}$ is $NH_2$. In embodiments, $R^{20}$ is

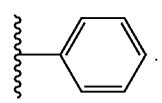

In embodiments, $R^{20}$ is

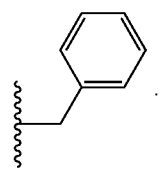 [SMILES: *Cc1ccccc1]

In embodiments, $R^{20}$ is

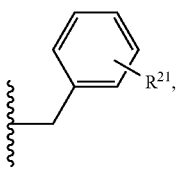

wherein $R^{21}$ is as described herein. In embodiments, $R^{20}$ is

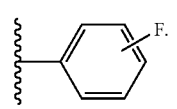

In embodiments, $R^{20}$ is

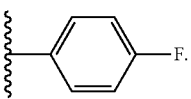

In embodiments, $R^{20}$ is

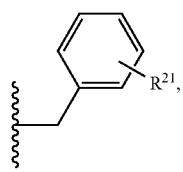

wherein $R^{21}$ is as described herein. In embodiments, $R^{20}$ is

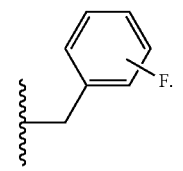

In embodiments, $R^{20}$ is

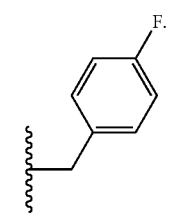 [SMILES: *Cc1ccc(F)cc1]

In embodiments, $R^{20}$ is

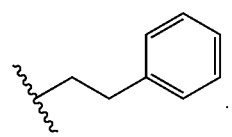 [SMILES: *CCc1ccccc1]

In embodiments, $R^{20}$ is

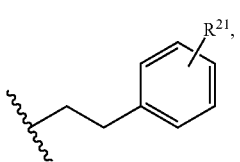

wherein $R^{21}$ is as described herein. In embodiments, $R^{20}$ is

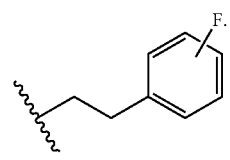

In embodiments, $R^{20}$ is

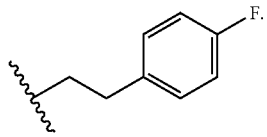 [SMILES: *CCc1ccc(F)cc1]

In embodiments, $R^{20}$ is

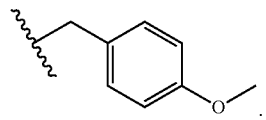 [SMILES: *Cc1ccc(OC)cc1]

In embodiments, $R^{20}$ is

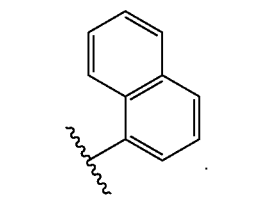

In embodiments, $R^{20}$ is

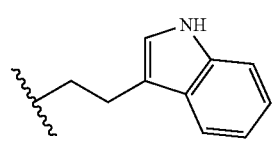

In embodiments, $R^{20}$ is

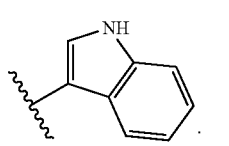

In embodiments, $R^{20}$ is

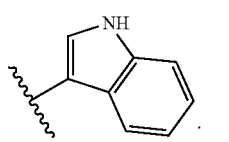 [SMILES: *c1c[nH]c2ccccc12]

In embodiments, $R^{21}$ is

In embodiments, $R^{21}$ is $OCH_3$. In embodiments, $R^{21}$ is halogen. In embodiments, $R^{21}$ is F. In embodiments, $R^{21}$ is methyl.

In embodiments, $R^3$ is hydrogen. In embodiments, $R^3$ is Br. In embodiments, $R^3$ is methyl. In embodiments, $R^3$ is $CH_2OH$. In embodiments, $R^3$ is COOH. In embodiments, $R^3$ is

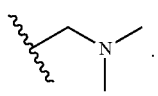 [SMILES: *CN(C)C]

In embodiments, $R^3$ is

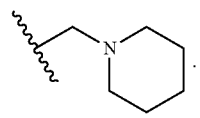

In embodiments, $R^3$ is

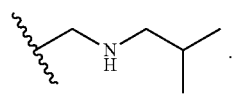

In embodiments, $R^3$ is

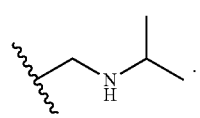 [SMILES: *CNC(C)C]

In embodiments, $R^3$ is

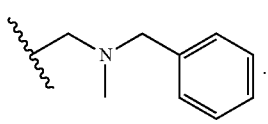 [SMILES: *CN(C)Cc1ccccc1]

In embodiments, $R^3$ is

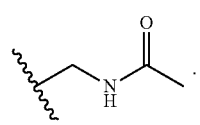 [SMILES: *CNC(C)=O]

In embodiments, $R^3$ is

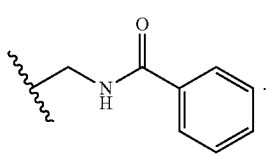 [SMILES: *CNC(=O)c1ccccc1]

In embodiments, $R^3$ is

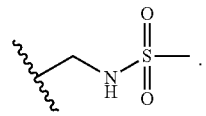

In embodiments, $R^3$ is

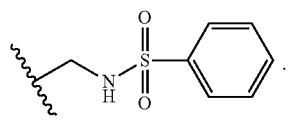 [SMILES: *CNS(=O)(=O)c1ccccc1]

In embodiments, $R^3$ is

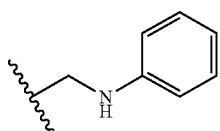

In embodiments, $R^3$ is

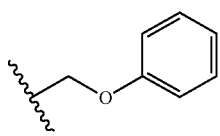

In embodiments, $R^3$ is

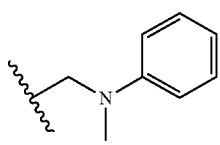

In embodiments, $R^3$ is

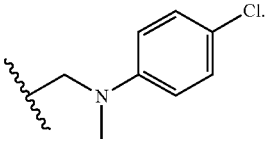 [SMILES: *CN(C)c1ccc(Cl)cc1]

In embodiments, $R^3$ is

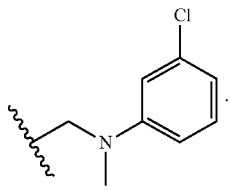 [SMILES: *CN(C)c1cccc(Cl)c1]

In embodiments, R³ is
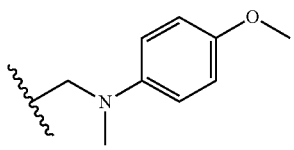
In embodiments, R³ is
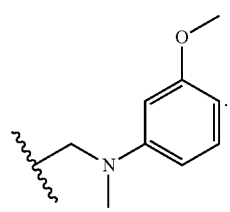 [SMILES: *CN(C)c1cccc(OC)c1]
In embodiments, R³ is
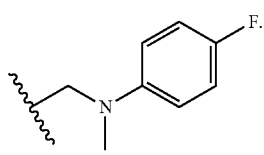 [SMILES: *CN(C)c1ccc(F)cc1]
In embodiments, R³ is
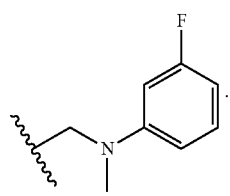
In embodiments, R³ is
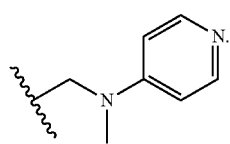 [SMILES: *CN(C)c1ccncc1]
In embodiments, R³ is
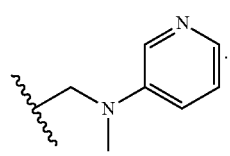 [SMILES: *CN(C)c1cccnc1]
In embodiments, R³ is
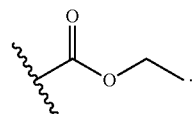 [SMILES: *C(=O)OCC]
In embodiments, $R^{30}$ is
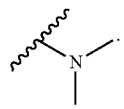
In embodiments, $R^{30}$ is
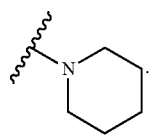 [SMILES: *N1CCCCC1]
In embodiments, $R^{30}$ is
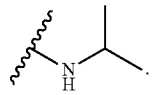
In embodiments, $R^{30}$ is
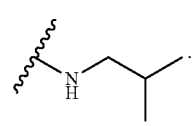 [SMILES: *NCC(C)C]
In embodiments, $R^{30}$ is
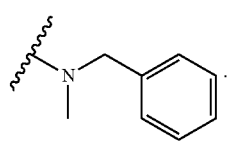 [SMILES: *N(C)Cc1ccccc1]
In embodiments, $R^{30}$ is
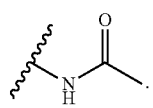

In embodiments, $R^{30}$ is
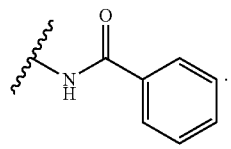 [SMILES: *NC(=O)c1ccccc1]
In embodiments, $R^{30}$ is
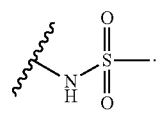
In embodiments, $R^{30}$ is
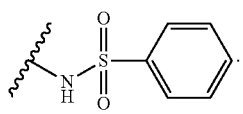 [SMILES: *NS(=O)(=O)c1ccccc1]
In embodiments, $R^{30}$ is
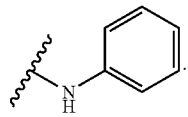 [SMILES: *Nc1ccccc1]
In embodiments, $R^{30}$ is
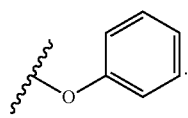
In embodiments, $R^{30}$ is
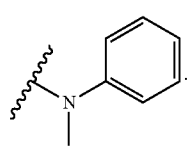 [SMILES: *N(C)c1ccccc1]
In embodiments, $R^{30}$ is
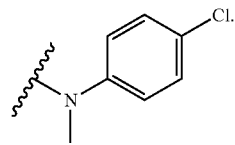 [SMILES: *N(C)c1ccc(Cl)cc1]
In embodiments, $R^{30}$ is
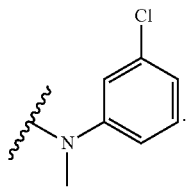 [SMILES: *N(C)c1cccc(Cl)c1]
In embodiments, $R^{30}$ is
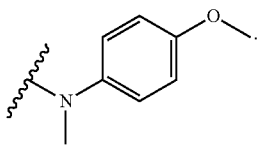 [SMILES: *N(C)c1ccc(OC)cc1]
In embodiments, $R^{30}$ is
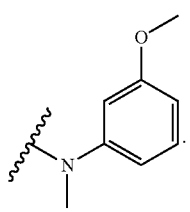 [SMILES: *N(C)c1cccc(OC)c1]
In embodiments, $R^{30}$ is
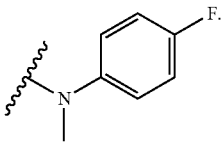 [SMILES: *N(C)c1ccc(F)cc1]
In embodiments, $R^{30}$ is
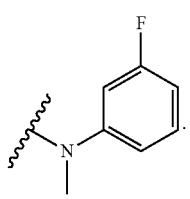 [SMILES: *N(C)c1cccc(F)c1]
In embodiments, $R^{30}$ is
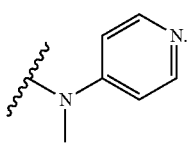 [SMILES: *N(C)c1ccncc1]

In embodiments, $R^{30}$ is

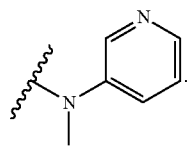 [SMILES: *N(C)c1cccnc1]

In embodiments, $R^{31}$ is methyl, —OCH$_3$, or halogen. In embodiments, $R^{31}$ is methyl. In embodiments, $R^{31}$ is OCH$_3$. In embodiments, $R^{31}$ is halogen. In embodiments, $R^{31}$ is F. In embodiments, $R^{31}$ is Cl.

In embodiments, $R^3$ is

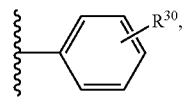

wherein $R^{30}$ is as described herein. In embodiments, $R^{30}$ is

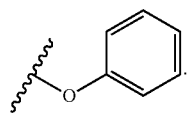

In embodiments, In embodiments, $R^{30}$ is COOH. In embodiments, $R^{30}$ is methyl. In embodiments, $R^{30}$ is

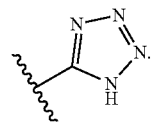

In embodiments, $R^{30}$ is

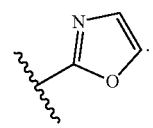

In embodiments, $R^4$ is methyl. In embodiments, $R^4$ is hydrogen. In embodiments, $R^4$ is COOH. In embodiments, $R^4$ is

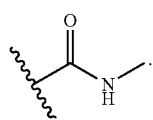 [SMILES: *C(=O)NC]

In embodiments, $R^4$ is

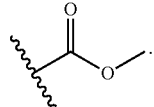 [SMILES: *C(=O)OC]

In embodiments, $R^4$ is

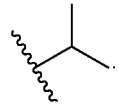 [SMILES: *C(C)C]

In embodiments, $R^4$ is

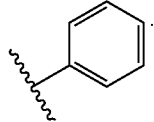

In embodiments, $R^4$ is

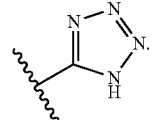 [SMILES: *c1nnn[nH]1]

In embodiments, $R^4$ is

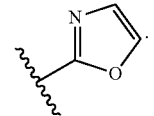

In embodiments, the compound is a compound described herein, including in an aspect, embodiment, claim, figure, table, example, or scheme. In embodiments, the compound is compound 1 of table 9. In embodiments, the compound is compound 2 of table 9. In embodiments, the compound is compound 3 of table 9. In embodiments, the compound is compound 4 of table 9. In embodiments, the compound is compound 5 of table 9. In embodiments, the compound is compound 6 of table 9. In embodiments, the compound is compound 7 of table 9. In embodiments, the compound is compound 8 of table 9. In embodiments, the compound is compound 9 of table 9. In embodiments, the compound is compound 10 of table 9. In embodiments, the compound is compound 11 of table 9. In embodiments, the compound is compound 12 of table 9. In embodiments, the compound is compound 13 of table 9. In embodiments, the compound is compound 14 of table 9. In embodiments, the compound is compound 15 of table 9. In embodiments, the compound is compound 16 of table 9. In embodiments, the compound is compound 17 of table 9. In embodiments, the compound is compound 18 of table 9. In embodiments, the compound is compound 19 of table 9. In embodiments, the compound is compound 20 of table 9. In embodiments, the compound is compound 21 of table 9. In embodiments, the compound is compound 22 of table 9. In embodiments, the compound is compound 23 of table 9. In embodiments, the compound is compound 24 of table 9. In embodiments, the compound is compound 25 of table 9. In embodiments, the compound is compound 26 of table 9. In embodiments, the compound is compound 27 of table 9. In embodiments, the compound is compound 28 of table 9. In embodiments, the compound is compound 29 of table 9. In embodiments, the compound is compound 30 of table 9. In embodiments, the compound is compound 31 of table 9. In embodiments, the compound is compound 32 of table 9. In embodiments, the compound is compound 33 of table 9. In embodiments, the compound is compound 34 of table 9. In embodiments, the compound is compound 35 of table 9. In embodiments, the compound is compound 36 of table 9. In embodiments, the compound is compound 37 of table 9. In embodiments, the compound is compound 38 of table 9. In embodiments, the compound is compound 39 of table 9. In embodiments, the compound is compound 40 of table 9. In embodiments, the compound is compound 41 of table 9. In embodiments, the compound is compound 42 of table 9. In embodiments, the compound is compound 43 of table 9. In embodiments, the compound is compound 44 of table 9. In embodiments, the compound is compound 45 of table 9. In embodiments, the compound is compound 46 of table 9. In embodiments, the compound is compound 47 of table 9. In embodiments, the compound is compound 48 of table 9. In embodiments, the compound is compound 49 of table 9. In embodiments, the compound is compound 50 of table 9. In embodiments, the compound is compound 51 of table 9. In embodiments, the compound is compound 52 of table 9. In embodiments, the compound is compound 53 of table 9. In embodiments, the compound is compound 54 of table 9. In embodiments, the compound is compound 55 of table 9. In embodiments, the compound is compound 56 of table 9. In embodiments, the compound is compound 57 of table 9. In embodiments, the compound is compound 58 of table 9. In embodiments, the compound is compound 59 of table 9. In embodiments, the compound is compound 60 of table 9. In embodiments, the compound is compound 61 of table 9. In embodiments, the compound is compound 62 of table 9. In embodiments, the compound is compound 63 of table 9. In embodiments, the compound is compound 64 of table 9. In embodiments, the compound is compound 65 of table 9. In embodiments, the compound is compound 66 of table 9. In embodiments, the compound is compound 67 of table 9. In embodiments, the compound is compound 68 of table 9. In embodiments, the compound is compound 69 of table 9. In embodiments, the compound is compound 70 of table 9. In embodiments, the compound is compound 71 of table 9. In embodiments, the compound is compound 101 of table 9. In embodiments, the compound is compound 102 of table 9. In embodiments, the compound is compound 103 of table 9. In embodiments, the compound is compound 104 of table 9. In embodiments, the compound is compound 107 of table 9. In embodiments, the compound is compound A11 of table 9. In embodiments, the compound is compound 112 of table 9. In embodiments, the compound is compound 118 of table 9. In embodiments, the compound is compound 119 of table 9. In embodiments, the compound is compound 131 of table 9. In embodiments, the compound is compound 133 of table 9. In embodiments, the compound is compound 142 of table 9. In embodiments, the compound is compound 143 of table 9. In embodiments, the compound is compound B4 of table 9. In embodiments, the compound is compound B12 of table 9. In embodiments, the compound is compound B13 of table 9. In embodiments, the compound is compound B15 of table 9. In embodiments, the compound is compound A9 of table 9. In embodiments, the compound is compound A10 of table 9. In embodiments, the compound is compound A11 of table 9. In embodiments, the compound is compound A12 of table 9. In embodiments, the compound is compound B11 of table 9. In embodiments, the compound is compound $C_4$ of table 9. In embodiments, the compound is compound A13 of table 9. In embodiments, the compound is compound F13 of table 9. In embodiments, the compound is compound 59-4 of table 9. In embodiments, the compound is compound 59-5 of table 9. In embodiments, the compound is compound 59-6-3Acid of table 9. In embodiments, the compound is compound 59-6-4Acid of table 9. In embodiments, the compound is compound 59-7-4Tet of table 9. In embodiments, the compound is compound 61-1-depro of table 9. In embodiments, the compound is compound 61-3 of table 9. In embodiments, the compound is compound 57-6bF of table 9. In embodiments, the compound is compound 62-4c of table 9. In embodiments, the compound is compound Z1 of table 9. In embodiments, the compound is compound Z2 of table 9. In embodiments, the compound is compound 56-NOH of table 9. In embodiments, the compound is compound F8 of table 9. In embodiments, the compound is compound #2-NH of table 9. In embodiments, the compound is compound 105 of table 9. In embodiments, the compound is compound 106 of table 9. In embodiments, the compound is compound 201 of table 9. In embodiments, the compound is compound E4 of table 9. In embodiments, the compound is compound 205 of table 9. In embodiments, the compound is compound 213 of table 9. In embodiments, the compound is compound E3 of table 9. In embodiments, the compound is compound E5 of table 9. In embodiments, the compound is compound E6 of table 9. In embodiments, the compound is compound 210 of table 9. In embodiments, the compound is compound 212 of table 9.

In embodiments, the compound is not a compound having the formula:

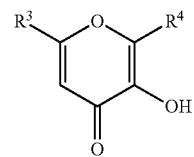

wherein $R^3$ and $R^4$ are as described below. In embodiments, the compound is not a compound having the formula:

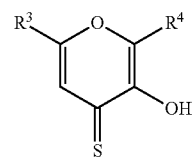

wherein $R^3$ and $R^4$ are as described below. In embodiments, the compound is not a compound having the formula:

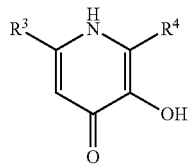

wherein $R^3$ and $R^4$ are as described below. In embodiments, the compound is not a compound having the formula:

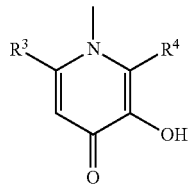

wherein $R^3$ and $R^4$ are as described below. In embodiments, the compound is not a compound having the formula:

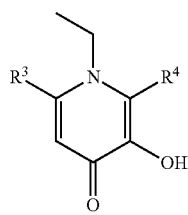

wherein $R^3$ and $R^4$ are as described below. In embodiments, the compound is not a compound having the formula:

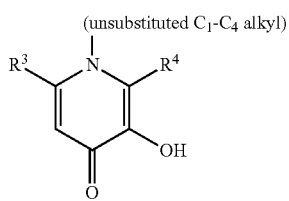

wherein $R^3$ and $R^4$ are as described below. In embodiments, the compound is not a compound having the formula:

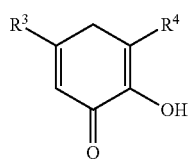

wherein $R^3$ and $R^4$ are as described below. In embodiments, the compound is not a compound having the formula:

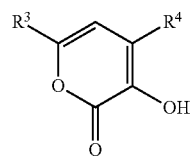

wherein $R^3$ and $R^4$ are as described below. In embodiments, the compound is not a compound having the formula:

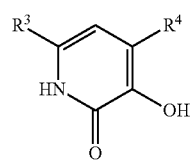

wherein $R^3$ and $R^4$ are as described below. In embodiments, the compound is not a compound having the formula:

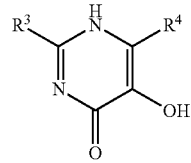

wherein $R^3$ and $R^4$ are as described below. In embodiments, the compound is not a compound having the formula:

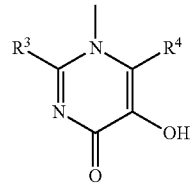

wherein $R^3$ and $R^4$ are as described below. In embodiments, the compound is not a compound having the formula:

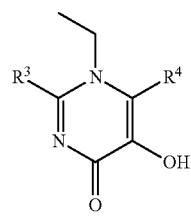

wherein $R^3$ and $R^4$ are as described below. In embodiments, the compound is not a compound having the formula:

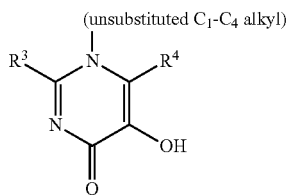

wherein $R^3$ and $R^4$ are as described below. In embodiments, the compound is not a compound having the formula:

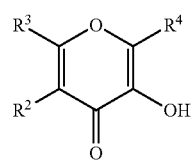

wherein $R^2$, $R^3$, and $R^4$ are as described below. In embodiments, the compound is not a compound having the formula:

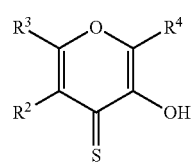

wherein $R^2$, $R^3$, and $R^4$ are as described below. In embodiments, the compound is not a compound having the formula:

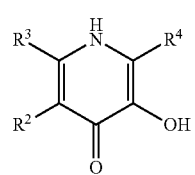

wherein $R^2$, $R^3$, and $R^4$ are as described below. In embodiments, the compound is not a compound having the formula:

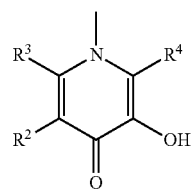

wherein $R^2$, $R^3$, and $R^4$ are as described below. In embodiments, the compound is not a compound having the formula:

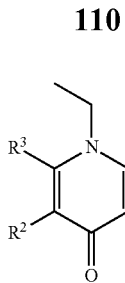

wherein $R^2$, $R^3$, and $R^4$ are as described below. In embodiments, the compound is not a compound having the formula:

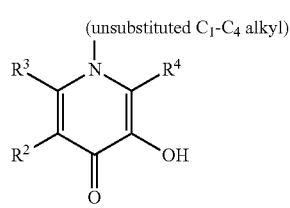

wherein $R^2$, $R^3$, and $R^4$ are as described below. In embodiments, the compound is not a compound having the formula:

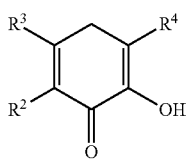

wherein $R^2$, $R^3$, and $R^4$ are as described below. In embodiments, the compound is not a compound having the formula:

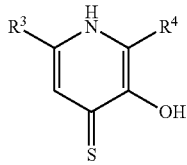

wherein $R^3$ and $R^4$ are as described below. In embodiments, the compound is not a compound having the formula:

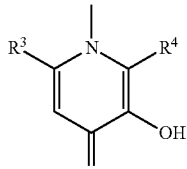

wherein $R^3$ and $R^4$ are as described below. In embodiments, the compound is not a compound having the formula:

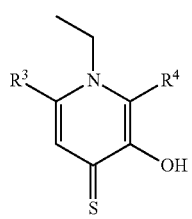

wherein $R^3$ and $R^4$ are as described below. In embodiments, the compound is not a compound having the formula:

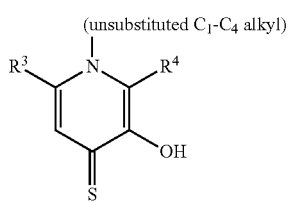

wherein $R^3$ and $R^4$ are as described below. In embodiments, the compound is not a compound having the formula:

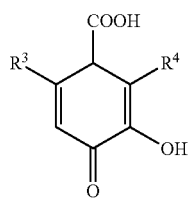

wherein $R^3$ and $R^4$ are as described below. In embodiments, the compound is not a compound having the formula:

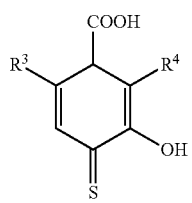

wherein $R^3$ and $R^4$ are as described below. In embodiments, the compound is not a compound having the formula:

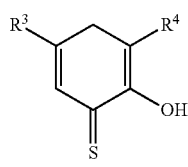

wherein $R^3$ and $R^4$ are as described below. In embodiments, the compound is not a compound having the formula:

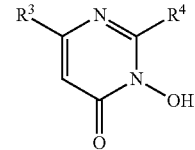

wherein $R^3$ and $R^4$ are as described below. In embodiments, the compound is not a compound having the formula:

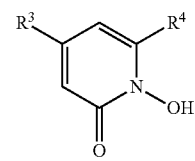

wherein $R^3$ and $R^4$ are as described below. In embodiments, the compound is not a compound having the formula:

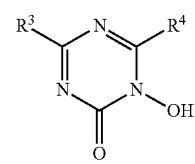

wherein $R^3$ and $R^4$ are as described below. In embodiments, the compound is not a compound having the formula:

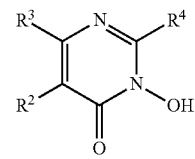

wherein $R^2$, $R^3$, and $R^4$ are as described below. In embodiments, the compound is not a compound having the formula:

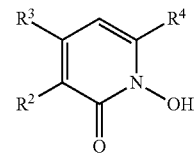

wherein $R^2$, $R^3$, and $R^4$ are as described below. In embodiments, the compound is not a compound having the formula:

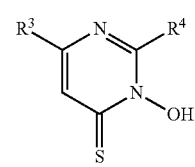

wherein $R^3$ and $R^4$ are as described below. In embodiments, the compound is not a compound having the formula:

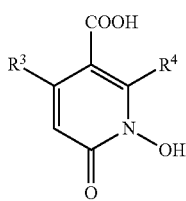

wherein R³ and R⁴ are as described below. In embodiments, the compound is not a compound having the formula:

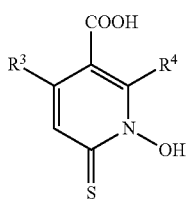

wherein R³ and R⁴ are as described below. In embodiments, the compound is not a compound having the formula:

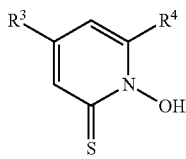

wherein R³ and R⁴ are as described below.

In embodiments, the compound is not a compound having the formula:

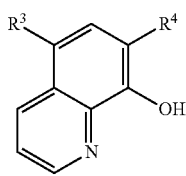

wherein R³ and R⁴ are as described below.

In embodiments, the compound is not a compound having the formula:

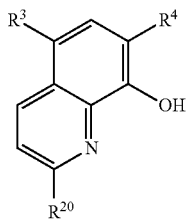

wherein $R^{20}$, $R^3$, and $R^4$ are as described below.

In embodiments, $R^{20}$ is independently halogen, —CX$^{20}$₃, —CHX$^{20}$₂, —CH₂X$^{20}$, —OCX$^{20}$₃, —OCH₂X$^{20}$, —OCHX$^{20}$₂, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O)NH₂, —NHSO₂H, —NHC=(O)H, —NHC(O)—OH, —NHOH, —OR²¹, —NHR²¹, —COOR²¹, —CONHR²¹, —SR²¹, —SO₂NHR²¹, —SO₂R²¹, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{20}$ is independently —F, —Cl, —Br, or —I. In embodiments, $R^{20}$ is hydrogen, OH-substituted $C_1$-$C_3$ alkyl, halogen-substituted $C_1$-$C_3$ alkyl, ($C_1$-$C_3$ alkyl), halogen (e.g., —Cl), —($C_1$-$C_3$ alkyl)-(halogen-substituted phenyl), or —($C_1$-$C_3$ alkyl). In embodiments, $R^{20}$ is hydrogen. In embodiments, $R^{20}$ is unsubstituted methyl. In embodiments, $R^{20}$ is unsubstituted $C_1$-$C_3$ alkyl. In embodiments, $R^{20}$ is unsubstituted ethyl. In embodiments, $R^{20}$ is —CH₂OH, —CH₂Cl, —CH₂F, —CH₂Br, —CH₂I, —CH₃, or —CH₂-(4-F phenyl). In embodiments, $R^{20}$ is —COOH. In embodiments, $R^{20}$ is —NH₂. In embodiments, $R^{20}$ is as described herein (e.g., in an embodiment).

In embodiments, the compound is not a compound having the formula:

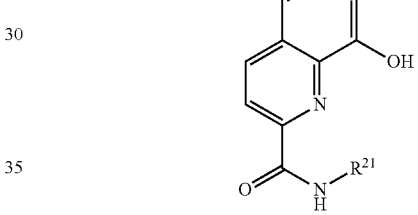

wherein $R^{21}$, $R^3$, and $R^4$ are as described below.

In embodiments, $R^{21}$ is hydrogen, OH-substituted $C_1$-$C_3$ alkyl, halogen-substituted $C_1$-$C_3$ alkyl, ($C_1$-$C_3$ alkyl), halogen (e.g., —Cl), —($C_1$-$C_3$ alkyl)-(halogen-substituted phenyl), or —($C_1$-$C_3$ alkyl). In embodiments, $R^{21}$ is hydrogen. In embodiments, $R^{21}$ is unsubstituted methyl. In embodiments, $R^{21}$ is unsubstituted $C_1$-$C_3$ alkyl. In embodiments, $R^{21}$ is unsubstituted ethyl. In embodiments, $R^{21}$ is —CH₂OH, —CH₂Cl, —CH₂F, —CH₂Br, —CH₂I, —CH₃, or —CH₂-(4-F phenyl). In embodiments, $R^3$, $R^4$, and $R^{21}$ are as described herein (e.g., each in an embodiment). In embodiments, $R^{21}$ is as described herein (e.g., in an embodiment).

In embodiments, the compound is not a compound having the formula:

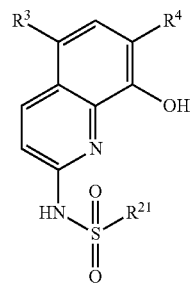

wherein $R^3$ and $R^4$ are as described below and $R^{21}$ is hydrogen, —CH$_2$OH, —CH$_2$Cl, —CH$_2$F, —CH$_2$Br, —CH$_2$I, —CH$_3$, -halogen (e.g., —Cl), —CH$_2$-(4-F phenyl), OH-substituted C$_1$-C$_3$ alkyl, halogen-substituted C$_1$-C$_3$ alkyl, (C$_1$-C$_3$ alkyl), —(C$_1$-C$_3$ alkyl)-(halogen-substituted phenyl), —(C$_1$-C$_3$ alkyl), unsubstituted phenyl, unsubstituted biphenyl, unsubstituted 5 to 6 membered heteroaryl (e.g., thienyl, furanyl, or pyrrolyl). In embodiments, $R^3$, $R^4$, and $R^{21}$ are as described herein (e.g., each in an embodiment).

In embodiments, the compound is not a compound having the formula:

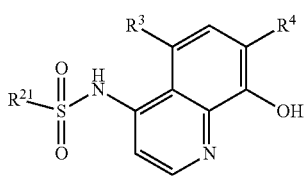

wherein $R^3$ and $R^4$ are as described below and $R^{21}$ is hydrogen, —CH$_2$OH, —CH$_2$Cl, —CH$_2$F, —CH$_2$Br, —CH$_2$I, —CH$_3$, -halogen (e.g., —Cl), —CH$_2$-(4-F phenyl), OH-substituted C$_1$-C$_3$ alkyl, halogen-substituted C$_1$-C$_3$ alkyl, (C$_1$-C$_3$ alkyl), —(C$_1$-C$_3$ alkyl)-(halogen-substituted phenyl), —(C$_1$-C$_3$ alkyl), unsubstituted phenyl, unsubstituted biphenyl, unsubstituted 5 to 6 membered heteroaryl (e.g., thienyl, furanyl, or pyrrolyl). In embodiments, $R^3$, $R^4$, and $R^{21}$ are as described herein (e.g., each in an embodiment).

In embodiments, the compound is not a compound having the formula:

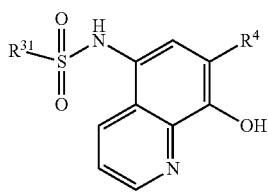

wherein $R^4$ is as described below and $R^{31}$ is hydrogen, —CH$_2$OH, —CH$_2$Cl, —CH$_2$F, —CH$_2$Br, —CH$_2$I, —CH$_3$, -halogen (e.g., —Cl), —CH$_2$-(4-F phenyl), OH-substituted C$_1$-C$_3$ alkyl, halogen-substituted C$_1$-C$_3$ alkyl, (C$_1$-C$_3$ alkyl), —(C$_1$-C$_3$ alkyl)-(halogen-substituted phenyl), —(C$_1$-C$_3$ alkyl), unsubstituted phenyl, unsubstituted biphenyl, unsubstituted 5 to 6 membered heteroaryl (e.g., thienyl, furanyl, or pyrrolyl). In embodiments, $R^4$ and $R^{31}$ are as described herein (e.g., each in an embodiment).

In embodiments, the compound is not a compound having the formula:

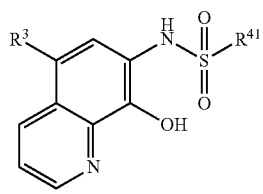

wherein $R^3$ is as described below and $R^{41}$ is hydrogen, —CH$_2$OH, —CH$_2$Cl, —CH$_2$F, —CH$_2$Br, —CH$_2$I, —CH$_3$, -halogen (e.g., —Cl), —CH$_2$-(4-F phenyl), OH-substituted C$_1$-C$_3$ alkyl, halogen-substituted C$_1$-C$_3$ alkyl, (C$_1$-C$_3$ alkyl), —(C$_1$-C$_3$ alkyl)-(halogen-substituted phenyl), —(C$_1$-C$_3$ alkyl), unsubstituted phenyl, unsubstituted biphenyl, unsubstituted 5 to 6 membered heteroaryl (e.g., thienyl, furanyl, or pyrrolyl). In embodiments, $R^3$ and $R^{41}$ are as described herein (e.g., each in an embodiment).

In embodiments, the compound is not raltegravir. In embodiments, the compound is not elvitegravir. In embodiments, the compound is not dolutegravir. In embodiments, the compound is not GS9160. In embodiments, the compound is not PICA. In embodiments, the compound is not RCD-1. In embodiments, the compound is not MK0536. In embodiments, the compound is not MK2048.

In embodiments, the compound is not a compound having the formula:

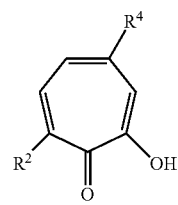

wherein $R^2$ and $R^4$ are as described below.

In embodiments, $R^2$ is hydrogen. In embodiments, $R^2$ is unsubstituted methyl. In embodiments, $R^3$ is unsubstituted ethyl. In embodiments, $R^2$ is unsubstituted C$_1$-C$_3$ alkyl. In embodiments, $R^3$ is —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$. In embodiments, $R^2$ is —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl)-(C$_1$-C$_3$ alkyl-substituted phenyl), —CONH(C$_1$-C$_3$ alkyl), or —CONH$_2$. In embodiments, $R^2$ is —C(O)NHR$^{2.4}$.

In embodiments, $R^3$ is hydrogen. In embodiments, $R^4$ is hydrogen. In embodiments, $R^3$ and $R^4$ are hydrogen. In embodiments, $R^3$ is unsubstituted methyl. In embodiments, $R^3$ is unsubstituted ethyl. In embodiments, $R^3$ is unsubstituted C$_1$-C$_3$ alkyl. In embodiments, $R^3$ is unsubstituted methyl and $R^4$ is hydrogen. In embodiments, $R^3$ is unsubstituted ethyl and $R^4$ is hydrogen. In embodiments, $R^3$ is unsubstituted C$_1$-C$_3$ alkyl and $R^4$ is hydrogen. In embodiments, $R^4$ is unsubstituted methyl. In embodiments, $R^4$ is unsubstituted ethyl. In embodiments, $R^4$ is unsubstituted C$_1$-C$_3$ alkyl. In embodiments, $R^4$ is unsubstituted methyl and $R^3$ is hydrogen. In embodiments, $R^4$ is unsubstituted ethyl and $R^3$ is hydrogen. In embodiments, $R^4$ is unsubstituted isopropyl and $R^3$ is hydrogen. In embodiments, $R^4$ is unsubstituted C$_1$-C$_3$ alkyl and $R^3$ is hydrogen. In embodiments, $R^3$ is —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$. In embodiments, R$^3$ is —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CSNHCH$_2$-(4-F phenyl), —CONHCH$_2$-(4-methyl phenyl), —CSNHCH$_2$-(4-methyl phenyl), —CONHCH$_3$, or —CONH$_2$ and R$^4$ is hydrogen.

In embodiments, R$^3$ is —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$ and R$^4$ is hydrogen, —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$. In embodiments, R$^4$ is —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$. In embodiments, R$^4$ is —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$ and R$^3$ is hydrogen. In embodiments, R$^4$ is —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$ and R$^3$ is hydrogen, —COOH, —CH$_2$OH, —CH$_2$Cl, —CH$_2$F, —CH$_2$Br, —CH$_2$I, —CH$_3$, —OH, halogen (e.g., —Cl), —CONHCH$_2$-(4-F phenyl), —CONHCH$_3$, or —CONH$_2$. In embodiments, R$^3$ is —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), —CONH(C$_1$-C$_3$ alkyl)-(C$_1$-C$_3$ alkyl-substituted phenyl), —CONH(C$_1$-C$_3$ alkyl), or —CONH$_2$. In embodiments, R$^3$ is —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), or —CONH$_2$ and R$^4$ is hydrogen. In embodiments, R$^3$ is —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), or —CONH$_2$ and R$^4$ is hydrogen, —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), or —CONH$_2$. In embodiments, R$^4$ is —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), —CONH(C$_1$-C$_3$ alkyl)-(C$_1$-C$_3$ alkyl-substituted phenyl), —CONH(C$_1$-C$_3$ alkyl), or —CONH$_2$. In embodiments, R$^4$ is —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), or —CONH$_2$ and R$^3$ is hydrogen. In embodiments, R$^4$ is —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), or —CONH$_2$ and R$^3$ is hydrogen, —COOH, OH-substituted C$_1$-C$_3$ alkyl, halogen-substituted C$_1$-C$_3$ alkyl, (C$_1$-C$_3$ alkyl), —OH, halogen (e.g., —Cl), —CONH(C$_1$-C$_3$ alkyl)-(halogen-substituted phenyl), —CONH(C$_1$-C$_3$ alkyl), or —CONH$_2$. In embodiments, R$^3$ is as described herein. In embodiments, R$^4$ is as described herein. In embodiments, R$^3$ is —C(O)NHR$^{3A}$. In embodiments, R$^4$ is —C(O)NHR$^{4A}$.

In embodiments, the compound has the formula:

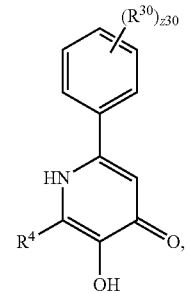

wherein R$^4$ and R$^{30}$ are as described herein. The symbol z30 is an integer from 0 to 5. In embodiments, z30 is 0. In embodiments, z30 is 1. In embodiments, z30 is 2. In embodiments, z30 is 3. In embodiments, z30 is 4. In embodiments, z30 is 5.

In embodiments, the compound has the formula:

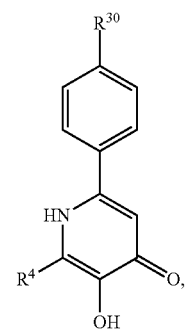

wherein R$^4$ and R$^{30}$ are as described herein.

In embodiments, the compound has the formula:

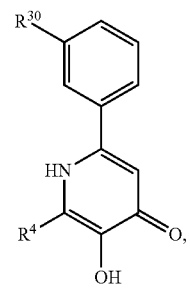

wherein R$^4$ and R$^{30}$ are as described herein.

In embodiments, the compound has the formula:

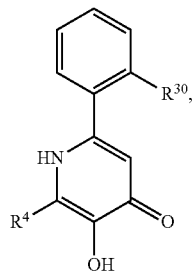

wherein $R^4$ and $R^{30}$ are as described herein.

In embodiments, the compound has the formula:

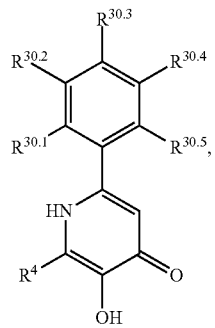

wherein $R^4$ is as described herein. $R^{30.1}$, $R^{30.2}$, $R^{30.3}$, $R^{30.4}$, and $R^{30.5}$ are each $R^{30}$ at a fixed position on the attached ring. $R^{30.1}$, $R^{30.2}$, $R^{30.3}$, $R^{30.4}$, and $R^{30.5}$ may be hydrogen or any substituent of $R^{30}$ described herein, including in any aspect, embodiment, example, figure, or claim. In embodiments, $R^{30.1}$, $R^{30.2}$, $R^{30.3}$, $R^{30.4}$, and $R^{30.5}$ may be hydrogen.

In embodiments, the compound has the formula:

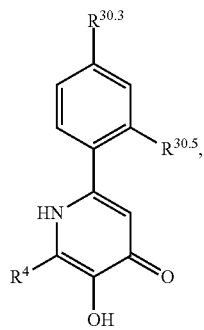

wherein $R^{30.3}$, $R^{30.5}$ and $R^4$ are as described herein, including embodiments.

In embodiments, $R^{30}$ is $R^{30}$-substituted or unsubstituted alkyl (e.g., $C_1$-$C_8$ alkyl, $C_1$-$C_6$ alkyl, or $C_1$-$C_4$ alkyl). In embodiments, $R^{30}$ is $R^{30}$-substituted alkyl (e.g., $C_1$-$C_8$ alkyl, $C_1$-$C_6$ alkyl, or $C_1$-$C_4$ alkyl). In embodiments, $R^{30}$ is an unsubstituted alkyl (e.g., $C_1$-$C_8$ alkyl, $C_1$-$C_6$ alkyl, or $C_1$-$C_4$ alkyl).

In embodiments, $R^{30}$ is $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^{30}$ is $R^{30}$-substituted heteroalkyl (e.g., 2 to 8 membered heteroalkyl, 2 to 6 membered heteroalkyl, or 2 to 4 membered heteroalkyl). In embodiments, $R^{30}$ is an unsubstituted heteroalkyl (e.g., 2 to 8 membered heteroalkyl, 2 to 6 membered heteroalkyl, or 2 to 4 membered heteroalkyl).

In embodiments, $R^{30}$ is $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{30}$ is $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{30}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{30}$ is $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{30}$ is $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{30}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{30}$ is $R^{30}$-substituted or unsubstituted aryl (e.g., $C_6$-$C_{10}$ aryl, $C_{10}$ aryl, or phenyl). In embodiments, $R^{30}$ is $R^{30}$-substituted aryl (e.g., $C_6$-$C_{10}$ aryl, $C_{10}$ aryl, or phenyl). In embodiments, $R^{30}$ is an unsubstituted aryl (e.g., $C_6$-$C_{10}$ aryl, $C_{10}$ aryl, or phenyl).

In embodiments, $R^{30}$ is $R^{30}$-substituted or unsubstituted heteroaryl (e.g., 5 to 10 membered heteroaryl, 5 to 9 membered heteroaryl, or 5 to 6 membered heteroaryl). In embodiments, $R^{30}$ is $R^{30}$-substituted heteroaryl (e.g., 5 to 10 membered heteroaryl, 5 to 9 membered heteroaryl, or 5 to 6 membered heteroaryl). In embodiments, $R^{30}$ is an unsubstituted heteroaryl (e.g., 5 to 10 membered heteroaryl, 5 to 9 membered heteroaryl, or 5 to 6 membered heteroaryl).

In embodiments, $R^{30}$ is

—$CH_3$, —$CH_2CH_3$, —$CH_2CH_2H_3$, unsubstituted $C_1$-$C_6$ alkyl, —$OCH_3$, —$SCH_3$, —COOH, wherein $R^{31}$ is as described herein. In embodiments, $R^{30}$ is —$CX^{30}{}_3$, —$CHX^{30}{}_2$, —$CH_2X^{30}$, —$OCX^{30}{}_3$, —$OCH_2X^{30}$, or —$OCHX^{30}{}_2$. In embodiments, $R^{30}$ is an unsubstituted methyl. In embodiments, $R^{30}$ is an unsubstituted $C_2$ alkyl. In embodiments, $R^{30}$ is an unsubstituted $C_3$ alkyl. In embodiments, $R^{30}$ is an unsubstituted $C_4$ alkyl. In embodiments, $R^{30}$ is an unsubstituted $C_5$ alkyl. In embodiments, $R^{30}$ is an unsubstituted $C_6$ alkyl. In embodiments, $R^{30}$ is an unsubstituted $C_7$ alkyl. In embodiments, $R^{30}$ is an unsubstituted $C_8$ alkyl.

In embodiments, $R^3$ is methyl. In embodiments, $R^3$ is unsubstituted isopropyl. In embodiments, $R^3$ is —OH. In embodiments, $R^3$ is unsubstituted phenyl. In embodiments, $R^3$ is

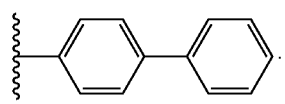 [SMILES: *c1ccc(-c2ccccc2)cc1]

In embodiments, $R^3$ is

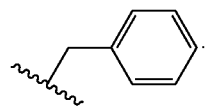

In embodiments, $R^3$ is

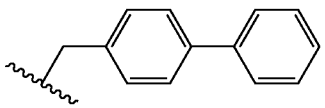

In embodiments, $R^3$ is

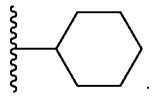

In embodiments, $R^3$ is

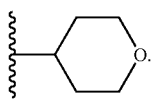

In embodiments, $R^3$ is

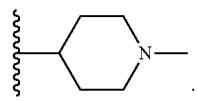

In embodiments, $R^3$ is

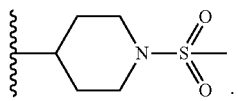

In embodiments, $R^3$ is

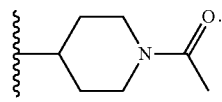

In embodiments, $R^3$ is

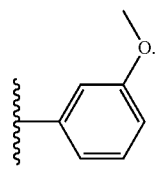

In embodiments, $R^3$ is

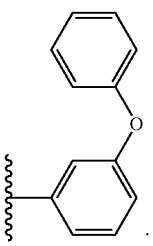 [SMILES: *c1cccc(Oc2ccccc2)c1]

In embodiments, $R^3$ is

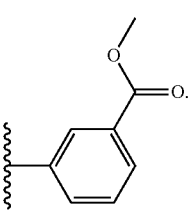 [SMILES: *c1cccc(C(=O)OC)c1]

In embodiments, $R^3$ is

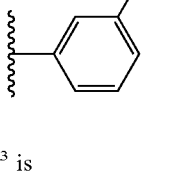

In embodiments, $R^3$ is

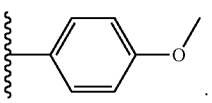

In embodiments, R³ is

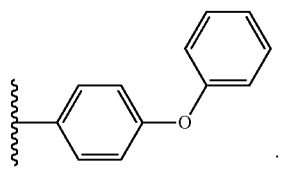 [SMILES: *c1ccc(Oc2ccccc2)cc1]

In embodiments, R³ is

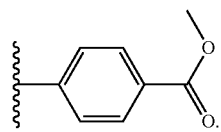

In embodiments, R³ is

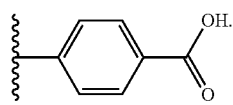 [SMILES: *c1ccc(C(=O)O)cc1]

In embodiments, R³ is

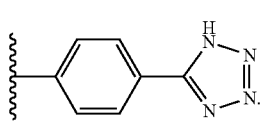

In embodiments, R³ is

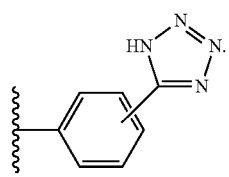

In embodiments, R³ is

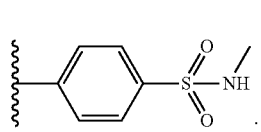 [SMILES: *c1ccc(S(=O)(=O)NC)cc1]

In embodiments, R³ is

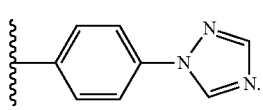

In embodiments, R³ is

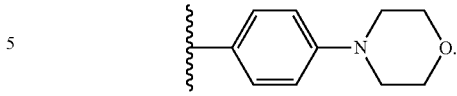

In embodiments, $R^{30}$ is unsubstituted phenyl. In embodiments, $R^{30}$ is —COOH. In embodiments, $R^{30}$ is —S(O)$_2$CH$_3$. In embodiments, $R^{30}$ is —OCH$_3$. In embodiments, $R^{30}$ is —COCH$_3$. In embodiments, $R^{30}$ is

In embodiments, $R^{30}$ is —C(O)OCH$_3$. In embodiments, $R^{30}$ is —S(O)$_2$NHCH$_3$. In embodiments, $R^{30}$ is

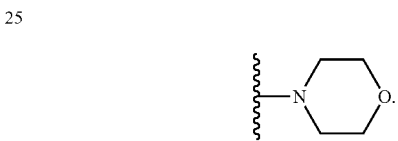

In embodiments, $R^{30}$ is

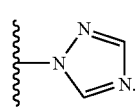

In embodiments, $R^{30}$ is

In embodiments, the compound is:

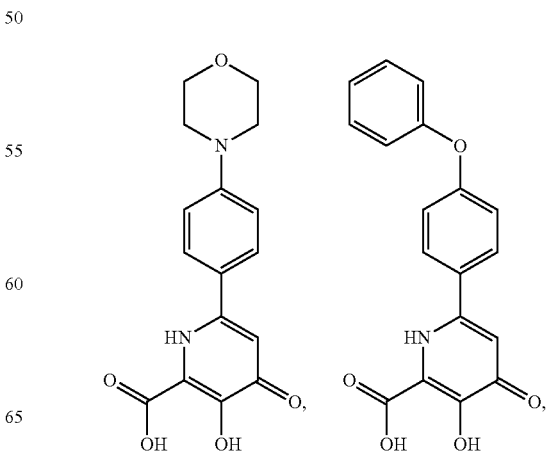

-continued
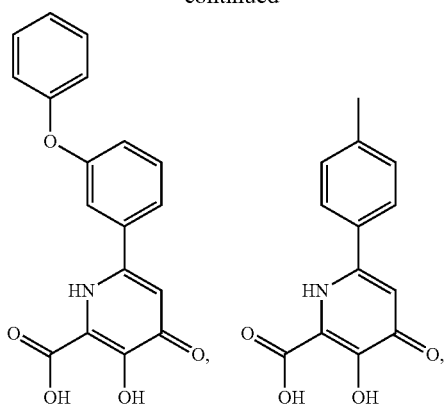
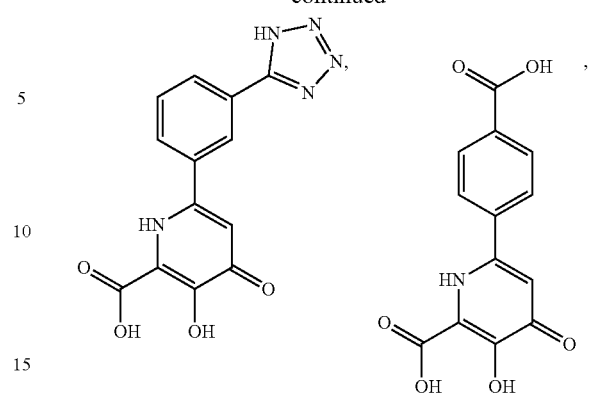
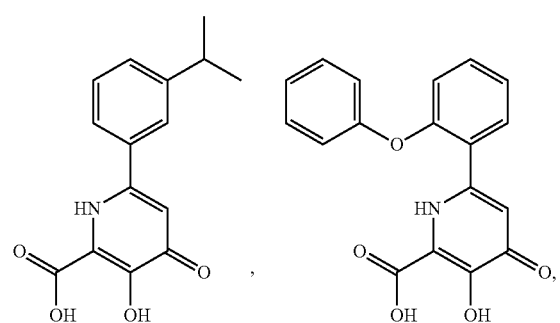
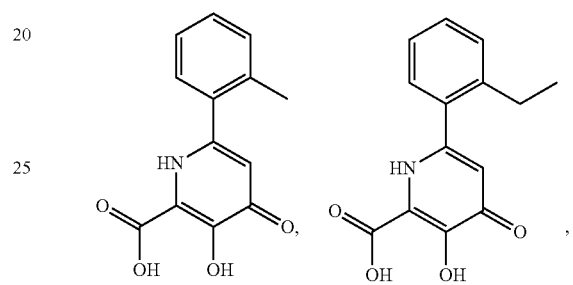
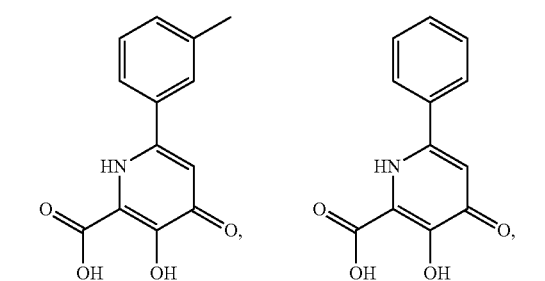
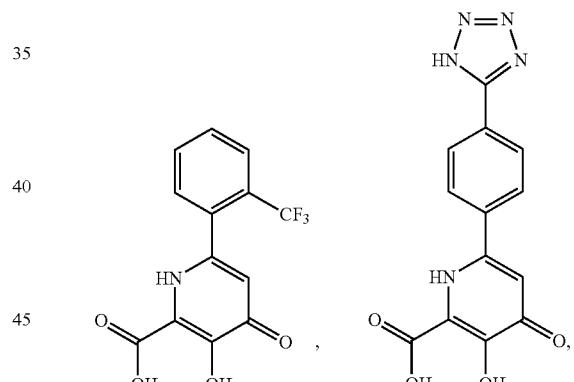
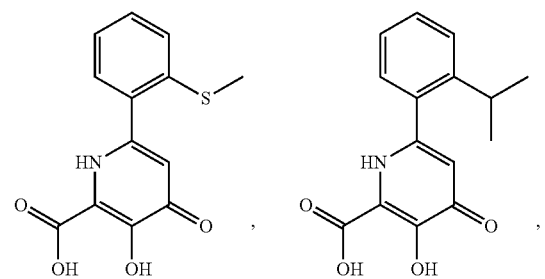
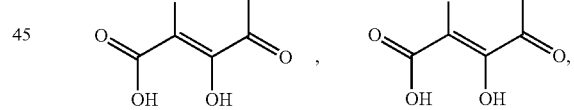
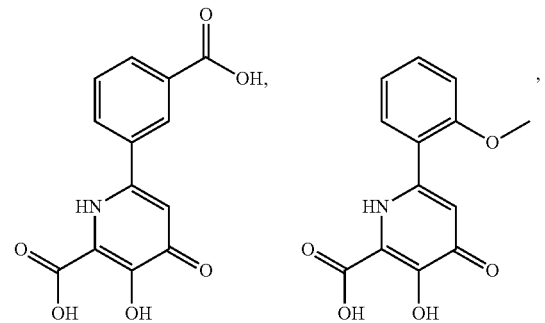
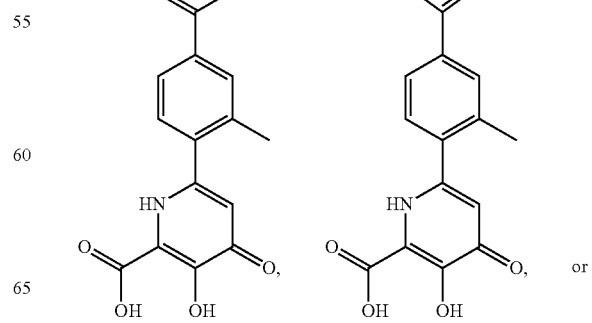
or

127

-continued

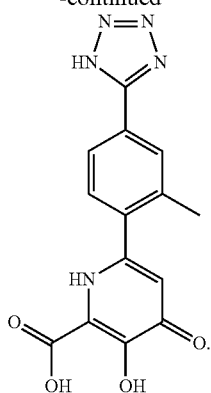

In embodiments, the compound has the formula:

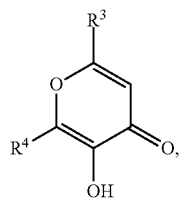

wherein $R^3$ and $R^4$ are as described herein, including embodiments.

In embodiments, the compound has the formula:

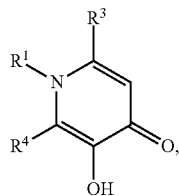

wherein $R^1$, $R^3$, and $R^4$ are as described herein, including embodiments.

In embodiments, the compound has the formula:

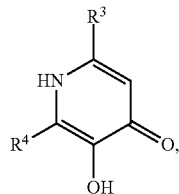

wherein $R^1$, $R^3$, and $R^4$ are as described herein, including embodiments.

128

In embodiments, the compound has the formula:

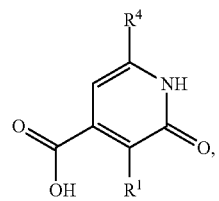

wherein $R^1$ and $R^4$ are as described herein, including embodiments.

In embodiments, the compound is not a compound having the formula:

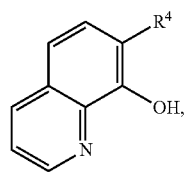

wherein $R^4$ is as described herein, including embodiments.

In embodiments, the compound is:

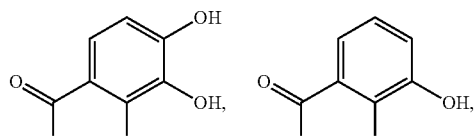

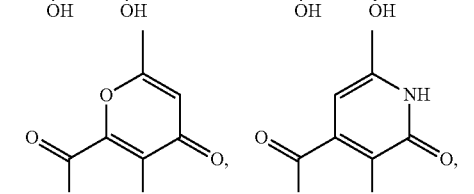

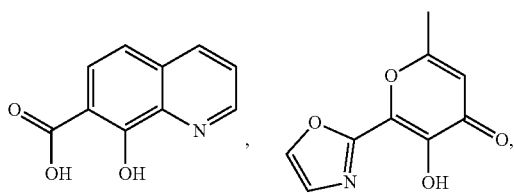

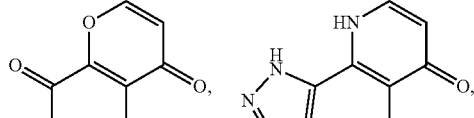

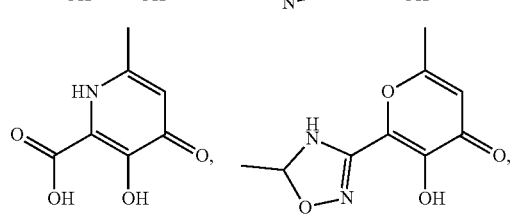

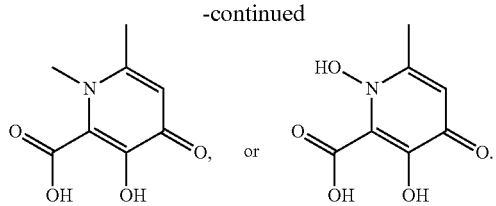
In embodiments, the compound is not a compound having the formula:
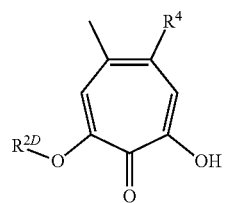
wherein $R^{2D}$ and $R^4$ are as described herein.
In embodiments, the compound is:
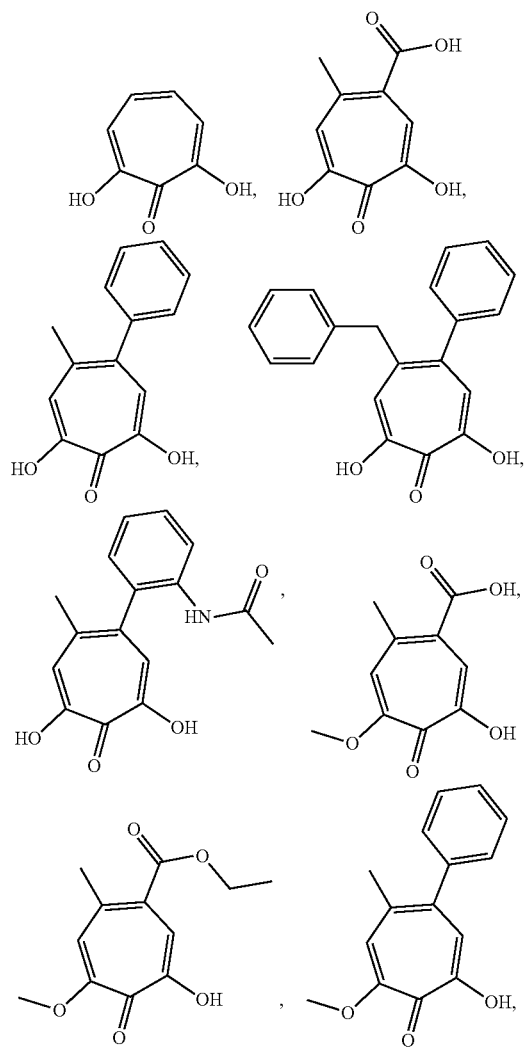
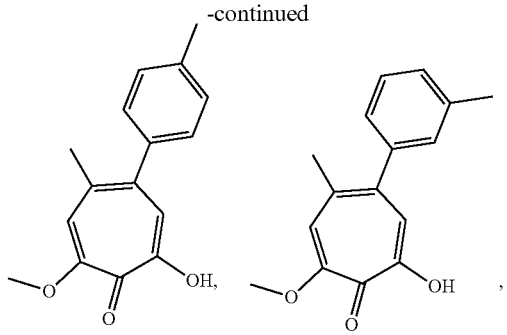
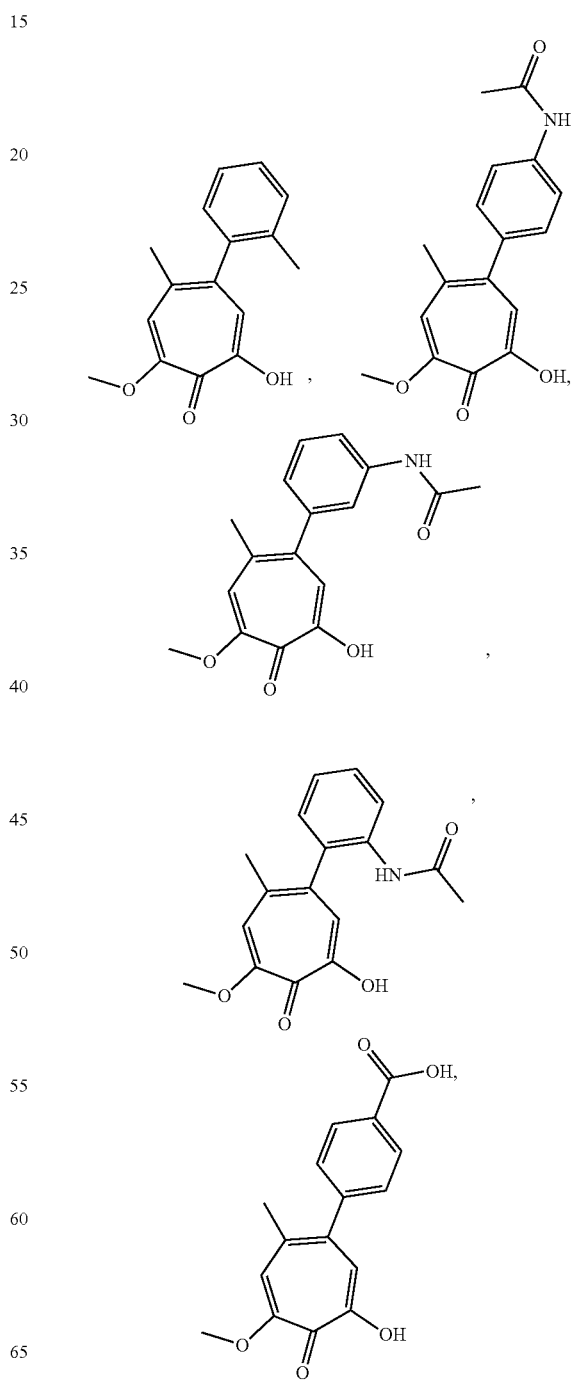

-continued
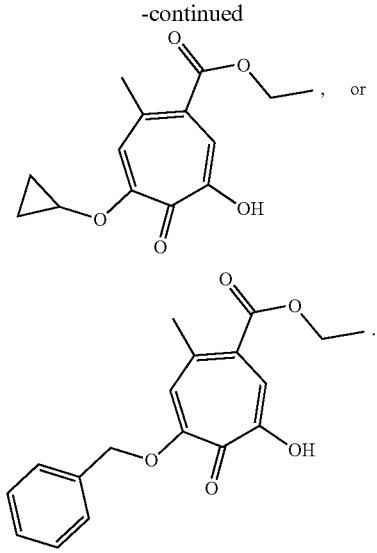, or
In embodiments, the compound is:
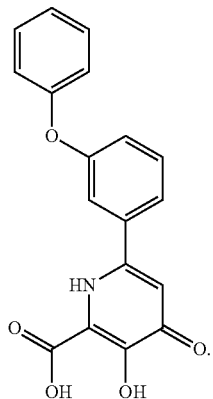
In embodiments, the compound is:
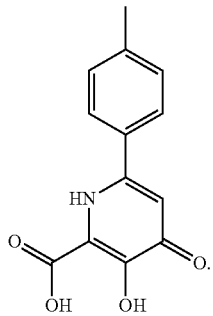
In embodiments, the compound is:
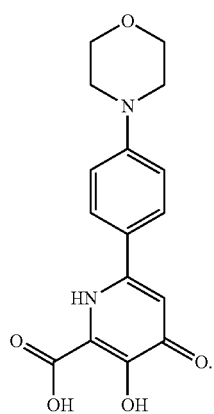 [SMILES: O=C(O)c1[nH]c(-c2ccc(N3CCOCC3)cc2)cc(=O)c1O]
In embodiments, the compound is:
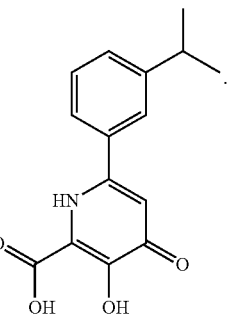
In embodiments, the compound is:
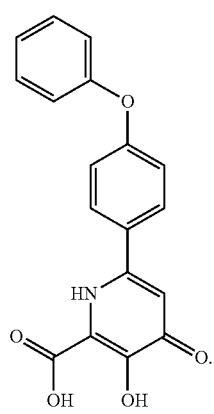 [SMILES: O=C(O)c1[nH]c(-c2ccc(Oc3ccccc3)cc2)cc(=O)c1O]
In embodiments, the compound is:
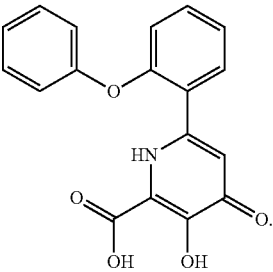 [SMILES: O=C(O)c1[nH]c(-c2ccccc2Oc2ccccc2)cc(=O)c1O]

In embodiments, the compound is:
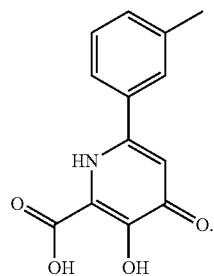 [SMILES: Cc1cccc(-c2cc(=O)c(O)c(C(=O)O)[nH]2)c1]
In embodiments, the compound is:
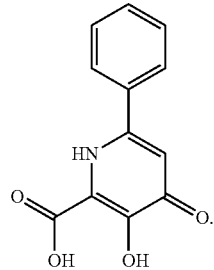 [SMILES: O=C(O)c1[nH]c(-c2ccccc2)cc(=O)c1O]
In embodiments, the compound is:
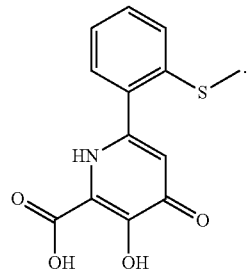 [SMILES: CSc1ccccc1-c1cc(=O)c(O)c(C(=O)O)[nH]1]
In embodiments, the compound is:
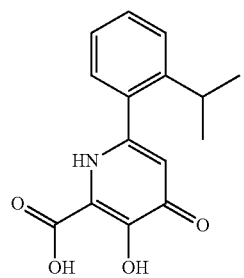
In embodiments, the compound is:
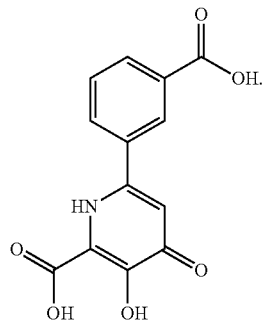 [SMILES: O=C(O)c1cccc(-c2cc(=O)c(O)c(C(=O)O)[nH]2)c1]
In embodiments, the compound is:
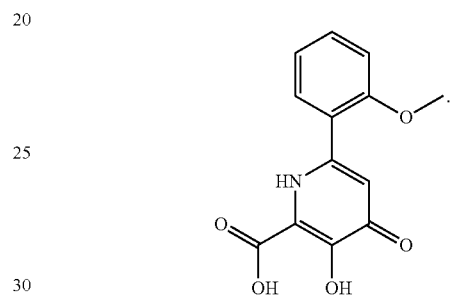
In embodiments, the compound is
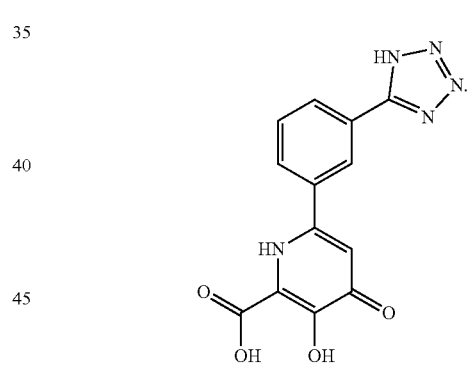
In embodiments, the compound is:
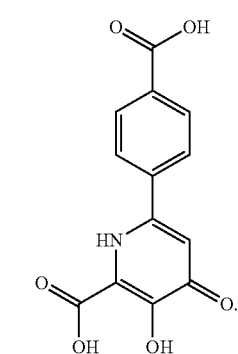 [SMILES: O=C(O)c1ccc(-c2cc(=O)c(O)c(C(=O)O)[nH]2)cc1]

In embodiments, the compound is:
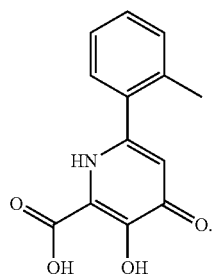 [SMILES: Cc1ccccc1-c1cc(=O)c(O)c(C(=O)O)[nH]1]
In embodiments, the compound is:
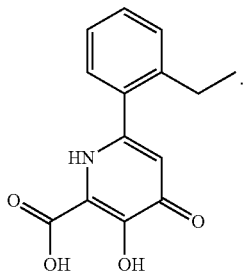
In embodiments, the compound is:
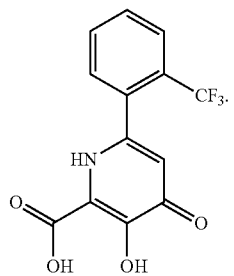 [SMILES: O=C(O)c1[nH]c(-c2ccccc2C(F)(F)F)cc(=O)c1O]
In embodiments, the compound is:
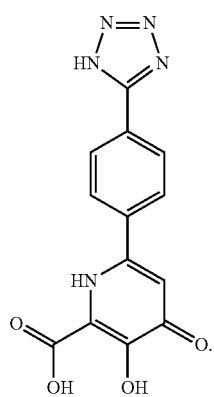
In embodiments, the compound is:
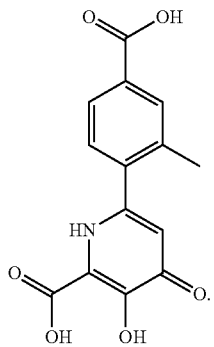
In embodiments, the compound is:
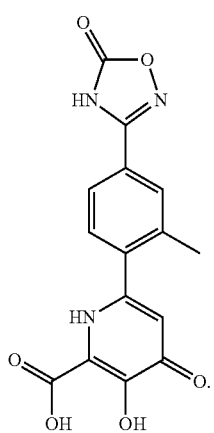 [SMILES: Cc1cc(-c2noc(=O)[nH]2)ccc1-c1cc(=O)c(O)c(C(=O)O)[nH]1]
In embodiments, the compound is:
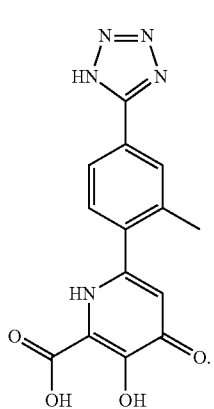 [SMILES: Cc1cc(-c2nnn[nH]2)ccc1-c1cc(=O)c(O)c(C(=O)O)[nH]1]
In embodiments, the compound is:
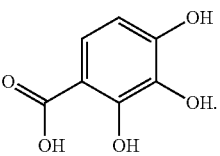 [SMILES: O=C(O)c1ccc(O)c(O)c1O]

In embodiments, the compound is:

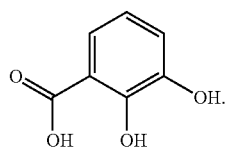

In embodiments, the compound is:

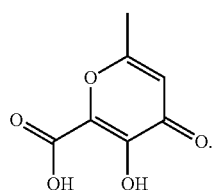

In embodiments, the compound is:

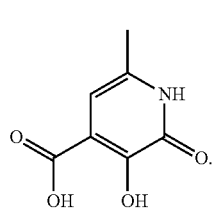

In embodiments, the compound is:

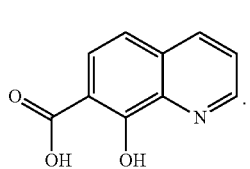 [SMILES: O=C(O)c1ccc2cccnc2c1O]

In embodiments, the compound is:

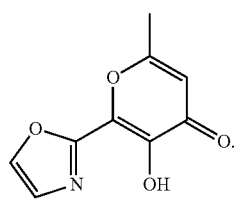

In embodiments, the compound is:

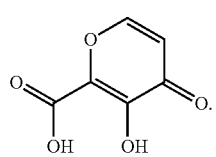 [SMILES: O=C(O)c1occc(=O)c1O]

In embodiments, the compound is:

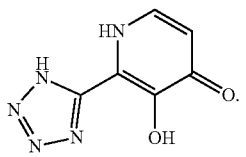 [SMILES: O=c1cc[nH]c(-c2nnn[nH]2)c1O]

In embodiments, the compound is:

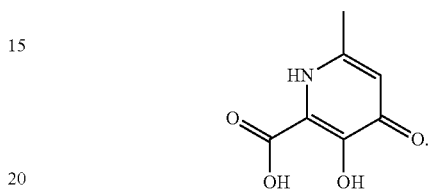

In embodiments, the compound is:

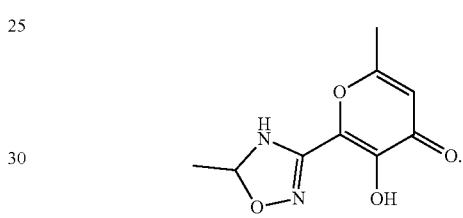

In embodiments, the compound is:

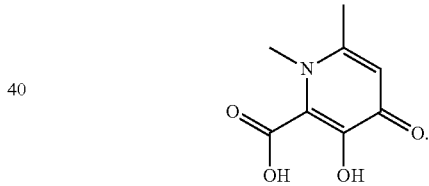

In embodiments, the compound is:

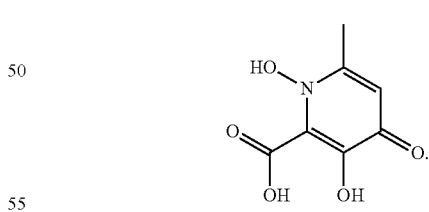

In embodiments, the compound is:

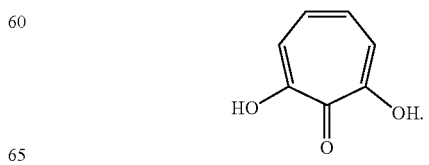

In embodiments, the compound is:
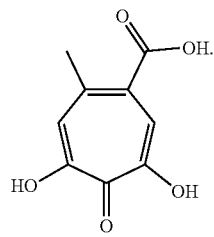
In embodiments, the compound is:
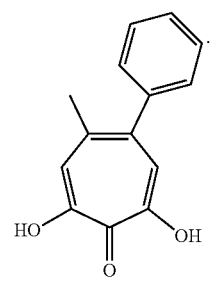
In embodiments, the compound is:
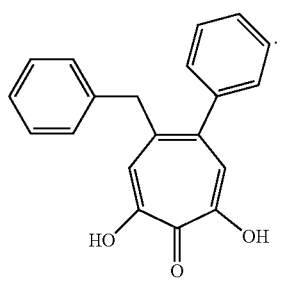 [SMILES: O=c1c(O)cc(Cc2ccccc2)c(-c2ccccc2)cc1O]
In embodiments, the compound is:
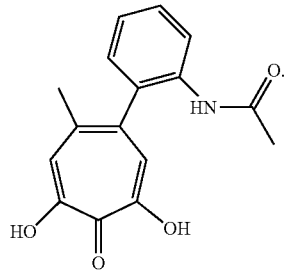 [SMILES: CC(=O)Nc1ccccc1-c1cc(O)c(=O)c(O)cc1C]
In embodiments, the compound is:
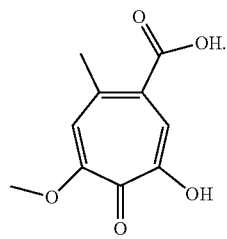
In embodiments, the compound is:
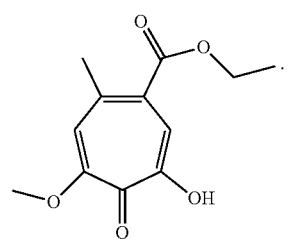 [SMILES: CCOC(=O)c1cc(O)c(=O)c(OC)cc1C]
In embodiments, the compound is:
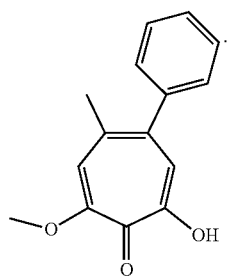 [SMILES: COc1cc(C)c(-c2ccccc2)cc(O)c1=O]
In embodiments, the compound is:
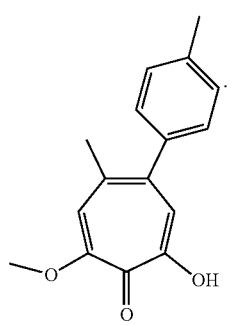 [SMILES: COc1cc(C)c(-c2ccc(C)cc2)cc(O)c1=O]

In embodiments, the compound is:

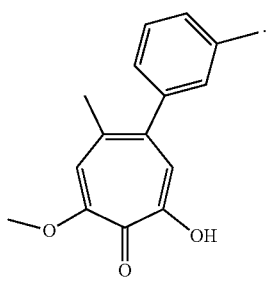

In embodiments, the compound is:

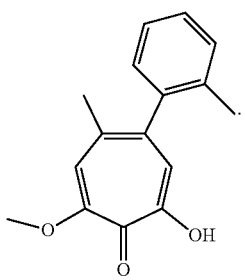

In embodiments, the compound is:

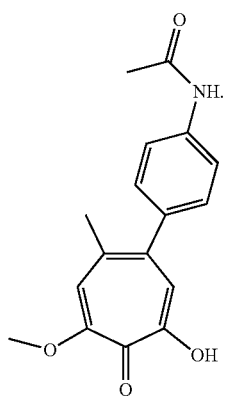 [SMILES: COc1cc(C)c(-c2ccc(NC(C)=O)cc2)cc(O)c1=O]

In embodiments, the compound is:

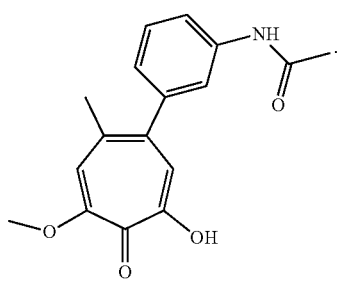 [SMILES: COc1cc(C)c(-c2cccc(NC(C)=O)c2)cc(O)c1=O]

In embodiments, the compound is:

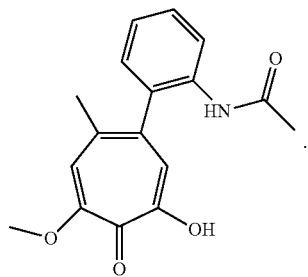 [SMILES: COc1cc(C)c(-c2ccccc2NC(C)=O)cc(O)c1=O]

In embodiments, the compound is:

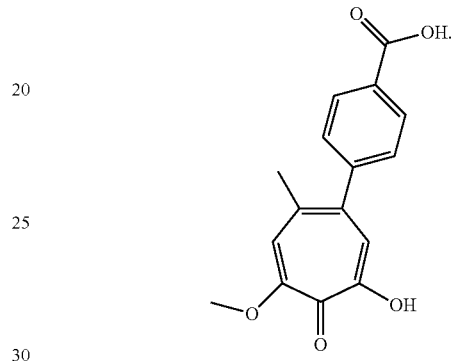

In embodiments, the compound is:

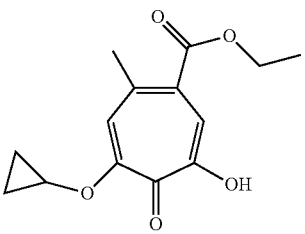

In embodiments, the compound is

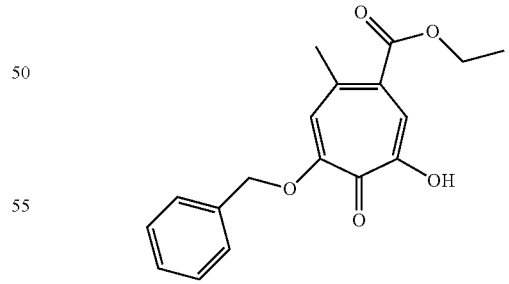

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating a viral infection. In embodiments of the pharmaceutical compositions, the second agent is an agent for treating an influenza infection. In embodiments of the pharmaceutical compositions, the second agent is an agent for treating an influenza A infection. In embodiments, the second agent is an anti-viral agent. In embodiments, the second agent is an anti-viral neuraminidase inhibitor selected from the group consisting of Oseltamivir, Zanamivir, Laninamivir, and Peramivir. In embodiments, the second agent is an anti-influenza agent. In embodiments, the second agent is an anti-influenza A agent. In embodiments, the anti-viral agent is a neuraminidase inhibitor selected from the group consisting of Oseltamivir, Zanamivir, Laninamivir, and Peramivir. In embodiments, the neuraminidase inhibitor is Oseltamivir. In embodiments, the neuraminidase inhibitor is Zanamivir. In embodiments, the antivial agent is a viral M2 protein inhibitor selected from the group consisting of Amantadine, Rimantadine, and Adapromine. In embodiments, the viral M2 protein inhibitor is Amantadine. In embodiments, the viral M2 protein inhibitor is Rimantadine.

IV. Methods of Treatment

In an aspect is provided a method of treating a viral infection associated with RNA-dependent RNA polymerase PA subunit endonuclease protein activity including administering to a subject in need thereof an effective amount of a compound described herein. In embodiments, the compound is included in a therapeutically effective amount. In embodiments, the viral infection is an influenza infection. In embodiments, the viral infection is an influenza A infection.

In an aspect is provided a method of treating an influenza virus infection including administering to a subject in need thereof an effective amount of a compound described herein. In embodiments, the viral infection is an influenza virus A infection.

In an aspect is provided a method of treating an influenza virus A infection including administering to a subject in need thereof an effective amount of a compound described herein.

In embodiments, the method includes administering a second agent (e.g. therapeutic agent). In embodiments, the method includes administering a second agent (e.g. therapeutic agent) in a therapeutically effective amount. In embodiments, the second agent is an agent for treating a viral infection. In embodiments, the second agent is an agent for treating an influenza infection. In embodiments, the second agent is an agent for treating an influenza A infection. In embodiments, the second agent is an anti-viral agent. In embodiments, the second agent is an anti-influenza agent. In embodiments, the second agent is an anti-influenza A agent. In embodiments, the anti-viral agent is a neuraminidase inhibitor selected from the group consisting of Oseltamivir, Zanamivir, Laninamivir, and Peramivir. In embodiments, the neuraminidase inhibitor is Oseltamivir. In embodiments, the neuraminidase inhibitor is Zanamivir. In embodiments, the antivial agent is a viral M2 protein inhibitor selected from the group consisting of Amantadine, Rimantadine, and Adapromine. In embodiments, the viral M2 protein inhibitor is Amantadine. In embodiments, the viral M2 protein inhibitor is Rimantadine.

V. Methods of Inhibition

In an aspect is provided a method of inhibiting RNA-dependent RNA polymerase PA subunit endonuclease protein activity including contacting the RNA-dependent RNA polymerase PA subunit endonuclease protein with an effective amount of a compound described herein. In embodiments, the RNA polymerase PA subunit endonuclease protein is an influenza virus (e.g., influenza virus type A) RNA polymerase PA subunit endonuclease. In embodiments, compound is provided in a therapeutically effective amount. In embodiments, the method includes contacting the the RNA-dependent RNA polymerase PA subunit endonuclease protein with an effective amount of a compound described herein.

In an aspect is provided a method of inhibiting an RNA-dependent RNA polymerase including an RNA-dependent RNA polymerase PA subunit endonuclease protein activity wherein the method includes contacting the RNA-dependent RNA polymerase (e.g., the RNA-dependent RNA polymerase PA subunit endonuclease included in the RNA-dependent RNA polymerase) protein with an effective amount of a compound described herein. In embodiments, the RNA-dependent RNA polymerase protein is an influenza virus (e.g., influenza virus type A) RNA-dependent RNA polymerase. In embodiments, compound is provided in a therapeutically effective amount. In embodiments, the method includes contacting the the RNA-dependent RNA polymerase (e.g. the included RNA-dependent RNA polymerase PA subunit endonuclease) protein with an effective amount of a compound described herein.

In embodiments, the compound contacts one or two divalent metal cations (e.g., $Mn^{2+}$ or $Mg^{2+}$) in an RNA-dependent RNA polymerase PA subunit endonuclease (e.g., influenza virus or influenza virus type A) and/or one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound contacts one or two divalent metal cations (e.g., $Mn^{2+}$ or $Mg^{2+}$) in RNA-dependent RNA polymerase PA subunit endonuclease (e.g., influenza virus or influenza virus type A) and one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound contacts one or two divalent $Mn^{2+}$ cations in RNA-dependent RNA polymerase PA subunit endonuclease (e.g., influenza virus or influenza virus type A), and/or one or more amino acids corresponding to Arg82, Lys34, Arg124, Lys24, and Tyr24 of influenza virus (e.g., influenza virus type A) RNA-dependent RNA polymerase PA subunit endonuclease. In embodiments, the compound contacts one or two divalent $Mn^{2+}$ cations in RNA-dependent RNA polymerase PA subunit endonuclease (e.g., influenza virus or influenza virus type A) and one or more amino acids corresponding to Arg82, Lys34, Arg124, Lys24, and Tyr24 of influenza virus (e.g., influenza virus type A) RNA-dependent RNA polymerase PA subunit endonuclease. In embodiments, compound contacts two divalent $Mn^{2+}$ cations in RNA-dependent RNA polymerase PA subunit endonuclease (e.g., influenza virus or influenza virus type A), and/or one or more amino acids corresponding to Arg82, Lys34, Arg124, Lys24, and Tyr24 of influenza virus (e.g., influenza virus type A) RNA-dependent RNA polymerase PA subunit endonuclease. In embodiments, compound contacts two divalent $Mn^{2+}$ cations in RNA-dependent RNA polymerase PA subunit endonuclease (e.g., influenza virus or influenza virus type A) and one or more amino acids corresponding to Arg82, Lys34, Arg124, Lys24, and Tyr24 of influenza virus (e.g., influenza virus type A) RNA-dependent RNA polymerase PA subunit endonuclease. In embodiments, compound contacts one or two divalent metal cations (e.g., $Mn^{2+}$ or $Mg^{2+}$) in RNA-dependent RNA polymerase PA subunit endonuclease (e.g., influenza virus or influenza virus type A). In embodiments, compound contacts two divalent metal cations (e.g., $Mn^{2+}$ or $Mg^{2+}$) in RNA-dependent RNA polymerase PA subunit endonuclease (e.g., influenza virus or influenza virus type A). In embodiments, compound contacts one or two divalent $Mn^{2+}$ cations in RNA-dependent RNA polymerase PA subunit endonuclease (e.g., influenza virus or influenza virus type A). In embodiments, compound contacts one divalent $Mn^{2+}$ cation in RNA-dependent RNA polymerase PA subunit endonuclease (e.g., influenza virus or influenza virus type A). In embodiments, compound contacts two divalent $Mn^{2+}$ cations in RNA-dependent RNA polymerase PA subunit endonuclease (e.g., influenza virus or influenza virus type A In embodiments, compound contacts one or more amino acids corresponding to Arg82, Lys34, Arg124, Lys24, and Tyr24 of influenza virus (e.g., influenza virus type A) RNA-dependent RNA polymerase PA subunit endonuclease. In embodiments, compound contacts one or more amino acids corresponding to Arg82, Lys34, Arg124, and Lys24 of influenza virus (e.g., influenza virus type A) RNA-dependent RNA polymerase PA subunit endonuclease. In embodiments, compound contacts one or two divalent $Mn^{2+}$ cations in influenza virus (e.g., influenza virus type A) RNA-dependent RNA polymerase PA subunit endonuclease and an amino acid corresponding to Arg82, Lys34, Arg124, Lys24, and Tyr24 of influenza virus (e.g., influenza virus type A) RNA-dependent RNA polymerase PA subunit endonuclease. In embodiments, compound contacts two divalent $Mn^{2+}$ cations in RNA-dependent RNA polymerase PA subunit endonuclease (e.g., influenza virus or influenza virus type A) and an amino acid corresponding to Arg82, Lys34, Arg124, Lys24, and Tyr24 of influenza virus (e.g., influenza virus type A) RNA-dependent RNA polymerase PA subunit endonuclease. In embodiments, In embodiments, compound contacts an amino acid corresponding to Arg82, Lys34, Arg124, Lys24, and Tyr24 of influenza virus (e.g., influenza virus type A) RNA-dependent RNA polymerase PA subunit endonuclease. In embodiments, In embodiments, compound contacts an amino acid corresponding to Arg82, Lys34, Arg124, and Lys24 of influenza virus (e.g., influenza virus type A) RNA-dependent RNA polymerase PA subunit endonuclease. In embodiments, compound contacts two divalent $Mn^{2+}$ cations in RNA-dependent RNA polymerase PA subunit endonuclease (e.g., influenza virus or influenza virus type A) and an amino acid corresponding to Arg82 of influenza virus (e.g., influenza virus type A) RNA-dependent RNA polymerase PA subunit endonuclease. In embodiments, compound contacts two divalent $Mn^{2+}$ cations in RNA-dependent RNA polymerase PA subunit endonuclease (e.g., influenza virus or influenza virus type A) and an amino acid corresponding to Lys34 of influenza virus (e.g., influenza virus type A) RNA-dependent RNA polymerase PA subunit endonuclease. In embodiments, compound contacts two divalent $Mn^{2+}$ cations in RNA-dependent RNA polymerase PA subunit endonuclease (e.g., influenza virus or influenza virus type A) and an amino acid corresponding to Lys24 of influenza virus (e.g., influenza virus type A) RNA-dependent RNA polymerase PA subunit endonuclease. In embodiments, compound contacts two divalent $Mn^{2+}$ cations in RNA-dependent RNA polymerase PA subunit endonuclease (e.g., influenza virus or influenza virus type A) and an amino acid corresponding to Tyr24 of influenza virus (e.g., influenza virus type A) RNA-dependent RNA polymerase PA subunit endonuclease. In embodiments, compound contacts one divalent $Mn^{2+}$ cation in RNA-dependent RNA polymerase PA subunit endonuclease (e.g., influenza virus or influenza virus type A) and an amino acid corresponding to Arg82 of influenza virus (e.g., influenza virus type A) RNA-dependent RNA polymerase PA subunit endonuclease. In embodiments, compound contacts one divalent $Mn^{2+}$ cation in RNA-dependent RNA polymerase PA subunit endonuclease (e.g., influenza virus or influenza virus type A) and an amino acid corresponding to Lys34 of influenza virus (e.g., influenza virus type A) RNA-dependent RNA polymerase PA subunit endonuclease. In embodiments, compound contacts one divalent $Mn^{2+}$ cation in RNA-dependent RNA polymerase PA subunit endonuclease (e.g., influenza virus or influenza virus type A) and an amino acid corresponding to Lys24, of influenza virus (e.g., influenza virus type A) RNA-dependent RNA polymerase PA subunit endonuclease. In embodiments, compound contacts one divalent $Mn^{2+}$ cation in RNA-dependent RNA polymerase PA subunit endonuclease (e.g., influenza virus or influenza virus type A) and an amino acid corresponding to Tyr24 of influenza virus (e.g., influenza virus type A) RNA-dependent RNA polymerase PA subunit endonuclease. In embodiments, compound contacts an amino acid corresponding to Arg82 of influenza virus (e.g., influenza virus type A) RNA-dependent RNA polymerase PA subunit endonuclease. In embodiments, compound contacts an amino acid corresponding to Lys34 of influenza virus (e.g., influenza virus type A) RNA-dependent RNA polymerase PA subunit endonuclease. In embodiments, compound contacts an amino acid corresponding to Arg124 influenza virus (e.g., influenza virus type A) RNA-dependent RNA polymerase PA subunit endonuclease. In embodiments, compound contacts an amino acid corresponding to Tyr24 of influenza virus (e.g., influenza virus type A) RNA-dependent RNA polymerase PA subunit endonuclease.

In embodiments, the inhibition is competitive inhibition. In embodiments, the inhibition is irreversible. In embodiments, the inhibition is reversible. In embodiments, the compound chelates to the two divalent $Mn^{2+}$ cations in influenza virus (e.g., influenza virus type A) RNA-dependent RNA polymerase PA subunit endonuclease.

In embodiments, the RNA-dependent RNA polymerase PA subunit endonuclease protein is an influenza virus protein.

In embodiments, the RNA-dependent RNA polymerase PA subunit endonuclease protein activity is endonuclease activity.

VI. Additional Embodiments

Embodiment P1

A compound with structure of Formula (I):

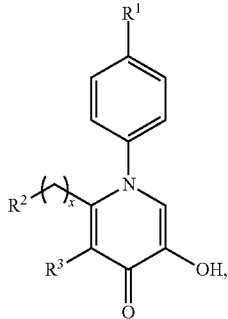

wherein $R^1$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, -substituted or unsubstituted heterocycloalkyl, -substituted or unsubstituted aryl, or substituted or unsubstituted heteroaryl; $R^2$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, -substituted or unsubstituted heterocycloalkyl, -substituted or unsubstituted aryl, or substituted or unsubstituted heteroaryl; $R^3$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, -substituted or unsubstituted heterocycloalkyl, -substituted or unsubstituted aryl, or substituted or unsubstituted heteroaryl; and x is an integer in the range 0-6.

Embodiment P2

The compound according to embodiment P1, said compound having the structure of Cmpd 71:

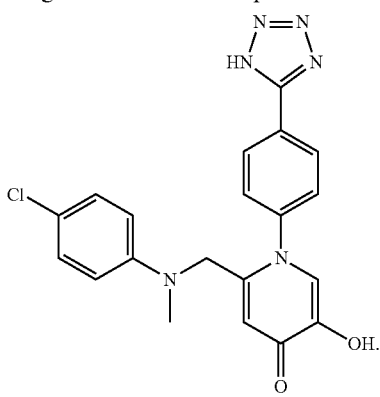

Embodiment P3

A method for inhibiting an influenza A RNA-dependent RNA polymerase PA subunit endonuclease, said method comprising contacting an influenza A RNA-dependent RNA polymerase PA subunit endonuclease with a compound of Formula (I).

Embodiment P4

A pharmaceutical composition comprising a compound of Formula (I) and a pharmaceutically acceptable excipient.

Embodiment P5

A method of treating an influenza A infection, said method comprising administering to a subject in need thereof an effective amount of a compound of Formula (I).

VII. Further Embodiments

Embodiment 1

A compound having the formula:

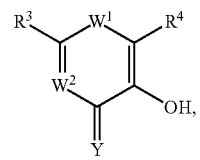 (I)

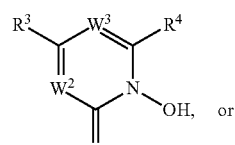 (II)

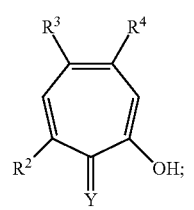 (III)

wherein,
Y is O, S, or NH;
$W^1$ is —O—, —CH($R^1$)—, or —N($R^1$)—;
$R^1$ is hydrogen, halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —NHC(O)$NR^{1A}R^{1B}$, —N(O)$_{m1}$, —$NR^{1A}R^{1B}$, —C(O)$R^{1C}$, —C(O)—$OR^{1C}$, —C(O)$NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$W^2$ is —C($R^2$)= or —N=;
$R^2$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —NHC(O)$NR^{2A}R^{2B}$, —N(O)$_{m2}$, —$NR^{2A}R^{2B}$, —C(O)$R^2$, —C(O)—$OR^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

W$^3$ is —C(R$^1$)═ or —N═;

R$^3$ is hydrogen, halogen, —CX$^3{}_3$, —CHX$^3{}_2$, —CH$_2$X$^3$, —OCX$^3{}_3$, —OCH$_2$X$^3$, —OCHX$^3{}_2$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —CX$^4{}_3$, —CHX$^4{}_2$, —CH$_2$X$^4$, —OCX$^4{}_3$, —OCH$_2$X$^4$, —OCHX$^4{}_2$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, and R$^{4D}$, is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl;

each X, X$^1$, X$^2$, X$^3$, and X$^4$ is independently —F, —Cl, —Br, or —I;

n1, n2, n3, and n4 are independently an integer from 0 to 4; and m1, m2, m3, m4, v1, v2, v3, and v4 are independently an integer from 1 to 2.

Embodiment 2

The compound of embodiment 1 having the formula:

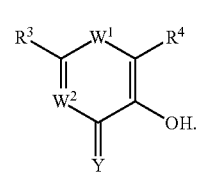

(I)

Embodiment 3

The compound of one of embodiments 1 to 2, wherein Y is S.

Embodiment 4

The compound of one of embodiments 1 to 2, wherein Y is O.

Embodiment 5

The compound of one of embodiments 1 to 4, wherein W$^1$ is —O—.

Embodiment 6

The compound of one of embodiments 1 to 4, wherein W$^1$ is —N(R$^1$)—.

Embodiment 7

The compound of embodiment 6, wherein R$^1$ is hydrogen, —CX$^1{}_3$, —CHX$^1{}_2$, —CH$_2$X$^1$, —CN, —C(O)R$^{1C}$, —C(O)—OR$^{1C}$, —C(O)NR$^{1A}$R$^{1B}$, —OR$^{1D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 8

The compound of embodiment 6, wherein R$^1$ is hydrogen.

Embodiment 9

The compound of embodiment 6, wherein R$^1$ is substituted or unsubstituted cycloalkyl, substituted or unsubstituted heterocycloalkyl, substituted or unsubstituted aryl, or substituted or unsubstituted heteroaryl.

Embodiment 10

The compound of embodiment 6, wherein R$^1$ is substituted or unsubstituted aryl or substituted or unsubstituted heteroaryl.

Embodiment 11

The compound of embodiment 6, wherein R$^1$ is substituted or unsubstituted phenyl.

Embodiment 12

The compound of embodiment 6, wherein R$^1$ is R$^{10}$-substituted phenyl; wherein, R$^{10}$ is independently oxo, halogen, $-CX^{10}_3$, $-CHX^{10}_2$, $-CH_2X^{10}$, $-OCX^{10}_3$, $-OCH_2X^{10}$, $-OCHX^{10}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OR^{11}$, $-NHR^{11}$, $-COOR^{11}$, $-CONHR^{11}$, $-SR^{11}$, $-SO_2NHR^{11}$, $-SO_2R^{11}$, $R^{11}$-substituted or unsubstituted alkyl, $R^{11}$-substituted or unsubstituted heteroalkyl, $R^{11}$-substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl; $X^{10}$ is independently $-F$, $-Cl$, $-Br$, or $-I$; $R^{11}$ is independently oxo, halogen, $-CX^{11}_3$, $-CHX^{11}_2$, $-CH_2X^{11}$, $-OCX^{11}_3$, $-OCH_2X^{11}$, $-OCHX^{11}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl; $X^{11}$ is independently $-F$, $-Cl$, $-Br$, or $-I$; $R^{12}$ is independently oxo, halogen, $-CX^{12}_3$, $-CHX^{12}_2$, $-CH_2X^{12}$, $-OCX^{12}_3$, $-OCH_2X^{12}$, $-OCHX^{12}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl; and $X^{12}$ is independently $-F$, $-Cl$, $-Br$, or $-I$.

Embodiment 13

The compound of embodiment 6, wherein $R^1$ is $R^{10}$-substituted phenyl; wherein, $R^{10}$ is independently unsubstituted tetrazolyl.

Embodiment 14

The compound of one of embodiments 1 to 13, wherein $W^2$ is $-N=$.

Embodiment 15

The compound of one of embodiments 1 to 13, wherein $W^2$ is $-C(R^2)=$.

Embodiment 16

The compound of embodiment 15, wherein $R^2$ is hydrogen, $-OR^{2D}$, $-C(O)R^{2C}$, $-C(O)-OR^{2C}$, $-C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 17

The compound of embodiment 15, wherein $R^2$ is hydrogen.

Embodiment 18

The compound of embodiment 15, wherein $R^2$ is $-C(O)OR^{2C}$ or $-C(O)NR^{2A}R^{2B}$.

Embodiment 19

The compound of embodiment 15, wherein $R^2$ is $-OR^{2D}$.

Embodiment 20

The compound of one of embodiments 1 to 19, wherein $R^3$ is hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 21

The compound of one of embodiments 1 to 19, wherein $R^3$ is hydrogen, halogen, substituted or unsubstituted alkyl, or substituted or unsubstituted heteroalkyl.

Embodiment 22

The compound of one of embodiments 1 to 19, wherein $R^3$ is hydrogen, halogen, $R^{30}$-substituted or unsubstituted alkyl, $R^{30}$-substituted or unsubstituted heteroalkyl, or $R^{30}$-substituted or unsubstituted aryl; wherein, $R^{30}$ is independently oxo, halogen, $-CX^{30}_3$, $-CHX^{30}_2$, $-CH_2X^{30}$, $-OCX^{30}_3$, $-OCH_2X^{30}$, $-OCHX^{30}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OR^{31}$, $-NHR^{31}$, $-N(CH_3)R^{31}$, $-COOR^{31}$, $-CONHR^{31}$, $-SR^{31}$, $-SO_2NHR^{31}$, $-SO_2R^{31}$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl; $X^{30}$ is independently $-F$, $-Cl$, $-Br$, or $-I$; $R^{31}$ is independently oxo, halogen, $-CX^{31}_3$, $-CHX^{31}_2$, $-CH_2X^{31}$, $-OCX^{31}_3$, $-OCH_2X^{31}$, $-OCHX^{31}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OR^{32}$, $-NHR^{32}$, $-N(CH_3)R^{32}$, $-COOR^{32}$, $-CONHR^{32}$, $-SR^{32}$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl; $X^{31}$ is independently $-F$, $-Cl$, $-Br$, or $-I$; $R^{32}$ is independently oxo, halogen, $-CX^{32}_3$, $-CHX^{32}_2$, $-CH_2X^{32}$, $-OCX^{32}_3$, $-OCH_2X^{32}$, $-OCHX^{32}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl, unsubstituted heteroalkyl, unsubstituted cycloalkyl, unsubstituted heterocycloalkyl, unsubstituted aryl, or unsubstituted heteroaryl; and $X^{32}$ is independently $-F$, $-Cl$, $-Br$, or $-I$.

Embodiment 23

The compound of embodiment 22, wherein $R^3$ is hydrogen, halogen, $R^{30}$-substituted or unsubstituted methyl, $R^{30}$- substituted or unsubstituted —CH$_2$N(CH$_3$)Ph, or R$^{30}$-substituted or unsubstituted phenyl.

Embodiment 24

The compound of one of embodiments 1 to 23, wherein R$^4$ is hydrogen, —C(O)R$^{4C}$, —C(O)—OR$^{4C}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 25

The compound of one of embodiments 1 to 23, wherein R$^4$ is hydrogen, —C(O)R$^{4C}$, —C(O)—OR$^{4C}$, —C(O)NR$^{4A}$R$^{4B}$, or substituted or unsubstituted heteroaryl.

Embodiment 26

The compound of one of embodiments 1 to 23, wherein R$^4$ is hydrogen, —C(O)OCH$_3$, —C(O)OH, —C(O)NHCH$_3$, or unsubstituted tetrazolyl.

Embodiment 27

The compound of embodiment 1 having the formula:

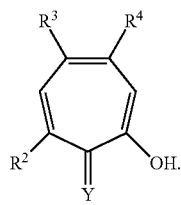

(III)

Embodiment 28

The compound of embodiment 27, wherein Y is S.

Embodiment 29

The compound of embodiment 27, wherein Y is O.

Embodiment 30

The compound of one of embodiments 27 to 29, wherein R$^2$ is hydrogen, —OR$^{2D}$, —C(O)R$^{2C}$, —C(O)OR$^{2C}$, or —C(O)NR$^{2A}$R$^{2B}$.

Embodiment 31

The compound of embodiment 30, wherein R$^2$ is hydrogen.

Embodiment 32

The compound of embodiment 30, wherein R$^2$ is —C(O)OR$^{2C}$ or —C(O)NR$^{2A}$R$^{2B}$.

Embodiment 33

The compound of embodiment 30, wherein R$^2$ is —OR$^{2D}$.

Embodiment 34

The compound of embodiment 30, wherein R$^2$ is —OCH$_3$.

Embodiment 35

The compound of embodiment 30, wherein R$^2$ is —OH.

Embodiment 36

The compound of one of embodiments 27 to 35, wherein R$^3$ is hydrogen, —C(O)OR$^{3C}$, —C(O)NR$^{3A}$R$^{3B}$, —OR$^{3D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 37

The compound of one of embodiments 27 to 35, wherein R$^3$ is hydrogen, —C(O)OH, —C(O)NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 38

The compound of one of embodiments 27 to 35, wherein R$^3$ is hydrogen, —C(O)OH, —C(O)NH$_2$, R$^{30}$-substituted or unsubstituted alkyl, or R$^{30}$-substituted or unsubstituted aryl; wherein, R$^{30}$ is independently oxo, halogen, —CX$^{30}_3$, —CHX$^{30}_2$, —CH$_2$X$^{30}$, —OCX$^{30}_3$, —OCH$_2$X$^{30}$, —OCHX$^{30}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{31}$-substituted or unsubstituted alkyl, R$^{31}$-substituted or unsubstituted heteroalkyl, R$^{31}$-substituted or unsubstituted cycloalkyl, R$^{31}$-substituted or unsubstituted heterocycloalkyl, R$^{31}$-substituted or unsubstituted aryl, or R$^{31}$-substituted or unsubstituted heteroaryl; X$^{30}$ is independently —F, —Cl, —Br, or —I; R$^{31}$ is independently oxo, halogen, —CX$^{31}_3$, —CHX$^{31}_2$, —CH$_2$X$^{31}$, —OCX$^{31}_3$, —OCH$_2$X$^{31}$, —OCHX$^{31}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —SR$^{32}$, R$^{32}$-substituted or unsubstituted alkyl, R$^{32}$-substituted or unsubstituted heteroalkyl, R$^{32}$-substituted or unsubstituted cycloalkyl, R$^{32}$-substituted or unsubstituted heterocycloalkyl, R$^{32}$-substituted or unsubstituted aryl, or R$^{32}$-substituted or unsubstituted heteroaryl; X$^{31}$ is independently —F, —Cl, —Br, or —I; R$^{32}$ is independently oxo, halogen, —CX$^{32}_3$, —CHX$^{32}_2$, —CH$_2$X$^{32}$, —OCX$^{32}_3$, —OCH$_2$X$^{32}$, —OCHX$^{32}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl; and X$^{32}$ is independently —F, —Cl, —Br, or —I.

Embodiment 39

The compound of one of embodiments 27 to 35, wherein $R^3$ is hydrogen, —C(O)OH, unsubstituted $C_1$-$C_3$ alkyl, or unsubstituted phenyl.

Embodiment 40

The compound of one of embodiments 27 to 39, wherein $R^4$ is hydrogen, —C(O)$OR^{4C}$, —C(O)$NR^{4A}R^{4B}$, —$OR^{4D}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 41

The compound of one of embodiments 27 to 39, wherein $R^4$ is hydrogen, —C(O)OH, —C(O)$NHR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 42

The compound of one of embodiments 27 to 39, wherein $R^4$ is hydrogen, —C(O)OH, —C(O)$NHR^{14}$, $R^{40}$-substituted or unsubstituted alkyl, or $R^{40}$-substituted or unsubstituted aryl; wherein, $R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl; $X^{40}$ is independently —F, —Cl, —Br, or —I; $R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$SR^{42}$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl; $X^{41}$ is independently —F, —Cl, —Br, or —I; $R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl; and $X^{42}$ is independently —F, —Cl, —Br, or —I.

Embodiment 43

The compound of one of embodiments 27 to 39, wherein $R^4$ is hydrogen, —C(O)OH, unsubstituted $C_1$-$C_3$ alkyl, or unsubstituted phenyl.

Embodiment 44

The compound of embodiment 1 having the formula:

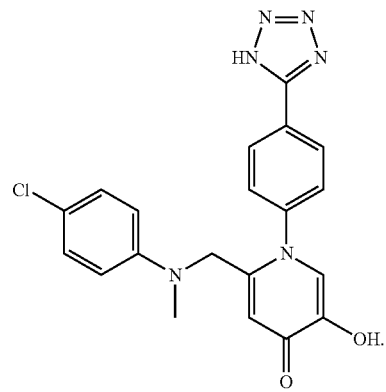 [SMILES: CN(Cc1cc(=O)c(O)cn1-c1ccc(-c2nnn[nH]2)cc1)c1ccc(Cl)cc1]

Embodiment 45

A pharmaceutical composition comprising the compound of any one of embodiments 1 to 44 and a pharmaceutically acceptable excipient.

Embodiment 46

A method of inhibiting RNA-dependent RNA polymerase PA subunit endonuclease protein activity, said method comprising contacting the RNA-dependent RNA polymerase PA subunit endonuclease protein with an effective amount of a compound of one of embodiments 1 to 44.

Embodiment 47

The method of embodiment 46, wherein the RNA-dependent RNA polymerase PA subunit endonuclease protein is an influenza virus protein.

Embodiment 48

The method of one of embodiments 46 to 47, wherein the activity is endonuclease activity.

Embodiment 49

The method of one of embodiments 46 to 47, wherein the activity is nucleic acid binding.

Embodiment 50

A method of treating a viral infection, said method comprising administering to a subject in need thereof an effective amount of a compound of one of embodiments 1 to 44.

Embodiment 51

The method of embodiment 50, wherein the viral infection is an influenza virus infection.

Embodiment 52

The method of embodiment 50, wherein the viral infection is an influenza virus A infection

EXAMPLES

Example 1: Protein Expression and Purification

Pandemic H1N1 N-terminal PA endonuclease was expressed from a pET-28a parent vector containing a kanamycin-resistance reporter gene, expression inducible by the Lac 1 operon. The endonuclease was expressed as an 8-histidine tagged fusion protein. Transformation protocol was adapted from pET system manual (Novagen) using single competent BL21 cells. Briefly, 1 µL of 25 ng/µL recombinant plasmid was used for transformation. Cells were mixed by flicking with plasmid and were heat shocked at 42° C. for 30 second followed by incubation on ice for 5 minutes. Outgrowth was plated on LB agarose plates contain 50 µg/mL kanamycin, and was incubated overnight at 37° C. One colony was scraped from the LB plate and added to 50 mL of SOC broth containing 50 µg/mL kanamycin, and was incubated for 5 hours at 37° C. with shaking at 125 rpm. Glycerol stocks of this culture were prepared (0.9 mL cultured media+0.1 mL 80% glycerol) and flash frozen for future expressions. 100 mL of SOC media containing 50 µg/mL kanamycin was combined with 1 mL frozen glycerol stock or 1 mL the previously mentioned 5-hour growth, and was incubated with shaking at 100-125 rpm overnight at 37° C. as a starter culture. This starter culture was then equally divided into 4×1 L batches of expression media (TB media with added 0.2% dextrose, 0.1 mM $MnCl_2$, and 0.1 mM $MgSO_4$) containing 50 µg/mL kanamycin. Cells were grown to the beginning of log phase ($OD_{600}$=between 0.6-0.8) at 37° C. with shaking at 100-125 rpm. Expression of PA endonuclease was then induced by the addition of IPTG to a final concentration of 0.8 mM. The media was grown with shaking overnight at ~18° C. After approximately 18 hours, the cells were harvested by centrifuging at 2000 g for 30 minutes at 4° C. The resulting paste was stored at -80° C. prior to lysis. Cell paste was thawed on ice for 2 hours, and re-suspended in 25-35 mL of lysis buffer (20 mM $Na_2PO_4$, 500 mM NaCl, 25 mM imidazole, 1 mM $MgCl_2$, 2 mM dithiothreitol (DTT), 0.2% Triton-X, pH=7.4) with presence of EDTA free protease inhibitor (Roche); and lysed by sonication—5×25 second pulses with 2-minute rest periods on ice. To the cell lysates was added DNAseI to a final concentration of 10-100 µg/mL, and the lysates were shaken at 125 rpm for 30-60 minutes on ice until the consistency of the lysate became free-flowing. Cell debris was then pelleted by centrifugation at 10000 rpm 35-45 minutes at 4° C. The supernatant was decanted from the pellet, and a HisTrap HP (Parmacia) column was utilized to isolate His-tagged fusion protein from the cell lysates according to the manufacturer's recommendations. Briefly, cell-free lysates from 4 L of growth were loaded on 1×5 mL column that had previously been charged with Ni ions. The column was then washed with a binding buffer (20 mM $Na_2PO_4$, 500 mM NaCl, 25 mM imidazole, pH=7.4) until fraction absorbance reached a steady baseline. Fusion protein was then eluted with a gradient from 0-100% elution buffer (20 mM $Na_2PO_4$, 500 mM NaCl, 500 mM imidazole, pH=7.4) over 45 minutes at a flow rate of 4 mL/min. Pure target protein eluted between 50-60% elution buffer.

Isolated protein was flash-frozen and stored at -80° C. SDS-PAGE analysis showed a single band of pure protein running at a molecular weight of ~23 kD.

Example 2: Endonuclease Activity Assay

Endonuclease activity assays were carried out in Black Costar 96-well plates. Each well contained a total volume of 100 µL comprised of: buffer (20 mM Tris, 150 mM NaCl, 2 mM $MnCl_2$, 10 mM β-mercaptoethanol, 0.2% Triton-X100, pH=8.0), influenza PA endonuclease (25 nM) prepared from Example 1, inhibitor (various concentrations) in buffer, and fluorescent ssDNA-oligo substrate (200 nM). A single-stranded, 17-mer DNA substrate labeled with a 5'-FAM fluorophore and a 3'-TAMRA quencher ([6-FAM] AATCGCAGGCAGCACTC[TAM]) (SEQ ID NO:2) synthesized by Sigma-Aldrich was employed to measure endonucleic cleavage. Upon addition of the substrate, the change in fluorescence was measured over 45 minutes at 37° C. (excitation: 485 nm; emission 528 nm). The positive control wells contained no inhibitor for preliminary screens, and were set as an arbitrary 100% activity. Compounds that exhibited >80% inhibition at a concentration of 200 µM were re-evaluated at a concentration of 50 µM. Confirmation screens employed EGCG (Epigallocatechin 3-gallate), a previously validated inhibitor, as a positive control. The gain was set to 100 and the first 10 data points (the first 10 minutes) were excluded from the activity calculations. Dose-response curves were generated, fitted, and analyzed using Origin8 graphing software. Dose-response curves were compiled and $IC_{50}$ values determined for compounds exhibiting >50% inhibition at 50 µM.

Example 3: MBP Library Screening to Identify Potent Inhibitor Scaffolds

Utilizing a fragment-based drug discovery approach, a 300 component metal-binding pharmacophore (MBP) library was screened in an effort to identify novel scaffolds for influenza A RNA-dependent RNA polymerase PA subunit endonuclease inhibitors. This screen identified pyromeconic acid and structural derivatives as moderately potent and efficient scaffolds for further derivatization (Table 1) as well as several similar, highly potent fragments containing a shared 'binding triad' motif (Table 2).

TABLE 1

Select MBP fragments that displayed potent inhibition against influenza PA endonuclease. $pIC_{50}$ is defined as $pIC_{50} = -\log(IC_{50})$ and is included to allow a linear comparison between $IC_{50}$ values. Ligand efficiency (LE) provides a measure of binding energy per non-hydrogen atom in the fragment molecule (see Reference 31).

| Number | Compound | $IC_{50}$ (µM) | $pIC_{50}$ | LE |
| --- | --- | --- | --- | --- |
| 1 | | 22.5 ± 1.0 µM | 4.6 | 0.79 |
| 2 | | 17.1 ± 1.5 µM | 4.8 | 0.73 |
| 3 | | >200 µM | <3.7 | N/A |
| 4 | | >50 µM | <4.3 | N/A |
| 5 | | 68 nM | 7.17 | 0.59 |
| 6 | | 3.5 ± 0.6 µM | 5.5 | 0.62 |
| 7 | | 4.4 ± 0.3 µM | 5.4 | 0.56 |
| 8 | | 12.3 ± 1.5 µM | 4.9 | 0.67 |

TABLE 1-continued

Select MBP fragments that displayed potent inhibition against influenza PA endonuclease. $pIC_{50}$ TABLE 2-continued
Highly potent MBP fragments that displayed potent inhibition against influenza PA endonuclease.
| Number | Compound | IC$_{50}$ (nM) | pIC$_{50}$ | LE |
|---|---|---|---|---|
| 102 | 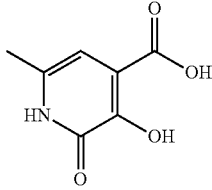 | 430 nM | 6.4 | 0.73 |
| 103 | 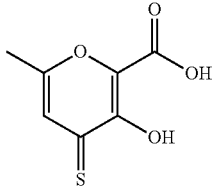 | 420 nM | 6.4 | 0.73 |
| 104 | 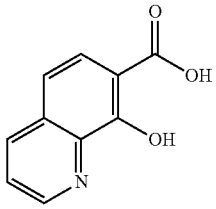 [SMILES: O=C(O)c1ccc2cccnc2c1O] | 260 nM | 6.6 | 0.65 |
| 105 | 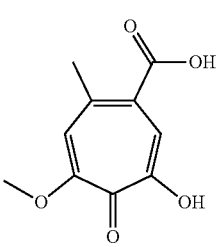 | 180 nM | 6.7 | 0.66 |
| 106 | 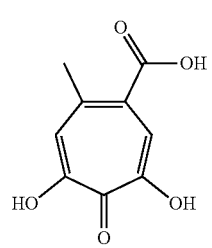 | 8.5 nM | 8 | 0.85 |
| 107 | 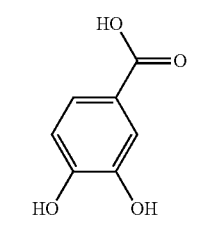 | 220 nM | 6.7 | 0.83 |

The fragments in Table 2 contained a common structural motif that imparted a large increase in potency, for example, a carboxylic acid alpha to the phenolic oxygen. Similar potency was also observed in several cases with the carboxylic acid beta to the phenolic oxygen.

In addition, a few MBP fragments based on compound 102 showed decreased activity, but may need further SAR studies.

B12

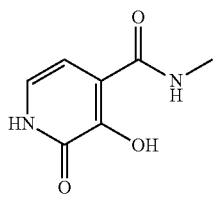

IC$_{50}$ > 50 uM

B13

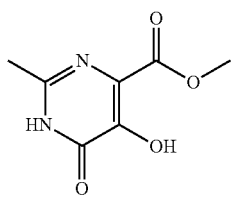

IC$_{50}$ = 1.6 uM

B15

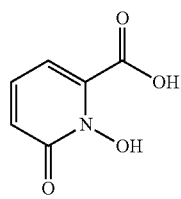

IC$_{50}$ = 7.5 uM

-continued

F8

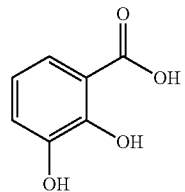

IC$_{50}$ = 6.4 uM

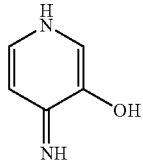

IC$_{50}$ > 200 uM

Figure 3:
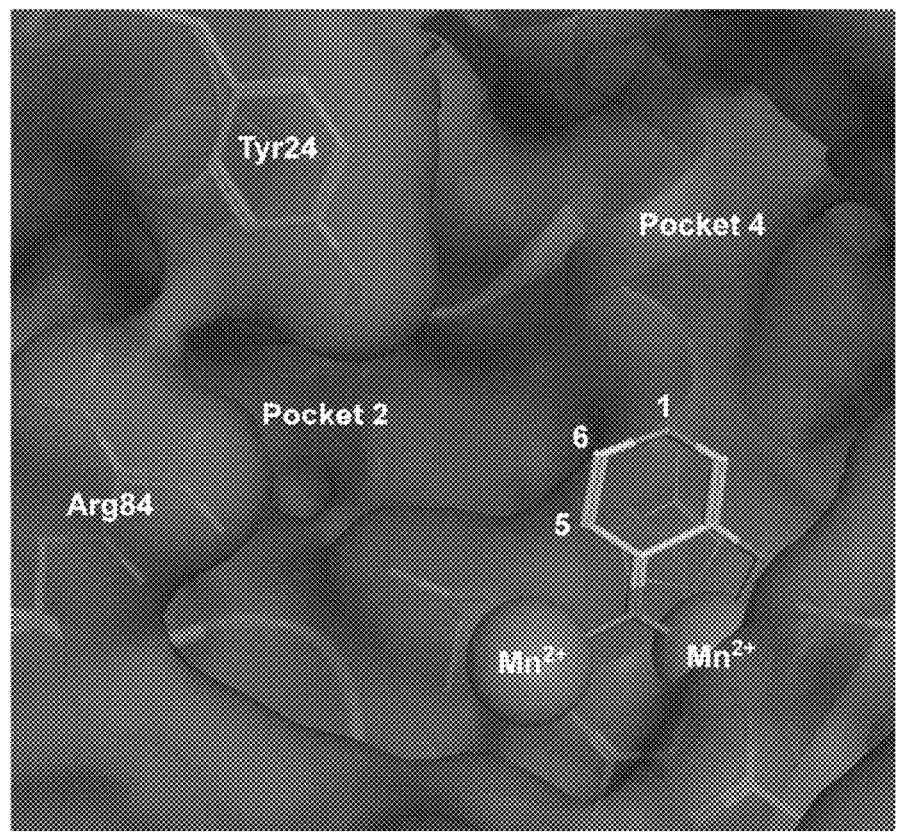
FIG. 3: Proposed binding of pyromeconic acid (compound 1) to the PA subunit active site.

Example 4: Possible Binding of Pyromeconic Acid (1) to the PA Subunit Active Site A proposed mode of metal coordination for compound 1 is shown in FIG. 3. This model is based on superposition of the donor-atoms in compound 1 with crystallographic water molecules present in X-ray structures of uninhibited influenza PA endonuclease and superposition of the pyrone ring with other similar cyclic metal-binding inhibitors that have been crystallographically validated against the endonuclease (see Reference 28). As shown in FIG. 3, positions 5- and 6- of the ring were deemed amenable to further derivatization for targeting hydrophobic pocket 2 and key residues Tyr24 and Arg84. Derivatization at the 1-position was proposed to probe interactions with pocket 4.

Example 5: Inhibition Evaluation of Various Pyromeconic Acid Derivatives

SAR from the initial screen combined with docking simulations guided the development of derivatives of pyromeconic acid at the 5-, and 6-positions of the ring, as detailed in Table 3.

TABLE 3

IC$_{50}$ and pIC$_{50}$ values of various 5- and 6- position derivatives of pyromeconic acid.

a)

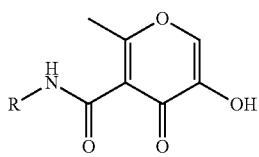

| Compound | R | IC$_{50}$(μM) | pIC$_{50}$ |
|---|---|---|---|
| 7 | | 4.4 ± 0.3 μM | 5.4 |

TABLE 3-continued
IC$_{50}$ and pIC$_{50}$ values of various 5- and 6- position derivatives of pyromeconic acid.
| | | | |
|---|---|---|---|
| 11 | 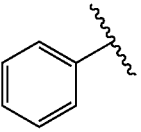 [SMILES: *c1ccccc1] | >50 μM | >4.3 |
| 12 | 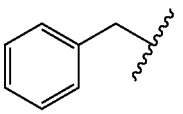 [SMILES: *Cc1ccccc1] | >50 μM | >4.3 |
| 13 | 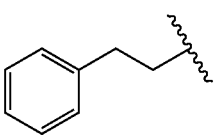 [SMILES: *CCc1ccccc1] | 11.3 ± 1.2 μM | 4.9 |
| 14 | 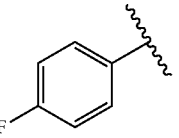 | >50 μM | >4.3 |
| 15 | 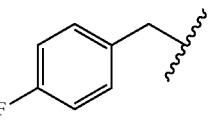 | 17.8 ± 1.5 μM | 4.7 |
| 16 | 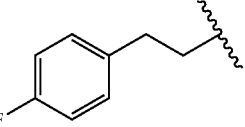 | 12.6 ± 0.6 μM | 4.9 |
| 17 | 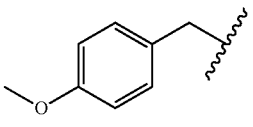 [SMILES: *Cc1ccc(OC)cc1] | 34.8 ± 0.6 μM | 4.5 |
| 18 | 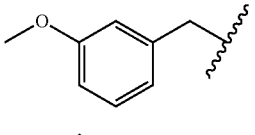 | 22.1 ± 0.6 μM | 4.7 |
| 19 | 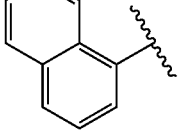 | >50 μM | >4.3 |
| 20 | 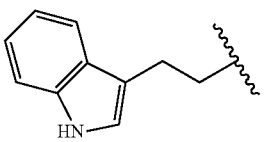 [SMILES: *CCc1c[nH]c2ccccc12] | 1.5 ± 0.3 μM | 5.8 |
b)
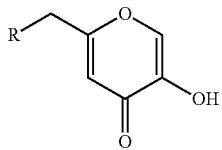

TABLE 3-continued

IC$_{50}$ and pIC$_{50}$ values of various 5- and 6- position derivatives of pyromeconic acid.

| Compound | R | IC$_{50}$(μM) | pIC$_{50}$ |
|---|---|---|---|
| 2 | H-NH- | 17.1 ± 1.5 μM | 4.8 |
| 21 | (CH$_3$)$_2$N- | 4.0 ± 1.3 μM | 5.4 |
| 22 | piperidin-1-yl | 5.5 ± 2.1 μM | 5.3 |
| 23 | iPrNH- | 3.9 ± 0.9 μM | 5.4 |
| 24 | cyclohexyl-NH- | 13.7 ± 2.1 μM | 4.9 |
| 25 | iBuNH- | 10.5 ± 0.7 μM | 5.0 |
| 26 | BnNH- | 2.7 ± 0.4 μM | 5.6 |
| 27 | BnN(Me)- | 3.4 ± 0.5 μM | 5.5 |
| 28 | CH$_3$C(O)NH- | 8.5 ± 1.1 μM | 5.1 |
| 29 | PhC(O)NH- | 4.3 ± 1.2 μM | 5.4 |
| 30 | CH$_3$S(O)$_2$NH- | 4.8 ± 0.7 μM | 5.3 |

TABLE 3-continued
IC$_{50}$ and pIC$_{50}$ values of various 5- and 6- position derivatives of pyromeconic acid.
| | | | |
|---|---|---|---|
| 31 | 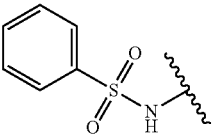 [SMILES: *NS(=O)(=O)c1ccccc1] | 1.7 ± 0.3 µM | 5.8 |
| 32 | 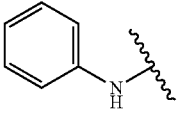 | 6.3 ± 0.4 µM | 5.2 |
| 33 | 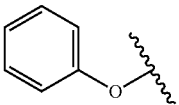 [SMILES: *Oc1ccccc1] | 4.8 ± 0.9 µM | 5.3 |
| 34 | 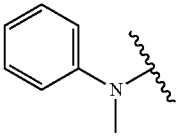 [SMILES: *N(C)c1ccccc1] | 2.9 ± 0.3 µM | 5.5 |
| 35 | 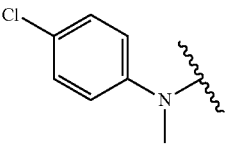 [SMILES: *N(C)c1ccc(Cl)cc1] | 0.94 ± 0.08 µM | 6.0 |
| 36 | 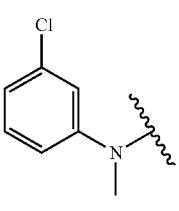 | 1.1 ± 0.1 µM | 6.0 |
| 37 | 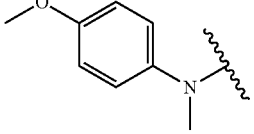 | 2.8 ± 0.2 µM | 5.6 |
| 38 | 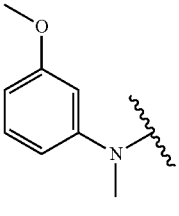 [SMILES: *N(C)c1cccc(OC)c1] | 2.2 ± 0.4 µM | 5.7 |
| 39 | 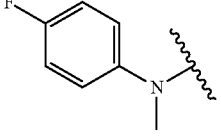 | 1.8 ± 0.2 µM | 5.7 |

TABLE 3-continued

IC$_{50}$ and pIC$_{50}$ values of various 5- and 6- position derivatives of pyromeconic acid.

| No. | Compound | IC$_{50}$ | pIC$_{50}$ |
|---|---|---|---|
| 40 | 3-fluorophenyl-N(Me)- | 3.2 ± 0.1 μM | 5.5 |
| 41 | pyridin-4-yl-N(Me)- | >100 μM | <4.0 |
| 42 | pyridin-3-yl-N(Me)- | >100 μM | <4.0 |

Figure 1B:
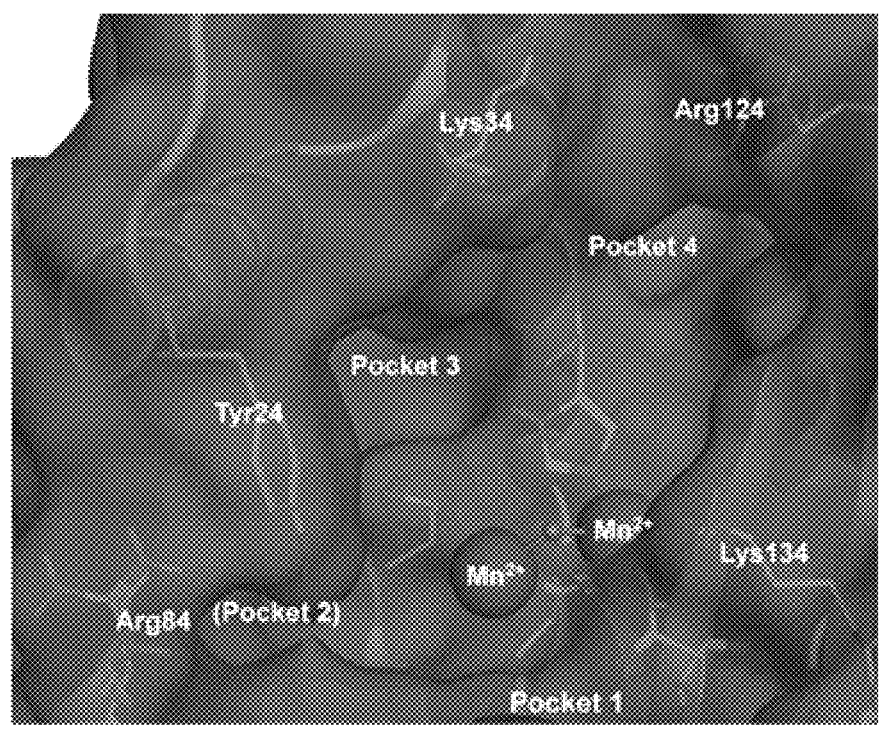

5-Position Derivatives:

Based on the SAR outlined in Table 1, initial efforts focused on exploring amide derivatives of compounds 6 and 7. Based on the modeling and prior crystallographic evidence (see References 18 and 28), it was proposed that aryl substituents at the 5-position could favorably interact with residues Tyr24 or Arg84, or make favorable hydrophobic interactions with pocket 2, as detailed in FIG. 1. A sub-library of 11 aryl amides derived from compound 6 were synthesized and evaluated for inhibitory activity, detailed in Table 3a. While the methyl amide compound 7 was equipotent to the parent fragment 6, other aryl amide derivatives except for compound 20 in Table 1a were found to be less active.

6-Position Derivatives:

Initial SAR (compounds 8 and 9) indicated that hydrophilic substituents at the 6-position were well tolerated. To continue probing interactions with pocket 2 shown in FIG. 2, a series of 6-aminomethyl derivatives were synthesized. Amine, amide, and sulfonamide derivatives were more active than kojic acid (compound 8) by from 3 to 18 fold, with compound 31 being the most potent. Aryl amine, aryl ether, and benzyl amine derivatives displayed similar activity, with tertiary amine derivatives being slightly more potent than secondary amine derivatives (e.g., compound 26 vs. compound 27; compound 32 vs. compound 34). The aryl ring substituent(s) in some cases provided added potency. However, the introduction of a pyridine moiety appeared to significantly decrease activity. Ultimately, compound 35 was identified as the most potent derivative among the compounds listed in Table 3b with an IC$_{50}$ value of 0.94±0.08 μM. Accordingly, screening results from these sub-library compounds listed in Table 3b indicated that aryl-aminomethyl and aryl-sulfonamidomethyl substituents at the 6 position were a key for increasing potency.

Example 6: Inhibition Evaluation of Various N-Functionalized Hydroxypyridinones

Figure 2:
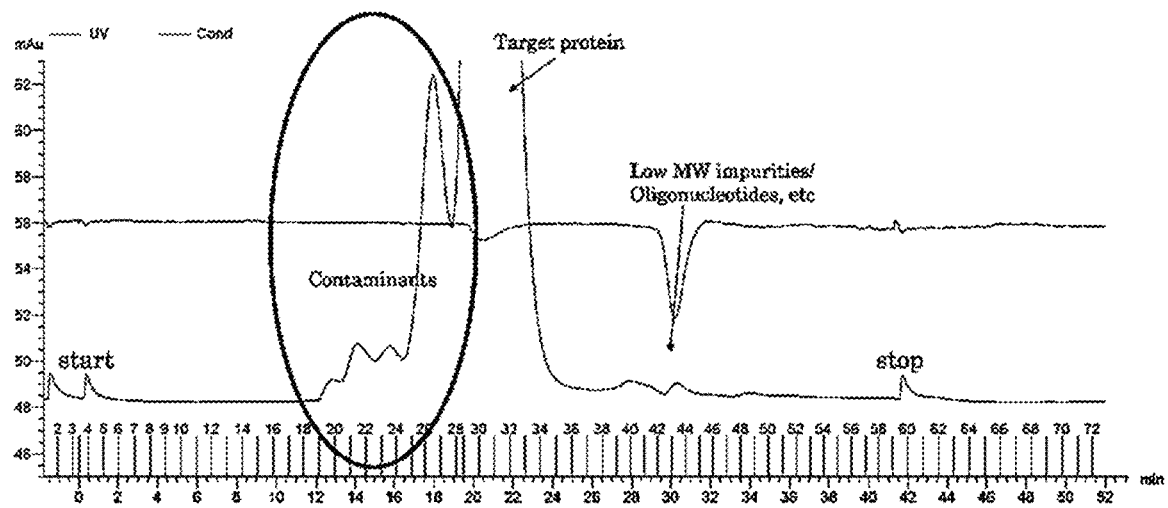
FIG. 2: Chromatogram of size-exclusion purification of the endonuclease construct.

Conversion of the pyrone ring to a pyridinone ring not only can increase ligand basicity (and hence metal binding), but also can afford a chemical handle for facile exploration of the large pocket located above the metal center active site of endonuclease, shown in FIG. 2. To probe this pocket, a sub-library of N-substituted pyridinones was synthesized and screened against endonuclease, detailed in Table 4.

TABLE 4

Inhibition values of various N-functionalized hydroxypyridinones

| No. | Compound | IC$_{50}$ (μM) | pIC$_{50}$ [a] |
|---|---|---|---|
| 43 | | 2.2 ± 0.2 μM | 5.7 |
| 44 | | 0.46 ± 0.06 μM | 6.3 |
| 45 | | 18 ± 2 μM | 4.7 |

TABLE 4-continued

Inhibition values of various N-functionalized hydroxypyridinones

| Compound | Structure | IC$_{50}$ (µM) | pIC$_{50}$ |
|---|---|---|---|
| 46 | biphenyl-N-pyridinone (2-methyl-3-OH) | 1.3 ± 0.2 µM | 5.9 |
| 47 | cyclohexyl-N-pyridinone (2-methyl-5-OH) | 0.18 ± 0.04 µM | 6.7 |
| 48 | cyclohexyl-N-pyridinone (2-methyl-3-OH) | 14 ± 3 µM | 4.9 |
| 49 | benzyl-N-pyridinone (2-methyl-5-OH) | 2.5 ± 0.5 µM | 5.6 |
| 50 | biphenylmethyl-N-pyridinone (2-methyl-5-OH) | 3.8 ± 0.8 µM | 5.4 |

TABLE 4-continued

Inhibition values of various N-functionalized hydroxypyridinones b)

[Structure: 2-methyl-5-hydroxy-pyridin-4(1H)-one with R on N]

| Compound | R | IC$_{50}$ (µM) | pIC$_{50}$ |
|---|---|---|---|
| 47 | cyclohexyl | 0.18 ± 0.04 µM | 6.7 |
| 51 | tetrahydropyran-4-yl | 0.73 ± 0.07 µM | 6.1 |
| 52 | 1-methylpiperidin-4-yl | 2.2 ± 0.3 µM | 5.7 |
| 53 | 1-(methylsulfonyl)piperidin-4-yl | 1.1 ± 0.2 µM | 6.0 |
| 54 | 1-acetylpiperidin-4-yl | 3.4 ± 0.4 µM | 5.5 |

It was found that both N-aryl and N-cycloalkyl pyridinones (compounds 44 and 47) were significantly more active than the parent fragment compound 10. Simple extension of the aryl substituent (compounds 46 and 50) did not improve activity. Accordingly, compounds 45 and 48 showed a significant loss in activity, consistent with the previously observed unfavorable effect of a substituent (i.e., —CH$_3$) at the 2-position of pyromeconic acid (i.e., compound 3 in Table 1). Further hydrophilic modifications of N-cycloalkyl pyridinones (compound 47) appeared to reduce activity.

Example 7: Inhibition Evaluation of Various Derivatives of 5-hydroxy-2-methyl-1-phenylpyridin-4(1H)-one A series of derivatives were synthesized exploring substituents at either the 3'- or 4'-positions of the N-phenyl ring, detailed in Table 5.

TABLE 5

Inhibition values and SAR of 3'- and 4'-position derivatives of 5-hydroxy-2-methyl-1-phenylpyridin-4(1H)-one.

a)

| Compound | R | IC$_{50}$ (nM) | pIC$_{50}$ |
|---|---|---|---|
| 44 | H– | 460 ± 60 nM | 6.3 |
| 55 | –O–CH$_3$ | 320 ± 40 nM | 6.5 |
| 56 | –O–Ph | 760 ± 50 nM | 6.1 |
| 57 | –C(O)–O–CH$_3$ | 460 ± 70 nM | 6.3 |
| 58 | –C(O)–OH | 410 ± 20 nM | 6.4 | b)

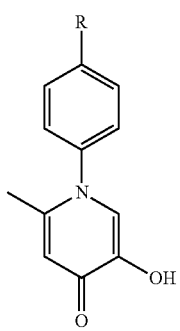

| Compound | R | IC$_{50}$ (nM) | pIC$_{50}$ |
|---|---|---|---|

TABLE 5-continued

Inhibition values and SAR of 3'- and 4'-position derivatives of 5-hydroxy-2-methyl-1-phenylpyridin-4(1H)-one.

| | | | |
|---|---|---|---|
| 44 | H– | 460 ± 60 nM | 6.3 |
| 59 | –O–CH$_3$ | 360 ± 40 nM | 6.4 |
| 60 | –O–Ph | 120 ± 20 nM | 6.9 |
| 61 | –C(O)–O–CH$_3$ | 440 ± 20 nM | 6.4 |
| 62 | –C(O)–OH | 130 ± 30 nM | 6.9 |
| 63 | tetrazole (HN–N=N–N=C–) | 36 ± 7 nM | 7.4 |
| 64 | –S(O)$_2$–NH–CH$_3$ | 850 ± 80 nM | 6.1 |
| 65 | 1,2,4-triazol-1-yl | 2300 ± 400 nM | 5.6 |
| 66 | morpholin-4-yl | 5300 ± 600 nM | 5.3 |

In general, 3' modifications yielded a flat SAR, with only small changes in activity, detailed in Table 1a. The SAR of the 4'-position derivatives was more varied, and revealed that the addition of an aryl ether (compound 60) or a carboxylic acid (compound 62) both afforded increased activity. While several other polar 4'-position derivatives resulted in a reduced potency (64, 65, 66), the addition of a tetrazole group to the 4'-position (63) resulted in a substantial increase in potency. Without wishing to be bound by theory, it is believed that the phenyl tetrazole moiety makes very favorable interactions with pocket 4. Compound 63 was identified as the most potent derivative of this series with an IC$_{50}$ value of 36±7 nM against PA endonuclease.

Example 8: Inhibition Evaluation of Various Derivatives by Fragment Merging

Computational modeling suggested that derivatives at the 5- and 6-position were likely interacting with pocket 2 in the endonuclease active site, and that N-substituted derivatives at the 1-position were interacting with pocket 4. It was decided to merge the most potent 5- or 6-position derivatives with the most potent N-aryl derivative of the 1-position to interact with both pockets simultaneously. Since the amide derivatization of compound 6 showed unnoticeable improvement to potency, incorporation of a 5-position carboxylic acid to N-substituted compounds 44, 60, and 63 was pursued, detailed in Table 6.

TABLE 6

Inhibition values of merged inhibitor compounds

| Compound | $R^{10}$ | $R^{30}$ | $R^2$ | $IC_{50}$ (nM) | $pIC_{50}$ |
|---|---|---|---|---|---|
| 67 | H | H | ethyl ester | 5300 ± 400 nM | 5.3 |
| 68 | phenoxy | H | ethyl ester | 5200 ± 800 nM | 5.3 |
| 69 | tetrazole (HN-N=N-N) | H | ethyl ester | 190 ± 60 nM | 6.7 |
| 70 | H | H | carboxylic acid (HO-C(=O)-) | 610 ± 30 nM | 6.2 |
| 71 | tetrazole (HN-N=N-N) | 4-chloro-N-methyl aniline | H | 14 ± 3 nM | 7.9 |

Ethyl esters 67, 68, and 69 surprisingly showed markedly decreased potency after the addition of the carboxylate group at the 5-position. Base catalyzed hydrolysis of these compounds failed to produce the corresponding carboxylic acid, resulting in complete degradation of these molecules. However, compound 70, synthesized via an alternate route, showed no improvement over the parent compound 44.

Extensive SAR of the 6-position revealed that aryl amine and sulfonamide derivatives were the most potent elaborations at this position, likely due to favorable hydrophobic interactions with pocket 2 and possible π-stacking interactions with Tyr24. As detailed in Table 6, the addition of a 4-chloro-N-methyl aniline substituent to the compound 63 resulted in an increase of potency from an $IC_{50}$ value of 36±7 nM to 14±3 nM for compound 71. While fragment merging did result in an overall more potent molecule, the fact that the observed potency increase was not simply additive may suggest either a conformational change in binding mode as compared to the original fragments or a possible overlap in binding pockets between the two substituents.

Example 9: Inhibition Evaluation of Various Derivatives of
3-Hydroxy-4-oxo-4H-pyran-2-carboxylic acid

TABLE 7

Inhibition values and SAR of various derivatives of 3-Hydroxy-4-oxo-4H-pyran-2-carboxylic acid

| Number | Compound | $IC_{50}$ | Number | Compound | $IC_{50}$ |
|---|---|---|---|---|---|
| 5 | | 68 nM | 118 | | 17 nM |
| A11 | | 4.1 μM | 119 | | 3900 nM |
| 101 | | 43 nM | 120 | | 85 nM |
| 108 | | 2.7 μm | B4 | | 13 μM |
| 112 | | 3.8 μM | 131 | | 25 nM |
| 6 | | 3.0 μM | 133 | | 63 nM |

TABLE 7-continued

Inhibition values and SAR of various derivatives of 3-Hydroxy-4-oxo-4H-pyran-2-carboxylic acid

| Number | Compound | IC$_{50}$ | Number | Compound | IC$_{50}$ |
|---|---|---|---|---|---|
| 103 | [structure] | 420 nM | 136 | [structure] | 37 nM |
| | | | 150 | [structure] | 1.2 µM |
| | | | 151 | [structure] | 71 nM |
| | | | 142 | [structure] | 5.6 nM |
| | | | 143 | [structure] | 22 nM |
| | | | 144 | [structure] | 1.6 nM |

TABLE 7-continued

Inhibition values and SAR of various derivatives of 3-Hydroxy-4-oxo-4H-pyran-2-carboxylic acid

| Number | Compound | IC$_{50}$ |
|---|---|---|
| 145 | [structure: 3-COOH-phenyl-pyridinone-carboxylic acid] | 2.0 nM |
| 146 | [structure: 3-methyl-phenyl-pyridinone-carboxylic acid] | 4.8 nM |
| 147 | [structure: 2-methyl-phenyl-pyridinone-carboxylic acid] | 2.0 nM |
| 148 | [structure: 4-(1H-tetrazol-5-yl)-phenyl-pyridinone-carboxylic acid] | 1.9 nM |

Several analogues based on compound 101 in Table 1 were assayed against influenza endonuclease, and revealed that any steric pressure applied alpha to the coordinating carboxylic acid resulted in a dramatic decrease in activity. The N—H isologue of compound 101 was found to have very similar activity as compound 101 (IC$_{50}$=17 nM and 43 nM, respectively). The 2-3 fold increase in activity was consistent with the same trends observed with other pyrone to pyridinone conversions (e.g., see Table 1). The N-methyl analogue (compound 119), however, was found to be 100-fold less active (IC$_{50}$=3900 nM) than compound 101. Similar difference in activity was also observed between compound 101 and compound 6. Without wishing to be bound by theory, it is believed that the difference of activity might be due to the steric prohibition of ideal metal-binding to compounds 119 and 6. The N—OH analog (compound 120), was found to have significantly improved activity (IC$_{50}$=85 nM) compared to the N-methyl analogue (compound 119). However, compound 120 was 4-fold less activie than the parent compound 101.

Compounds 131 and 133 were assayed for inhibitory activity against influenza endonuclease. It was found that the bromine at the 6-position had no negative effect on the activity of the fragment (IC$_{50}$=25 nM). The tetrazole analogue 133 was found to still inhibit endonuclease strongly, although the activity dropped by ~two-fold (IC$_{50}$=63 nM) as compared to the carboxylic acid analogue. Compound 136 was found to have similar activity compared to the bromo-analog compound 133. It was interesting to note that the similarity in activity indicates that the coordinating carboxylic acid was effectively replaced by the tetrazole; that the tetrazole might likely coordinate in a similar fashion as observed in compound 71. Other heteroaryl, for example 5-methyl-1,2,4-oxadiazol-3-yl and oxazol-2-yl were also used for the replacement of the tetrazole; and corresponding compounds 150 and 151 were assayed for inhibitory activity against influenza endonuclease. It was found that the 2-oxazole compound 151 still inhibit endonuclease strongly, but with reduced activity by about two-fold (IC$_{50}$=71 nM) as compared to the tetrazole analogue. Compound 150 with the 5-methyl-1,2,4-oxadiazol-3-yl had significant reduced activity compared to the tetrazole compound 136.

Compounds 142 and 143 were assayed against influenza endonuclease. Compound 142, the phenyl derivative, was found to have an $IC_{50}$ value of 5.6 nM. The increase of activity was consistent with previously established SAR in Table 4. However, compound 143 was found to less active than compound 142, with an $IC_{50}$ value of 22 nM (equipotent with the parent compound 101). In Table 5, the 4-phenyl ether derivative of allomaltol (compound 60) was found to be equipotent with the 4-carboxylic acid analogue (compound 62), and ~5 fold more active than the undecorated phenyl derivative (compound 44 in Table 4). Compounds 144, 145, 146, 147, and 148 with varies substituents around the phenyl ring were found to be more active or equipotent with the parent compound 142. More varieties and positions of substituents around the phenyl ring based on compound 142 may lead further SARs.

Example 10: Inhibition Evaluation of Various Derivatives of α-Hydroxy Tropolone

TABLE 8

Inhibition values and SAR of various derivatives of α-hydroxy tropolone

| Number | Compound | $IC_{50}$ | Number | Compound | $IC_{50}$ |
|---|---|---|---|---|---|
| 201 | | 8.8 μM | 105 | | 180 nM |
| E4 | | 11 μm | 106 | | 8.5 nM |
| 205 | | 12 nM | 213 | | 5.0 nM |

Compound 106 was found to have an IC$_{50}$ value of 8.5 nM by an optimized fluorescence assay. Because this value was well below the detection limits of the assay, further validation was evaluated using a FEB chip reader. Compound 106 was found to have sub-nanomolar affinity for endonuclease with a Ki of 0.82±0.03 nM. Co-crystal structures of compound 106 in the endonuclease active site showed that no appreciable interactions were made between the carboxylic acid and the active site, and no ordered water network was observed interacting with the carboxylic acid at obtainable resolutions. To further evaluating the observed inhibitory activity, other α-hydroxy tropolone derivatives were pursued including a non-functionalized α-hydroxy tropolone.

α-Hydroxy tropolone (compound 205) was shown to have similar activity to the functionalized compound 101 (IC$_{50}$=12 nM and 8.5 nM, respectively). This was further evidence that the carboxylic acid of compound 106 was not a major factor in the observed activity of the fragment. This revelation also indicates that this carboxylic acid is a viable handle for further synthetic elaboration.

Compound 213 was found to be even more active than compound 106 with an observed IC$_{50}$ value of 5.0 nM. The level of inhibition was consistent with picomolar Kd values and compound 213 is the most active influenza endonuclease known to date.

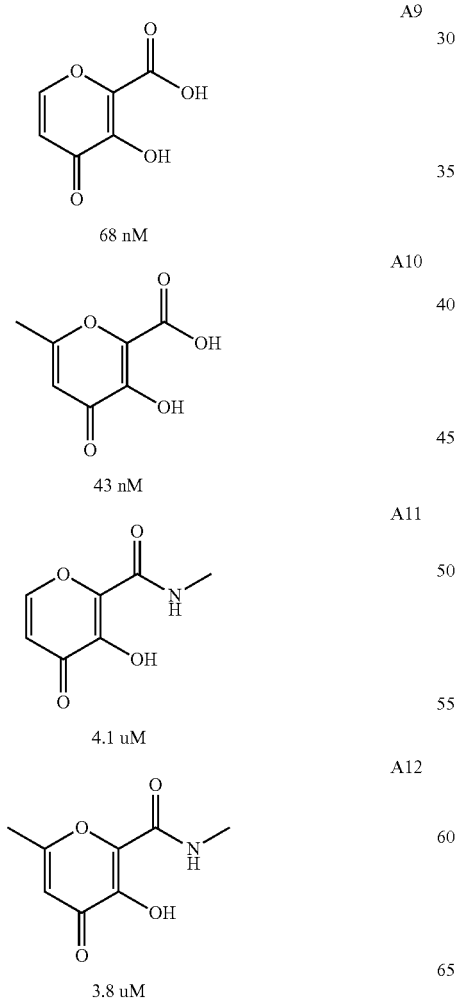

A9
68 nM

A10
43 nM

A11
4.1 uM

A12
3.8 uM

-continued

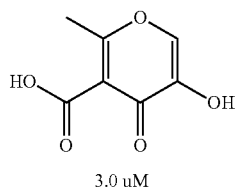

A13
3.0 uM

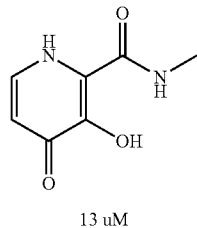

B4
13 uM

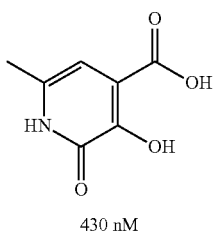

B11
430 nM

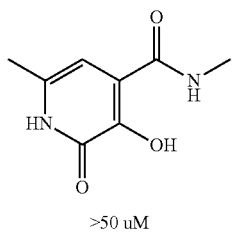

B12
>50 uM

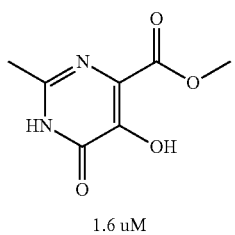

B13
1.6 uM

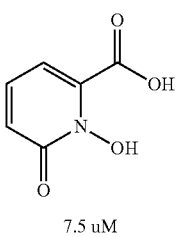

B15
7.5 uM

C4

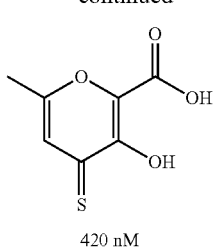

420 nM

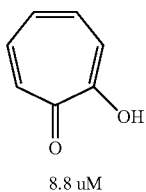

8.8 uM

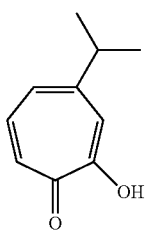

11 uM

E5

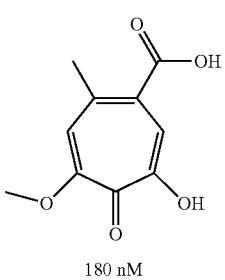

180 nM

E6

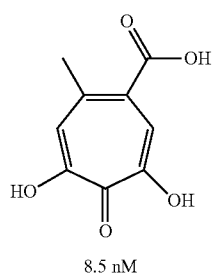

8.5 nM

F13

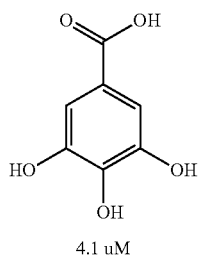

4.1 uM

It is interesting to note that despite the structural similarity between E6 and gallic acid (F13), there remains a 500-fold disparity in affinity between these two MBPs. Brief computational studies were performed to analyze the pKa of the hydroxyl groups on both of these molecules. While the pKa of the last deprotonated hydroxyl group of E6 was predicted at around 11, the analogous pKa of the final deprotonated hydroxyl of F13 was predicted between 14-15. Because 3 successive deprotonation events are required for full metal complexation of F13, coupled with the resultant very high negative charge density, it is predicted that binding will be both slow as well as weaker than in the α-hydroxy tropolone system. Analyzing the deprotonation of E6 reveals that the negative charge generated following a first deprotonation even is effectively delocalized over both the phenol and the adjacent carboxyl group. The subsequent deprotonation also results in delocalization of charge over the three oxygen atoms. This is responsible for the lower pKa of α-hydroxy tropolone as compared to gallic acid. The observed delocalization of charge facilitating deprotonation, coupled with only two deprotonation events being necessary for full metal binding, helps explain the disparity between these two structurally similar MBPs.

Example 11: Synthesis of Compounds in Table 1 to 8

Example 11.1: General Experimental Details

All reagents and solvents were obtained from commercial sources and used without further purification. All reactions, unless otherwise stated, were done under nitrogen atmosphere. Reactions were monitored using either aluminum or glass-backed silica TLC plates impregnated with a fluorescent indicator, absorbing at 254 nm. Silica gel column chromatography was performed on a CombiFlash Rf Teledyne ISCO system using hexane, ethyl acetate, methylene chloride, or methanol as eluent. Reverse phase column chromatography (C18 column) was performed on the same instrument using 0.1% formic acid in methanol, acetonitrile, or water as eluent. Separations were monitored by mass spectrometry via a Teledyne ISCO RF+ Purlon ESI-MS or APCI-MS detector with 1 Da resolution. $^1$H NMR spectra were obtained on a Varian (400 MHz) spectrometers in the Department of Chemistry and Biochemistry at U.C. San Diego. The purity of all compounds used in assays was determined to be ≥95% by $^1$H NMR spectroscopy and confirmed by high-resolution mass spectrometry (HRMS) experiments using an Agilent 6230 Accurate-Mass LC-TOFMS at the U.C. San Diego Molecular Mass Spectrometry Facility (MMSF). Standard resolution MS was performed either at U.C. San Diego Molecular Mass Spectrometry Facility or on the aforementioned Teledyne ISCO RF+ Purlon MS. Microwave reactions were performed using a CEM Discover series S-class microwave reactor in pressure-sealed vessels. Compounds 3 and 8 were obtained from commercial suppliers.

Experiment 11.2: Synthesis of Compounds in Table 1

Compounds 1, 2, 3, 4, 6, and 8 were previously reported (see Reference 30).

5-(Benzyloxy)-1,2-dimethylpyridin-4(1H)-one (10)

A mixture of 5-(benzyloxy)-2-methyl-4H-pyran-4-one (compound 82 in Scheme 3) (250 mg, 1.156 mmol), methylamine (0.154 mL, 3.47 mmol), and acetic acid (0.199 ml, 3.47 mmol) in ethanol (3 mL) and water (1.5 mL) was added to a 10 mL microwave vessel. The reaction mixture was heated with stirring at 125° C. for 3 hours. After cooling, the solvent was evaporated under vacuum, and the resulting solid purified by silica chromatography (gradient of 0-10% MeOH in CH₂Cl₂) to yield compound 10 (188 mg, 71%) as a light pink solid. ¹H NMR (400 MHz, CD₃OD): δ 7.46 (s, 1H), 6.36 (s, 1H), 3.68 (s, 3H), 2.35 (s, 3H). HR-ESI-MS Experimental: 162.0522. Calculated for [C₇H₉NO₂Na]⁺: 162.0525.

Experiment 9.4: Synthesis of Compounds in Table 3a

Scheme 1
Synthetic route from bromopyruvic acid (72)

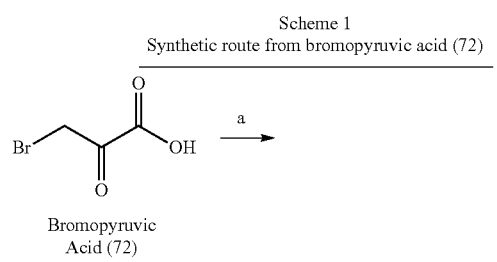

Bromopyruvic Acid (72)

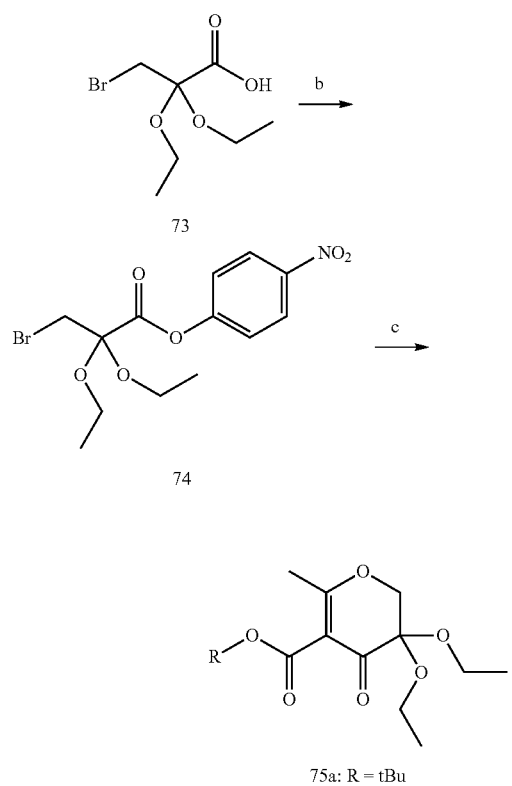

75a: R = tBu
75b: R = Et

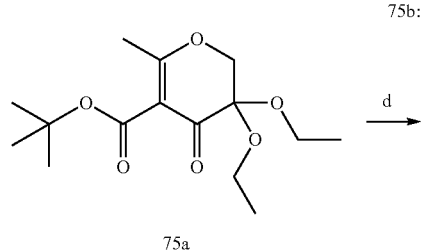

75a

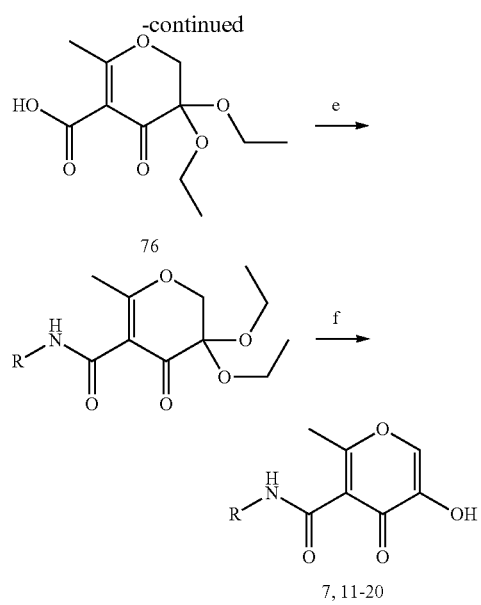

7, 11-20

Reagents and conditions: (a) triethyl orthoformate, H₂SO₄ (catalytic), rt, 24 h; (b) 4-nitrophenyl trifluoroacetate, pyridine, rt, 18 h; (c) ethyl or tert-butyl acetoacetate, NaH, reflux in dry THF, 4-6 h; (d) TFA, CH₂Cl₂, rt, 2-4 h; (e) HATU, triethyl amine, DMF, 60° C., o/n; (f) 1:1 HCOOH:H₂O, 80° C., 2-6 h.

Synthesis of 5-hydroxy-2-methyl-4-oxo-4H-pyran-3-carboxamide derivatives is outlined in Scheme 1. Bromopyruvic acid was transformed to bromodiethoxypropanoic acid by treatment with triethyl orthoformate in the presence of catalytic sulfuric acid. The acetal-protected propanoic acid was then activated as the p-nitrophenyl ester compound 74. Pyrone ring formation was achieved over two steps by the slow addition of compound 74 to a solution of ethyl or tert-butyl acetoacetate that was deprotonated by sodium hydride prior to the addition. After the initial nucleophilic attack of the activated ester by the acetoacetate, ring closing was accomplished via nucleophilic addition by heating the reaction mixture to reflux for 4-6 hours. The pyrone-acetal compound 75a was saponified by stirring briefly with trifluoroacetic acid (TFA) in CH₂Cl₂. The tert-butyl ester was removed selectively by controlling the time of the reaction, as the ester is more labile in the absence of water than the acetal. Key intermediate compound 76 was used to prepare various amides using analogous conditions; specifically, compound 76 was activated with HATU and triethyl amine in DMF. Addition of the amine was followed by heating and stirring for ~18 hours at 60° C. After isolation of the formed amide, the acetal was deprotected in water and acid to reveal the 3-keto intermediate, which rapidly tautomerizes to form the desired 3-hydroxide species.

General Procedure for the Preparation of Compounds 7, 11-20:

To a solution of 3,3-diethoxy-6-methyl-4-oxo-3,4-dihydro-2H-pyran-5-carboxylic acid (76) (100 mg, 0.409 mmol) in dimethylformamide (DMF) (15 mL) was added triethylamine (TEA) (0.068 mL, 0.491 mmol). The mixture was stirred briefly, and 1-[bis(dimethylamino)methylene]-1H-1,2,3-triazolo[4,5-b]pyridinium 3-oxid hexafluorophosphate (HATU) (187 mg, 0.491 mmol) was added. A primary amine or aniline (0.491 mmol) was then added and the mixture was heated to 55° C. and stirred overnight. The reaction mixture was concentrated to dryness under vacuum, taken up in ethyl acetate, washed twice with saturated bicarbonate solution, and dried over MgSO₄. The organic solution was concentrated to dryness and purified by silica column chromatography (gradient of 0-50% ethyl acetate in hexanes). This acetal intermediate was then taken up in 1:1 water:formic acid (20 mL) and heated to 80° C. for 2-6 h hours. The reaction mixture was concentrated to dryness under vacuum, and the residue was purified by silica column chromatography eluting with a gradient of 0-10% MeOH in $CH_2Cl_2$.

5-Hydroxy-N, 2-dimethyl-4-oxo-4H-pyran-3-carboxamide (7)

Compound 7 was prepared according to the procedure described above in 68% yield over 2 steps, and was isolated as a white solid (51 mg). $^1$H NMR (400 MHz, $CD_3OD$): δ 7.25 (s, 1H), 3.23 (s, 3H), 2.68 (s, 3H). HR-ESI-MS Experimental: 182.0456. Calculated for $[C_8H_8NO_4]^-$: 182.0459.

5-Hydroxy-2-methyl-4-oxo-N-phenyl-4H-pyran-3-carboxamide (11)

Compound 11 was prepared according to the procedure described above in 50% yield over 2 steps, and was isolated as a beige solid (49 mg). $^1$H NMR (400 MHz, Acetone-$d_6$): δ 11.56 (s, 1H), 8.16 (s, 1H), 7.72 (d, J=7.7 Hz, 2H), 7.35 (t, J=7.9 Hz, 2H), 7.11 (t, J=7.4 Hz, 1H), 3.10 (s, 3H). HR-ESI-MS Experimental: 244.0613. Calculated for $[C_{13}H_{10}NO_4]^-$: 244.0615.

N-benzyl-5-hydroxy-2-methyl-4-oxo-4H-pyran-3-carboxamide (12)

Compound 12 was prepared according to the general procedure in 65% yield over 2 steps, and was isolated as a white solid (76 mg). $^1$H NMR (400 MHz, $CD_3OD$): δ 9.72 (s, 1H), 7.93 (s, 1H), 7.35 (m, 4H), 7.24 (t, J=6.9 Hz, 1H), 4.54 (s, 2H), 2.56 (s, 3H). HR-ESI-MS Experimental: 285.0772. Calculated for $[C_{14}H_{12}NO_4]^-$: 285.0772.

5-Hydroxy-2-methyl-4-oxo-N-phenethyl-4H-pyran-3-carboxamide (13)

Compound 13 was prepared according to the procedure described above in 69% yield over 2 steps, and was isolated as a pink solid (77 mg). $^1$H NMR (400 MHz, $CD_3OD$) δ: 9.36 (s, 1H), 7.90 (s, 1H), 7.26 (bd, J=2.4 Hz, 5H), 4.87 (t, J=5.1 Hz, 2H), 3.59 (t, J=5.2 Hz, 2H), 2.47 (s, 3H). HR-ESI-MS Experimental: 272.0929. Calculated for $[C_{15}H_{14}NO_4]^-$: 272.0928.

N-(4-fluorophenyl)-5-hydroxy-2-methyl-4-oxo-4H-pyran-3-carboxamide (14)

Compound 14 was prepared according to the procedure described above in 53% yield over 2 steps, and was isolated as a white solid (57 mg). $^1$H NMR (400 MHz, Acetone-$d_6$): δ 11.58 (s, 1H), 8.16 (s, 1H), 7.75 (dd, J=8.9, 4.9 Hz, 2H), 7.13 (t, J=8.8 Hz, 2H), 2.79 (s, 3H). HR-ESI-MS Experimental: 262.0522. Calculated for $[C_{13}H_9FNO_4]^-$: 262.0521.

N-(4-fluorobenzyl)-5-hydroxy-2-methyl-4-oxo-4H-pyran-3-carboxamide (15)

Compound 15 was prepared according to the procedure described above in 55% yield over 2 steps, and was isolated as a light brown solid (62 mg). $^1$H NMR (400 MHz, $CDCl_3$): δ 9.78 (s, 1H), 7.85 (s, 1H), 7.31 (dd, J=8.4, 5.5 Hz, 2H), 7.01 (t, J=8.7 Hz, 2H), 4.56 (d, J=5.6 Hz, 2H), 2.85 (s, 3H). HR-ESI-MS Experimental: 276.0679. Calculated for $[C_{14}H_{11}FNO_4]^-$: 276.0678.

N-(4-fluorophenethyl)-5-hydroxy-2-methyl-4-oxo-4H-pyran-3-carboxamide (16)

Compound 16 was prepared according to the procedure described above in 71% yield over 2 steps, and was isolated as a pink solid (84 mg). $^1$H NMR (400 MHz, $CDCl_3$): δ 9.44 (s, 1H), 7.78 (s, 1H), 7.20 (dd, J=7.7, 5.7 Hz, 2H), 6.97 (t, J=8.5 Hz, 2H), 3.66-3.60 (m, 2H), 2.87 (t, J=7.2 Hz, 2H), 2.80 (s, 3H). HR-ESI-MS Experimental: 290.0835. Calculated for $[C_{15}H_{13}FNO_4]^-$: 290.0834.

5-Hydroxy-N-(4-methoxybenzyl)-2-methyl-4-oxo-4H-pyran-3-carboxamide (17)

Compound 17 was prepared according to the procedure described above in 65% yield over 2 steps, and was isolated as a white solid (77 mg). $^1$H NMR (400 MHz, $CD_3OD$): δ 7.89 (s, 1H), 7.25 (d, J=8.2 Hz, 2H), 6.84 (d, J=8.2 Hz, 2H), 4.44 (s, 2H), 3.73 (s, 3H), 2.54 (s, 3H). HR-ESI-MS Experimental: 288.0878. Calculated for $[C_{15}H_{14}NO_5]^-$: 288.0877.

5-Hydroxy-N-(3-methoxybenzyl)-2-methyl-4-oxo-4H-pyran-3-carboxamide (18)

Compound 18 was prepared according to the procedure described above in 62% yield over 2 steps, and was isolated as a light yellow solid (73 mg). $^1$H NMR (400 MHz, Acetone-$d_6$): δ 9.66 (s, 1H), 8.09 (s, 1H), 7.24 (t, J=7.9 Hz, 1H), 7.06-6.87 (m, 2H), 6.82 (dd, J=8.2, 2.1 Hz, 1H), 4.56 (d, J=5.8 Hz, 2H), 3.78 (s, 3H), 2.72 (s, 3H). HR-ESI-MS Experimental: 288.0878. Calculated for $[C_{15}H_{14}NO_5]^-$: 288.0877.

5-Hydroxy-2-methyl-N-(naphthalen-1-yl)-4-oxo-4H-pyran-3-carboxamide (19)

Compound 19 was prepared according to the procedure described above in 51% yield over 2 steps, and was isolated as a white solid (62 mg). $^1$H NMR (400 MHz, DMSO-$d_6$): δ 11.69 (s, 1H), 9.63 (s, 1H), 8.30 (d, J=8.0 Hz, 1H), 8.10 (d, J=7.5 Hz, 1H), 7.97 (d, J=7.7 Hz, 1H), 7.77 (d, J=8.2 Hz, 1H), 7.55 (dt, J=22.1, 7.7 Hz, 3H), 2.65 (s, 3H). HR-ESI-MS Experimental: 294.0773. Calculated for $[C_{17}H_{12}NO_4]^-$: 294.0772.

N-(2-(1H-indol-3-yl)ethyl)-5-hydroxy-2-methyl-4-oxo-4H-pyran-3-carboxamide (20)

Compound 20 was prepared according to the procedure described above in 47% yield over 2 steps, and was isolated as a red solid (60 mg). $^1$H NMR (400 MHz, $CD_3OD$): δ 10.20 (s, 1H), 9.34 (s, 1H), 7.91 (s, 1H), 7.58 (d, J=7.8 Hz, 1H), 7.32 (d, J=7.9 Hz, 1H), 7.11 (d, J=15.2 Hz, 1H), 7.07 (t, J=7.4 Hz, 1H), 6.98 (t, J=7.4 Hz, 1H), 3.81-3.57 (m, 2H), 3.04 (t, J=7.1 Hz, 2H), 2.46 (s, 3H). HR-ESI-MS Experimental: 311.1036. Calculated for $[C_{17}H_{15}N_2O_4]^-$: 311.1037.

Example 11.5: Synthesis of Compounds in Table 3b

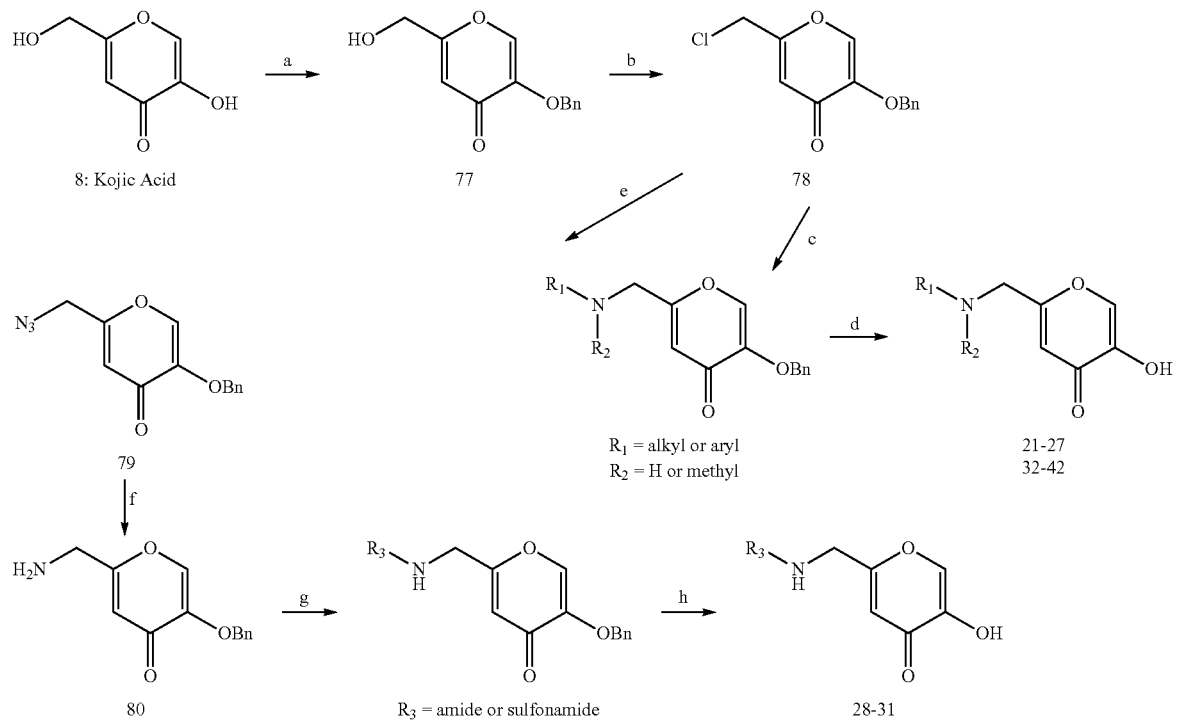

Scheme 2
Synthetic route from Kojic acid (compound 8)

$R_1$ = alkyl or aryl
$R_2$ = H or methyl
$R_3$ = amide or sulfonamide

[a]Reagents and conditions: (a) benzyl bromide, $K_2CO_3$, DMF, 80° C., 8-12 h; (b) thionyl chloride, $CH_2Cl_2$, rt, 8 h; (c) $R_1R_2NH$, triethyl amine, DMF, 75° C., o/n; (d) 5:5:1 HOAc:HCl:TFA, rt to 40° C., 24-48 h; (e) sodium azide, DMF, rt, o/n; (f) triphenylphosphine, THF, rt, 30-60 min; (g) acid chloride or sulfonyl chloride, $CH_2Cl_2$, rt, o/n; (h) $BCl_3$, $CH_2Cl_2$, 0° C., 30 min, rt, 30 min.

To acquire SAR at the 6-position, a library of amine derivatives was prepared from commercially available kojic acid, outlined in Scheme 2. The phenolic oxygen of 8 was selectively protected as a benzyl ether by treatment with benzyl bromide in the presence of potassium carbonate in DMF at 80° C. Compound 78 was prepared quantitatively by reacting compound 77 with thionyl chloride. Nucleophilic addition of various primary and secondary amines, followed by selective hydrolysis of the benzyl ether in a mixture of TFA, concentrated HCl, and glacial acetic acid afforded aminomethyl pyrones in good yields. Amide and sulfonamide derivatives were generated by the nucleophilic addition of sodium azide to compound 78, following by reduction of compound 79 with triphenylphosphine to afford compound 80 as a key intermediate. Compound 80 was reacted with various acid chlorides and sulfonyl chlorides to generate compounds 28-31, after deprotection of the phenol by boron trichloride.

5-(Benzyloxy)-2-(hydroxymethyl)-4H-pyran-4-one (77)

Kojic acid (15 g, 106 mmol) and potassium carbonate (32.1 g, 232 mmol) were dissolved in DMF (200 mL) and stirred. Benzyl bromide (15.07 mL, 127 mmol) was added and the mixture was heated to 80° C. for 6-8 hours. Solvent was then evaporated under vacuum, and the residue was recrystallized in water to give compound 77 (24.7 g, 72%) as white, needle-like crystals. $^1$H NMR (400 MHz, $CDCl_3$): δ 7.52 (s, 1H), 7.44-7.29 (m, 5H), 6.52 (s, 1H), 5.04 (s, 2H). HR-ESI-MS Experimental: 255.0636. Calculated for $[C_{13}H_{12}O_4Na]^+$: 255.0634.

5-(Benzyloxy)-2-(chloromethyl)-4H-pyran-4-one (78)

To a rapidly stirring suspension of compound 77 (2.5 g, 10.76 mmol) in $CH_2Cl_2$ (100 mL) at room temperature was added thionyl chloride (0.903 mL, 12.38 mmol), dropwise over the course of 20 minutes. Throughout the addition, the suspension tended to clump. When clumping occurred, the addition was paused to allow the solution to return to homogeneity. After addition, the reaction was stirred for 6-8 hours, during which time the solution turned from cloudy white, to a pale translucent yellow, to a cloudy white. After 6-8 hours, the solution was dried under vacuum, co-evaporated with methanol to remove all residual HCl, and purified via silica column chromatography, eluting with a gradient of 0-5% methanol in $CH_2Cl_2$ to afford compound 78 (2.23 g, 83%) as a white solid yield. $^1$H NMR (400 MHz, $CDCl_3$): δ 7.56 (s, 1H), 7.37 (dd, J=12.9, 4.6 Hz, 5H), 6.48 (s, 1H), 5.08 (s, 2H). ESI-MS $[M+H]^+$: 251.24.

General Procedure for the Preparation of 21-27, 32-42

To a solution of 5-(benzyloxy)-2-(chloromethyl)-4H-pyran-4-one (78) (250 mg, 0.997 mmol) and aryl or alkyl, primary, or secondary amine (1.995 mmol) in DMF (15 mL) was added TEA (0.306 mL, 2.194 mmol). The mixture was heated to 75° C. and stirred overnight. The reaction was then evaporated to dryness under vacuum, and the residue purified by column chromatography (0-5% methanol in $CH_2Cl_2$). The benzyl ether protected intermediate was then stirred in a 5:5:1 mixture of concentrated hydrochloric acid, glacial acetic acid, and TFA for 24-48 hours. Solvent was removed under high vacuum, the residue co-evaporated several times with methanol, and resulting solids purified by C18 column chromatography in a methanol-water system with added 0.1% formic acid.

2-((Dimethylamino)methyl)-5-hydroxy-4H-pyran-4-one (21)

Compound 21 was prepared according to the general procedure in 58% yield over 2 steps, and was isolated as a red oily solid (97 mg). $^1$H NMR (400 MHz, $CD_3OD$): δ 8.08 (s, 1H), 6.71 (s, 1H), 4.38 (s, 2H), 2.96 (s, 6H). HR-ESI-MS Experimental: 170.0811. Calculated for $[C_8H_{12}NO_3]^+$: 170.0812.

5-Hydroxy-2-(piperidin-1-ylmethyl)-4H-pyran-4-one (22)

Compound 22 was prepared according to the procedure described above in 78% yield over 2 steps, and was isolated as a beige solid (161 mg). $^1$H NMR (400 MHz, $CD_3OD$): δ 7.96 (s, 1H), 6.47 (s, 1H), 3.41 (s, 2H), 2.47 (s, 4H), 1.60 (dt, J=11.0, 5.6 Hz, 4H), 1.45 (d, J=5.1 Hz, 2H). HR-ESI-MS Experimental: 210.1123. Calculated for $[C_{11}H_{16}NO_3]^+$: 210.1125.

5-Hydroxy-2-((isopropylamino)methyl)-4H-pyran-4-one (23)

Compound 23 was prepared according to the procedure described above in 66% yield over 2 steps, and was isolated as a red oily solid (120 mg). $^1$H NMR (400 MHz, $CDCl_3$): δ 7.82 (s, 1H), 7.26 (s, 1H), 6.49 (s, 1H), 3.68 (s, 2H), 2.82 (dt, J=12.4, 6.3 Hz, 1H), 1.08 (d, J=6.2 Hz, 6H). HR-ESI-MS Experimental: 184.0968. Calculated for $[C_9H_{14}NO_3]^+$: 184.0968.

2-((Cyclohexylamino)methyl)-5-hydroxy-4H-pyran-4-one (24)

Compound 24 was prepared according to the procedure described above in 74% yield over 2 steps, and was isolated as a white solid (163 mg). $^1$H NMR (400 MHz, $CDCl_3$): δ 7.82 (s, 1H), 7.26 (s, 1H), 6.50 (s, 1H), 3.70 (s, 2H), 2.43 (dd, J=12.0, 8.4 Hz, 1H), 1.86 (d, J=11.6 Hz, 2H), 1.73 (d, J=13.0 Hz, 2H), 1.61 (d, J=11.0 Hz, 1H), 1.21 (dd, J=22.9, 10.7 Hz, 3H), 1.13-1.06 (m, 2H). HR-ESI-MS Experimental: 224.1280. Calculated for $[C_{12}H_{18}NO_3]$: 224.1281.

5-Hydroxy-2-((isobutylamino)methyl)-4H-pyran-4-one (25)

Compound 25 was prepared according to the procedure described above in 62% yield over 2 steps, and was isolated as a pink solid (120 mg). $^1$H NMR (400 MHz, $CDCl_3$): δ 7.83 (d, J=5.8 Hz, 1H), 7.27 (d, J=5.7 Hz, 1H), 6.50 (d, J=5.6 Hz, 1H), 3.67 (d, J=5.3 Hz, 2H), 2.43 (t, J=6.1 Hz, 2H), 1.74 (dd, J=13.1, 6.6 Hz, 1H), 0.92 (t, J=6.1 Hz, 6H). HR-ESI-MS Experimental: 198.1122. Calculated for $[C_{10}H_{16}NO_3]^+$: 198.1125.

2-((Benzylamino)methyl)-5-hydroxy-4H-pyran-4-one (26)

Compound 26 was prepared according to the procedure described above in 76% yield over 2 steps, and was isolated as a pink solid (242 mg). $^1$H NMR (400 MHz, $CD_3OD$): δ 7.97 (s, 1H), 7.36 (d, J=6.8 Hz, 5H), 6.49 (s, 1H), 3.90 (s, 2H), 3.79 (s, 2H). HR-ESI-MS Experimental: 323.0966. Calculated for $[C_{13}H_{14}NO_3]$: 323.0968.

2-((Benzyl(methyl)amino)methyl)-5-hydroxy-4H-pyran-4-one (27)

Compound 27 was prepared according to the procedure described above in 64% yield over 2 steps, and was isolated as a beige solid (155 mg). $^1$H NMR (400 MHz, $CD_3OD$): δ 7.93 (s, 1H), 7.29 (d, J=6.7 Hz, 5H), 6.49 (s, 1H), 3.56 (s, 2H), 3.42 (s, 2H), 2.24 (s, 3H). HR-ESI-MS Experimental: 246.1120. Calculated for $[C_{14}H_{16}NO_3]^+$: 246.1125.

5-Hydroxy-2-((phenylamino)methyl)-4H-pyran-4-one (32)

Compound 32 was prepared according to the procedure described above in 51% yield over 2 steps, and was isolated as a white solid (110 mg). $^1$H NMR (400 MHz, $CD_3OD$): δ 7.96 (s, 1H), 7.11 (t, J=7.9 Hz, 2H), 6.70-6.58 (m, 3H), 6.41 (s, 1H), 4.86 (s, 6H), 4.23 (s, 2H), 3.31 (d, J=1.5 Hz, 3H). HR-ESI-MS Experimental: 218.0813. Calculated for $[C_{12}H_{12}NO_3]$: 218.0812.

5-Hydroxy-2-(phenoxymethyl)-4H-pyran-4-one (33)

Compound 33 was prepared according to the procedure described above in 43% yield over 2 steps, and was isolated as a yellow oily solid (92 mg). $^1$H NMR (400 MHz, $CDCl_3$): δ 7.88 (s, 1H), 7.31 (t, J=7.9 Hz, 2H), 7.02 (t, J=7.3 Hz, 1H), 6.93 (d, J=8.3 Hz, 2H), 6.65 (s, 1H), 4.88 (s, 2H). HR-ESI-MS Experimental: 219.0651. Calculated for $[C_{12}H_{11}NO_4]^+$: 219.0652.

5-Hydroxy-2-((methyl(phenyl)amino)methyl)-4H-pyran-4-one (34)

Compound 34 was prepared according to the procedure described above in 69% yield over 2 steps, and was isolated as a white solid (157 mg). $^1$H NMR (400 MHz, $CD_3OD$): δ 7.96 (s, 1H), 7.19 (t, J=7.7 Hz, 2H), 6.81-6.66 (m, 3H), 6.24 (s, 1H), 4.43 (s, 2H), 3.05 (s, 3H). HR-ESI-MS Experimental: 232.0968. Calculated for $[C_{13}H_{14}NO_3]^+$: 232.0968.

2-(((4-Chlorophenyl)(methyl)amino)methyl)-5-hydroxy-4H-pyran-4-one (35)

Compound 35 was prepared according to the procedure described above in 55% yield over 2 steps, and was isolated as a white solid (144 mg). $^1$H NMR (400 MHz, $CD_3OD$): δ 7.96 (s, 1H), 7.16 (d, J=9.1 Hz, 2H), 6.73 (d, J=9.0 Hz, 2H), 6.24 (s, 1H), 4.44 (s, 2H), 3.05 (s, 3H). HR-ESI-MS Experimental: 266.0584. Calculated for [C$_{13}$H$_{13}$ClNO$_3$]$^+$: 266.0578.

2-(((3-Chlorophenyl)(methyl)amino)methyl)-5-hydroxy-4H-pyran-4-one (36)

Compound 36 was prepared according to the procedure described above in 60% yield over 2 steps, and was isolated as a white solid (157 mg). $^1$H NMR (400 MHz, CDCl$_3$): δ 7.84 (s, 1H), 7.14 (t, J=8.1 Hz, 1H), 6.75 (d, J=7.8 Hz, 1H), 6.66 (s, 1H), 6.55 (d, J=8.3 Hz, 1H), 6.32 (s, 1H), 4.33 (s, 2H), 3.05 (s, 3H). HR-ESI-MS Experimental: 266.0583. Calculated for [C$_{13}$H$_{13}$ClNO$_3$]$^+$: 266.0578.

5-Hydroxy-2-(((4-methoxyphenyl)(methyl)amino)methyl)-4H-pyran-4-one (37)

Compound 37 was prepared according to the procedure described above in 57% yield over 2 steps, and was isolated as a light yellow solid (134 mg). $^1$H NMR (400 MHz, CDCl$_3$): δ 7.82 (s, 1H), 6.82 (d, J=9.1 Hz, 2H), 6.68 (d, J=9.1 Hz, 2H), 6.37 (s, 1H), 4.24 (s, 2H), 3.74 (s, 3H), 2.96 (s, 3H). HR-ESI-MS Experimental: 284.0891. Calculated for [C$_{14}$H$_{15}$NO$_4$Na]$^+$: 284.0893.

5-Hydroxy-2-(((3-methoxyphenyl)(methyl)amino)methyl)-4H-pyran-4-one (38)

Compound 38 was prepared according to the procedure described above in 68% yield over 2 steps, and was isolated as a light yellow solid (168 mg). $^1$H NMR (400 MHz, CDCl$_3$): δ 7.83 (s, 1H), 7.14 (t, J=8.0 Hz, 1H), 6.44-6.29 (m, 3H), 6.24 (s, 1H), 4.33 (s, 2H), 3.78 (s, 3H), 3.47 (s, 1H), 3.04 (s, 3H). HR-ESI-MS Experimental: 284.0892. Calculated for [C$_{14}$H$_{15}$NO$_4$Na]$^+$: 284.0893.

2-(((4-Fluorophenyl)(methyl)amino)methyl)-5-hydroxy-4H-pyran-4-one (39)

Compound 39 was prepared according to the procedure described above in 62% yield over 2 steps, and was isolated as a white solid (153 mg). $^1$H NMR (400 MHz, CDCl$_3$): δ 7.83 (s, 1H), 6.94 (t, J=8.7 Hz, 2H), 6.72-6.60 (m, 2H), 6.35 (s, 1H), 4.29 (s, 2H), 3.01 (s, 3H). HR-ESI-MS Experimental: 272.0692. Calculated for [C$_{13}$H$_{12}$FNO$_3$Na]$^+$: 272.0693.

2-(((3-Fluorophenyl)(methyl)amino)methyl)-5-hydroxy-4H-pyran-4-one (40)

Compound 40 was prepared according to the procedure described above in 74% yield over 2 steps, and was isolated as a white solid (183 mg). $^1$H NMR (400 MHz, CDCl$_3$): δ 7.85 (s, 1H), 7.17 (dd, J=15.5, 7.7 Hz, 1H), 6.57-6.30 (m, 4H), 4.34 (s, 2H), 3.06 (s, 3H). HR-ESI-MS Experimental: 250.0876. Calculated for [C$_{13}$H$_{13}$FNO$_3$]$^+$: 250.0874.

5-Hydroxy-2-((methyl(pyridin-4-yl)amino)methyl)-4H-pyran-4-one (41)

Compound 41 was prepared according to the procedure described above in 48% yield over 2 steps, and was isolated as a pink solid (110 mg). $^1$H NMR (400 MHz, CD$_3$OD): δ 8.33 (s, 1H), 8.16 (s, 1H), 7.98 (s, 1H), 6.95 (s, 2H), 6.56 (s, 1H), 5.37 (s, 2H), 3.01 (s, 3H). HR-ESI-MS Experimental: 233.0922. Calculated for [C$_{12}$H$_{13}$N$_2$O$_3$]$^+$: 233.0921.

5-Hydroxy-2-((methyl(pyridin-3-yl)amino)methyl)-4H-pyran-4-one (42)

Compound 42 was prepared according to the procedure described above in 53% yield over 2 steps, and was isolated as a pink solid (122 mg). $^1$H NMR (400 MHz, CD$_3$OD): δ 8.33 (s, 1H), 8.16 (s, 1H), 7.98 (s, 1H), 6.95 (s, 2H), 6.56 (s, 1H), 5.37 (s, 2H), 3.01 (s, 3H). HR-ESI-MS Experimental: 233.0922. Calculated for [C$_{12}$H$_{13}$N$_2$O$_3$]$^+$: 233.0921.

2-(Azidomethyl)-5-(benzyloxy)-4H-pyran-4-one (79)

To a stirring solution of compound 78 (1.5 g, 5.98 mmol) in DMF (25 mL) was added sodium azide (0.408 g, 6.28 mmol) slowly. The mixture was left to stir overnight at room temperature. To the reaction mixture was added 5 mL of saturated sodium bicarbonate and the solution stirred for 5 minutes. Solvent was removed under reduced pressure, and the residue was purified via a silica column chromatography, eluting with a gradient of 0-5% methanol in CH$_2$Cl$_2$. Purification yielded compound 79 as a light brown solid (1.2 g, 78%). 1H NMR (400 MHz, CDCl$_3$): δ 7.52 (s, 1H), 7.34 (dd, J=26.9, 19.0 Hz, 5H), 6.52 (s, 1H), 5.04 (s, 2H), 4.44 (s, 2H). ESI-MS [M+H]$^+$: 258.09.

2-(Aminomethyl)-5-(benzyloxy)-4H-pyran-4-one (80)

Compound 79 (1 g, 4 mmol) in THF (50 mL) was stirred at room temperature. Triphenylphosphine (1.259 g, 4.8 mmol) was added slowly to the stirring solution, and was left to react for 30-60 minutes. To the reaction was added aq. 1 M HCl, and the mixture was washed with 3×100 mL chloroform. The organics were discarded, and the pH of the aqueous phase was raised to ~12 with 6 M NaOH. The basic aqueous phase was extracted with 3×100 mL ethyl acetate. Organics were combined and dried, then concentrated to yield compound 80 as a dark red, oily solid. NMR analysis indicated traces of triphenylphosphine oxide were still present. However, compound 80 was used without further purification. ESI-MS [M+H]$^+$: 232.16.

N-((5-(benzyloxy)-4-oxo-4H-pyran-2-yl)methyl) acetamide (28)

Compound 80 (250 mg, 0.934 mmol) was dissolved in CH$_2$Cl$_2$ (15 mL) and stirred. To the stirring mixture was added acetic anhydride (0.5 mL, 5.3 mmol) slowly, and the reaction mixed overnight. The reaction was quenched by the addition of water (50 mL) and stirred 15 minutes. To this mixture was added 1 M NaOH (25 mL) and CH$_2$Cl$_2$ (100 mL). The layers were separated and the organic layer was dried under reduced pressure. This residue was then taken up directly in dry CH$_2$Cl$_2$ (25 mL) and cooled in an ice bath to 0° C. Boron trichloride (1 M in CH$_2$Cl$_2$, 3 mL) was then added dropwise and the reaction stirred for 30 minutes on ice and 30 minutes at room temperature. The reaction was quenched by the slow addition of methanol, concentrated under vacuum, co-evaporated with methanol, and purified by C18 column chromatography, in a water:methanol system with added 0.1% formic acid. Purification yielded compound 28 (100 mg) in 59% yield as a white solid. $^1$H NMR (400 MHz, DMSO-d$_6$): δ 8.44 (s, 1H), 8.02 (s, 1H), 6.22 (s, 1H), 4.10 (d, J=5.8 Hz, 2H), 1.87 (s, 3H). HR-ESI-MS Experimental: 184.0602. Calculated for [C$_8$H$_{10}$NO$_4$]$^+$: 184.0604.

N-((5-(benzyloxy)-4-oxo-4H-pyran-2-yl)methyl) benzamide (29)

Compound 29 was prepared similarly to compound 28, substituting benzoyl chloride for acetic anhydride, in 66% yield and was isolated as a white solid (150 mg). $^1$H NMR (400 MHz, DMSO-$d_6$): δ 8.05 (s, 1H), 7.88 (d, J=8.0 Hz, 2H), 7.54 (d, J=7.4 Hz, 1H), 7.48 (t, J=7.5 Hz, 2H), 6.27 (s, 1H), 4.34 (d, J=5.5 Hz, 2H), 3.35 (s, 3H). HR-ESI-MS Experimental: 246.0760. Calculated for $[C_{13}H_{12}NO_4]^+$: 246.0761.

N-((5-(benzyloxy)-4-oxo-4H-pyran-2-yl)methyl) methanesulfonamide (30)

Compound 30 was prepared similarly to compound 28, substituting methanesuflonyl chloride for acetic anhydride, in 47% yield and was isolated as an off-white solid (95 mg). $^1$H NMR (400 MHz, DMSO-$d_6$): δ 8.06 (s, 1H), 6.36 (s, 1H), 4.05 (s, 2H), 2.94 (s, 3H). HR-ESI-MS Experimental: 220.0279. Calculated for $[C_{13}H_{12}NO_4]^+$: 220.0274.

N-((5-(benzyloxy)-4-oxo-4H-pyran-2-yl)methyl) benzenesulfonamide (31)

Compound 31 was prepared similarly to compound 28, substituting benzoyl chloride for acetic anhydride, in 52% yield and was isolated as a white solid (135 mg). $^1$H NMR (400 MHz, DMSO-$d_6$): δ 7.87 (s, 1H), 7.82-7.75 (m, 2H), 7.61 (d, J=7.0 Hz, 1H), 7.55 (t, J=7.3 Hz, 2H), 6.22 (s, 1H), 3.93 (s, 2H). HR-ESI-MS Experimental: 282.0434. Calculated for $[C_{12}H_{12}NO_5S]^+$: 282.0431.

Example 11.6: Synthesis of Compounds in Tables 4 and 5

Scheme 3
Synthetic route from Compound 8

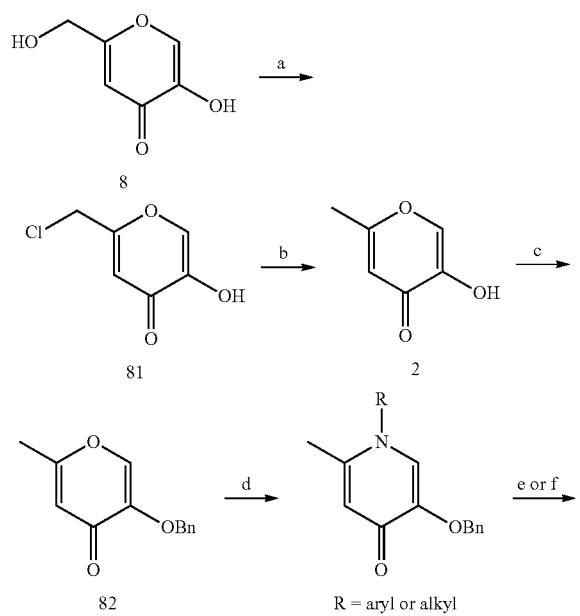

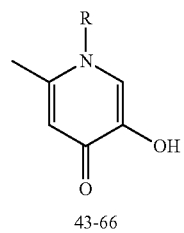

Reagents and conditions: (a) thionyl chloride, $CH_2Cl_2$, rt, 4-6 h; (b) Zinc dust, HCl, water, 70° C., 4-6 h; (c) benzyl bromide, $K_2CO_3$, DMF, 80° C., 8-12 h; (d) aryl or alkyl amine, HOAc, 3:1 EtOH:$H_2O$, MW 125° C., 90-120 min; (e) $BCl_3$, $CH_2Cl_2$, 0° C., 30 min, rt, 30 min; (f) 5:5:1 HOAc:HCl:TFA, rt-40° C., 24-48 h.

Preparation of pyridinone derivatives of allomaltol (2) possessing N-aryl and -alkyl substituents is described generally in Scheme 3. Kojic chloride (81) was derived from compound 8, and reduced to compound 2 using metallic zinc and strong acid. While dehydration of the hydroxypyrone ring to afford hydroxypyridinone derivatives was shown to be possible, benzyl protection of the hydroxyl group prior to dehydration greatly improved yields and suppressed formation of side-products. Key intermediate compound 82 was irradiated in a microwave reactor in the presence of excess amine and acetic acid to produce a wide variety of pyridinone derivatives. Microwave heating under increased pressure greatly accelerated reaction rates; dehydration using conventional heating could be accomplished, but required refluxing reactants in ethanol for a period of days. Removal of the benzyl ether after dehydration was shown to be accomplished quickly and efficiently employing boron trichloride as a dealkylating agent, or less efficiently using a 5:5:1 mixture of concentrated hydrochloric acid, glacial acetic acid, and TFA as a milder alternative to boron trihalides.

2-(Chloromethyl)-5-hydroxy-4H-pyran-4-one (81)

To a rapidly stirring suspension of Kojic acid (8) (10 g, 70.4 mmol) in $CH_2Cl_2$ (250 mL) at room temperature was added thionyl chloride (5.91 mL, 81 mmol), dropwise over the course of 25 minutes. Throughout the addition, the suspension tended to clump. When clumping occurred, the addition was paused to allow the solution to return to homogeneity. After 4-6 hours of stirring, the suspension was filtered, and the solids were recrystallized from ethanol to afford Kojic chloride (9.0 g) in 81% yield as white needles. 1H NMR (400 MHz, DMSO-$d_6$): δ 8.12 (s, 1H), 6.56 (s, 1H), 4.65 (s, 2H). ESI-MS $[M+H]^+$: 159.14.

5-Hydroxy-2-methyl-4H-pyran-4-one (2)

A stirring solution of compound 81 (10 g, 62.3 mmol) in water (150 mL) was heated to 50° C. To this vigorously stirring solution was added zinc powder (8.14 g 125 mmol) slowly, and the temperature was raised to 70° C. To this solution was added concentrated HCl (25 mL, 823 mmol) dropwise, maintaining the internal temperature of the solution below 80° C. The mixture was stirred for an additional 4 hours at 70° C. At this point the reaction was hot filtered to remove residual zinc. The cooled filtrate was extracted 5 times with 50 mL $CH_2Cl_2$+10 mL ethyl acetate. The resulting organics were dried and concentrated, to yield compound 2 (allomaltol) (6.5 g) as a white powder in 83% yield.

1H NMR (400 MHz, Acetone-$d_6$): δ 7.82 (s, 1H), 6.21 (s, 1H), 2.28 (d, J=0.5 Hz, 3H). ESI-MS [M−H]⁻: 125.22.

5-(Benzyloxy)-2-methyl-4H-pyran-4-one (82)

Allomaltol (2) (2 g, 15.86 mmol) was dissolved in DMF (100 mL) and stirred. To this solution was added potassium carbonate (4.82 g, 34.9 mmol) and benzyl bromide (2.26 mL, 19 mmol). The reaction mixture was heated to 80° C. overnight. The reaction was then concentrated under vacuum, taken up in water, extracted 3 times with $CH_2Cl_2$. The combined extracts were back-extracted once with 1 M NaOH, dried, and concentrated to afford compound 82 (3.2 g) as a white powder in 93% yield. 1H NMR (400 MHz, Acetone-$d_6$): δ 7.88 (s, 1H), 7.46-7.42 (m, 2H), 7.41-7.31 (m, 3H), 6.16 (d, J=0.6 Hz, 1H), 5.03 (s, 2H), 2.25 (d, J=0.5 Hz, 3H). ESI-MS [M+Na]⁺: 239.27.

General Procedure for the Preparation of Compounds 43-66:

A mixture of 5-(benzyloxy)-2-methyl-4H-pyran-4-one (82) (250 mg, 1.156 mmol), aryl or alkyl amine (3.47 mmol), and acetic acid (0.199 mL, 3.47 mmol) in ethanol (3 mL) and water (1.5 mL) was added to a 10 mL microwave vessel. The reaction mixture was irradiated with stirring at 125° C. for 3 hours. After cooling, the solvent was evaporated under vacuum, and the resulting solid purified by silica chromatography (0-5% methanol in $CH_2Cl_2$). The isolated benzyl ether intermediate was deprotected by one of two methods: (method 1) the benzyl ether intermediate was stirred in a 5:5:1 mixture of concentrated hydrochloric acid, glacial acetic acid, and TFA for 24-48 hours. Solvent was removed under high vacuum, the residue co-evaporated several times with methanol; (method 2) alternatively, boron trichloride (1 M in $CH_2Cl_2$, 3.3 mL) was added dropwise to the isolated intermediate and the reaction stirred for 30 minutes on ice and 30 minutes at room temperature. The reaction was quenched by the slow addition of methanol, concentrated under vacuum, and co-evaporated with methanol. The resultant solids of either deprotection method were purified by C18 column chromatography in a water:methanol system with added 0.1% formic acid.

5-Hydroxy-1-isopropyl-2-methylpyridin-4(1H)-one (43)

Compound 43 was prepared according to the general procedure described above employing deprotection method 2 in 62% yield over 2 steps, and was isolated as a light orange solid (120 mg). ¹H NMR (400 MHz, DMSO-$d_6$): δ 7.45 (s, 1H), 6.03 (s, 1H), 2.28 (s, 3H), 1.31 (d, J=6.6 Hz, 6H). HR-ESI-MS Experimental: 190.0838. Calculated for $[C_{12}H_{13}N_2O_3Na]^+$: 190.0838.

5-Hydroxy-2-methyl-1-phenylpyridin-4(1H)-one (44)

Compound 44 was prepared according to the procedure described above employing deprotection method 2 in 78% yield over 2 steps, as a white solid (181 mg). ¹H NMR (400 MHz, $CD_3OD$): δ 8.04 (s, 1H), 7.68 (s, 3H), 7.53 (d, J=4.1 Hz, 2H), 7.25 (s, 1H), 2.32 (d, J=6.7 Hz, 3H). HR-ESI-MS Experimental: 202.0861. Calculated for $[C_{12}H_{12}NO_2]^+$: 202.0863.

3-Hydroxy-2-methyl-1-phenylpyridin-4(1H)-one (45)

Compound 45 was prepared according to the procedure described above employing deprotection method 2 in 78% yield over 2 steps, and was isolated as a white solid (181 mg). ¹H NMR (400 MHz, $CD_3OD$): δ 7.59 (ddd, J=5.5, 3.1, 1.4 Hz, 4H), 7.46-7.35 (m, 2H), 6.53-6.41 (m, 1H), 2.11 (d, J=1.3 Hz, 3H). HR-ESI-MS Experimental: 224.0681. Calculated for $[C_{12}H_{11}NO_2Na]^+$: 224.0682.

1-([1,1'-Biphenyl]-4-yl)-5-hydroxy-2-methylpyridin-4(1H)-one (46)

Compound 46 was prepared according to the procedure described above employing deprotection method 2 in 64% yield over 2 steps, and was isolated as a pink solid (200 mg). ¹H NMR (400 MHz, $CD_3OD$): δ 8.10 (s, 1H), 7.90 (t, J=8.6 Hz, 2H), 7.75-7.66 (m, 2H), 7.59 (d, J=7.8 Hz, 2H), 7.48 (d, J=7.2 Hz, 3H), 5.27 (s, 1H), 2.36 (s, 3H). HR-ESI-MS Experimental: 300.0997. Calculated for $[C_{18}H_{15}NO_2Na]^+$: 300.0995.

1-Cyclohexyl-5-hydroxy-2-methylpyridin-4(1H)-one (47)

Compound 47 was prepared according to the procedure described above employing deprotection method 2 in 63% yield over 2 steps, and was isolated as a white solid (151 mg). ¹H NMR (400 MHz, DMSO-$d_6$): δ 7.50 (s, 1H), 6.09 (s, 1H), 4.01 (t, J=11.6 Hz, 1H), 2.30 (s, 3H), 1.78 (d, J=11.1 Hz, 4H), 1.74-1.52 (m, 3H), 1.38 (dd, J=25.1, 12.5 Hz, 2H), 1.21 (t, J=12.9 Hz, 1H). HR-ESI-MS Experimental: 208.1330. Calculated for $[C_{12}H_{18}NO_2]^+$: 208.1332.

1-Cyclohexyl-3-hydroxy-2-methylpyridin-4(1H)-one (48)

Compound 48 was prepared according to the procedure described above employing deprotection method 2 in 61% yield over 2 steps, and was isolated as a white solid (146 mg). ¹H NMR (400 MHz, $CD_3OD$) (7.76 (d, J=7.4 Hz, 1H), 6.44 (d, J=7.4 Hz, 1H), 4.29-4.12 (m, 1H), 2.47 (s, 3H), 1.93 (dd, J=23.4, 9.0 Hz, 4H), 1.82-1.64 (m, 3H), 1.52 (dt, J=16.3, 13.1 Hz, 2H), 1.37-1.27 (m, 1H). HR-ESI-MS Experimental: 208.1333. Calculated for $[C_{12}H_{18}NO_2]^+$: 208.1332.

1-Benzyl-5-hydroxy-2-methylpyridin-4(1H)-one (49)

Compound 49 was prepared according to the procedure described above employing deprotection method 1 in 65% yield over 2 steps, and was isolated as a pink solid (162 mg). ¹H NMR (400 MHz, DMSO-$d_6$): δ 7.52 (s, 1H), 7.37 (t, J=7.4 Hz, 2H), 7.30 (d, J=7.3 Hz, 1H), 7.07 (d, J=7.4 Hz, 2H), 6.11 (s, 1H), 5.14 (s, 2H), 2.14 (s, 3H). HR-ESI-MS Experimental: 238.0837. Calculated for $[C_{13}H_{13}NO_2Na]^+$: 238.0838.

1-([1,1'-Biphenyl]-4-ylmethyl)-5-hydroxy-2-methylpyridin-4(1H)-one (50)

Compound 50 was prepared according to the procedure described above employing deprotection method 1 in 55% yield over 2 steps, and was isolated as a white solid (186 mg). ¹H NMR (400 MHz, DMSO-$d_6$): δ 7.65 (dd, J=13.3, 7.8 Hz, 4H), 7.58 (s, 1H), 7.44 (t, J=7.4 Hz, 2H), 7.35 (t, J=7.1 Hz, 1H), 7.17 (d, J=7.9 Hz, 2H), 6.16 (s, 1H), 5.20 (s, 2H), 2.20 (s, 3H). HR-ESI-MS Experimental: 314.1153. Calculated for $[C_{19}H_{17}NO_2Na]^+$: 314.1151.

5-Hydroxy-2-(tetrahydro-2H-pyran-4-yl)pyridin-4(1H)-one (51)

Compound 51 was prepared according to the procedure described above employing deprotection method 1 in 51% yield over 2 steps, and was isolated as a white solid (124 mg). $^1$H NMR (400 MHz, DMSO-d$_6$): δ 7.46 (s, 1H), 6.05 (s, 1H), 4.28 (t, J=11.6 Hz, 1H), 3.93 (dd, J=11.3, 3.9 Hz, 2H), 3.47 (s, 2H), 2.33 (s, 3H), 2.02-1.87 (m, 2H), 1.73 (d, J=9.9 Hz, 2H). HR-ESI-MS Experimental: 232.0943. Calculated for [C$_{11}$H$_{15}$NO$_3$Na]$^+$: 232.0944.

5-Hydroxy-2-methyl-1-(1-methylpiperidin-4-yl)pyridin-4(1H)-one (52)

Compound 52 was prepared according to the procedure described above employing deprotection method 1 in 42% yield over 2 steps, and was isolated as a white solid (108 mg). $^1$H NMR (400 MHz, DMSO-d$_6$): δ 11.49-11.23 (m), 8.07 (s), 7.28 (s), 4.87 (d, J=2.2 Hz), 3.54 (s), 3.30 (s), 2.74 (s), 2.64 (s), 2.38 (s), 2.24 (s). HR-ESI-MS Experimental: 223.1442. Calculated for [C$_{12}$H$_{19}$N$_2$O$_2$]$^+$: 223.1441.

5-Hydroxy-2-methyl-1-(1-(methylsulfonyl)piperidin-4-yl)pyridin-4(1H)-one (53)

Compound 53 was prepared according to the procedure described above employing deprotection method 1 in 62% yield over 2 steps, and was isolated as a white solid (206 mg). $^1$H NMR (400 MHz, DMSO-d$_6$): δ 7.49 (s, 1H), 6.08 (s, 1H), 4.20 (s, 1H), 3.67 (d, J=10.7 Hz, 3H), 2.95-2.91 (m, 3H), 2.50-2.47 (m, 1H), 2.32 (s, 3H), 1.93 (dd, J=39.8, 11.9 Hz, 4H). HR-ESI-MS Experimental: 309.0876. Calculated for [C$_{12}$H$_{18}$N$_2$O$_4$SNa]$^+$: 309.0879.

1-(1-Acetylpiperidin-4-yl)-5-hydroxy-2-methylpyridin-4(1H)-one (54)

Compound 54 was prepared according to the procedure described above employing deprotection method 1 in 69% yield over 2 steps, and was isolated as a white solid (200 mg). $^1$H NMR (400 MHz, CD$_3$OD): δ 8.47 (s), 7.30 (s), 4.75 (s), 4.52 (d, J=12.1 Hz), 3.95 (d, J=12.7 Hz), 3.25 (t, J=12.5 Hz), 3.02 (d, J=5.3 Hz), 2.12-1.95 (m), 1.94-1.80 (m), 1.70 (d, J=8.8 Hz), 1.18 (t, J=7.1 Hz). HR-ESI-MS Experimental: 273.1212. Calculated for [C$_{13}$H$_{18}$N$_2$O$_3$Na]$^+$: 273.1210.

5-Hydroxy-1-(3-methoxyphenyl)-2-methylpyridin-4(1H)-one (55)

Compound 55 was prepared according to the procedure described above employing deprotection method 1 in 76% yield over 2 steps, and was isolated as a white solid (196 mg). $^1$H NMR (400 MHz, CD$_3$OD): δ 7.46 (dd, J=18.5, 10.5 Hz, 2H), 7.19-7.08 (m, 1H), 7.06-6.91 (m, 2H), 6.44 (s, 1H), 3.85 (s, 3H), 2.10 (s, 3H). HR-ESI-MS Experimental: 254.0788. Calculated for [C$_{13}$H$_{13}$NO$_3$Na]$^+$: 254.0788.

5-Hydroxy-2-methyl-1-(3-phenoxyphenyl)pyridin-4(1H)-one (56)

Compound 56 was prepared according to the procedure described above employing deprotection method 1 in 61% yield over 2 steps, and was isolated as a white solid (210 mg). $^1$H NMR (400 MHz, DMSO-d$_6$): δ 7.53 (t, J=8.4 Hz, 1H), 7.41 (dd, J=8.4, 7.5 Hz, 2H), 7.33 (s, 1H), 7.19 (ddd, J=6.3, 3.1, 1.5 Hz, 2H), 7.14-7.05 (m, 4H), 6.19 (s, 1H), 1.98 (s, 3H). HR-ESI-MS Experimental: 316.0943. Calculated for [C$_{18}$H$_{15}$NO$_3$Na]$^+$: 316.0944.

Methyl 3-(5-hydroxy-2-methyl-4-oxopyridin-1(4H)-yl)benzoate (57)

Compound 57 was prepared according to the procedure described above employing deprotection method 1 in 52% yield over 2 steps, and was isolated as a light grey solid (155 mg). $^1$H NMR (400 MHz, DMSO-d$_6$): δ 8.07 (d, J=7.5 Hz, 1H), 7.92 (s, 1H), 7.76 (d, J=7.7 Hz, 1H), 7.70 (d, J=7.8 Hz, 1H), 7.34 (s, 1H), 6.22 (s, 1H), 3.87 (s, 3H), 1.94 (s, 3H). HR-ESI-MS Experimental: 282.0736. Calculated for [C$_{14}$H$_{13}$NO$_4$Na]$^+$: 282.0737.

3-(5-Hydroxy-2-methyl-4-oxopyridin-1(4H)-yl)benzoic acid (58)

Compound 58 was prepared according to the procedure described above employing deprotection method 1 in 67% yield over 2 steps, and was isolated as a white solid (190 mg). $^1$H NMR (400 MHz, DMSO-d$_6$): δ 8.04 (d, J=7.0 Hz, 1H), 7.86 (s, 1H), 7.66 (d, J=11.2 Hz, 2H), 7.34 (s, 1H), 6.22 (s, 1H), 1.95 (s, 3H). HR-ESI-MS Experimental: 268.0577. Calculated for [C$_{13}$H$_{11}$NO$_4$Na]$^+$: 268.0580.

5-Hydroxy-1-(4-methoxyphenyl)-2-methylpyridin-4(1H)-one (59)

Compound 59 was prepared according to the procedure described above employing deprotection method 1 in 53% yield over 2 steps, and was isolated as a white solid (149 mg). $^1$H NMR (400 MHz, DMSO-d$_6$): δ 7.35 (d, J=8.5 Hz, 2H), 7.23 (s, 1H), 7.05 (d, J=8.5 Hz, 2H), 6.19 (s, 1H), 3.80 (s, 3H), 1.93 (s, 3H). HR-ESI-MS Experimental: 254.0787. Calculated for [C$_{13}$H$_{13}$NO$_3$Na]$^+$: 254.0788.

5-Hydroxy-2-methyl-1-(4-phenoxyphenyl)pyridin-4(1H)-one (60)

Compound 60 was prepared according to the procedure described above employing deprotection method 1 in 81% yield over 2 steps, and was isolated as a pink solid (263 mg). $^1$H NMR (400 MHz, CD$_3$OD): δ 7.43 (t, J=7.7 Hz, 3H), 7.37 (d, J=8.6 Hz, 2H), 7.22 (d, J=7.5 Hz, 1H), 7.10 (t, J=9.0 Hz, 4H), 6.44 (s, 1H), 2.10 (s, 3H). HR-ESI-MS Experimental: 316.0943. Calculated for [C$_{13}$H$_{13}$NO$_3$Na]$^+$: 316.0944.

Methyl 4-(5-hydroxy-2-methyl-4-oxopyridin-1(4H)-yl)benzoate (61)

Compound 61 was prepared according to the procedure described above employing deprotection method 1 in 58% yield over 2 steps, and was isolated as a white solid (168 mg). $^1$H NMR (400 MHz, DMSO-d$_6$): δ 8.08 (d, J=8.3 Hz, 2H), 7.61 (d, J=8.3 Hz, 2H), 7.33 (d, J=5.3 Hz, 1H), 6.23 (s, 1H), 3.88 (s, 3H), 1.97 (s, 3H). HR-ESI-MS Experimental: 282.0736. Calculated for [C$_{14}$H$_{13}$NO$_4$Na]$^+$: 282.0737.

4-(5-Hydroxy-2-methyl-4-oxopyridin-1(4H)-yl)benzoic acid (62)

Compound 62 was prepared according to the procedure described above employing deprotection method 1 in 57% yield over 2 steps, and was isolated as a beige solid (162 mg). $^1$H NMR (400 MHz, DMSO-d$_6$): δ 8.08 (d, J=8.5 Hz, 2H), 7.61 (d, J=8.5 Hz, 2H), 7.54 (s, 1H), 6.51 (s, 1H), 2.03 (s, 3H). HR-ESI-MS Experimental: 268.0583. Calculated for [$C_{13}H_{11}NO_4Na$]$^+$: 268.0580.

1-(4-(H-tetrazol-5-yl)phenyl)-5-hydroxy-2-methylpyridin-4(1H)-one (63)

Compound 63 was prepared according to the procedure described above employing deprotection method 1 in 42% yield over 2 steps, and was isolated as a white solid (131 mg). $^1$H NMR (400 MHz, DMSO-$d_6$): δ 8.17 (d, J=7.9 Hz, 2H), 7.69 (d, J=7.8 Hz, 2H), 7.39 (s, 1H), 6.27 (s, 1H), 2.02 (s, 3H). HR-ESI-MS Experimental: 292.0806. Calculated for [$C_{13}H_{11}N_5O_2Na$]$^+$: 292.0805.

4-(5-Hydroxy-2-methyl-4-oxopyridin-1(4H)-yl)-N-methylbenzenesulfonamide (64)

Compound 64 was prepared according to the procedure described above employing deprotection method 1 in 52% yield over 2 steps, and was isolated as a white solid (117 mg). $^1$H NMR (400 MHz, DMSO-$d_6$): δ 7.90 (d, J=8.5 Hz, 2H), 7.70 (d, J=8.4 Hz, 2H), 7.38 (s, 1H), 6.24 (s, 1H), 3.15 (s, 3H), 1.98 (s, 3H). HR-ESI-MS Experimental: 317.0567. Calculated for [$C_{13}H_{14}N_2O_4SNa$]$^+$: 317.0566.

1-(4-(1H-1,2,4-triazol-1-yl)phenyl)-5-hydroxy-2-methylpyridin-4(1H)-one (65)

Compound 65 was prepared according to the procedure described above employing deprotection method 1 in 66% yield over 2 steps, and was isolated as a white solid (205 mg). $^1$H NMR (400 MHz, CD$_3$OD): δ 10.44 (s, 1H), 8.98 (s, 1H), 8.28 (d, J=6.4 Hz, 2H), 8.18 (s, 1H), 7.90 (d, J=6.5 Hz, 2H), 7.33 (s, 1H), 2.39 (s, 3H). HR-ESI-MS Experimental: 291.0849. Calculated for [$C_{13}H_{14}N_2O_4SNa$]$^+$: 291.0852.

5-Hydroxy-2-methyl-1-(4-morpholinophenyl)pyridin-4(1H)-one (66)

Compound 66 was prepared according to the procedure described above employing deprotection method 1 in 74% yield over 2 steps, and was isolated as a red solid (245 mg). $^1$H NMR (400 MHz, DMSO-$d_6$): δ 7.71 (s, 1H), 7.33 (d, J=8.5 Hz, 2H), 7.07 (d, J=8.7 Hz, 2H), 6.82 (s, 1H), 3.73 (d, J=4.6 Hz, 4H), 3.20 (s, 4H), 2.09 (s, 3H). HR-ESI-MS Experimental: 309.1211. Calculated for [$C_{13}H_{14}N_2O_4SNa$]$^+$: 309.1210.

Example 11.7: Synthesis of Compounds in Table 6

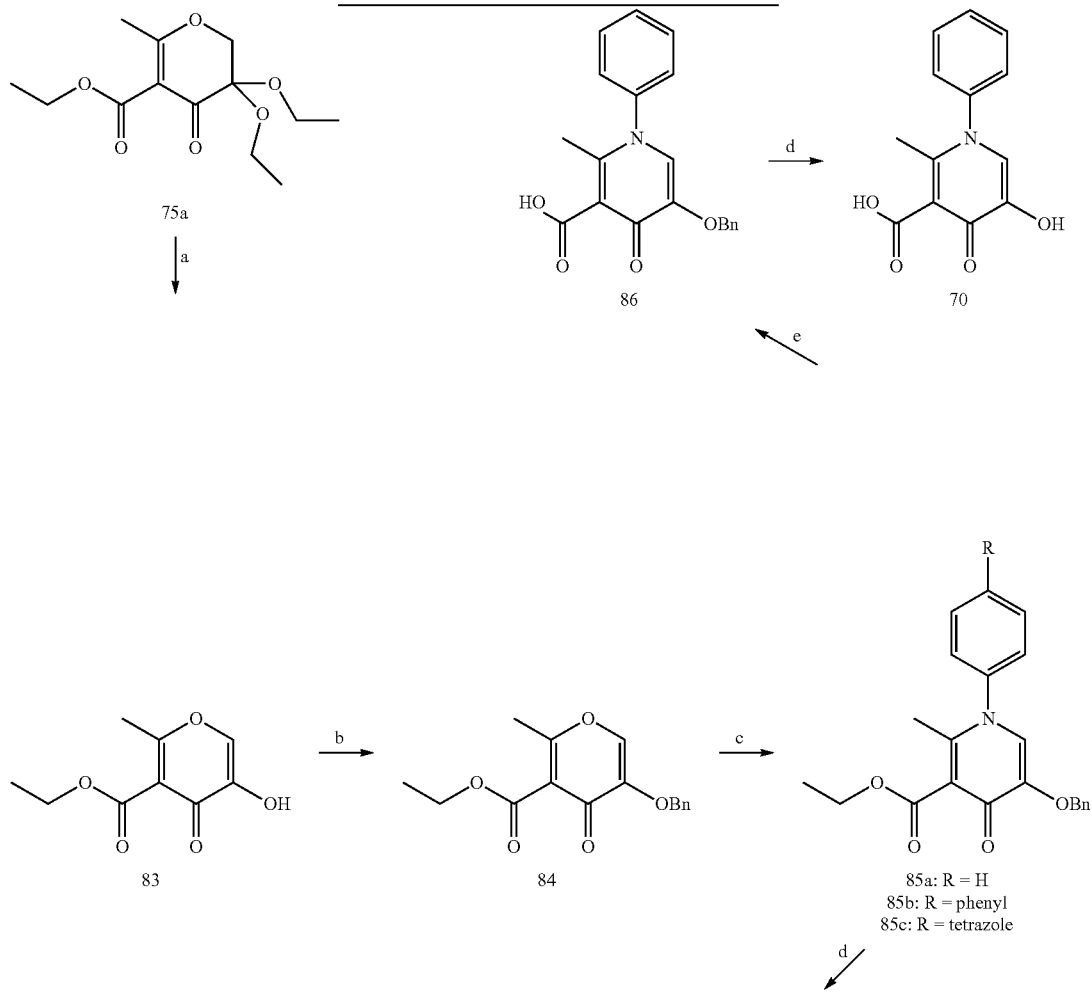

Scheme 4
Synthetic routes from compound 75a and compound 78

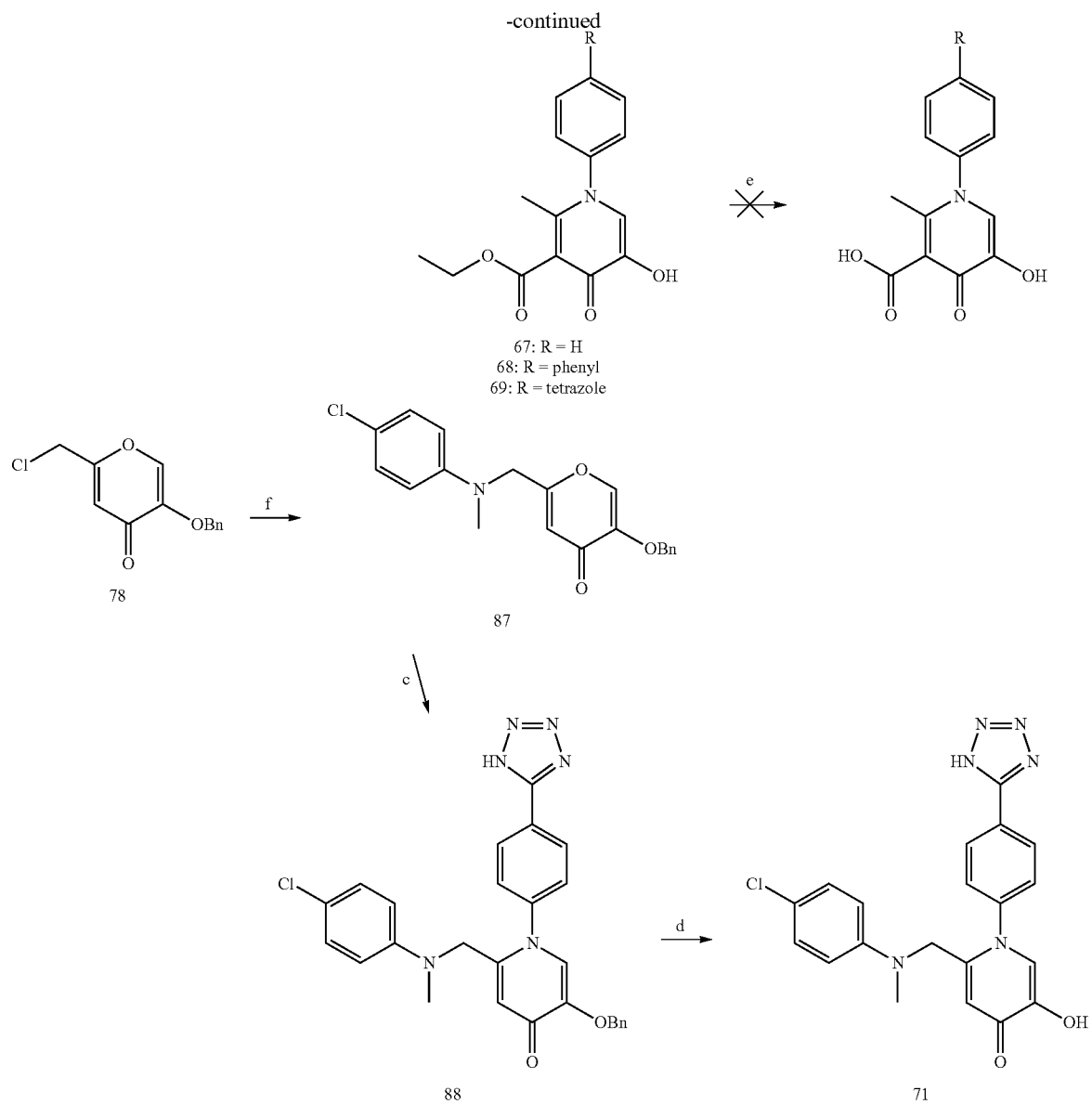

Reagents and conditions: (a) 1:1 HCOOH:H₂O, 80° C., 2-6 h; (b) benzyl bromide, K₂CO₃, DMF, 80° C., 8-12 h; (c) aryl amine, HOAc, 3:1 EtOH:H₂O, MW 130° C., 3-5 h; (d) 5:5:1 HOAc:HCl:TFA, rt-40° C., 24-48 h; (e) 4% KOH, 1:2:1 THF:MeOH:water, rt, o/n; (f) RCH₃NH, triethyl amine, DMF, 75° C., o/n.

The preparation of the fragment merging compounds was accomplished as shown in Scheme 4. Merging of N-aryl pyridinones with 5-position carboxylates began with advanced intermediate compound 76a. Hydrolysis of the acetal followed by tautomerization yielded compound 83. After benzyl protection of the phenol, dehydration was accomplished with microwave heating using dry ethanol as a solvent. Hydrolysis of only the benzyl ether using strong acid afforded compounds 67-69 in moderate yields; hydrolysis of both ester and ether was not observed. Further base catalyzed hydrolysis of the ethyl ester proved difficult, and ultimately resulted in the decomposition of the ring system. As an alternative route, compound 86 was hydrolyzed to the free carboxylic acid by stirring in 4% KOH and methanol for several hours. This reaction proceeded almost quantitatively with no apparent decomposition of the starting material. Compound 86 was found to be stable to strongly acidic conditions, and was hydrolyzed to compound 70 using a mixture of strong acids with good yields. Synthesis of compound 71 began with chloride compound 78. Nucleophilic substitution with 4-chloro-N-methylaniline afforded pyrone compound 87. Dehydration, as previously described, yielded compound 88 in moderate to low yields. Hydrolysis in the presence of strong acid afforded compound 71.

Ethyl 5-hydroxy-2-methyl-4-oxo-4H-pyran-3-carboxylate (83)

To a stirring solution of ethyl 3,3-diethoxy-6-methyl-4-oxo-3,4-dihydro-2H-pyran-5-carboxylate (75a) (1.5 g, 5.51 mmol) in ethanol (20 mL) and water (2.000 mL) was added formic acid (5 mL, 5.51 mmol). The mixture was heated to reflux for 2-3 hours. Solvent was removed under vacuum and the residue was purified by silica chromatography eluting with a gradient of 20-40% ethyl acetate in hexanes to provide compound 83 (786 mg, 72%). ¹H NMR (400

MHz, CDCl$_3$): δ 6.93 (d, J=9.0 Hz, 1H), 3.61 (d, J=7.1 Hz, 2H), 2.23 (s, 3H), 1.30 (s, 3H). HR-ESI-MS Experimental: 197.0454. Calculated for [C$_9$H$_9$O$_5$]$^-$: 197.1450.

Ethyl 5-(benzyloxy)-2-methyl-4-oxo-4H-pyran-3-carboxylate (84)

To a solution of ethyl 5-hydroxy-2-methyl-4-oxo-4H-pyran-3-carboxylate (4 g, 20.18 mmol) in DMF (20 mL) was added benzyl bromide (2.64 mL, 22.20 mmol) and potassium carbonate (5.86 g, 42.4 mmol). The mixture was heated to 85° C. and stirred for 18 hours. Solvent was removed under vacuum and the residue was taken up in ethyl acetate, washed once with 1 M NaOH, dried and concentrated, then purified by silica column chromatography to yield compound 84 (4.7 g, 81%). $^1$H NMR (400 MHz, CDCl$_3$): δ 7.46 (s, 1H), 7.40-7.10 (m, 5H), 4.97 (s, 2H), 4.30 (d, J=7.1 Hz, 2H), 2.25 (s, 3H), 1.29 (t, J=7.1 Hz, 3H). HR-ESI-MS Experimental: 311.0892. Calculated for [C$_{16}$H$_{16}$O$_5$Na]$^+$: 311.0896.

Ethyl 5-(benzyloxy)-2-methyl-4-oxo-1-phenyl-1,4-dihydropyridine-3-carboxylate (85a)

To a 10 mL microwave vessel containing ethanol (3 mL) were added ethyl 5-(benzyloxy)-2-methyl-4-oxo-4H-pyran-3-carboxylate (250 mg, 0.867 mmol), aniline (0.238 mL, 2.60 mmol), and acetic acid (0.149 mL, 2.60 mmol). The mixture was irradiated with stirring to 130° C. for 2.5 hours, after which time the mixture was concentrated under vacuum and purified by silica column chromatography to yield compound 85a (191 mg, 61%). $^1$H NMR (400 MHz, CDCl$_3$): δ 7.54-7.47 (m, 3H), 7.39 (d, J=6.9 Hz, 2H), 7.34-7.26 (m, 3H), 7.20-7.14 (m, 2H), 7.04 (s, 1H), 5.17 (s, 2H), 4.41 (d, J=7.1 Hz, 2H), 2.01 (s, 3H), 1.39 (s, 3H). ESI-MS [M+H]$^+$: 364.

Ethyl 5-(benzyloxy)-2-methyl-4-oxo-1-(4-phenoxyphenyl)-1,4-dihydropyridine-3-carboxylate (85b)

Compound 85b was prepared similarly to compound 85a, substituting 4-phenoxyaniline (482 mg, 2.60 mmol) for aniline and irradiating at 13° C. for 8 hours, and compound 85b (165 mg) was isolated in a 42% Yield. $^1$H NMR (400 MHz, CDCl$_3$): δ 7.40 (d, J=7.6 Hz, 3H), 7.35-7.25 (m, 3H), 7.21 (t, J=7.4 Hz, 1H), 7.15-6.97 (m, 7H), 5.17 (s, 2H), 4.41 (q, J=7.1 Hz, 2H), 2.03 (s, 3H), 1.38 (s, 3H). ESI-MS [M+H]$^+$: 456.

Ethyl 1-(4-(1H-tetrazol-5-yl)phenyl)-5-(benzyloxy)-2-methyl-4-oxo-1,4-dihydropyridine-3-carboxylate (85c)

Compound 85c was prepared similarly to 85a, substituting 4-(1H-tetrazol-5-yl)aniline (402 mg, 2.60 mmol) for aniline and irradiating at 135° C. for 8 hours, and compound 85c (134 mg) was isolated in a 36% Yield. $^1$H NMR (400 MHz, CDCl$_3$): δ 7.54-7.47 (m, 3H), 7.39 (d, J=6.9 Hz, 2H), 7.34-7.26 (m, 3H), 7.20-7.14 (m, 2H), 7.04 (s, 1H), 5.17 (s, 2H), 4.41 (d, J=7.1 Hz, 2H), 2.01 (s, 3H), 1.39 (s, 3H). ESI-MS [M+H]$^+$: 432.

Ethyl 5-hydroxy-2-methyl-4-oxo-1-phenyl-1,4-dihydropyridine-3-carboxylate (67)

Compound 85a was dissolved and stirred in a 5:5:1 mixture of concentrated hydrochloric acid, glacial acetic acid, and TFA for 24-48 h. Solvent was removed under high vacuum and the residue co-evaporated several times with methanol. The resultant solids were purified by C18 column chromatography in a water:methanol system with added 0.1% formic acid to yield compound 67 (124 mg, 84%). $^1$H NMR (400 MHz, CD$_3$OD): δ 7.59 (d, J=6.2 Hz, 3H), 7.42 (d, J=7.9 Hz, 3H), 4.36 (d, J=7.1 Hz, 2H), 2.07 (s, 3H), 1.35 (t, J=7.1 Hz, 3H). HR-ESI-MS Experimental: 296.0898. Calculated for [C$_{15}$H$_{15}$NO$_4$Na]$^+$: 296.0893.

Ethyl 5-hydroxy-2-methyl-4-oxo-1-(4-phenoxyphenyl)-, 4-dihydropyridine-3-carboxylate (68)

Compound 68 was prepared from compound 85b in a similar manner as compound 67, and compound 68 (115 mg) was isolated in a 74% Yield. $^1$H NMR (400 MHz, CD$_3$OD): δ 7.48-7.34 (m, 5H), 7.21 (t, J=7.4 Hz, 1H), 7.16-7.05 (m, 4H), 4.36 (d, J=7.1 Hz, 2H), 2.10 (s, 3H), 1.35 (t, J=7.1 Hz, 3H). HR-ESI-MS Experimental: 388.1156. Calculated for [C$_{21}$H$_{19}$NO$_5$Na]$^+$: 388.1155.

Ethyl 1-(4-(1H-tetrazol-5-yl)phenyl)-5-hydroxy-2-methyl-4-oxo-1,4-dihydropyridine-3-carboxylate (69)

Compound 69 was prepared from compound 85c in a similar manner as compound 67, and compound 69 (87 mg) was isolated in a 69% Yield. $^1$H NMR (400 MHz, DMSO-d$_6$): δ 8.18 (d, J=7.1 Hz, 2H), 7.75 (d, J=7.0 Hz, 2H), 7.44 (s, 1H), 4.25 (d, J=7.1 Hz, 2H), 1.97 (s, 3H), 1.25 (s, 3H). HR-ESI-MS Experimental: 342.1196. Calculated for [C$_{16}$H$_{15}$N$_5$O$_4$]$^+$: 342.1197.

5-(Benzyloxy)-2-methyl-4-oxo-1-phenyl-1,4-dihydropyridine-3-carboxylic acid (86)

Compound 85a was dissolved and stirred in a 1:2:1 THF:MeOH: 1M NaOH solvent mixture at room temperature for 18 hours. The reaction mixture was then neutralized with 1 M HCl and concentrated under vacuum to yield a solid. The crude solid was purified by C18 column chromatography in a water: methanol system with added 0.1% formic acid to yield compound 86 (76 mg, 77%). $^1$H NMR (400 MHz, CD$_3$OD): δ 7.56-7.46 (m, 3H), 7.41-7.25 (m, 5H), 7.17 (d, J=3.3 Hz, 2H), 7.04 (s, 1H), 5.17 (s, 2H), 2.01 (s, 3H). ESI-MS [M+Na]$^+$: 358.38.

5-Hydroxy-2-methyl-4-oxo-1-phenyl-1,4-dihydropyridine-3-carboxylic acid (70)

Compound 86 was dissolved and stirred in a 5:5:1 mixture of concentrated hydrochloric acid, glacial acetic acid, and TFA for 24-48 hours. Solvent was removed under high vacuum and the residue co-evaporated several times with methanol. The resultant solids were purified by C18 column chromatography in a water:methanol system with added 0.1% formic acid to yield compound 70 (52 mg, 69%). $^1$H NMR (400 MHz, DMSO-d$_6$): δ 7.69 (s, 1H), 7.59 (s, 3H), 7.54 (s, 2H), 2.44 (s, 3H). HR-ESI-MS Experimental: 268.0582. Calculated for [C$_{13}$H$_{11}$NO$_4$Na]$^+$: 268.0580.

5-(Benzyloxy)-2-(((4-chlorophenyl)(methyl)amino)methyl)-4H-pyran-4-one (87)

To a solution of 5-(benzyloxy)-2-(chloromethyl)-4H-pyran-4-one (250 mg, 0.997 mmol) and 4-chloro-N-methylaniline (282 mg, 1.995 mmol) in DMF (15 mL) was added triethylamine (0.306 mL, 2.194 mmol). The mixture was then heated to 60° C. and stirred overnight. The mixture was then evaporated to dryness under vacuum and purified by column chromatography to give compound 87 (201 mg, 79%). $^1$H NMR (400 MHz, CDCl$_3$): δ 7.52 (s, 1H), 7.36 (dd, J=12.7, 4.4 Hz, 5H), 7.16 (d, J=9.0 Hz, 2H), 6.59 (d, J=9.0 Hz, 2H), 6.26 (s, 1H), 5.05 (s, 2H), 4.25 (s, 2H), 3.01 (s, 3H). ESI-MS [M+H]$^+$: 356.

1-(4-(1H-tetrazol-5-yl)phenyl)-5-(benzyloxy)-2-(((4-chlorophenyl)(methyl)amino)methyl) pyridin-4(1H)-one (88)

5-(benzyloxy)-2-(((4-chlorophenyl)(methyl)amino) methyl)-4H-pyran-4-one (87) (300 mg, 0.84 mmol), 4-(1H-tetrazol-5-yl)aniline (340 mg, 2.11 mmol), and acetic acid (0.072 mL, 1.27 mmol) in ethanol (3 mL) water (1.5 mL) was added to a 10 mL microwave vessel. The reaction mixture was irradiated with stirring at 140° C. for 18 hours. After cooling, the solvent was evaporated under vacuum, and the resulting solid purified by C18 column chromatography in a water:methanol system with added 0.1% formic acid to give compound 87 (84 mg, 27%). $^1$H NMR (400 MHz, DMSO-d$_6$): δ 8.15 (d, J=8.1 Hz, 2H), 7.80 (d, J=8.2 Hz, 2H), 7.43 (s, 1H), 7.10 (d, J=8.9 Hz, 2H), 6.56 (d, J=8.9 Hz, 2H), 5.98 (s, 1H), 4.16 (s, 2H), 2.85 (s, 3H). ESI-MS [M−H]$^−$: 497.

1-(4-(1H-tetrazol-5-yl)phenyl)-2-(((4-chlorophenyl)(methyl)amino)methyl)-5-hydroxypyridin-4(1H)-one (71)

Compound 88 was dissolved and stirred in a 5:5:1 mixture of concentrated hydrochloric acid, glacial acetic acid, and TFA for 24-48 hours. Solvent was removed under high vacuum and the residue co-evaporated several times with methanol. The resultant solids were purified by C18 column chromatography in a water:methanol system with added 0.1% formic acid to yield compound 71 (38 mg, 66%). $^1$H NMR (400 MHz, DMSO-d$_6$): (8.15 (d, J=8.1 Hz, 2H), 7.80 (d, J=8.2 Hz, 2H), 7.43 (s, 1H), 7.10 (d, J=8.9 Hz, 2H), 6.56 (d, J=8.9 Hz, 2H), 5.98 (s, 1H), 4.16 (s, 2H), 2.85 (s, 3H). HR-ESI-MS Experimental: 431.0995. Calculated for [C$_{20}$H$_{17}$ClN$_6$O$_2$Na]$^+$: 431.0994.

Example 11.8: Synthesis of Compounds in Table 7

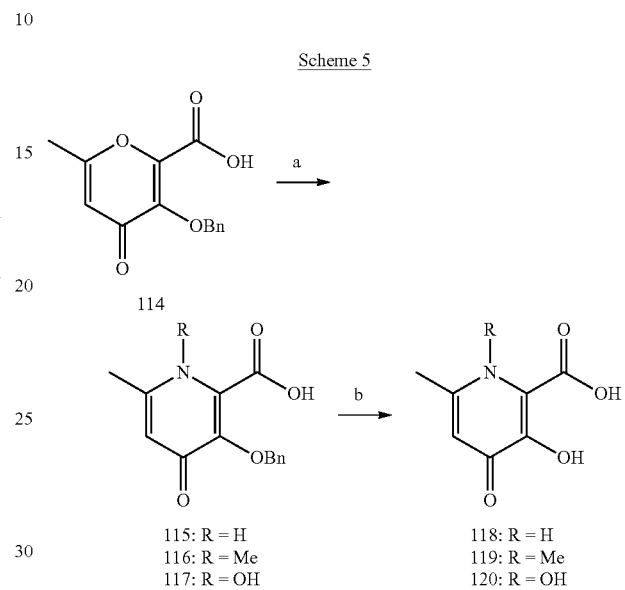

Scheme 5

115: R = H
116: R = Me
117: R = OH

118: R = H
119: R = Me
120: R = OH

Reaction conditions: (a) NH$_2$R, MeOH, water, 75° C., sealed vessel, 18-24 h; (b) 5:5:1 HCl(conc.):HOAc:TFA, rt, 3 d.

Advanced intermediate 114 had been previously synthesized and was allowed for direct synthesis of pyridinones compounds 115-117 by dehydration (N-insertion), as detailed in Scheme 5. The synthesis was effectively optimized against by controlling the means of heating (conventional as opposed to microwave synthesis), by including water as a primary solvent, and by maintaining low pH by the addition of excess amine and sealing the reaction vessel.

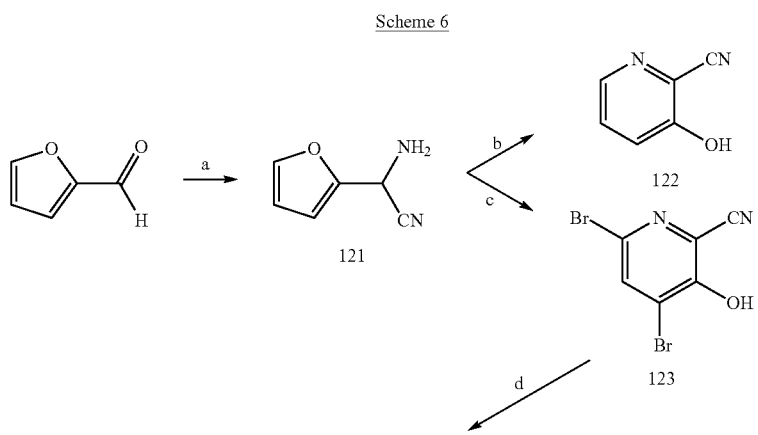

Scheme 6

-continued

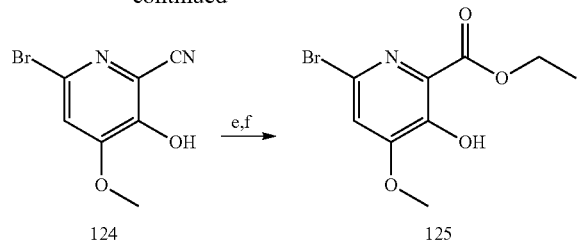

Reaction conditions: (a) NH₄OAc, KCN, EtOAc, water, rt, 18 h; (b) NBS, HBr, water, rt, 8 h; (c) Br₂, HBr, water, 0-25° C., 36 h; (d) NaOMe, DMSO, 55-60° C., 24 h; (e) 75% sulfuric acid, 95° C., 24 h; (f) EtOH, H₂SO₄(cat.), reflux, 18 hours.

As detailed in Scheme 6, the key dibromo picolinonitrile intermediate 123 was generated from furfural as a starting material. The aldehyde was converted to the aminonitrile by the Strecker reaction in a biphasic system. In the presence of weak bromine sources, such as NBS, the aminonitrile 121 will rearrange to generate the picolinonitrile 122. In the presence of strong brominating reagents such as Br₂, further bromination will subsequently produce compound 123 in moderate yields. Selective nucleophilic aromatic substitution at the 4 position is achieved by using a strong alkoxide nucleophile and controlling the reaction temperature. At temperatures below 65° C., substitution is only observed at the 4 position. At higher temperatures, a mixture of products is obtained. The presence of the phenoxy anion alpha to the 4-bromine both inductively and resonatively facilitates the S$_N$Ar intermediate and is the driving cause of selective substitution at this position. The phenyl ether product 124 can be subsequently hydrolyzed to afford the trapped picolinic acid, as the ether prevents tautomerization to the 3,4—HOPO. Due to the low solubility of 124, either 70% sulfuric acid or a 5:5:1 mixture of concentrated HCl:HOAc:TFA are necessary to solubilize and hydrolyze the nitrile intermediate, even at high temperatures.

Scheme 7A

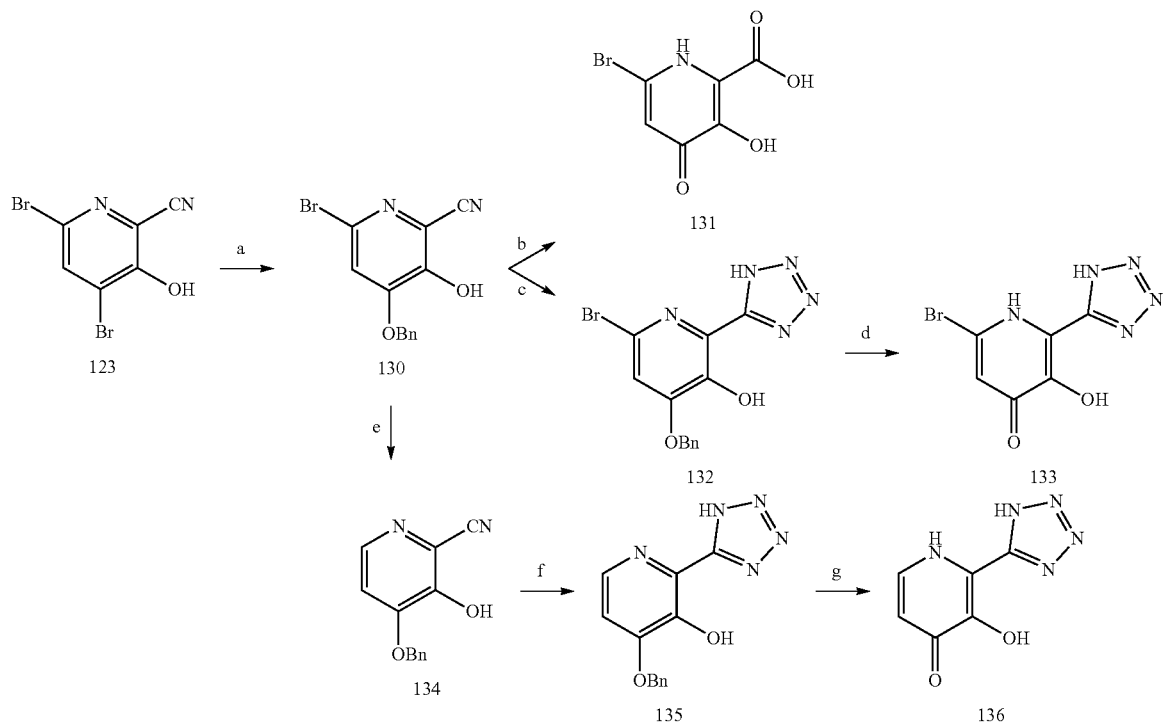

Reaction conditions: (a) BnOH, NaH, DMSO, 55-60° C., 24 h; (b) 5:5:1 HCl(conc.):HOAc:TFA, 80° C., 18 h; (c), (f) NaN3, NH4Cl, DMF, 110-120° C., 8 h; (e) Zn(dust), 20% KOH(aq) rt, 18 h; (d), (g) 5:5:1 HCl(conc.):HOAc:TFA, rt, 18 h.

As detailed in Scheme 7A, the dibromo intermediate 123 was transformed to the benzyl ether picolinonitrile 130 under the same conditions uses to synthesize the methyl ether analogue. While the sodium benzyloxide had to be generated in situ with sodium hydride and benzyl alcohol, and the reaction proceeded at a slower rate, the overall yield was very similar. Hydrolysis and deprotection of 30 to generate the compound 131 was preformed in a mixture of 5:5:1 HCl:HOAc:TFA at 80° C. Compound 130 was selectively reduced to compound 134 with zinc dust in 20% KOH, and both compounds 132 and 134 readily cyclized to form the tetrazole under the conditions as described in the scheme 7A. Benzyl ethers were removed by stirring in 5:5:1 HCl:HOAc:TFA at room temperature for 3 days to afford compounds 133 and 136.

Scheme 7B

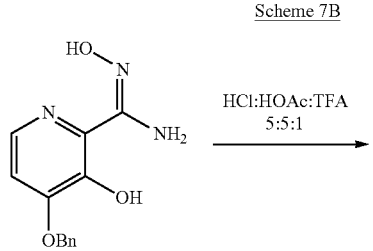

As shown in Scheme 7B, Compound 150 was prepared by cyclization in a 5:5:1 mixture of concentrated hydrochloric acid, glacial acetic acid, and trifluoroacetic acid.

Scheme 8

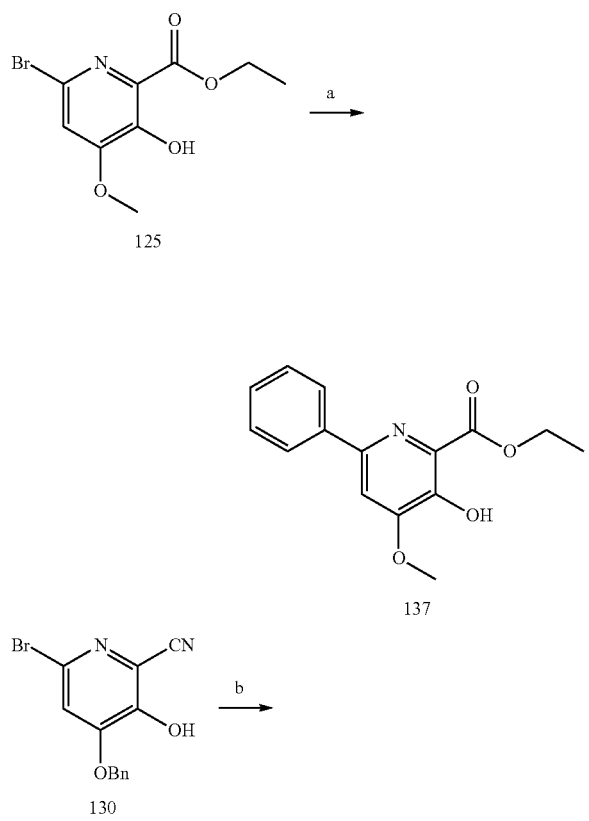

-continued

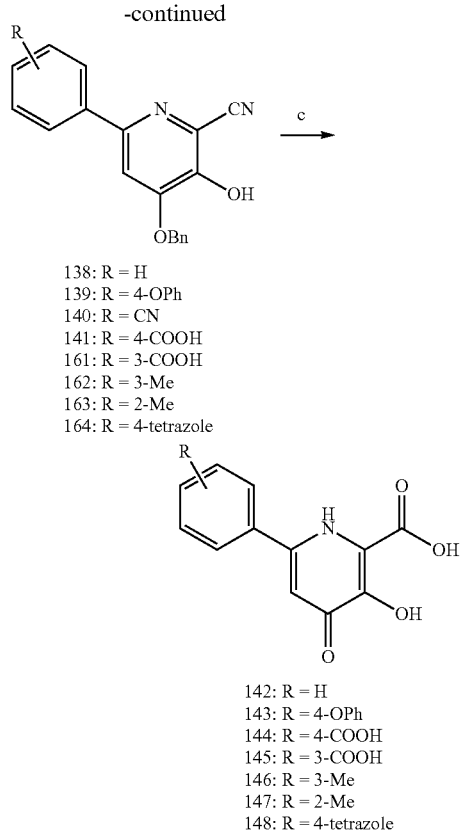

138: R = H
139: R = 4-OPh
140: R = CN
141: R = 4-COOH
161: R = 3-COOH
162: R = 3-Me
163: R = 2-Me
164: R = 4-tetrazole 142: R = H
143: R = 4-OPh
144: R = 4-COOH
145: R = 3-COOH
146: R = 3-Me
147: R = 2-Me
148: R = 4-tetrazole An initial survey of 5 different palladium ligands in a water/dioxanes solvent system with carbonate bases led to good yields overall, with a 2:1 combination of S-phos and DPPF palladium ligands being ideal for the system at a temperature of 90-100° C. Under these conditions, coupling of phenylboronic acid proceeded very well with isolated yields in excess of 85%. As detailed in Scheme 7, several simple boronic acids were coupled with compound 130. Phenyl and phenyl ether derivatives 138 and 139 were isolated in good yields. Other derivatives 141, 161, 162, 163, and 164 were isolated in various yields (46%, 44%, 87%, 56%, and 41% accordingly). Isolated picolinonitriles were hydrolyzed and deprotected in one pot in 5:5:1 HCl(conc.):HOAc:TFA at 80 to 85° C. Compound 142, 143, 146, and 147 were isolated in moderate yields. Other compounds 144, 145, and 148 were isolated to have enough materials for the assay against the endonuclease enzyme.

3-(Benzyloxy)-6-methyl-4-oxo-1,4-dihydropyridine-2-carboxylic acid (115)

3-(benzyloxy)-6-methyl-4-oxo-4H-pyran-2-carboxylic acid (200 mg, 0.769 mmol) was taken up in a 1:1 mixture of water (10 ml) and methanol (10 ml) in a sealable vessel. Ammonium hydroxide (30%) (328 ul, 2.306 mmol) was added and the vessel was sealed and heated to 75° C. for 18-24 h. After this time, the reaction was cooled and concentrated under vacuum, diluted with 1M HCl and concentrated under vacuum to remove ammonium salts, and the resultant solids were purified by C18 column chromatography utilizing a MeOH/water system to afford 3-(benzyloxy)-6-methyl-4-oxo-1,4-dihydropyridine-2-carboxylic acid (122 mg, 0.469 mmol, 61% yield) as a white powder.

¹H NMR (400 MHz, CD3OD) δ 7.45 (t, J=5.6 Hz, 4H), 7.31 (dd, J=15.9, 6.3 Hz, 8H), 5.18 (s, 4H), 2.62 (s, 5H).

3-(Benzyloxy)-1,6-dimethyl-4-oxo-1,4-dihydropyridine-2-carboxylic acid (116)

3-(benzyloxy)-6-methyl-4-oxo-4H-pyran-2-carboxylic acid (200 mg, 0.769 mmol) was taken up in a 1:1 mixture of water (10 ml) and methanol (10 ml) in a sealable vessel. Methylamine (200 ul, 2.306 mmol) was added and the vessel was sealed and heated to 75° C. for 18-24 hours. After this time, the reaction was cooled and concentrated under vacuum, diluted with 1M HCl and concentrated under vacuum to remove methylammonium salts, and the resultant solids were purified by C18 column chromatography utilizing a MeOH/water system to afford 3-(benzyloxy)-1,6-dimethyl-4-oxo-1,4-dihydropyridine-2-carboxylic acid (100 mg, 0.366 mmol, 47% yield) as a white solid. ¹H NMR (400 MHz, CD3OD) δ 7.47-7.26 (m, 6H), 5.16 (s, 2H), 3.92 (s, 3H), 2.64 (s, 3H).

3-(Benzyloxy)-1-hydroxy-6-methyl-4-oxo-1,4-dihydropyridine-2-carboxylic acid (117)

3-(benzyloxy)-6-methyl-4-oxo-4H-pyran-2-carboxylic acid (200 mg, 0.769 mmol) was taken up in a 1:1 mixture of water (10 ml) and methanol (10 ml) in a sealable vessel. Hydroxylamine hydrochloride (160 mg, 2.306 mmol) was added and the vessel was sealed and heated to 75° C. for 18-24 hours. After this time, the reaction was cooled and concentrated under vacuum and the resultant solids were purified by C18 column chromatography utilizing a MeOH/water system to afford 3-(benzyloxy)-1-hydroxy-6-methyl-4-oxo-1,4-dihydropyridine-2-carboxylic acid (71.9 mg, 0.261 mmol, 34% yield) as a white solid. ¹H NMR (400 MHz, CD3OD) δ 7.45 (d, J=6.7 Hz, 2H), 7.30 (s, 4H), 6.37 (s, 1H), 5.17 (s, 2H), 2.34 (s, 3H).

General Procedure for the Deprotection of Compounds 18-20:

Benzyl protected pyridinone compounds 18-20 was taken up in a 5:5:1 mixture of concentrated HCl:HOAC:TFA and was stirred at room temperature for 48 h. After this time, acids were removed under vacuum, the resultant solids were co-evaporated several times with methanol, and were purified by C18 column chromatography eluting in a water/MeOH system to yield pure target compound.

3-Hydroxy-6-methyl-4-oxo-1,4-dihydropyridine-2-carboxylic acid (118)

compound 118 was isolated as a white solid in 74% yield, according to the general procedure. ¹H NMR (400 MHz, DMSO) δ 6.92 (s, 1H), 2.48-2.38 (m, 3H).

3-Hydroxy-1,6-dimethyl-4-oxo-1,4-dihydropyridine-2-carboxylic acid (119)

compound 119 was isolated as a white solid in 66% yield, according to the general procedure. ¹H NMR (400 MHz, DMSO) δ 6.98 (s, 1H), 4.13 (s, 3H), 2.48 (s, 3H).

4,6-Dibromo-3-hydroxypicolinonitrile (123)

In a rapidly stirring biphasic solution of EtOAc (50 ml) and Water (12.50 ml) were suspended ammonium acetate (13.96 g, 181 mmol) and potassium cyanide (4.13 g, 63.4 mmol). Furfural (5 ml, 60.4 mmol) was added slowly at room temperature, and the mixture stirred over-night. The reaction mixture was then diluted with 25 ml of saturated bicarbonate solution, and the two layers were separated. After phase separation, the organic layer (containing the amino-nitrile intermediate) was extracted once with 50 ml of 5% aqueous HBr with ample agitation (vent often). The organic layer was then further extracted with 2×20 ml of water. The combined aqueous layers were combined and cooled to ~5° C. and bromine (12.44 ml, 241 mmol) was added dropwise maintaining the reaction at ice-bath temperatures. After addition, the mixture was allowed to warm to room temperature and was stirred overnight. A yellow precipitate formed. The reaction mixture was then cooled to 5-10° C. and 25 ml of a 25% aqueous solution of sodium bisulfite (NaHSO₃) was added slowly, maintaining ice-bath temperatures, to quench excess bromine. The resulting suspension was stirred for 30 min then filtered. The filter cake was washed twice with water and dried. Small quantities of the mono-bromo species may be present by NMR. This afforded the product, 4,6-dibromo-3-hydroxypicolinonitrile (8.44 g, 30.4 mmol, 50.3% yield) as a tan solid (50% yield over 4 steps). ¹H NMR (400 MHz, DMSO) δ 8.25 (q, J=0.7 Hz, 1H).

4-(Benzyloxy)-6-bromo-3-hydroxypicolinonitrile (130)

In a flame-dried flask sodium hydride (2.52 g, 63.0 mmol) was stirred in dry DMSO (20 ml). Benzyl alcohol (9.35 ml, 90 mmol) was added dropwise to the mixture. When the reaction was complete, as evidenced by the cessation of hydrogen evolution, 4,6-dibromo-3-hydroxypicolinonitrile (5 g, 17.99 mmol) in dry DMSO (10 ml) was added dropwise to the stirring solution and the mixture was heated to 60° C. for 24 hours. Monitor by TLC for conversion. When the reaction was complete, the mixture was moved to an ice-bath and 150 ml water was added. The mixture continued to stir for 10 minutes, during which time the solution clouded and then clarified. To remove residual benzyl alcohol, the aqueous solution was extracted with diethyl ether. Residual ether was then removed from the aqueous portion under vacuum and the solution was cooled to 5° C. on ice. The addition of 4 M hydrochloric acid (until the pH was around 2.5) resulted in the precipitation of a white solid. At this pH, the mixture was stirred for 30 minutes on ice. The resultant solids were filtered, rinsed with water, and dried. Purification via silica gel chromatography in an EtOAc/hexanes system afforded 4-(benzyloxy)-6-bromo-3-hydroxypicolinonitrile (compound 130) (4.18 g, 13.70 mmol, 76% yield) as an off-white solid. ¹H NMR (400 MHz, Acetone) δ 10.38 (s, 1H), 7.51 (d, J=6.5 Hz, 2H), 7.47-7.35 (m, 4H), 5.30 (s, 2H).

6-Bromo-3-hydroxy-4-oxo-1,4-dihydropyridine-2-carboxylic acid (131)

4-(benzyloxy)-6-bromo-3-hydroxypicolinonitrile (2 g, 6.55 mmol) was suspended in a 10:10:1 mixture of concentrated hydrochloric acid, glacial acetic acid, and trifluoroacetic acid. The mixture was then heated to 85-90° C. for 24 hours. At reflux the solids dissolved. After 4 hours, a new solid formed. At this time water was added to dissolve the solids, and the mixture continued to reflux. Acids and water were removed under vacuum and the residue was co-evaporated with methanol twice. The resultant tan residue was taken up in 1M NaOH (20 ml) and was washed once with ether (to remove benzyl alcohol and any other junk).

The aqueous layer was isolated and residual ether was removed under vacuum. The aqueous solution was then cooled to 5° C. with stirring and was precipitated with 4 M HCl. The precipitate was stirred for a further 20 minutes and was isolated by filtration to afford compound 131 (1.24 g, 5.30 mmol, 81% yield) as a tan solid. $^1$H NMR (400 MHz, DMSO) δ 6.84 (s, 1H).

6-Bromo-4-(benzyloxy)-2-(1H-tetrazol-5-yl)pyridin-3-ol (132)

6-Bromo-4-(benzyloxy)-3-hydroxypicolinonitrile (300 mg, 1.326 mmol) or 6-bromo-3-hydroxy-4-methoxypicolinonitrile (600 mg) was dissolved in DMF (15 ml). Ammonium chloride (106 mg, 1.989 mmol) and sodium azide (129 mg, 1.989 mmol) were added and the mixture stirred at between 110-120° C. for 3-4 hours. The mostly-clear suspension turned opaque over this time. When starting material was consumed by TLC analysis (50% EtOAc/Hex) a new spot was identified that gave a positive iron chloride test. DMF was removed under vacuum and the residual was taken up in water and sonicated. The mixture was put on ice with stirring and 4 M HCl was added very carefully (only a few drops) to adjust the pH to acidic. The resultant solids were stirred on ice for 30 minutes and were isolated by filtration to afford compound 132 (240 mg, 0.520 mmol, 59% yield) as a white solid. $^1$H NMR (400 MHz, DMSO) δ 8.30 (s, 1H), 7.48 (d, J=7.6 Hz, 2H), 7.41 (t, J=7.4 Hz, 2H), 7.36 (d, J=7.3 Hz, 1H), 7.31 (s, 1H), 5.26 (s, 2H).

6-Bromo-3-hydroxy-2-(1H-tetrazol-5-yl)pyridin-4(1H)-one (133)

6-Bromo-4-(benzyloxy)-2-(1H-tetrazol-5-yl)pyridin-3-ol was taken up in a 5:5:1 mixture of concentrated HCl:HOAC:TFA and was stirred at room temperature for 48 hours. After this time, acids were removed under vacuum, the resultant solids were co-evaporated several times with methanol, and were purified by C18 column chromatography eluting in a water/MeOH system to yield pure compound 133 (74% yield) as a pink solid. $^1$H NMR (400 MHz, DMSO) δ 7.11 (d, J=0.7 Hz, 1H).

4-(Benzyloxy)-3-hydroxypicolinonitrile (134)

A suspension of 4-(benzyloxy)-6-bromo-3-hydroxypicolinonitrile (750 mg, 2.458 mmol) and zinc (dust) (321 mg, 4.92 mmol) in 20% KOH (aq) (25 ml) was stirred overnight at rt. The reaction mixture will turn from a grey suspension to a clear solution. After completion, by TLC and MS, the reaction mixture was filtered through a pad of celite to remove residual zinc powder. The aqueous filtrate was cooled to 5° C. and adjusted to a pH of 3-4 with HCl. The resultant precipitate was stirred for 30 minutes on ice and isolated by filtration. Some residual product is found in the aqueous rinse but was not recovered. Drying the solids afforded 4-(benzyloxy)-3-hydroxypicolinonitrile (468 mg, 2.069 mmol, 84% yield) as a white solid. $^1$H NMR (400 MHz, DMSO) δ 11.07 (s, 1H), 8.03 (dd, J=5.3, 0.6 Hz, 1H), 7.50 (d, J=7.3 Hz, 2H), 7.38 (d, J=7.9 Hz, 2H), 7.36-7.29 (m, 2H), 5.29 (s, 2H).

4-(Benzyloxy)-2-(1H-tetrazol-5-yl)pyridin-3-ol (135)

4-(benzyloxy)-3-hydroxypicolinonitrile (300 mg, 1.326 mmol) or 6-bromo-3-hydroxy-4-methoxypicolinonitrile (600 mg) was dissolved in DMF (15 ml). Ammonium chloride (106 mg, 1.989 mmol) and sodium azide (129 mg, 1.989 mmol) were added and the mixture stirred at between 110-120° C. for 3-4 hours. The mostly-clear suspension turned opaque over this time. When starting-material was consumed by TLC analysis (50% EtOAc/Hex) a new spot was identified that gave a positive iron chloride test. DMF was removed under vacuum and the residual was taken up in water and sonicated. The mixture was put on ice with stirring and 4M HCl was added very carefully (only a few drops) to adjust the pH to acidic. The resultant solids were stirred on ice for 30 minutes and were isolated by filtration to afford compound 135 (140 mg, 0.520 mmol, 39.2% yield) as a white solid. $^1$H NMR (400 MHz, DMSO) δ 8.20 (d, J=5.5 Hz, 1H), 7.51 (d, J=7.2 Hz, 2H), 7.41 (t, J=7.5 Hz, 2H), 7.38-7.33 (m, 2H), 5.34 (s, 2H).

3-Hydroxy-2-(1H-tetrazol-5-yl)pyridin-4(1H)-one (136)

4-(benzyloxy)-2-(1H-tetrazol-5-yl)pyridin-3-ol was taken up in a 5:5:1 mixture of concentrated HCl:HOAC:TFA and was stirred at room temperature for 48 h. After this time, acids were removed under vacuum, the resultant solids were co-evaporated several times with methanol, and were purified by C18 column chromatography eluting in a water/MeOH system to yield pure compound 136 (61% yield) as a pink solid. $^1$H NMR (400 MHz, DMSO) δ 7.11 (d, J=0.7 Hz, 1H).

General Procedure for the Optimized Suzuki Coupling of Compounds 138-141 and 161-164

4-(Benzyloxy)-6-bromo-3-hydroxypicolinonitrile (500 mg, 1.639 mmol) was dissolved in a mixture of dioxane (15 ml) and Water (5 ml) and was stirred. S-Phos (67.3 mg, 0.164 mmol), potassium carbonate (679 mg, 4.92 mmol), and boronic acid (1.966 mmol) were added and the mixture stirred at rt under vacuum for 10 minutes to degas. PdCl$_2$ (DPPF) (60.0 mg, 0.082 mmol) was added and the mixture was heated to 90° C. for 24 hours. After this time the solution turned a dark black color. 4 M HCl was added to quench excess potassium carbonate and to re-protonate the phenoxide anion. Solvent was then removed under vacuum and the residue was taken up in methanol and loaded on to silica, and was subsequently purified by column chromatography in an ethyl acetate/hexanes system eluting 0-100% ethyl acetate.

4-(Benzyloxy)-3-hydroxy-6-phenylpicolinonitrile (138)

Compound 138 was prepared according to the general procedure, as a white solid in 87% yield. $^1$H NMR (400 MHz, CD3OD) δ 7.80 (d, J=8.1 Hz, 2H), 7.50 (d, J=5.1 Hz, 3H), 7.36 (ddd, J=12.3, 10.7, 6.2 Hz, 6H), 5.32 (s, 2H).

4-(Benzyloxy)-3-hydroxy-6-(4-phenoxyphenyl)picolinonitrile (139)

Compound 139 was prepared according to the general procedure, as a white solid in 71% yield. $^1$H NMR (400 MHz, CDCl3) δ 7.72 (d, J=8.6 Hz, 2H), 7.39-7.30 (m, 7H), 7.24 (s, 1H), 7.13 (dd, J=10.7, 4.1 Hz, 1H), 7.01 (dd, J=8.7, 2.0 Hz, 4H), 5.18 (s, 2H).

4-(Benzyloxy)-6-(4-cyanophenyl)-3-hydroxypicolinonitrile (140)

Compound 140 was prepared according to the general procedure, as a white solid in 52% yield.

4-(4-(Benzyloxy)-6-cyano-5-hydroxypyridin-2-yl)benzoic acid (141)

Compound 141 was prepared according to the general procedure, as a white solid in 46% yield. $^1$H NMR (400 MHz, DMSO) δ 11.35 (s, 1H), 8.13 (d, J=7.5 Hz, 2H), 8.01 (d, J=7.5 Hz, 2H), 7.95 (s, 1H), 7.56 (d, J=8.0 Hz, 2H), 7.42 (t, J=7.6 Hz, 2H), 7.35 (d, J=6.3 Hz, 1H), 5.46 (s, 2H).

3-(4-(benzyloxy)-6-cyano-5-hydroxypyridin-2-yl)benzoic acid (161)

Compound 161 was prepared according to the general procedure, as a white solid in 44% yield.

4-(benzyloxy)-3-hydroxy-6-(m-tolyl)picolinonitrile (162)

Compound 162 was prepared according to the general procedure, as a white solid in 87% yield.

4-(benzyloxy)-3-hydroxy-6-(o-tolyl)picolinonitrile (163)

Compound 163 was prepared according to the general procedure, as a white solid in 56% yield.

6-(4-(1H-tetrazol-5-yl)phenyl)-4-enyl)-3-hydroxypicolinonitrile (164)

Compound 164 was prepared according to the general procedure, as a white solid in 41% yield.

General Procedure for the Optimized Suzuki Coupling of Compounds 142-148:

4-(benzyloxy)-3-hydroxy-6-phenylpicolinonitrile (or its derivatives) was suspended in a 5:5:1 mixture of concentrated hydrochloric acid, glacial acetic acid, and trifluoroacetic acid. The mixture was then heated to 85-90° C. for 24 h. After this time acids and water were removed under vacuum and the residue was co-evaporated with methanol twice before loading on celite and purifying by reverse phase C18 column chromatography eluting a water/methanol system.

3-Hydroxy-4-oxo-6-phenyl-1,4-dihydropyridine-2-carboxylic acid (142)

Compound 142 was prepared according to the general deprotection procedure in 43% yield as a white solid. $^1$H NMR (400 MHz, DMSO) δ 7.81-7.73 (m, 2H), 7.48 (dd, J=4.1, 2.3 Hz, 3H), 7.31 (s, 1H).

3-Hydroxy-4-oxo-6-(4-phenoxyphenyl)-1,4-dihydropyridine-2-carboxylic acid (143)

Compound 143 was prepared according to the general deprotection procedure in 34% yield as a white solid. $^1$H NMR (400 MHz, DMSO) δ 7.79 (d, J=8.7 Hz, 2H), 7.42 (t, J=7.9 Hz, 2H), 7.27 (s, 1H), 7.19 (t, J=7.4 Hz, 1H), 7.07 (dd, J=8.1, 3.8 Hz, 4H).

6-(4-carboxyphenyl)-3-hydroxy-4-oxo-1,4-dihydropyridine-2-carboxylic acid (144)

Compound 144 (12 mg) was prepared according to the general deprotection procedure.

6-(3-carboxyphenyl)-3-hydroxy-4-oxo-1,4-dihydropyridine-2-carboxylic acid (145)

Compound 145 (24 mg) was prepared according to the general deprotection procedure.

3-hydroxy-4-oxo-6-(m-tolyl)-1,4-dihydropyridine-2-carboxylic acid (146)

Compound 146 (121 mg) was prepared according to the general deprotection procedure.

3-hydroxy-4-oxo-6-(o-tolyl)-1,4-dihydropyridine-2-carboxylic acid (147)

Compound 147 (150 mg) was prepared according to the general deprotection procedure.

6-(4-(1H-tetrazol-5-yl)phenyl)-3-hydroxy-4-oxo-1,4-dihydropyridine-2-carboxylic acid (148)

Compound 148 (16 mg) was prepared according to the general deprotection procedure.

Example 11.9: Synthesis of Compounds in Table 8

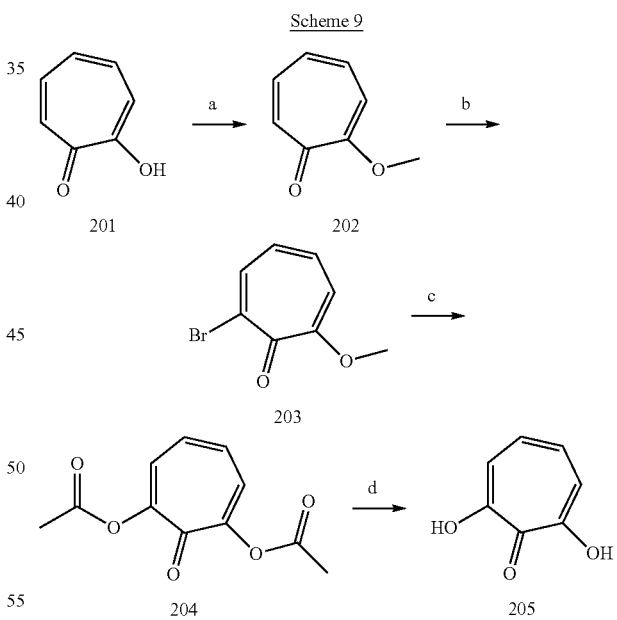

Reaction conditions: (a) MeI, K2CO3, DBU, acetonitrile, 70° C. (sealed vessel), 18 h; (b) NBS, benzene, reflux, 8 h; (c) acetic anhydride, TFA, HOAc, neat, 85° C. (sealed vessel) 8 h; (d) 4M HCl, reflux, 12 h.

As detailed in Scheme 9, α-hydroxy tropolone was prepared by bromination and subsequent solvolytic acetylation of methoxy tropolone. Cleavage of the acetyl esters of the compound 204 in refluxing 4 M HCl afforded α-hydroxy tropolone, albeit in low yields overall (due only to the limits of saponification; all other reactions were optimized to >85% yield).

Scheme 10

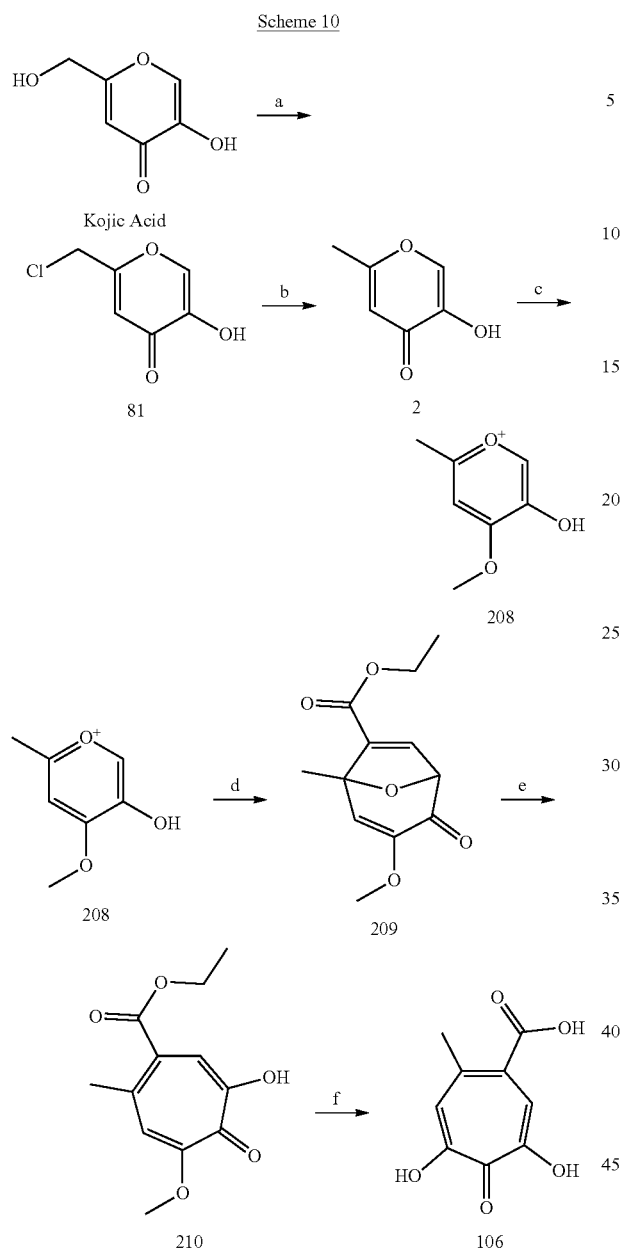

Reaction conditions: (a) thionyl chloride, DCM, r.t., 18 h; (b) Zn (dust), 6M HCl, water, 70° C., 4-6 h; (c) methyl triflate, DMC, chloroform, reflux, 18 h; (d) ethyl propiolate, DIPEA, chloroform, 125° C., microwave reactor, 25 min; (e) BCl$_3$, chloroform, 0-25° C., 1 h; (f) BBr$_3$, chloroform, reflux, 3d.

Compound 106 was synthesized as detailed in Scheme 10. Briefly, kojic acid was chlorinated at the allyl position with thionyl chloride and was subsequently reduced with zinc dust and acid to yield allomaltol (compound 2). Selective alkylation of the carbonyl oxygen by methyl triflate afforded the carbonyl ylide triflate salt (compound 208). The activated carbonyl ylide was irritated in a microwave reactor in either neat or concentrated ethyl propiolate with stoichiometric DIPEA to afford the 3+2 dipolar cycloaddition product (compound 209). Selective ring opening with boron trichloride afforded the α-methoxy tropolone ethyl ester. Subsequent deprotection with boron tribromide in refluxing chloroform yielded compound 106.

Scheme 11

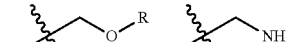

The scope of the dipolar cycloaddition with the carbonyl ylide triflate salt was explored as a route to further α-hydroxy tropolone derivatization, as briefly detailed in Scheme 11. Methyl propargyl ketone was found to undergo cycloaddition with the carbonyl ylide, but subsequent ring opening led to a complex mixture of products. Of the simple alkynes explored, phenyl acetylene gave robust cycloaddition product in a good yield. The phenyl cycloaddition adduct was tolerant of BCl₃ ring opening, but showed much greater decomposition as compared to the ethyl ester analogue. Further removal of the methoxy group with BBr₃ resulted in the target compound 213 in ~30% yield.

2-Methoxycyclohepta-2,4,6-trien-1-one (202)

Tropolone (500 mg, 4.09 mmol) and DBU (0.062 ml, 0.409 mmol) were dissolved in acetonitrile (5 ml) in a sealable vessel. Iodomethane (0.765 ml, 12.28 mmol) was added in one portion and the reaction was sealed. The stirring mixture was heated to 70° C. for 18 hours, after which time the reaction was cooled and a 30% ammonium hydroxide solution was added to quench excess iodomethane. Water and DCM were added, and the mixture was extracted 3× with DCM. The combined organics were dried and concentrated, and the resultant oil was loaded onto silica and was purified via column chromatography, eluting a 0-100% EtOAc in hexanes gradient over 15 minutes to afford 2-methoxycyclohepta-2,4,6-trien-1-one (425 mg, 3.12 mmol, 76% yield) as a yellow oil. $^1$H NMR (400 MHz, CDCl3) δ 7.10 (ddd, J=4.2, 2.1, 1.0 Hz, 2H), 7.02-6.94 (m, 1H), 6.75 (d, J=0.5 Hz, 1H), 6.64 (d, J=9.9 Hz, 1H), 3.82 (s, 3H).

2-Bromo-7-methoxycyclohepta-2,4,6-trien-1-one (203)

A solution of 2-methoxycyclohepta-2,4,6-trien-1-one (850 mg, 6.24 mmol) and NBS (1333 mg, 7.49 mmol) were heated to reflux in benzene for 4 hours. NHS precipitated over the course of the reaction. After 4 hours, the reaction was cooled to rt and was filtered. The filtrate was concentrated under vacuum, and the resultant solids were loaded on silica and purified on an EtOAc/hexanes gradient, with the desired product eluting at ~50% EtOAc to yield 2-bromo-7-methoxycyclohepta-2,4,6-trien-1-one (1.21 g, 5.63 mmol, 90% yield) as a light orange solid. $^1$H NMR (400 MHz, CDCl3) δ 8.19 (dd, J=9.5, 0.9 Hz, 1H), 7.15 (t, J=10.3 Hz, 1H), 6.79 (d, J=10.0 Hz, 1H), 6.69 (dd, J=10.4, 9.8 Hz, 1H), 3.95 (s, 3H).

2-Oxocyclohepta-3,5,7-triene-1,3-diyl diacetate (204)

2-bromo-7-methoxycyclohepta-2,4,6-trien-1-one (1000 mg, 4.65 mmol) was taken up in a mixture of acetic anhydride (8775 μl, 93 mmol), TFA (1075 μl, 13.95 mmol), and acetic acid (399 μl, 6.98 mmol) and was heated with stirring in a sealed vessel at 85° C. for 24 hours. After 24 hours the acids were removed under vacuum and the resultant solid was purified via a silica column in a 50% EtOAc/hexanes system to afford 2-oxocyclohepta-3,5,7-triene-1,3-diyl diacetate (186 mg, 0.837 mmol, 18% yield) as a white solid. $^1$H NMR (400 MHz, CDCl3) δ 7.25 (s, 1H), 7.03 (d, J=4.1 Hz, 1H), 2.27 (s, 3H).

2,7-Dihydroxycyclohepta-2,4,6-trien-1-one (205)

2-oxocyclohepta-3,5,7-triene-1,3-diyl diacetate (100 mg, 0.450 mmol) was taken up in 4 M HCl and was refluxed overnight. After completion, solvent was removed under vacuum and the resultant solids were purified by reverse phase C18 chromatography eluting a water/methanol system to afford 2,7-dihydroxycyclohepta-2,4,6-trien-1-one (29.8 mg, 0.216 mmol, 48% yield) as a white solid. $^1$H NMR (400 MHz, CDCl3) δ 7.25 (d, J=9.1 Hz, 1H), 7.09 (s, 1H), 6.81 (d, J=9.5 Hz, 2H), 3.89 (s, 3H), 2.31 (s, 3H).

2-(Chloromethyl)-5-hydroxy-4H-pyran-4-one (81)

To a rapidly stirring suspension of Kojic acid (10 g, 70.4 mmol) in CH₂Cl₂ (250 mL) at room temperature was added thionyl chloride (5.91 mL, 81 mmol), dropwise over the course of 25 minutes. Throughout the addition, the suspension tends to clump. When clumping occurred, the addition was paused to allow the solution to return to homogeneity. After 4-6 hours of stirring, the suspension was filtered, and the solids were recrystallized from ethanol to afford Kojic chloride in 81% (9.0 g) yield as white needles. $^1$H NMR (400 MHz, DMSO-d₆): δ 8.12 (s, 1H), 6.56 (s, 1H), 4.65 (s, 2H). ESI-MS [M+H]⁺: 159.14

5-Hydroxy-2-methyl-4H-pyran-4-one (2)

A stirring solution of 81 (10 g, 62.3 mmol) in water (150 mL) was heated to 50° C. To this vigorously stirring solution was added zinc powder (8.14 g 125 mmol) slowly, and the temperature was raised to 70° C. To this solution was added concentrated HCl (25 mL, 823 mmol) dropwise, maintaining the internal temperature of the solution below 80° C. The mixture was stirred for a further 4 hours at 70° C. At this point the reaction was hot filtered to remove residual zinc. The cooled filtrate was extracted 5 times with 50 mL CH₂Cl₂+10 mL ethyl acetate. The resulting organics were dried and concentrated, to yield 2 (allomaltol) as a white powder in 83% (6.5 g) yield. $^1$H NMR (400 MHz, Acetone-d₆): δ 7.82 (s, 1H), 6.21 (s, 1H), 2.28 (d, J=0.5 Hz, 3H). ESI-MS [M−H]⁻: 125.22

5-Hydroxy-4-methoxy-2-methylpyrylium triflate (208)

Allomaltol (5.4 g, 42.8 mmol) was stirred in a mixture of DCM (10 ml) and chloroform (30.0 ml). To the mixture was added fresh methyl trifluoromethansulfonate (7.07 ml, 64.2 mmol), slowly. The mixture was then heated to reflux and vigorously stirred. Note: Reaction mixture may form 2 layers at lower temperatures. The mixture was heated to reflux o/n and the reaction progress was monitored by TLC (5% MeOH in DCM) and stained with Iron chloride. Iron test alone can give false negatives for reaction progress as some residual allomaltol always remains unreacted and the free phenol of the product stains at high concentrations. After ~18 hours the reaction mixture was cooled and evaporated to dryness under high vacuum to remove solvent and residual methyl triflate. The resultant dark oil was then taken up in minimal ethyl acetate. White crystals will form upon introduction of ethyl acetate. The mixture was heated to dissolve any solids, and the solution was cooled on ice with swirling. Solids were isolated by filtration and washed 3× with ethyl acetate. A second crop of crystals can be gathered from the concentrated filtrate. Drying the isolate white crystals afforded 5-hydroxy-4-methoxy-2-methylpyrylium, Triflic acid- (9.4 g, 32.4 mmol, 76% yield). $^1$H NMR (400 MHz, DMSO) δ 8.99 (s, 1H), 7.91 (s, 1H), 4.25 (s, 3H), 2.73 (s, 3H).

Ethyl 3-methoxy-5-methyl-2-oxo-8-oxabicyclo [3.2.1]octa-3,6-diene-6-carboxylate (209)

5-hydroxy-4-methoxy-2-methylpyrylium, Triflic acid- (250 mg, 0.861 mmol) was added to chloroform (1 ml) in a 10 ml MW vessel. To the mixture was added ethyl propiolate (0.611 ml, 6.03 mmol) followed by N,N-diisopropylethylamine (0.181 ml, 1.034 mmol). The mixture was stirred briefly, sealed, and then irradiated at 125° C. for 25 minutes with stirring in a microwave reactor. Upon completion, the crude mixture was evaporated under high vacuum to remove ethyl propiolate and purified by silica chromatography employing a stepwise gradient from 6% to 12% ethyl acetate in hexanes, affording ethyl 3-methoxy-5-methyl-2-oxo-8-oxabicyclo[3.2.1]octa-3,6-diene-6-carboxylate (130 mg, 0.546 mmol, 63.3% yield) as a yellow solid. $^1$H NMR (400 MHz, CDCl3) δ 7.08 (d, J=2.5 Hz, 1H), 6.08 (s, 1H), 5.01 (dd, J=2.5, 0.5 Hz, 1H), 4.25 (qd, J=7.1, 6.6 Hz, 2H), 3.55 (s, 3H), 1.77 (s, 3H), 1.32 (td, J=7.1, 0.6 Hz, 3H).

Ethyl 3-hydroxy-5-methoxy-7-methyl-4-oxocyclohepta-1,5-diene-1-carboxylate (210)

Ethyl 3-methoxy-5-methyl-2-oxo-8-oxabicyclo[3.2.1]octa-3,6-diene-6-carboxylate (300 mg, 1.259 mmol) was taken up in dry DCM (50 ml) and stirred at 5° C. To the cooled solution was added boron trichloride (3.78 ml, 3.78 mmol) dropwise and the mixture stirred for 30 minutes on ice. The solution was then warmed to room temperature for a further 30 minutes, upon which time the reaction was quenched by the addition of methanol. The resultant solution was evaporated under vacuum and isolated solids were purified by column chromatography to afford ethyl 3-hydroxy-5-methoxy-7-methyl-4-oxocyclohepta-1,5-diene-1-carboxylate (206 mg, 0.856 mmol, 68% yield) as a pink solid. $^1$H NMR (400 MHz, CD3OD) δ 7.47 (s, 1H), 7.21 (s, 1H), 4.37 (d, J=7.1 Hz, 2H), 4.00 (s, 3H), 2.51 (s, 3H), 1.38 (t, J=7.1 Hz, 3H).

3-Methoxy-5-methyl-6-phenyl-8-oxabicyclo[3.2.1]octa-3,6-dien-2-one (211)

5-hydroxy-4-methoxy-2-methylpyrylium, Triflic acid- (500 mg, 1.723 mmol) was added to Chloroform (1 ml) in a 10 ml MW vessel. To the mixture was added phenylacetylene (0.946 ml, 8.61 mmol) followed by N,N-diisopropylethylamine (0.361 ml, 2.067 mmol). The mixture was stirred briefly, sealed, and then irradiated at 125° C. for 25 minutes with stirring in a microwave reactor. Upon completion, the crude mixture was evaporated under high vacuum to remove phenylacetylene and purified by silica chromatography employing a stepwise gradient from 6% to 12% ethyl acetate in hexanes affording 3-methoxy-5-methyl-6-phenyl-8-oxabicyclo[3.2.1]octa-3,6-dien-2-one (210 mg, 0.867 mmol, 50.3% yield) as a white solid. $^1$H NMR (400 MHz, CDCl3) δ 7.44-7.28 (m, 5H), 6.28 (d, J=2.4 Hz, 1H), 6.19 (s, 1H), 4.99 (d, J=2.5 Hz, 1H), 3.60 (s, 3H), 1.68 (s, 3H).

7-Hydroxy-2-methoxy-4-methyl-5-phenylcyclohepta-2,5-dien-1-one (212)

3-methoxy-5-methyl-6-phenyl-8-oxabicyclo[3.2.1]octa-3,6-dien-2-one (500 mg, 2.064 mmol) was taken up in dry DCM (50 ml) and stirred at 5° C. To the cooled solution was added boron trichloride (6.78 ml, 6.78 mmol) dropwise and the mixture stirred for 30 minutes on ice. The solution was then warmed to room temperature for a further 30 minutes, upon which time the reaction was quenched by the addition of methanol. The result and solution was evaporated under vacuum and isolated solids were purified by column chromatography to afford 7-hydroxy-2-methoxy-4-methyl-5-phenylcyclohepta-2,5-dien-1-one (302 mg, 1.238 mmol, 60% yield) as a grey solid. $^1$H NMR (400 MHz, CDCl3) δ 7.44-7.34 (m, 4H), 7.22 (dd, J=6.7, 1.5 Hz, 2H), 7.15 (s, 1H), 4.01 (d, J=1.2 Hz, 3H), 2.26 (d, J=1.5 Hz, 3H).

2,7-Dihydroxy-4-methyl-5-phenylcyclohepta-2,4,6-trien-1-one (213)

2-hydroxy-7-methoxy-5-methyl-4-phenylcyclohepta-2,4,6-trien-1-one (200 mg, 0.826 mmol) was taken up in DCM (20 ml) and was cooled to 5° C. in an ice bath. To the cooled solution was added boron tribromide (2.477 ml, 2.477 mmol) dropwise. The mixture stirred for 30 minutes on ice and then was warmed to rt and stirred a further 60 minutes after which time the reaction was quenched by the addition of methanol. Solvents were evaporated and the resultant black solid was purified by silica chromatography on a 0-100% EtOAc/hexanes system. The isolate product was insufficiently pure and was further purified by C18 reverse phase chromatography in a water/MeOH system to afford 2,7-dihydroxy-4-methyl-5-phenylcyclohepta-2,4,6-trien-1-one (58.4 mg, 0.256 mmol, 31% yield) as a black solid. $^1$H NMR (400 MHz, CD3OD) δ 7.49 (s, 1H), 7.41-7.30 (m, 4H), 7.18 (d, J=7.7 Hz, 2H), 2.14 (s, 3H).

Example 12: Computational Modeling/Docking

To gain insight into the mode of binding of fully elaborated inhibitor molecules, docking analysis was performed using Molecular Operating Environment (MOE) software.

Constrained docking and minimization studies were performed starting from a reported endonuclease crystal structure with a bound hydroxypyridinone-based inhibitor (see Reference 28). The bound inhibitor was removed from the structure and replaced with compound 71, utilizing the position of the metal-coordinating donor atoms of the co-crystallized inhibitor as an initial guide for the binding mode of compound 71 (PDB: 4M4Q). Constrained minimizations were then performed on this model in which the metal-binding oxygen atoms of 71 were fixed in optimal geometries based on several parameters, primarily previous crystal structures of inhibitors with similar ligand donor atom identity and geometry (see References 26 and 27). These constrained simulations ensured that a reasonable metal binding geometry was maintained; as MM-docking simulations do not appropriately account for metal-ligand interactions (see References 33 and 34). Flexible receptor modeling (induced fit) was employed in which active site residue side chains proximal to the inhibitor molecule were allowed to move, while residue backbones were more constrained. In the simulation the coordinating phenolic oxygen atom on compound 71 was deprotonated, and the charge on each metal center was assigned as 2+ (i.e. $Mn^{2+}$). Two water molecules coordinated to one of the $Mn^{2+}$ centers in the template structure (PDB: 4M4Q, Mn302) were retained in the simulation and their positions were fixed relative to the metal center.

As illustrated in FIGS. 3A-3B, compound 71 was predicted to make key interactions with several binding pocket and key residues, including Arg82, Lys34, Arg124, Lys134, and transient hydrophobic interactions with Tyr24. The docking Analysis showed that compound 71 chelated one of the active-site metal ions, with the carbonyl oxygen atom replacing the bridging water molecule, and the hydroxyl oxygen atom binding one metal center and forming a hydrogen bond with Lys134. The phenylaminomethyl moiety at the 6-position was found to be too short to allow for π-stacking with Tyr24, but allowed for hydrophobic interactions with pocket 2. The 4-chloro substituent was also positioned to allow for halogen bonding with the backbone carbonyl of Arg82. The N-phenyltetrazole moiety at the 1-position was found to fit well into pocket 4, with the aryl ring making hydrophobic interactions with the hydrophobic wall of the pocket and the tetrazole making favorable contacts with the basic residues found at the end of the pocket. It was found that the tetrazole was able to hydrogen bond with two nitrogen atoms from the guanidine moiety of Arg124 and simultaneously hydrogen bond with the terminal nitrogen of Lys34.

Without wishing to be bound by theory, it is believed that compounds disclosed herein inhibit influenza PA endonuclease by chelating the catalytic Mn2+ ions in the active site of the enzyme, thereby blocking to the ability of the protein to polarize and hydrolytically cleave the phosphodiester bonds found in the backbone of nucleic acids.

Example 13: Cellular Cytotoxicity and Antiviral Activity

Example 13.1: General Procedure of Cellular Cytotoxicity and Antiviral Activity Influenza A virus was obtained from the American Tissue Culture Collection (H1N1, ATCC VR-1737). Virus stocks were prepared by propagation of virus on Marvin-Darby canine kidney cells (MDCK; ATCC CCL-34) and infectious titers were determined by Hemagglutination assay (see Reference 3). MDCK cells were cultured using DMEM/Ham's F-12 (1:1) medium containing 10% fetal bovine serum (FBS, Gibco, Grand Island, N.Y., USA) and 1% antibiotic-antimycotic solution (10.000 Units/mL penicillin, 10 mg/mL streptomycin sulphate, 25 mg/mL amphotericin B) at 37° C. in an incubator with 5% $CO_2$.

Cytotoxicity assays of compounds towards MDCK cells were measured using CellTiter-Glo luminescent cell viability assay (Promega) according to the manufacturer protocol. To begin the assay, MDCK cells were counted with a hemocytometer and diluted with fresh medium to the proper concentration and seeded (2×104 cells/well) in an opaque-wall 96 well plate. Cells were then incubated at 37° C. with 5% $CO_2$ for 6 hours prior to treatment with inhibitors to allow for cell adhesion. Then the cells were treated with various concentrations of inhibitor compounds (ranging from 0.5 µM to 512 NM) for 48 h. Each concentration was screened in triplicate in one trial and repeated 2-3 times. After 48 hours, the assay was concluded by the addition of 100 µL per well of reconstituted reagent from the CellTiter-Glo luminescent assay kit. The assay plate was gently shaken for 3 minutes and incubated for 10 minutes at room temperature before reading. Luminescence was read using a BioTek Synergy HT microplate reader.

For the antiviral assay, MDCK cells were seeded at 2×104 cells/well in an opaque-wall 96 well plate, and were incubated for 5 hours at 37° C. and 5.0% $CO_2$ to form an 80% confluent monolayer. Stock solutions on endonuclease inhibitors were diluted to various concentrations by infection medium (DMEM/Ham's F-12 (1:1) containing 5 µg/mL trypsin, and 1% antibiotic solution). Virus stock was diluted in infection medium (DMEM/Ham's F-12 (1:1) containing 5 g/mL Trypsin and 1% antibiotics) to a theoretical multiplicity of infection (MOI) of 0.05. After removal of the culture medium and a washing step with PBS, diluted virus solution (50 µl) and diluted inhibitor solution (50 µL) were added together to each well. As a control, the virus suspension was replaced by infection medium in several wells. Each treatment was conducted in four replicates. After incubation at 37° C. and 5% $CO_2$ for 48 hours, each well was observed under microscope for apparent cytotoxicity and precipitate formation. Cell viability was then determined using CellTiter-Glo luminescent cell viability assay (Promega). 100 µL of reconstituted reagent was added to each well, which contained 100 µL of infection medium, and plates were gently shaken for 3 minutes and incubated for 10 minutes at room temperature before reading. Luminescence (RLU) was measured using Synergy HT plate reader (Biotek).

Relative luminescence, as compared to control wells, was used to determine $EC_{50}$ value using Origin8 graphing software. Upper and lower asymptotes of the sigmoidal curve were defined by the relative luminescence of untreated uninfected cells and untreated infected cells, respectively. $CC_{50}$ values were obtained by titrating inhibitor compound in uninfected MDCK cells and similarly fitting the response, with the upper asymptote being defined by the RLU of untreated uninfected cells.

Figure 4A:
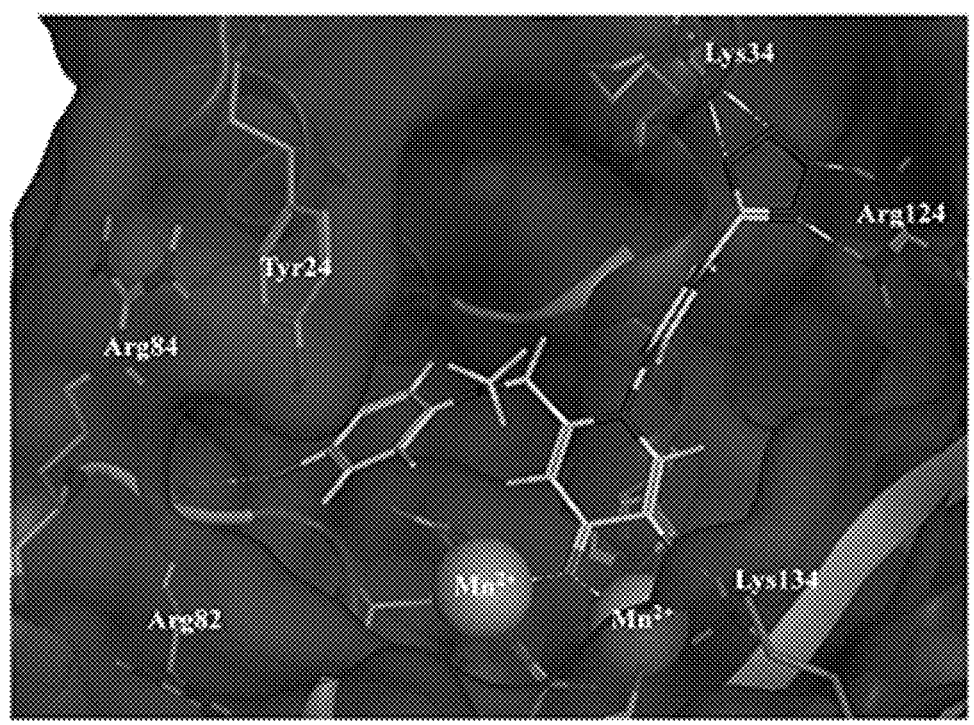
FIGS. 4A-4B.
Figure 4B:
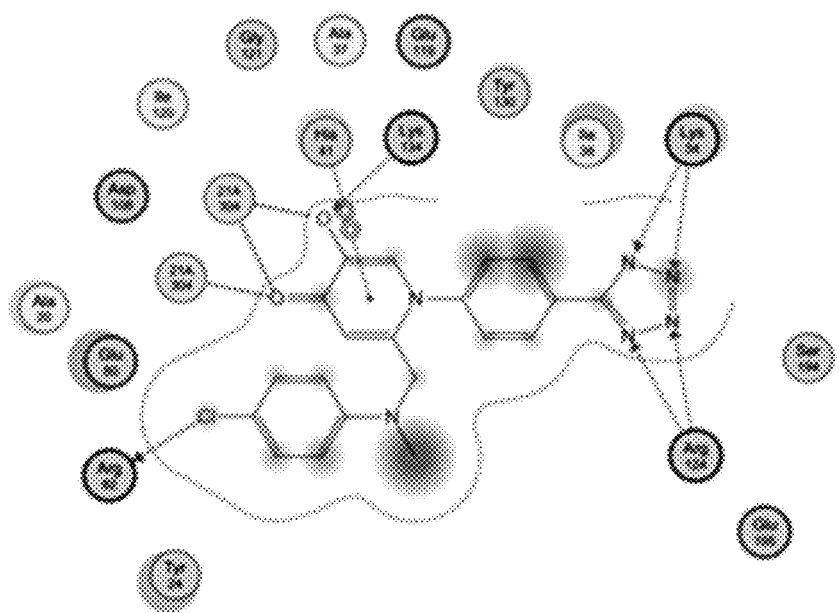
Figure 5A:
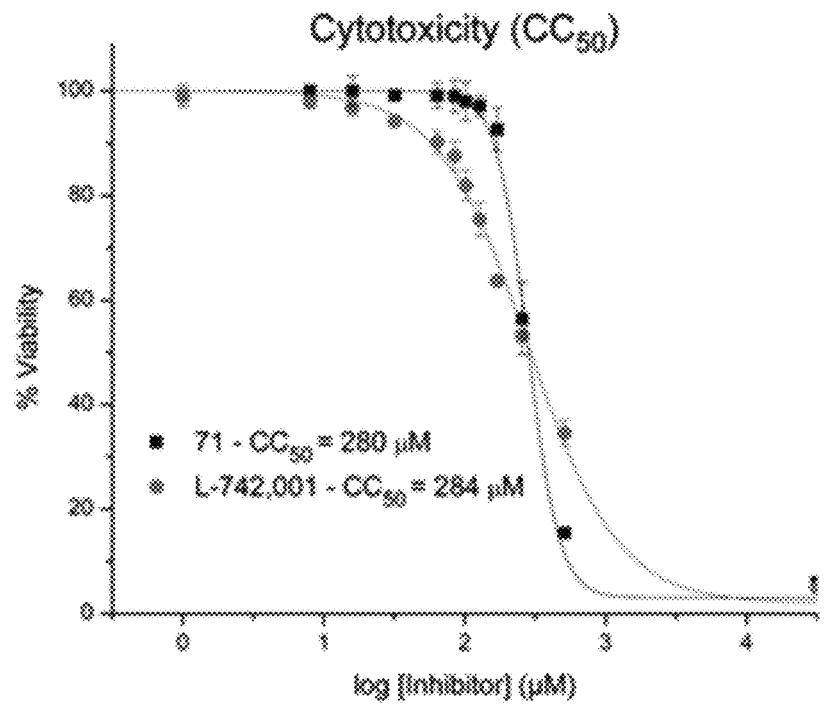
FIGS. 5A-5B.
Figure 5B:
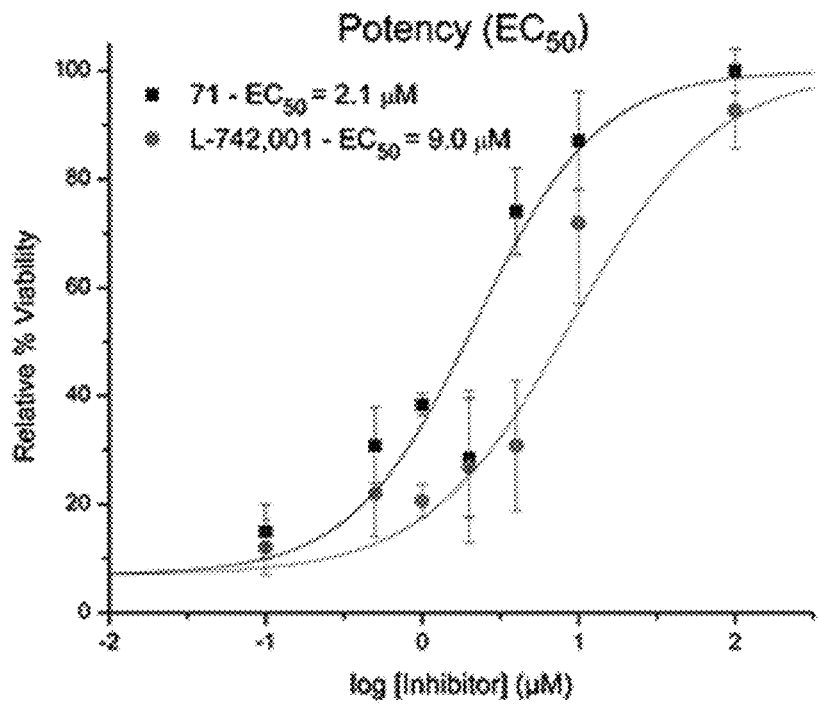

Example 13.2: Evaluation of Compound 71 for Cellular Cytotoxicity and Antiviral Activity The most potent compound, compound 71, was evaluate for cytotoxicity and antiviral activity in Marvin-Darby canine kidney (MDCK) cells. MDCK cells were incubated for a period of 48 hours in the presence of varying concentrations compound 71 or the commercially available inhibitor L-742,001, as a control. Cell viability was then determined using CellTiter-Glo luminescent assay. Antiviral activity was determined by exposing MDCK cells to a lethal challenge of influenza A virus, in the presence of varying concentrations of inhibitor. Compound 71 was found to have a $CC_{50}$ value of 280 µM and an $EC_{50}$ value of 2.1 µM (FIGS. 4A-4B). Both of these values were comparable to the control molecule, with compound 71 being 4- to 5-fold more potent than the control in the viral challenge assay.

Example 14: Endonuclease Construct

The particular endonuclease construct as described herein was isolated directly from H1N1 influenza A and then truncated, and was different from the two previous reported constructs that had been successfully crystalized and diffracted. The first reported structures were initially truncated from H3N2 influenza A and modified by PCR mutagenesis to more accurately resemble reported H1N1 primary sequences. More recent constructs have been reported (which afforded much higher quality of diffraction when crystalized) that were modified to remove the highly flexible A-loop of endonuclease, which was reported to be the cause of the poor-quality diffraction common to endonuclease.

The endonuclease construct was designed with a tobacco-etch virus (TEV) protease cleavage sequence between the His-tag and the N-terminal endonuclease domain. TEV is a highly-active and very specific protease that was found to efficiently cleave the His-tag and have minimal off-target activity in our system. After elution from the IMAC column, endonuclease-containing fractions (prepared from Example 1) were combined in dialysis tubing. To this solution was added pro-TEV plus (BioPioneer) TEV protease per manufacturer's instructions according to the concentration of endonuclease in the given solution. Pro-TEV plus is, itself, a His-tagged construct which allows for facile removal of both the protease and cleaved His-tags via a second IMAC column post-cleavage. This protease has also been optimized to maintain high turnover even in high-salt, high-imidazole buffers even at low temperatures. The reaction mixture was sealed in the dialysis tubing and was dialyzed for 4 hours at room temperature in a buffer containing 100 mM NaCl, 2 mM $MnCl_2$, 1 mM DTT, 20 mM Tris, 0.1% CHAPS, 5% glycerol, pH=8.0. After this initial dialysis, the reaction was further dialyzed in buffer (100 mM NaCl, 2 mM $MnCl_2$, 1 mM DTT, 20 mM Tris, pH=8.0; without CHAPS and glycerol) at 4° C. for 12-16 hours, changing buffer 2-3 times.

Dialyzed protein was purified over a HisTrap HP (Parmacia) column pre-equilibrated with the same buffer used for final dialysis. Eluent was analyzed, and fractions containing endonuclease protein were concentrated using an Amicon Ultra-15 10K centrifugal filter device (Millipore) at 5000×g per manufacturer's instructions. Protein was concentrated to between 5-10 mg/ml (if possible) and was further purified by size-exclusion chromatography. A Superdex 75 (GE Healthcare) gel-permeation column was employed according to manufacturer's instructions. Briefly, 500 µL of concentrated protein was filtered through a 0.45-micron filter and loaded on a pre-equilibrated column. Protein was eluted at a constant flow-rate of 1.0 ml/min in buffer containing 150 mM NaCl, 2 mM $MnCl_2$, 20 mM HEPES, pH=7.0. Resultant protein was concentrated in spin-Amicons to a final concentration of ~5 mg/ml. Analysis of the column trace revealed that while the protein was mostly pure after cleavage, several contaminants were present which had impeded crystallization efforts (FIG. 2). Indeed, crystal condition screens using both purified and crude protein illustrated the necessity of final protein cleanup via size-exclusion. Furthermore, by excluding all but the centermost fractions of the elution peak, the quality of crystals generated improved significantly.

Example 15: Protein Crystallography

All reported crystallization conditions for influenza $PA_N$ endonuclease employ both high salt concentrations for protein stability as well as high molecular weight PEG as a primary precipitant. The reported pH varies, but reports of crystallization at pH below 7.0 always involved a buffer exchange to a higher pH of isolated crystals before ligand soaking and diffraction. Hanging drop crystallization is also reported to be superior to sitting drop for this system. Taking these factors into account, the simple conditions (33% PEG-4000, 200 mM NaOAc, 100 mM Tris, pH=8.0) were used as a starting point for condition screenings, initially combining endonuclease at 5-10 mg/ml in a 1:1 ratio with precipitant solution. These conditions initially resulted in very few, small crystals which did not diffract nor polarize light when inspected. However, the quality of protein was found to be very important for crystallization under these conditions; further purified protein gave substantially greater consistency in producing protein crystals. The primary product of these crystallization experiments was a large amount to 'bad' precipitate (i.e. precipitated protein that did not re-solubilize upon dilution). This result indicated that too much precipitant had been employed. A screen of different ratio of precipitant:protein was performed, varying from 2:1 to 1:4, sequentially. Results indicated that a ratio of 1:2, precipitant-to-protein, was ideal; this resulted in the consistent formation of large numbers of small crystals at a protein concentration of 5 mg/ml. These crystals were of higher quality than those initially obtained; however, they did not diffract below 4 Å at our home-source. Furthermore, precipitation was still a problem with these conditions.

The high concentration of PEG was deemed to be the probable cause of both the bad-precipitation as well as the faster-than-desirable nucleation which resulted in many, small crystals as opposed to fewer, larger crystals. To optimize PEG concentration, screens were conducted varying the concentration of PEG from 33%-20%. The concentration of protein relative to precipitant was also varied in these screens from 7.5 mg/ml to 3 mg/ml. Crystals that diffracted well were obtained at many ratios of PEG to protein. Notably, an inverse correlation was observed between concentration of PEG and concentration of protein. Repeated screenings at all conditions which resulted in diffracting crystals indicated that a protein concentration of 5 mg/ml with a precipitant concentration of ~25% PEG was ideal to repeatably generate high quality crystals. The effect of pH was also studied, and it was found that a pH of 7.5-7.75 gave the best crystals.

Figure 6A:
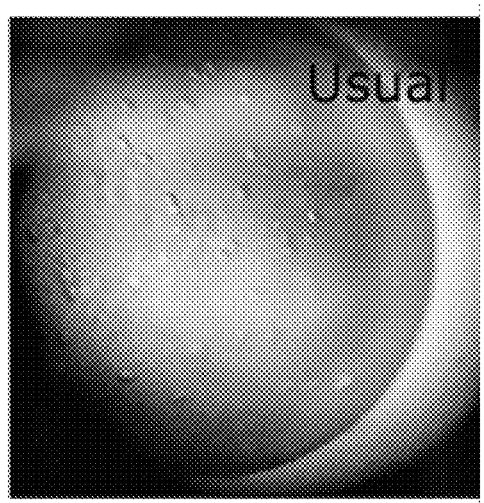
FIG. 6A-6B: Images of obtained crystals of purified endonuclease construct.
Figure 6B:
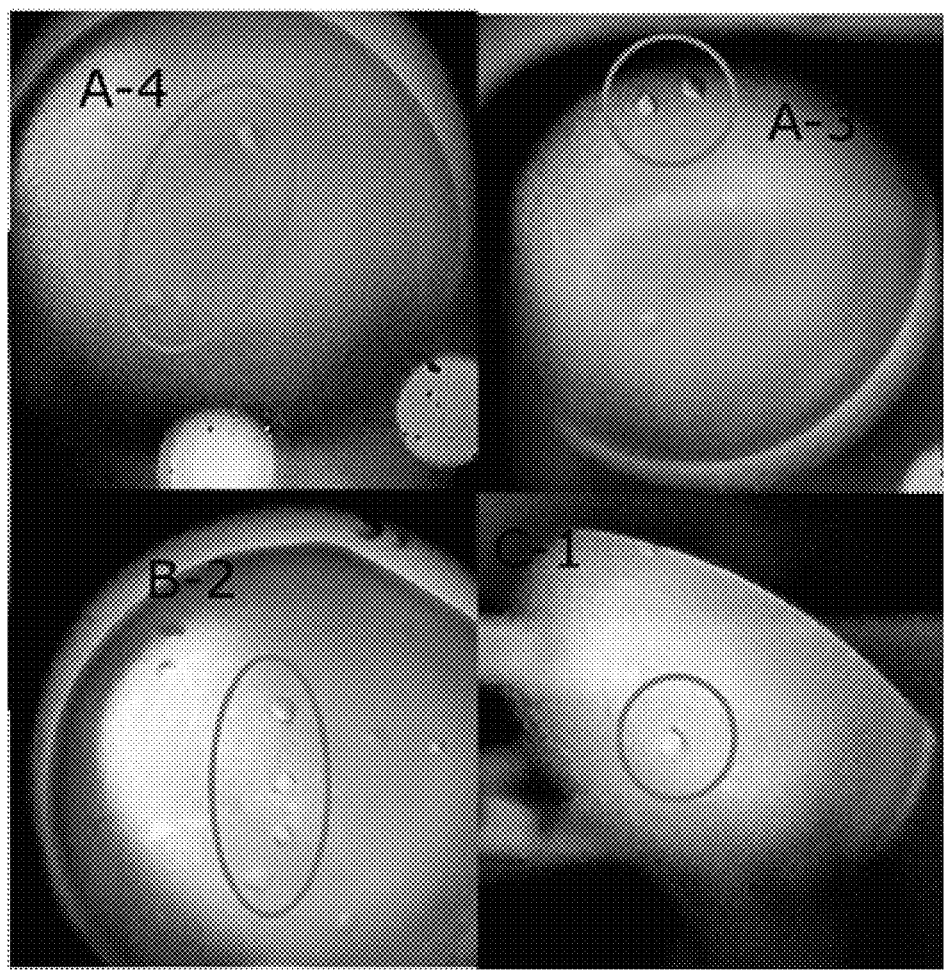
Figure 7A:
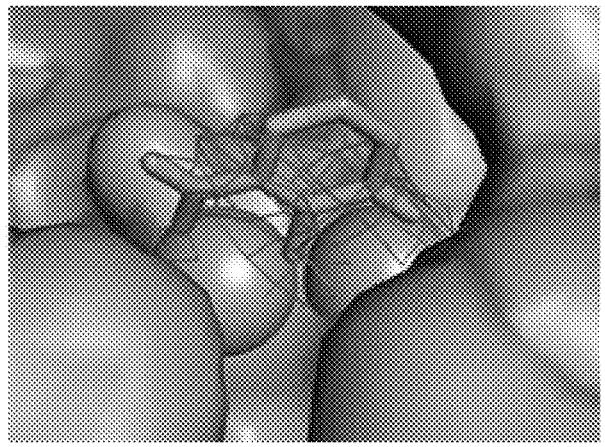
FIG. 7A-7E.
Figure 7B:
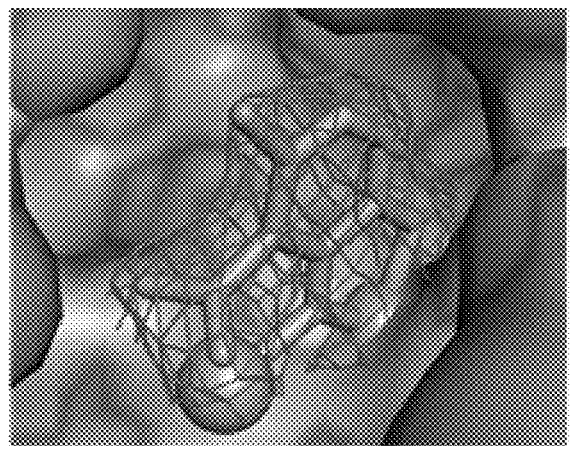
Figure 7C:
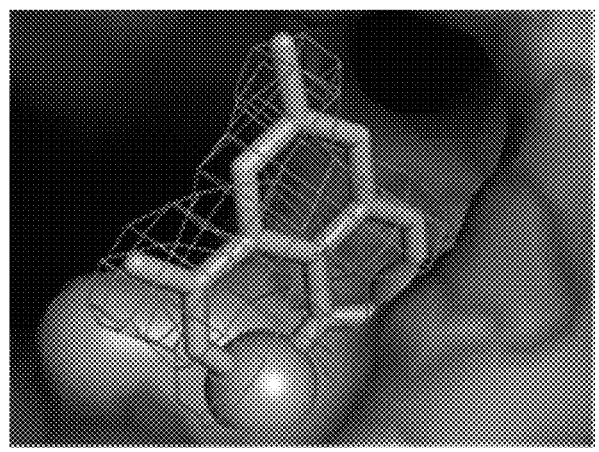
Figure 7D:
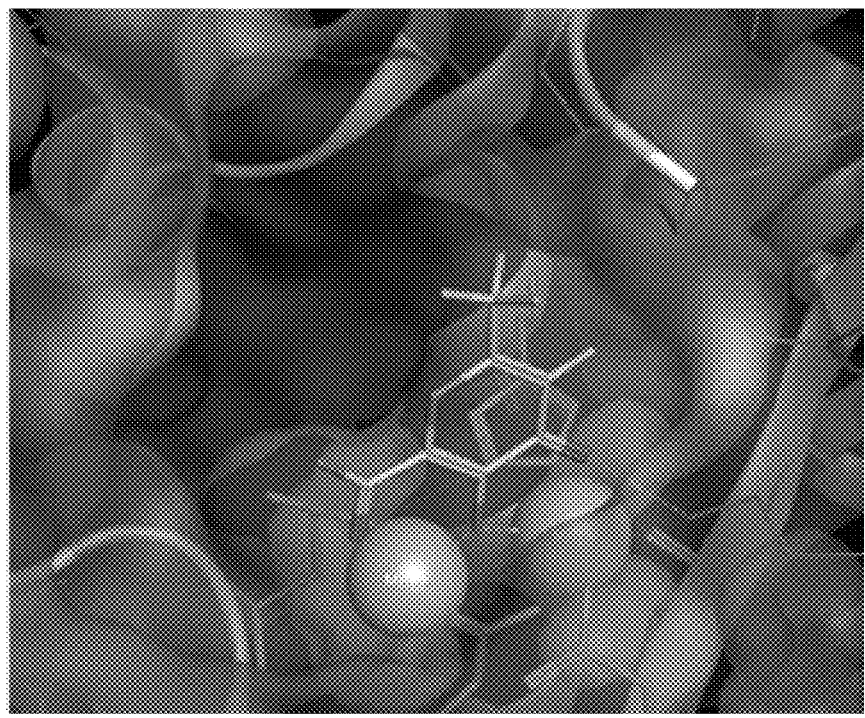
Figure 7E:
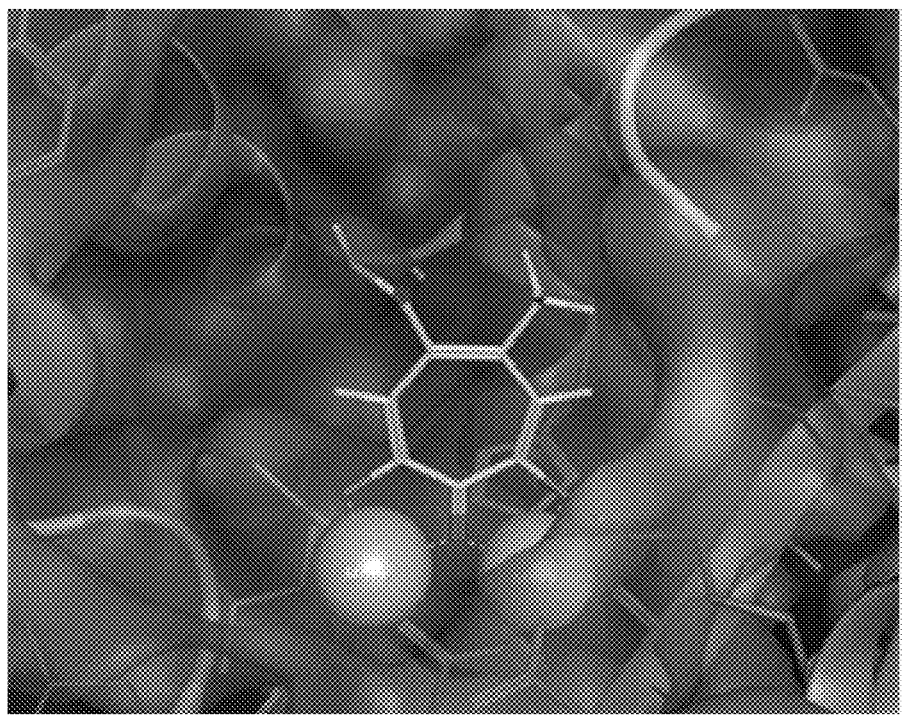
Figure 8A:
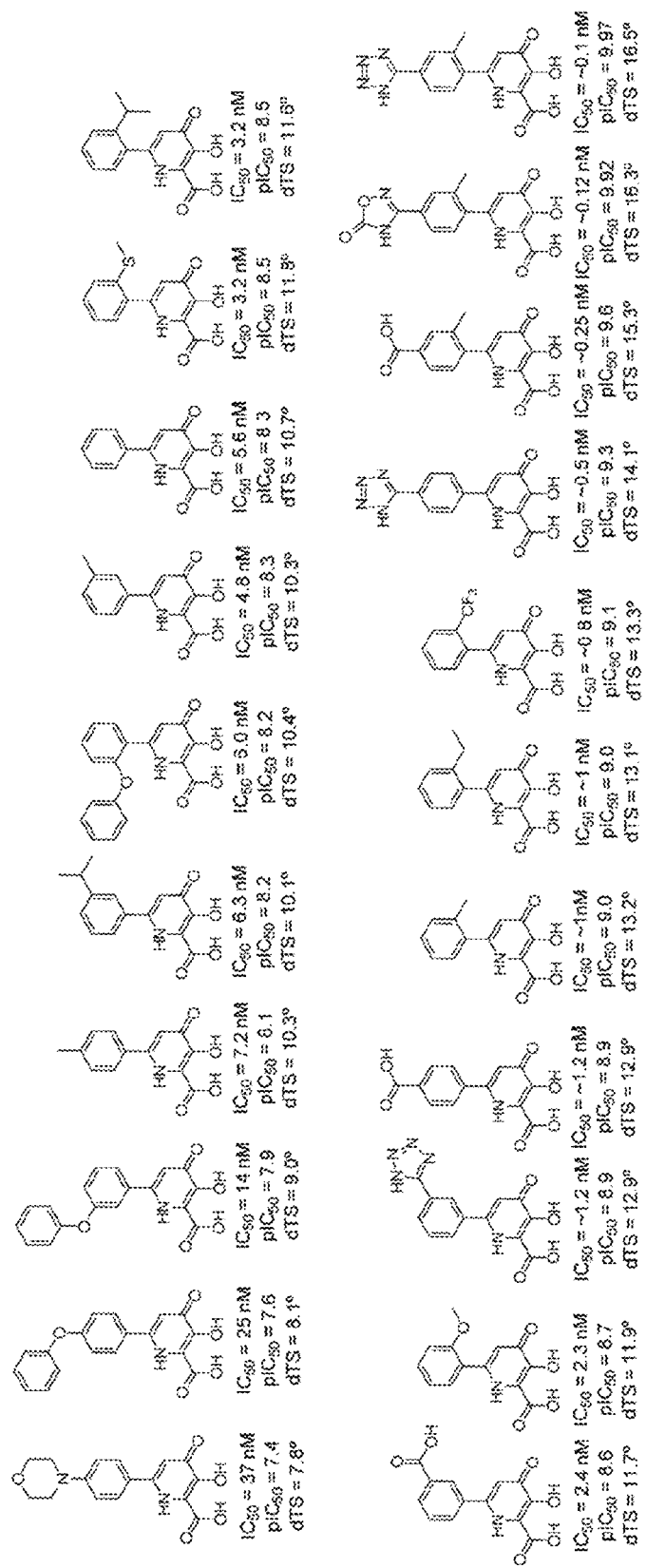
FIGS. 8A-8C. A selection of inhibitors and their respective activity.
Figure 8B:
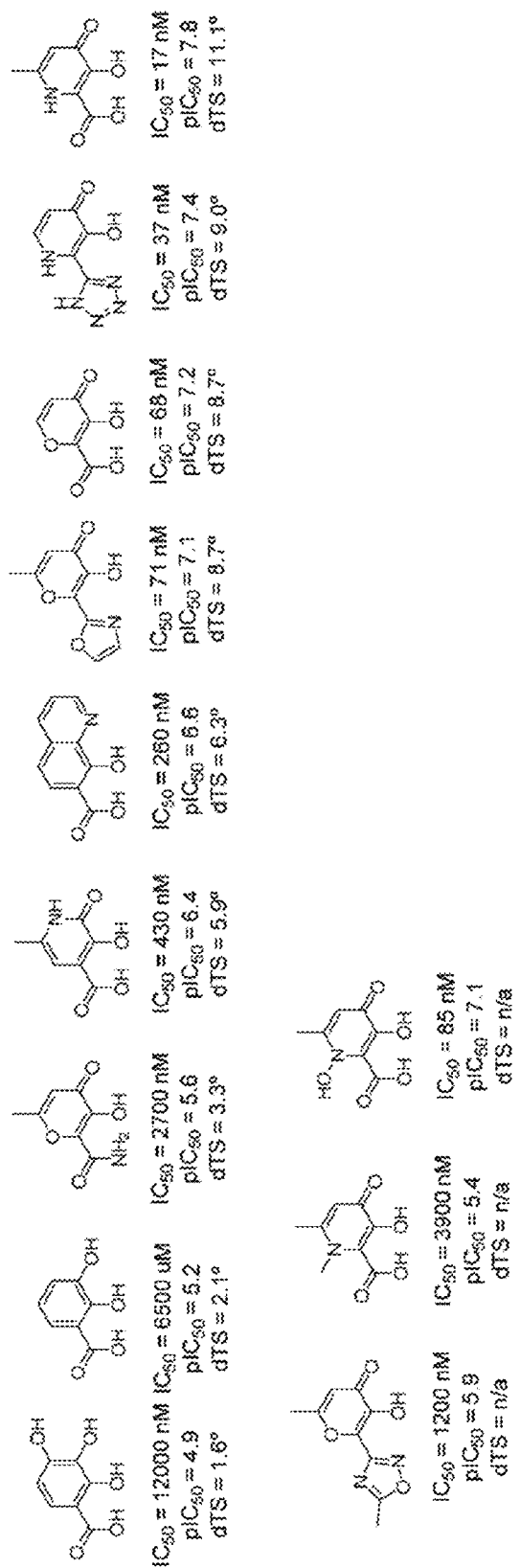
Figure 8C:
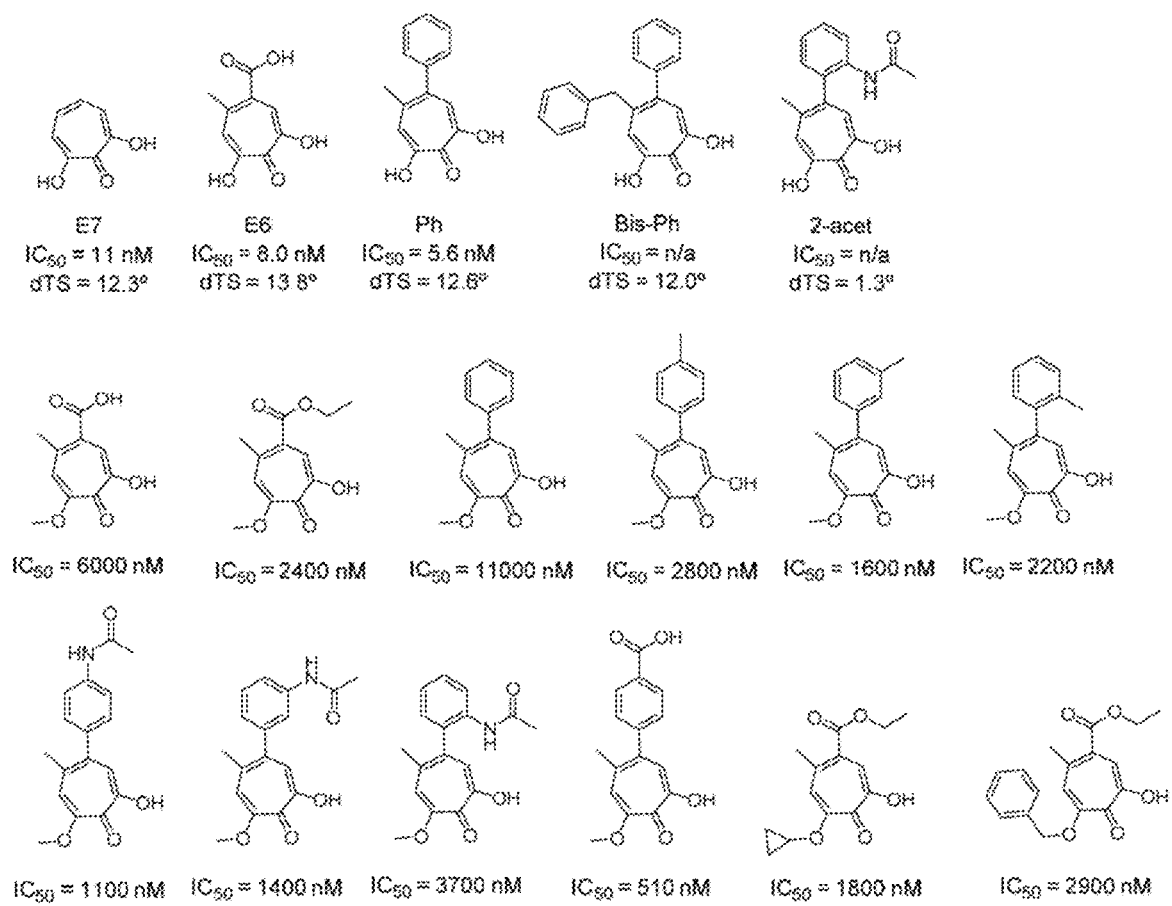

In spite of extensive optimization, the size of observed crystals was always small, and when crystals did form they formed in large number. In an effort to slow nucleation, crystallization experiments were performed at temperatures between 4-18° C. It was found that at temperatures at or below 15° C. precipitation with no crystal growth occurred regardless of protein concentration or concentration of precipitant. Higher temperatures were also explored and screening from 25-37° C. resulted in much greater success. Crystals formed at all temperatures explored, with the largest and highest quality crystals growing between 35-37° C. after incubation for 3-5 days at this temperature. Without being bond to a particular theory, the higher temperature either enhanced the solubility of the endonuclease or facilitated the thermodynamically driven process of Ostwald ripening to generate crystals that were approximately 8-10 times larger in volume than crystals grown at room temperature (see FIG. 6A-6B).

Diffraction experiments were run at the UCSD crystallography facility using a copper X-ray source. The native structure of the endonuclease construct described herein was solved and gratifyingly shown to be highly similar to other reported structures.

Example 16: X-Ray Structures of Various Inhibitors in Influenza Endonuclease

The active site of this crystal prepared in Example 15 was also not occluded by symmetry mates, allowing for facile generation of co-crystals by soaking. Soaking experiments were performed with compounds 5, 6, 101 and 106.

Co-crystal X-ray structures of compounds 5, 6, 101 and 106 in influenza endonuclease are shown in FIG. 7A-7E. The co-crystal structures of compounds 5, 6, and 101 depicted the reason for the observed disparity in activity of these 3 fragments. In compound 6, the methyl group was found to prevent the carboxylic acid from coordinating the manganese center with the preferred, head-on geometry. The methyl group in compound 101 was found not to prevent ideal metal binding and have very similar activity to compound 5 ($IC_{50}$=43 nM and 68 nM, respectively). Both compounds 101 and 106 were shown to make minimal contact with the active site aside from metal binding, giving evidence that the low nanomolar activity of these fragments may come from ideal metal interactions.

TABLE 9
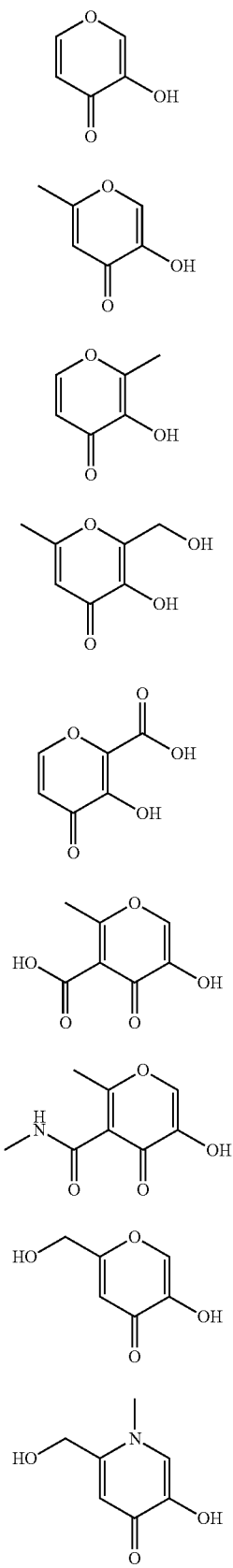
TABLE 9-continued
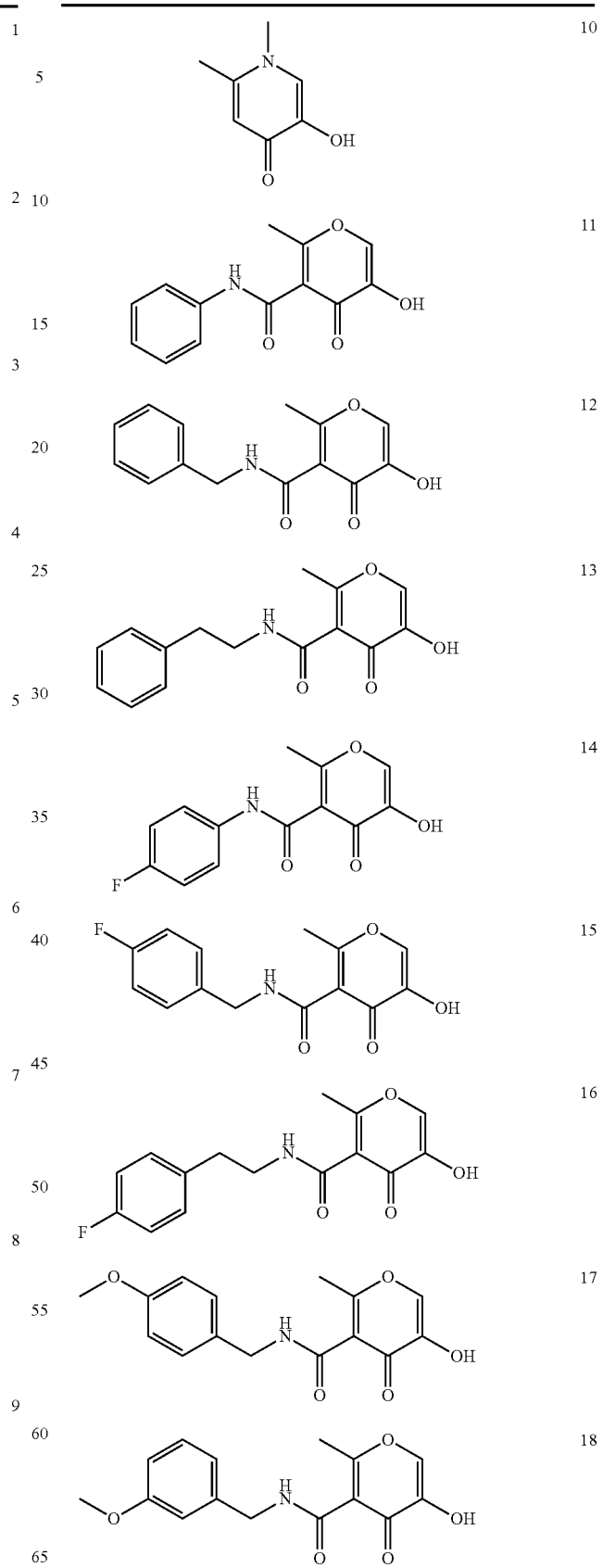

TABLE 9-continued
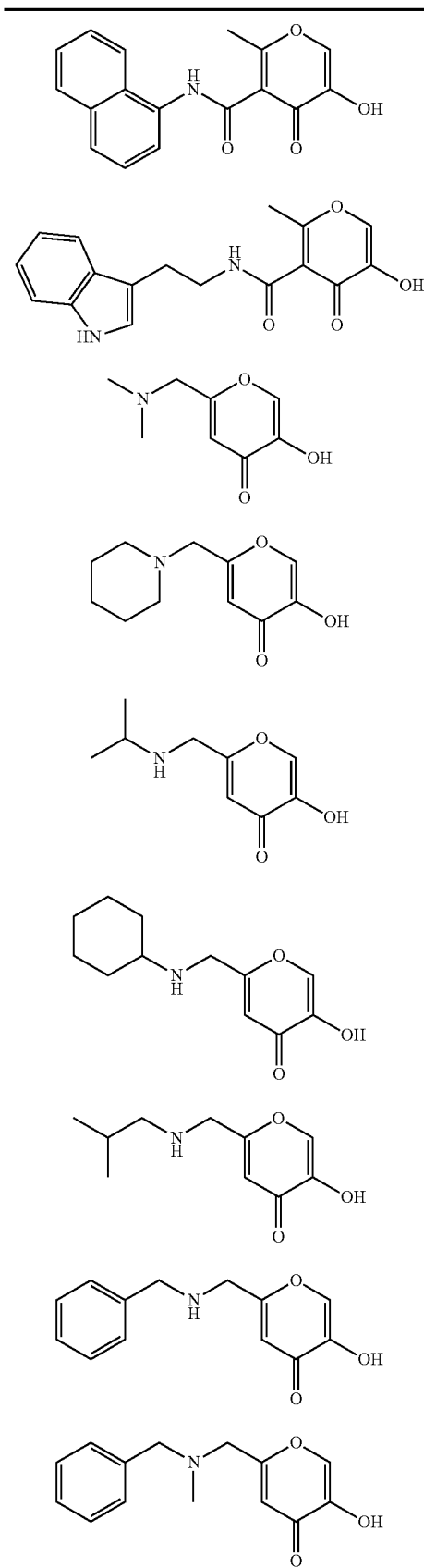
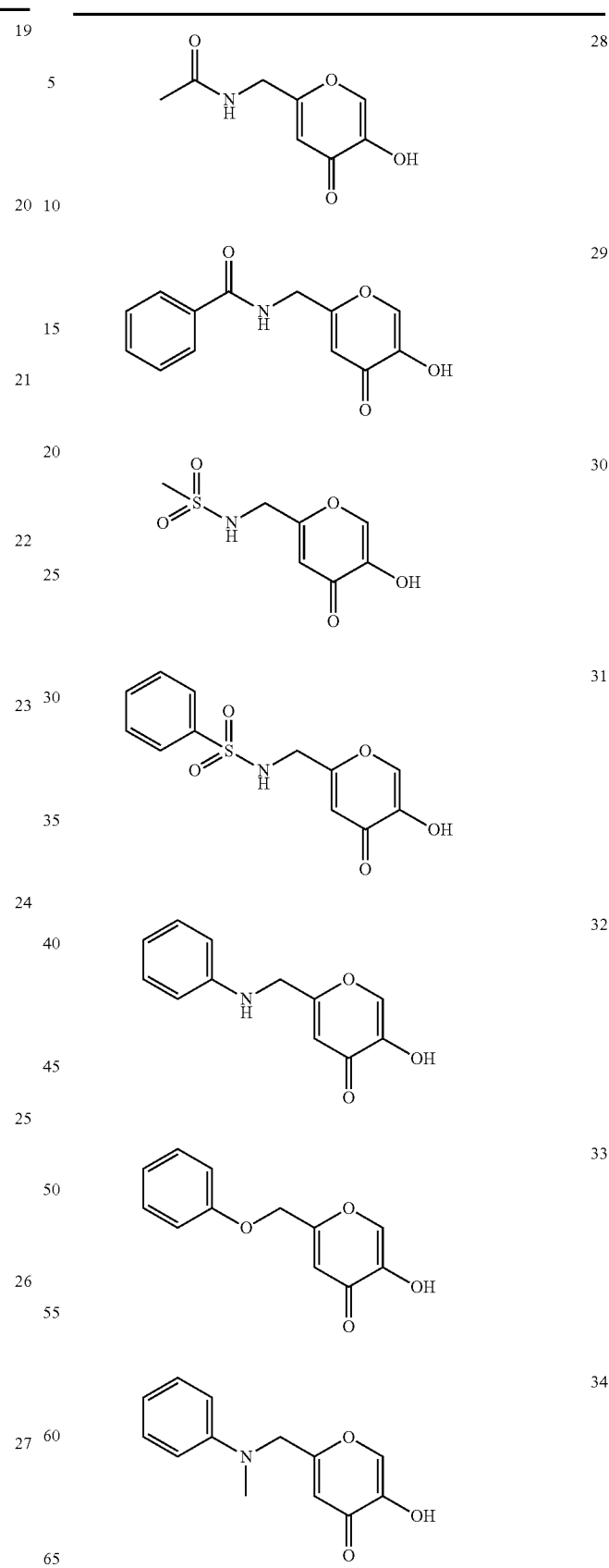

TABLE 9-continued
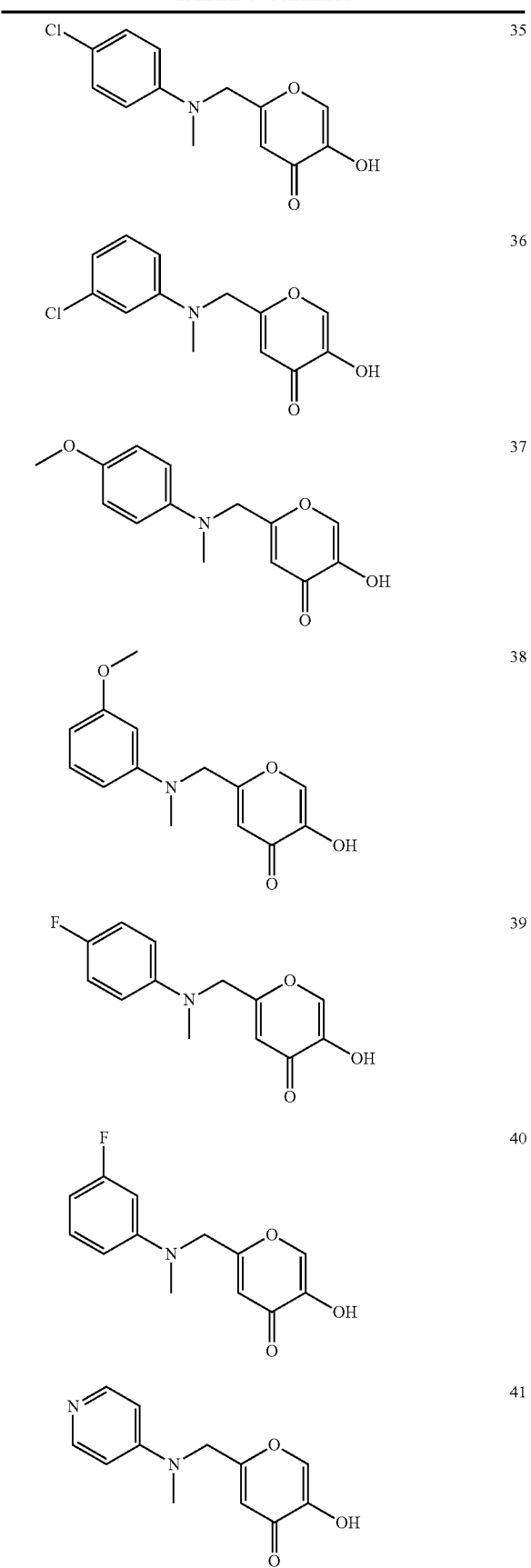
TABLE 9-continued
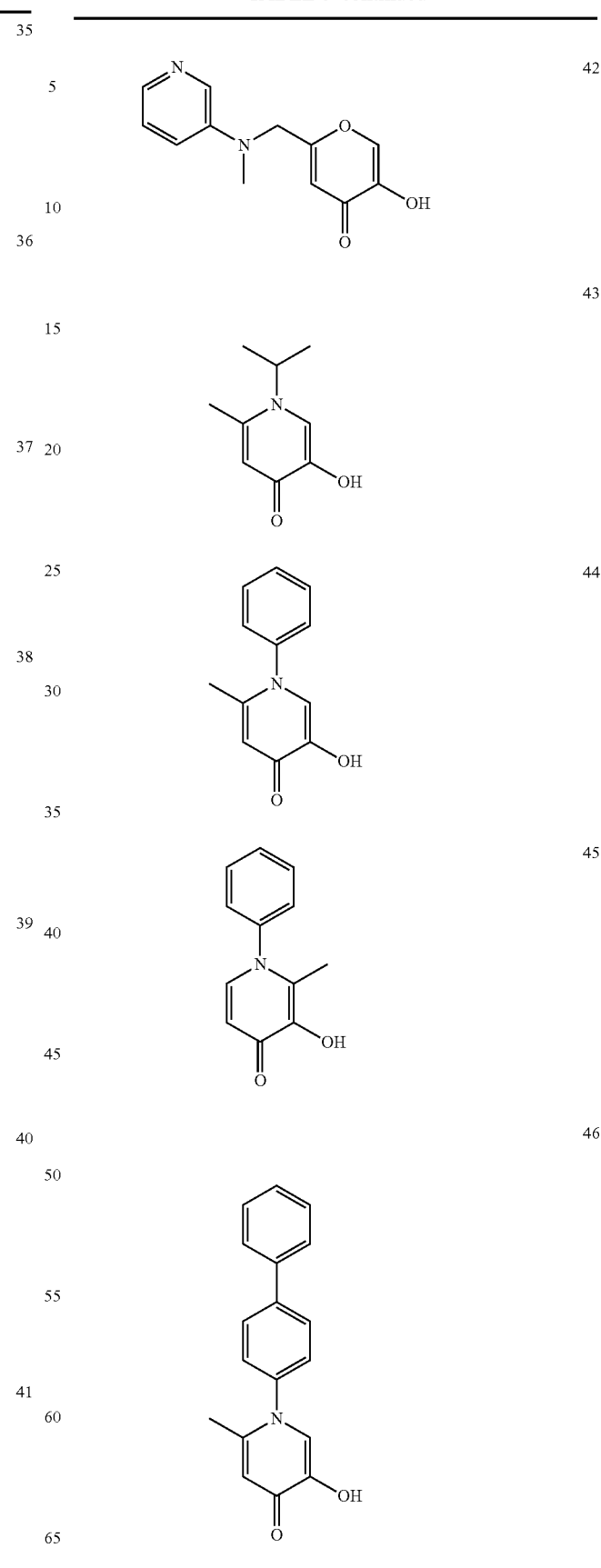

TABLE 9-continued
| | |
|---|---|
| 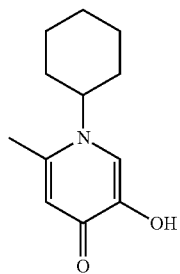 | 47 |
| 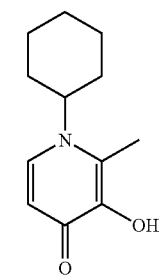 | 48 |
| 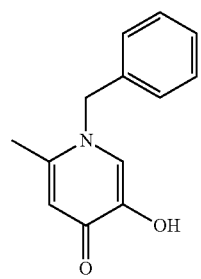 [SMILES: Cc1cc(=O)c(O)cn1Cc1ccccc1] | 49 |
| 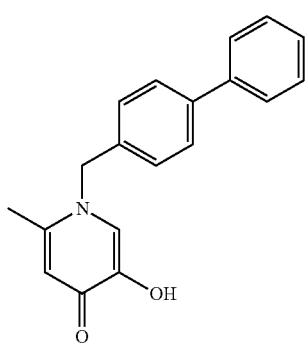 [SMILES: Cc1cc(=O)c(O)cn1Cc1ccc(-c2ccccc2)cc1] | 50 |
| 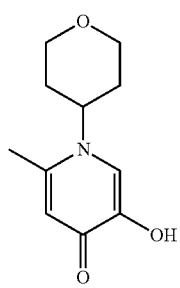 | 51 |
TABLE 9-continued
| | |
|---|---|
| 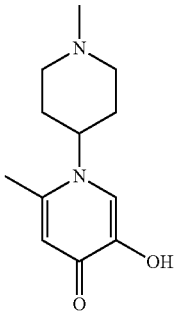 [SMILES: Cc1cc(=O)c(O)cn1C1CCN(C)CC1] | 52 |
| 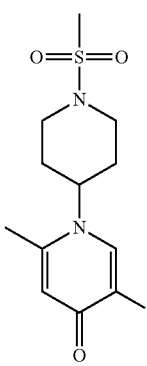 | 53 |
| 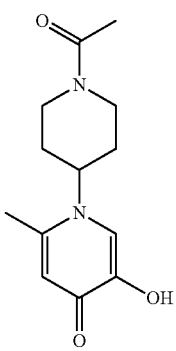 [SMILES: CC(=O)N1CCC(n2cc(O)c(=O)cc2C)CC1] | 54 |
| 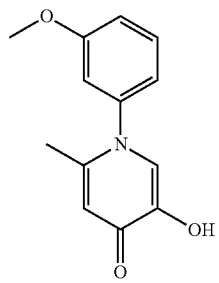 [SMILES: COc1cccc(-n2cc(O)c(=O)cc2C)c1] | 55 |
| 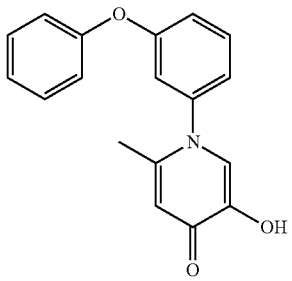 [SMILES: Cc1cc(=O)c(O)cn1-c1cccc(Oc2ccccc2)c1] | 56 |

TABLE 9-continued
57 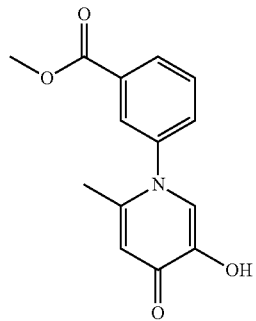 [SMILES: COC(=O)c1cccc(-n2cc(O)c(=O)cc2C)c1]
58 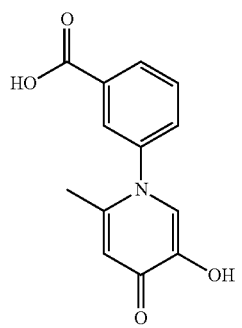 [SMILES: Cc1cc(=O)c(O)cn1-c1cccc(C(=O)O)c1]
59 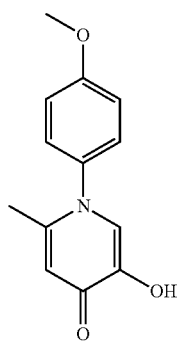 [SMILES: COc1ccc(-n2cc(O)c(=O)cc2C)cc1]
60 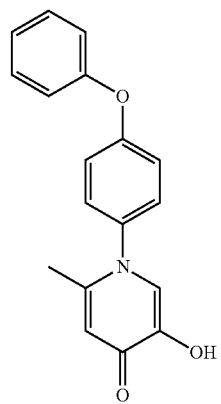 [SMILES: Cc1cc(=O)c(O)cn1-c1ccc(Oc2ccccc2)cc1]
TABLE 9-continued
61 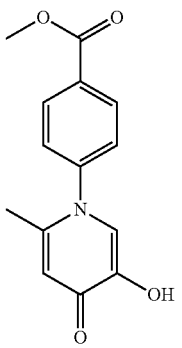 [SMILES: COC(=O)c1ccc(-n2cc(O)c(=O)cc2C)cc1]
62 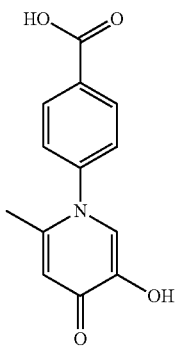 [SMILES: Cc1cc(=O)c(O)cn1-c1ccc(C(=O)O)cc1]
63 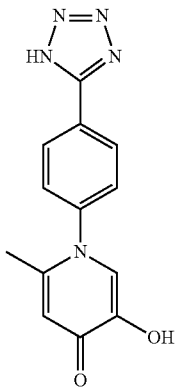 [SMILES: Cc1cc(=O)c(O)cn1-c1ccc(-c2nnn[nH]2)cc1]
64 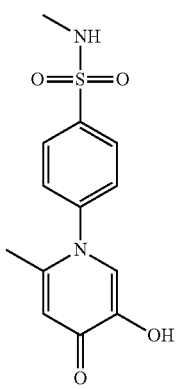 [SMILES: CNS(=O)(=O)c1ccc(-n2cc(O)c(=O)cc2C)cc1]

TABLE 9-continued
65
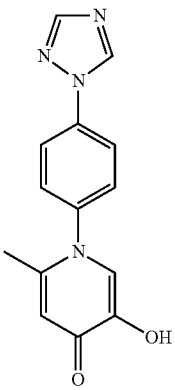 [SMILES: Cc1cc(=O)c(O)cn1-c1ccc(-n2cncn2)cc1]
66
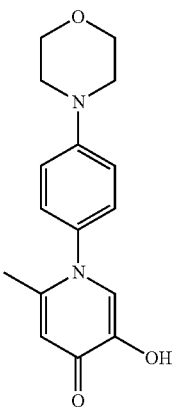 [SMILES: Cc1cc(=O)c(O)cn1-c1ccc(N2CCOCC2)cc1]
67
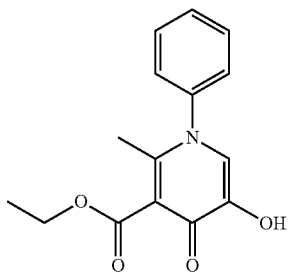 [SMILES: CCOC(=O)c1c(C)n(-c2ccccc2)cc(O)c1=O]
68
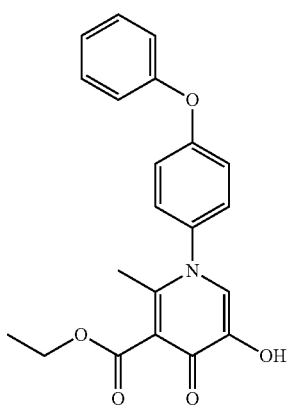 [SMILES: CCOC(=O)c1c(C)n(-c2ccc(Oc3ccccc3)cc2)cc(O)c1=O]
TABLE 9-continued
69
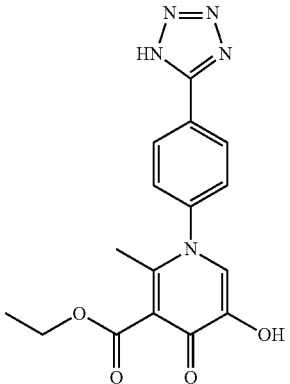 [SMILES: CCOC(=O)c1c(C)n(-c2ccc(-c3nnn[nH]3)cc2)cc(O)c1=O]
70
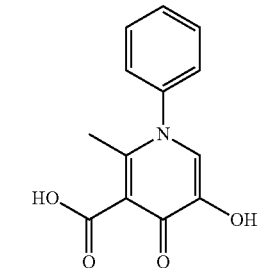 [SMILES: Cc1c(C(=O)O)c(=O)c(O)cn1-c1ccccc1]
71
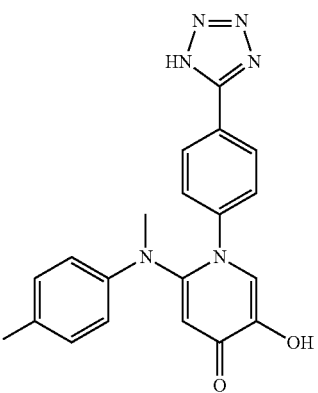
101
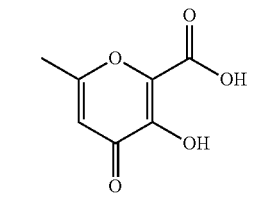
102
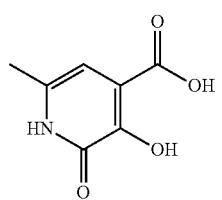

TABLE 9-continued

| 103 |
| 104 |
| 107 |
| A11 |
| 112 |
| 118 |
| 119 |

TABLE 9-continued

| 131 |
| 133 |
| 142 |
| 143 |
| B4 |
| B12 |
| B13 |

TABLE 9-continued

| Structure | Label |
|---|---|
| (B15) 1-hydroxy-6-oxo-1,6-dihydropyridine-2-carboxylic acid | B15 |
| (A9) 3-hydroxy-4-oxo-4H-pyran-2-carboxylic acid | A9 |
| (A10) 3-hydroxy-6-methyl-4-oxo-4H-pyran-2-carboxylic acid | A10 |
| (A11) 3-hydroxy-N-methyl-4-oxo-4H-pyran-2-carboxamide | A11 |
| (A12) 3-hydroxy-N,6-dimethyl-4-oxo-4H-pyran-2-carboxamide | A12 |
| (B11) 3-hydroxy-6-methyl-2-oxo-1,2-dihydropyridine-4-carboxylic acid | B11 |
| (C4) 3-hydroxy-6-methyl-4-thioxo-4H-pyran-2-carboxylic acid | C4 |
| (A13) 5-hydroxy-2-methyl-4-oxo-4H-pyran-3-carboxylic acid | A13 |

TABLE 9-continued

| Structure | Label |
|---|---|
| 3,4,5-trihydroxybenzoic acid | F13 |
| 3-hydroxy-4-oxo-6-(o-tolyl)-1,4-dihydropyridine-2-carboxylic acid | 59-4 |
| 3-hydroxy-4-oxo-6-(m-tolyl)-1,4-dihydropyridine-2-carboxylic acid | 59-5 |
| 6-(3-carboxyphenyl)-3-hydroxy-4-oxo-1,4-dihydropyridine-2-carboxylic acid | 59-6-3Acid |
| 6-(4-carboxyphenyl)-3-hydroxy-4-oxo-1,4-dihydropyridine-2-carboxylic acid | 59-6-4Acid |
| 3-hydroxy-4-oxo-6-(4-(1H-tetrazol-5-yl)phenyl)-1,4-dihydropyridine-2-carboxylic acid | 59-7-4Tet |

TABLE 9-continued
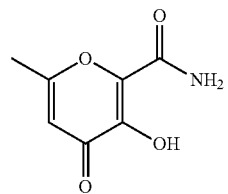
61-1-depro
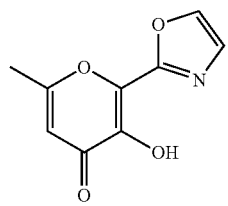
57-6bF
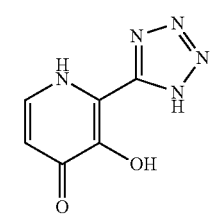 [SMILES: O=c1cc[nH]c(-c2nnn[nH]2)c1O]
62-4c
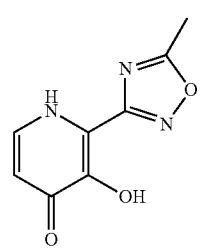
Z1
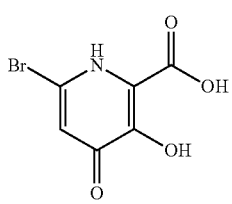
Z2
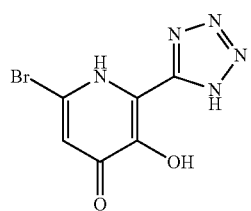 [SMILES: O=c1cc(Br)[nH]c(-c2nnn[nH]2)c1O]
56-NOH
TABLE 9-continued
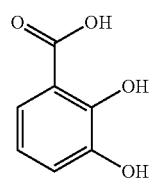 [SMILES: O=C(O)c1cccc(O)c1O]
61-3
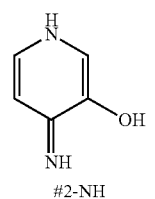
2-NH
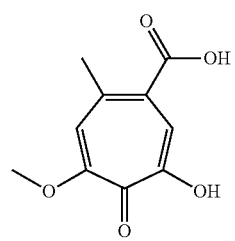
105
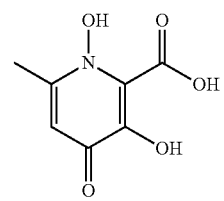
106
201
E4
205

TABLE 9-continued

| | |
|---|---|
| 213 | 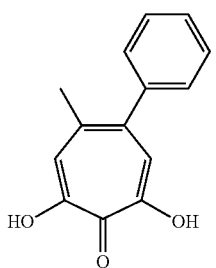 |
| E3 | 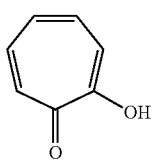 |
| E5 | 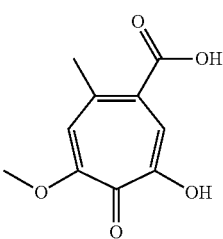 |
| E6 | 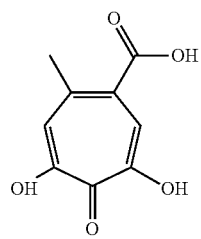 |
| 212 | 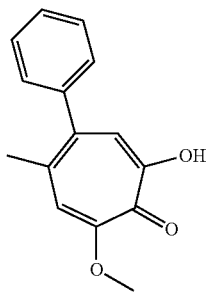 |
| 210 | 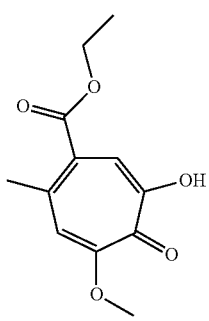 |

REFERENCES

[1] Dunning, J.; Baillie, J. K.; Cao, B.; Hayden, F. G.; International Severe Acute, R.; Emerging Infection, C., Antiviral combinations for severe influenza. *Lancet Infect. Dis.* 2014, 14 (12), 1259-1270.

[2] Mills, C. E.; Robins, J. M.; Lipsitch, M., Transmissibility of 1918 pandemic influenza. *Nature* 2004, 432 (7019), 904-906.

[3] Adjusted vaccine effectiveness estimates for influenza seasons from 2005-2015. www.cdc.gov/flu/professionals/vaccination/effectiveness-studies.htm (accessed Feb. 26, 2016).

[4] Monod, A.; Swale, C.; Tarus, B.; Tissot, A.; Delmas, B.; Ruigrok, R. W.; Crepin, T.; Slama-Schwok, A., Learning from structure-based drug design and new antivirals targeting the ribonucleoprotein complex for the treatment of influenza. *Expert Opin. Drug Discov.* 2015, 10 (4), 345-371.

[5] Stiver, G., The treatment of influenza with antiviral drugs. *Can. Med. Assoc. J.* 2003, 168 (1), 49-57.

[6] Administration, U. S. F. a. D. Tamiflu pediatric adverse events: questions and answers. www.fda.gov/Drugs/DrugSafety/PostmarketDrugSafetylnformationforPatientsandProviders/ucm 107840.htm (accessed Feb. 26, 2016).

[7] Furuse, Y.; Suzuki, A.; Oshitani, H., Large-scale sequence analysis of M gene of influenza A viruses from different species: mechanisms for emergence and spread of amantadine resistance. *Antimicrob. Agents Chemother.* 2009, 53 (10), 4457-4463.

[8] Fiore, A. E.; Fry, A.; Shay, D.; Gubareva, L.; Bresee, J. S.; Uyeki, T. M.; Centers for Disease, C.; Prevention, Antiviral agents for the treatment and chemoprophylaxis of influenza—recommendations of the Advisory Committee on Immunization Practices (ACIP). *MMWR Recomm. Rep.* 2011, 60 (1), 1-24.

[9] Huang, T. S.; Palese, P.; Krystal, M., Determination of influenza virus proteins required for genome replication. *J. Virol.* 1990, 64 (11), 5669-5673.

[10] Drake, J. W., Rates of spontaneous mutation among RNA viruses. *Proc. of the Natl. Acad. Sci. USA* 1993, 90 (9), 4171-4175.

[11] Fodor, E., The RNA polymerase of influenza a virus: mechanisms of viral transcription and replication. *Acta. Virol.* 2013, 57 (2), 113-122.

[12] Plotch, S. J.; Bouloy, M.; Ulmanen, I.; Krug, R. M., A unique cap(m7GpppXm)-dependent influenza virion endonuclease cleaves capped RNAs to generate the primers that initiate viral RNA transcription. *Cell* 1981, 23 (3), 847-858.

[13] Dias, A.; Bouvier, D.; Crepin, T.; McCarthy, A. A.; Hart, D. J.; Baudin, F.; Cusack, S.; Ruigrok, R. W., The cap-snatching endonuclease of influenza virus polymerase resides in the PA subunit. *Nature* 2009, 458 (7240), 914-918.

[14] Beaton, A. R.; Krug, R. M., Selected host cell capped RNA fragments prime influenza viral RNA transcription in vivo. *Nucleic Acids Res.* 1981, 9 (17), 4423-4436.

[15] Xie, L.; Wartchow, C.; Shia, S.; Uehara, K.; Steffek, M.; Warne, R.; Sutton, J.; Muiru, G. T.; Leonard, V. H.; Bussiere, D. E.; Ma, X., Molecular basis of mRNA cap recognition by Influenza B polymerase PB2 subunit. *J. Biol. Chem.* 2015.

[16] Hatakeyama, D.; Shoji, M.; Yamayoshi, S.; Hirota, T.; Nagae, M.; Yanagisawa, S.; Nakano, M.; Ohmi, N.; Noda, T.; Kawaoka, Y.; Kuzuhara, T., A novel functional site in the PB2 subunit of influenza A virus essential for acetyl- CoA interaction, RNA polymerase activity, and viral replication. *J. Biol. Chem.* 2014, 289 (36), 24980-24994.

[17] Blok, V.; Cianci, C.; Tibbles, K. W.; Inglis, S. C.; Krystal, M.; Digard, P., Inhibition of the influenza virus RNA-dependent RNA polymerase by antisera directed against the carboxy-terminal region of the PB2 subunit. *J. Gen. Virol.* 1996, 77 (Pt 5), 1025-1033.

[18] DuBois, R. M.; Slavish, P. J.; Baughman, B. M.; Yun, M. K.; Bao, J.; Webby, R. J.; Webb, T. R.; White, S. W., Structural and biochemical basis for development of influenza virus inhibitors targeting the PA endonuclease. *PLoS Pathog.* 2012, 8 (8), e1002830.

[19] Nakazawa, M.; Kadowaki, S. E.; Watanabe, I.; Kadowaki, Y.; Takei, M.; Fukuda, H., PA subunit of RNA polymerase as a promising target for anti-influenza virus agents. *Antiviral Res.* 2008, 78 (3), 194-201.

[20] Tomassini, J.; Selnick, H.; Davies, M. E.; Armstrong, M. E.; Baldwin, J.; Bourgeois, M.; Hastings, J.; Hazuda, D.; Lewis, J.; McClements, W.; et al., Inhibition of cap (m7GpppXm)-dependent endonuclease of influenza virus by 4-substituted 2,4-dioxobutanoic acid compounds. *Antimicrob. Agents Chemother.* 1994, 38 (12), 2827-2837.

[21] Hastings, J. C.; Selnick, H.; Wolanski, B.; Tomassini, J. E., Anti-influenza virus activities of 4-substituted 2,4-dioxobutanoic acid inhibitors. *Antimicrob. Agents Chemother.* 1996, 40 (5), 1304-1307.

[22] Cianci, C.; Chung, T. D. Y.; Meanwell, N.; Putz, H.; Hagen, M.; Colonno, R. J.; Krystal, M., Identification of N-hydroxamic acid and N-hydroxyimide compounds that inhibit the influenza virus polymerase. *Antivir. Chem. Chemother.* 1996, 7 (6), 353-360.

[23] Tomassini, J. E.; Davies, M. E.; Hastings, J. C.; Lingham, R.; Mojena, M.; Raghoobar, S. L.; Singh, S. B.; Tkacz, J. S.; Goetz, M. A., A novel antiviral agent which inhibits the endonuclease of influenza viruses. *Antimicrob. Agents Chemother.* 1996, 40 (5), 1189-1193.

[24] Kuzuhara, T.; Iwai, Y.; Takahashi, H.; Hatakeyama, D.; Echigo, N., Green tea catechins inhibit the endonuclease activity of influenza A virus RNA polymerase. *PLoS Curr.* 2009, 1, RRN1052.

[25] Kowalinski, E.; Zubieta, C.; Wolkerstorfer, A.; Szolar, O. H.; Ruigrok, R. W.; Cusack, S., Structural analysis of specific metal chelating inhibitor binding to the endonuclease domain of influenza pH1N1 (2009) polymerase. *PLoS Pathog.* 2012, 8 (8), e1002831.

[26] Sagong, H. Y.; Bauman, J. D.; Patel, D.; Das, K.; Arnold, E.; LaVoie, E. J., Phenyl substituted 4-hydroxypyridazin-3(2H)-ones and 5-hydroxypyrimidin-4(3H)-ones: inhibitors of influenza A endonuclease. *J. Med. Chem.* 2014, 57 (19), 8086-8098.

[27] Parhi, A. K.; Xiang, A.; Bauman, J. D.; Patel, D.; Vijayan, R. S.; Das, K.; Arnold, E.; Lavoie, E. J., Phenyl substituted 3-hydroxypyridin-2(1H)-ones: inhibitors of influenza A endonuclease. *Bioorg. Med. Chem.* 2013, 21 (21), 6435-6446.

[28] Bauman, J. D.; Patel, D.; Baker, S. F.; Vijayan, R. S.; Xiang, A.; Parhi, A. K.; Martinez-Sobrido, L.; LaVoie, E. J.; Das, K.; Arnold, E., Crystallographic fragment screening and structure-based optimization yields a new class of influenza endonuclease inhibitors. *ACS Chem. Biol.* 2013, 8 (11), 2501-2508.

[29] Baughman, B. M.; Jake Slavish, P.; DuBois, R. M.; Boyd, V. A.; White, S. W.; Webb, T. R., Identification of influenza endonuclease inhibitors using a novel fluorescence polarization assay. *ACS Chem Biol* 2012, 7 (3), 526-534.

[30] Jacobsen, J. A.; Fullagar, J. L.; Miller, M. T.; Cohen, S. M., Identifying chelators for metalloprotein inhibitors using a fragment-based approach. *J. Med. Chem.* 2011, 54 (2), 591-602.

[31] Hopkins, A. L.; Groom, C. R.; Alex, A., Ligand efficiency: a useful metric for lead selection. *Drug. Discov. Today* 2004, 9 (10), 430-431.

[32] Sanna, D.; Buglyo, P.; Biro, L.; Micera, G.; Garribba, E., Coordinating properties of pyrone and pyridinone derivatives, tropolone and catechol toward the VO2+ ion: an experimental and computational approach. *Eur. J. Inorg. Chem.* 2012, (7), 1079-1092.

[33] Raha, K.; Merz, K M., Jr., A quantum mechanics-based scoring function: study of zinc ion-mediated ligand binding. *J. Am. Chem. Soc.* 2004, 126 (4), 1020-1021.

[34] Zhang, J.; Yang, W.; Piquemal, J. P.; Ren, P., Modeling structural coordination and ligand binding in zinc proteins with a polarizable potential. *J. Chem. Theory Comput.* 2012, 8 (4), 1314-1324.

[35] Stevaert, A.; Dallocchio, R.; Dessi, A.; Pala, N.; Rogolino, D.; Sechi, M.; Naesens, L., Mutational analysis of the binding pockets of the diketo acid inhibitor L-742, 001 in the influenza virus PA endonuclease. *J Virol.* 2013, 87 (19), 10524-10538.

[36] Sagong, H. Y.; Parhi, A.; Bauman, J. D.; Patel, D.; Vijayan, R. S.; Das, K.; Arnold, E.; LaVoie, E. J., 3-Hydroxyquinolin-2(1H)-ones as inhibitors of influenza A endonuclease. *ACSMed. Chem. Lett.* 2013, 4 (6), 547-550.

[37] Bohm, H. J.; Flohr, A.; Stahl, M., Scaffold hopping. *Drug Discov. Today Technol.* 2004, 1 (3), 217-224.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

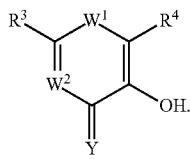

wherein,
Y is O, S, or NH;
$W^1$ is —CH($R^1$)—, or —N($R^1$)—;
$R^1$ is hydrogen;
$W^2$ is —C($R^2$)=;
$R^2$ is hydrogen, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is substituted or unsubstituted cycloalkyl, substituted or unsubstituted heterocycloalkyl, substituted or unsubstituted aryl, or substituted or unsubstituted heteroaryl;
$R^4$ is halogen, —$CX^4_3$, —$CHX^4_2$, —$CH_2X^4$, —$OCX^4_3$, —$OCH_2X^4$, —$OCHX^4_2$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —C(O)—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
each $R^{2A}$, $R^{2B}$, $R^{2C}$, $R^{2D}$, $R^{4A}$, $R^{4B}$, and $R^{4D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;
$R^{1D}$ is hydrogen;
$R^{4C}$ is hydrogen;
each X, $X^2$, and $X^4$ is independently —F, —Cl, —Br, or —I;
n2 and n4 are independently an integer from 0 to 4; and m2, m4, v2 and v4 are independently an integer from 1 to 2.

2. The compound of claim 1, wherein Y is S or O.

3. The compound of claim 1, wherein $W^1$ is —N($R^1$)—.

4. The compound of claim 1, wherein $W^2$ is —C($R^2$)=.

5. The compound of claim 4, wherein $R^2$ is hydrogen, —$OR^{2D}$, —$C(O)R^{2C}$, —C(O)—$OR^{2C}$, —$C(O)NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

6. The compound of claim 1, wherein $R^3$ is substituted or unsubstituted aryl, or substituted or unsubstituted heteroaryl.

7. The compound of claim 1, wherein $R^4$ is halogen, —$C(O)R^{4c}$, —C(O)—$OR^{4c}$, —$C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

8. A pharmaceutical composition comprising the compound of claim 1 and a pharmaceutically acceptable excipient.

9. A method of inhibiting RNA-dependent RNA polymerase PA subunit endonuclease protein activity, said method comprising contacting the RNA-dependent RNA polymerase PA subunit endonuclease protein with an effective amount of a compound of claim 1, wherein the RNA-dependent RNA polymerase PA subunit endonuclease protein is an influenza virus protein.

10. A method of treating a viral infection, said method comprising administering to a subject in need thereof an effective amount of a compound of claim 1, wherein the viral infection is an influenza virus infection.

11. The method of claim 10, wherein the viral infection is an influenza virus A infection.

12. The compound of claim 1 having the formula:

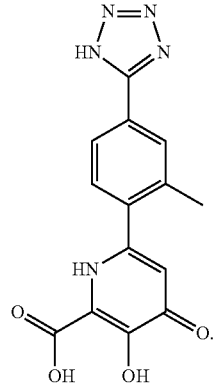 [SMILES: Cc1cc(-c2nnn[nH]2)ccc1-c1cc(=O)c(O)c(C(=O)O)[nH]1]

13. The compound of claim 1, wherein $R^3$ is $R^{30}$-substituted or unsubstituted aryl;
wherein,
$R^{30}$ is independently oxo, halogen, —$CX^{30}_3$, —$CHX^{30}_2$, —$CH_2X^{30}$, —$OCX^{30}_3$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OR^{31}$, —$NHR^{31}$, —N($CH_3$)$R^{31}$, —$COOR^{31}$, —$CONHR^{31}$, —$SR^{31}$, —$SO_2NHR^{31}$, —$SO_2R^{31}$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl;

$X^{30}$ is independently —F, —Cl, —Br, or —I;

$R^{31}$ is independently oxo, halogen, —CX$^{31}_3$, —CHX$^{31}_2$, —CH$_2$X$^{31}$, —OCX$^{31}_3$, —OCH$_2$X$^{31}$, —OCHX$^{31}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OR$^{32}$, —NHR$^{32}$, —N(CH$_3$)R$^{32}$, —COOR$^{32}$, —CONHR$^{32}$, —SR$^{32}$, R$^{32}$-substituted or unsubstituted alkyl, R$^{32}$-substituted or unsubstituted heteroalkyl, R$^{32}$-substituted or unsubstituted cycloalkyl, R$^{32}$-substituted or unsubstituted heterocycloalkyl, R$^{32}$-substituted or unsubstituted aryl, or R$^{32}$-substituted or unsubstituted heteroaryl;

$X^{31}$ is independently —F, —Cl, —Br, or —I;

$R^{32}$ is independently oxo, halogen, —CX$^{32}_3$, —CHX$^{32}_2$, —CH$_2$X$^{32}$, —OCX$^{32}_3$, —OCH$_2$X$^{32}$, —OCHX$^{32}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl, unsubstituted heteroalkyl, unsubstituted cycloalkyl, unsubstituted heterocycloalkyl, unsubstituted aryl, or unsubstituted heteroaryl; and $X^{32}$ is independently —F, —Cl, —Br, or —I.

14. The compound of claim 13, wherein R$^3$ is R$^{30}$-substituted or unsubstituted —CH$_2$N(CH$_3$)Ph, or R$^{30}$-substituted or unsubstituted phenyl.

15. The compound of claim 1, wherein R$^4$ is —C(O)R$^{4C}$, —C(O)—OR$^{4C}$, —C(O)NR$^{4A}$R$^{4B}$, or substituted or unsubstituted heteroaryl.

16. The compound of claim 15, wherein R$^4$ is —C(O)OH, —C(O)NHCH$_3$, or unsubstituted tetrazolyl.

* * * * *

SEQUENCE LISTING

<160> NUMBER OF SEQ ID NOS: 2

<210> SEQ ID NO 1
<211> LENGTH: 241
<212> TYPE: PRT
<213> ORGANISM: Influenza A virus

<400> SEQUENCE: 1

Met Ala His His His His His His Ser Arg Ala Trp Arg His Pro Gln
1               5                   10                  15

```
Phe Gly Gly His His His His His Ala Leu Glu Val Leu Phe Gln
            20                  25                  30

Gly Pro Leu Gly Ser Met Glu Asp Phe Val Arg Gln Cys Phe Asn Pro
            35                  40                  45

Met Ile Val Glu Leu Ala Glu Lys Ala Met Lys Glu Tyr Gly Glu Asp
 50                  55                  60

Pro Lys Ile Glu Thr Asn Lys Phe Ala Ala Ile Cys Thr His Leu Glu
 65                  70                  75                  80

Val Cys Phe Met Tyr Ser Asp Phe His Phe Ile Asp Glu Arg Gly Glu
                     85                  90                  95

Ser Ile Ile Val Glu Ser Gly Asp Pro Asn Ala Leu Leu Lys His Arg
                    100                 105                 110

Phe Glu Ile Ile Glu Gly Arg Asp Arg Ile Met Ala Trp Thr Val Val
                115                 120                 125

Asn Ser Ile Cys Asn Thr Thr Gly Val Glu Lys Pro Lys Phe Leu Pro
130                 135                 140

Asp Leu Tyr Asp Tyr Lys Glu Asn Arg Phe Ile Glu Ile Gly Val Thr
145                 150                 155                 160

Arg Arg Glu Val His Ile Tyr Tyr Leu Glu Lys Ala Asn Lys Ile Lys
                    165                 170                 175

Ser Glu Lys Thr His Ile His Ile Phe Ser Phe Thr Gly Glu Glu Met
                180                 185                 190

Ala Thr Lys Ala Asp Tyr Thr Leu Asp Glu Glu Ser Arg Ala Arg Ile
                195                 200                 205

Lys Thr Arg Leu Phe Thr Ile Arg Gln Glu Met Ala Ser Arg Ser Leu
                210                 215                 220

Trp Asp Ser Phe Arg Gln Ser Glu Arg Gly Glu Glu Thr Val Glu Glu
225                 230                 235                 240

Arg

<210> SEQ ID NO 2
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with 6-FAM
<220> FEATURE:
<221> NAME/KEY: misc_feature
<222> LOCATION: (17)..(17)
<223> OTHER INFORMATION: Residue modified with TAMRA

<400> SEQUENCE: 2
aatcgcaggc agcactc                                               17
```